(12) United States Patent
Lys et al.

(10) Patent No.: US 11,266,081 B2
(45) Date of Patent: Mar. 8, 2022

(54) METHODS, APPARATUS, AND SYSTEMS FOR LIGHTING AND DISTRIBUTED SENSING IN CONTROLLED AGRICULTURAL ENVIRONMENTS

(71) Applicant: Agnetix, Inc., San Diego, CA (US)

(72) Inventors: Ihor Lys, La Jolla, CA (US); Nicholas Maderas, Richmond, CA (US)

(73) Assignee: Agnetix, Inc., San Diego, CA (US)

( * ) Notice: Subject to any disclaimer, the term of this patent is extended or adjusted under 35 U.S.C. 154(b) by 0 days.

(21) Appl. No.: 17/216,291

(22) Filed: Mar. 29, 2021

(65) Prior Publication Data

US 2021/0235632 A1      Aug. 5, 2021

Related U.S. Application Data

(63) Continuation of application No. 16/828,521, filed on Mar. 24, 2020, now Pat. No. 10,959,383, which is a (Continued)

(51) Int. Cl.
*G01K 3/14* (2006.01)
*A01G 9/24* (2006.01)
(Continued)

(52) U.S. Cl.
CPC .............. *A01G 9/24* (2013.01); *A01G 7/045* (2013.01); *A01G 9/245* (2013.01); *A01G 9/246* (2013.01);
(Continued)

(58) Field of Classification Search
CPC .......... A01G 7/045; A01G 9/249; A01G 9/24; A01G 9/246; A01G 31/02; A01G 9/1423;
(Continued)

(56) References Cited

U.S. PATENT DOCUMENTS 3,869,605 A    3/1975 Davis
4,300,623 A   11/1981 Meckler
(Continued)

FOREIGN PATENT DOCUMENTS

CA       2632307 A1   11/2009
CN    101737694 A    6/2010
(Continued)

OTHER PUBLICATIONS

U.S. Appl. No. 16/114,088, filed Aug. 27, 2018, Lys et al.
(Continued)

*Primary Examiner* — Gail Kaplan Verbitsky
(74) *Attorney, Agent, or Firm* — Smith Baluch LLP

(57) ABSTRACT

A distributed sensor grid may be used to monitor the growth conditions of plants in an agricultural environment. In one example, a distributed sensor grid may include sensors that are arranged as a grid defined by a vertical axis and a first horizontal axis. The sensors may each be coupled to a cable and/or a port that provides operating power and/or network communications access. In some implementations, a plurality of lighting fixtures disposed in the agricultural environment may be configured to provide the power and network communications access to one or more sensors, thus alleviating use of excess cabling for connectivity and simplifying installation. The sensors may be correspondingly disposed within the vicinity of respective lighting fixtures to monitor growth conditions for a portion of the agricultural environment. The sensors used may also be packaged as an integrated sensor assembly, further simplifying installation and deployment.

30 Claims, 90 Drawing Sheets
(13 of 90 Drawing Sheet(s) Filed in Color)

Related U.S. Application Data continuation of application No. PCT/US2019/030889, filed on May 6, 2019.

(60) Provisional application No. 62/684,641, filed on Jun. 13, 2018, provisional application No. 62/667,217, filed on May 4, 2018.

(51) Int. Cl.

| | |
|---|---|
| *F21V 29/56* | (2015.01) |
| *A01G 7/04* | (2006.01) |
| *F21V 23/06* | (2006.01) |
| *G01K 1/02* | (2021.01) |
| *G01N 33/00* | (2006.01) |
| *G01N 33/24* | (2006.01) |
| *F21Y 115/10* | (2016.01) |
| *A01G 31/02* | (2006.01) |

(52) U.S. Cl.
CPC .............. *A01G 9/249* (2019.05); *F21V 23/06* (2013.01); *F21V 29/56* (2015.01); *G01K 1/026* (2013.01); *G01N 33/0075* (2013.01); *G01N 33/0098* (2013.01); *G01N 33/246* (2013.01); *A01G 31/02* (2013.01); *F21Y 2115/10* (2016.08); *G01K 3/14* (2013.01); *G01N 2033/245* (2013.01)

(58) Field of Classification Search
CPC .......... A01G 9/247; A01G 9/245; A01G 9/14; A01G 25/16; A01G 25/00; A01G 7/02; A01G 13/06; A01G 22/05; G01K 1/026; G01K 3/14; G01N 2033/245; G01N 33/0075; G01N 33/0098; G01N 33/246; G01N 33/075; F21V 29/56; F21V 23/06; F21Y 2115/10
See application file for complete search history.

(56) References Cited

U.S. PATENT DOCUMENTS

| | | | |
|---|---|---|---|
| 5,012,609 A | 5/1991 | Ignatius et al. |
| 6,431,723 B1 | 8/2002 | Schubert et al. |
| 6,683,970 B1 | 1/2004 | Satake et al. |
| 6,880,952 B2 | 4/2005 | Kiraly et al. |
| 7,095,053 B2 | 8/2006 | Mazzochette et al. |
| 7,252,408 B2 | 8/2007 | Mazzochette et al. |
| 7,456,733 B2 | 11/2008 | Joy et al. |
| 7,635,205 B2 | 12/2009 | Yu et al. |
| 7,905,051 B2 | 3/2011 | Lysa |
| 7,933,060 B2 | 4/2011 | Ishii et al. |
| 8,192,053 B2 | 6/2012 | Owen et al. |
| 8,297,782 B2 | 10/2012 | Bafetti et al. |
| 8,358,097 B2 | 1/2013 | Cartwright |
| 8,373,361 B2 | 2/2013 | Smits et al. |
| 8,390,454 B2 | 3/2013 | Lyon et al. |
| 8,558,413 B1 | 10/2013 | Lepard |
| 8,651,704 B1 | 2/2014 | Gordin et al. |
| 8,668,350 B2 | 3/2014 | Wells et al. |
| 8,850,742 B2 | 10/2014 | Dube |
| 8,920,001 B2 | 12/2014 | Part |
| 9,137,874 B2 | 9/2015 | Maxik et al. |
| 9,310,027 B2 | 4/2016 | Wells |
| 9,310,049 B2 | 4/2016 | Wells |
| 9,392,753 B2 | 7/2016 | Krijn et al. |
| 9,404,648 B2 | 8/2016 | Druchinin |
| D768,901 S | 10/2016 | Hillberg et al. |
| 9,516,822 B2 | 12/2016 | Gonyer et al. |
| 9,644,828 B1 | 5/2017 | May |
| 9,688,951 B2 | 6/2017 | Krenbrink et al. |
| 9,693,512 B2 | 7/2017 | Chen et al. |
| 9,857,068 B2 | 1/2018 | Nguyen et al. |
| 10,021,838 B1 | 7/2018 | Gustafik |
| 10,034,435 B2 | 7/2018 | Helene et al. |
| 10,175,215 B2 | 1/2019 | Ozcan et al. |
| 10,188,046 B2 | 1/2019 | Wik et al. |
| 10,261,493 B2 | 4/2019 | Hillberg et al. |
| 10,339,380 B2 | 7/2019 | Greenberg et al. |
| 10,426,099 B2 | 10/2019 | Clendinning et al. |
| 10,512,221 B2 | 12/2019 | Wells |
| 10,517,226 B2 | 12/2019 | Lee |
| 10,555,466 B2 | 2/2020 | Gonyer et al. |
| 10,627,785 B2 | 4/2020 | King et al. |
| 10,635,274 B2 | 4/2020 | Greenberg et al. |
| 10,660,170 B2 | 5/2020 | Wells |
| 10,674,677 B2 | 6/2020 | Pohjanvouri et al. |
| 10,750,671 B2 | 8/2020 | Wik et al. |
| 10,856,470 B2 | 12/2020 | Lys et al. |
| 10,881,051 B2 | 1/2021 | Lys et al. |
| 10,925,219 B2 | 2/2021 | Nguyen et al. |
| 10,949,974 B2 | 3/2021 | King et al. |
| 10,959,383 B2 * | 3/2021 | Lys .................... G01N 33/0098 |
| 10,999,976 B2 * | 5/2021 | Lys ......................... F21V 15/01 |
| 11,013,078 B2 | 5/2021 | Lys et al. |
| 11,044,854 B2 | 6/2021 | Lys et al. |
| 11,076,536 B2 | 8/2021 | Lys et al. |
| 2003/0216837 A1 | 11/2003 | Reich et al. |
| 2004/0120156 A1 | 6/2004 | Ryan |
| 2005/0103473 A1 | 5/2005 | Todd et al. |
| 2005/0152143 A1 | 7/2005 | Lee et al. |
| 2005/0162850 A1 | 7/2005 | Luk et al. |
| 2008/0205030 A1 | 8/2008 | Hargreaves |
| 2009/0027888 A1 | 1/2009 | Yu et al. |
| 2009/0040759 A1 | 2/2009 | Zhang et al. |
| 2010/0321950 A1 | 12/2010 | Wong |
| 2011/0037369 A1 | 2/2011 | Van Elmpt |
| 2012/0033431 A1 | 2/2012 | Martinez et al. |
| 2012/0162976 A1 | 6/2012 | Claeys |
| 2012/0211201 A1 | 8/2012 | Kunstwadl et al. |
| 2012/0250302 A1 | 10/2012 | Edwards et al. |
| 2012/0257375 A1 | 10/2012 | Tickner et al. |
| 2013/0003382 A1 | 1/2013 | Ohura et al. |
| 2013/0006401 A1 | 1/2013 | Shan |
| 2013/0057247 A1 | 3/2013 | Russell et al. |
| 2013/0293156 A1 | 11/2013 | Wells |
| 2014/0259920 A1 | 9/2014 | Wilson |
| 2014/0301067 A1 | 10/2014 | Morgan |
| 2015/0003070 A1 | 1/2015 | Medendorp, Jr. et al. |
| 2015/0250106 A1 | 9/2015 | Wik et al. |
| 2015/0254738 A1 | 9/2015 | Wright, III et al. |
| 2015/0313092 A1 | 11/2015 | Pocock et al. |
| 2015/0356894 A1 | 12/2015 | Petrocy et al. |
| 2016/0007424 A1 | 1/2016 | Maxik et al. |
| 2016/0081178 A1 | 3/2016 | D'Onofrio |
| 2016/0113211 A1 | 4/2016 | MacKenzie |
| 2016/0113213 A1 | 4/2016 | Berinsky |
| 2016/0183351 A1 * | 6/2016 | Snyder .................. H04L 12/413 315/152 |
| 2016/0209020 A1 | 7/2016 | Sprankle et al. |
| 2016/0217562 A1 | 7/2016 | Ulman |
| 2016/0235013 A1 | 8/2016 | Pohjanvouri et al. |
| 2016/0262313 A1 | 9/2016 | Szeto et al. |
| 2016/0278300 A1 | 9/2016 | Clendinning et al. |
| 2016/0360712 A1 | 12/2016 | Yorio et al. |
| 2016/0366833 A1 | 12/2016 | Pohjanvouri et al. |
| 2017/0023193 A1 | 1/2017 | Thosteson et al. |
| 2017/0055474 A1 | 3/2017 | Storey |
| 2017/0074474 A1 * | 3/2017 | Bailey ..................... F21V 17/16 |
| 2017/0095639 A1 | 4/2017 | Trzecieski |
| 2017/0134623 A1 | 5/2017 | Lee |
| 2017/0146226 A1 | 5/2017 | Storey et al. |
| 2017/0215252 A1 | 7/2017 | Wells |
| 2017/0231169 A1 | 8/2017 | Gillard et al. |
| 2017/0241632 A1 | 8/2017 | Nguyen et al. |
| 2017/0244934 A1 | 8/2017 | Chien |
| 2017/0303478 A1 | 10/2017 | Smith et al. |
| 2017/0311414 A1 | 10/2017 | Kido et al. |
| 2017/0339839 A1 | 11/2017 | Carstensen et al. |
| 2018/0007845 A1 | 1/2018 | Martin |
| 2018/0014485 A1 | 1/2018 | Whitcher et al. |
| 2018/0054985 A1 | 3/2018 | Li |
| 2018/0116025 A1 | 4/2018 | Adams et al. |

(56) References Cited

U.S. PATENT DOCUMENTS

| | | | |
|---|---|---|---|
| 2018/0128472 A1 | 5/2018 | Nguyen et al. | |
| 2018/0177008 A1 | 6/2018 | Jiang et al. | |
| 2018/0259550 A1 | 9/2018 | Nakamura et al. | |
| 2018/0309941 A1 | 10/2018 | Lopez et al. | |
| 2018/0313760 A1 | 11/2018 | Kramer et al. | |
| 2018/0363886 A1 | 12/2018 | Narayanaswamy et al. | |
| 2019/0008096 A1 | 1/2019 | Lee | |
| 2019/0364743 A1 | 1/2019 | Lys et al. | |
| 2019/0116739 A1 | 4/2019 | Lys et al. | |
| 2019/0141911 A1 | 5/2019 | Nguyen et al. | |
| 2019/0221044 A1 | 7/2019 | Motta et al. | |
| 2019/0234797 A1 | 8/2019 | Ramer et al. | |
| 2019/0244417 A1 | 8/2019 | Ashdown et al. | |
| 2019/0244428 A1 | 8/2019 | Greenberg et al. | |
| 2019/0246278 A1 | 8/2019 | Dorfman et al. | |
| 2019/0303164 A1 | 10/2019 | King | |
| 2019/0338934 A1 | 11/2019 | Ray et al. | |
| 2019/0353341 A1 | 11/2019 | Spiro | |
| 2020/0077598 A1 | 3/2020 | Wells | |
| 2020/0134741 A1 | 4/2020 | Bongartz et al. | |
| 2020/0163183 A1 | 5/2020 | Lys et al. | |
| 2020/0236862 A1 | 7/2020 | Lys et al. | |
| 2020/0236870 A1 | 7/2020 | Lys et al. | |
| 2021/0000097 A1* | 1/2021 | Marchesini | G05D 1/102 |
| 2021/0059123 A1 | 3/2021 | Lys et al. | |
| 2021/0120748 A1 | 4/2021 | Lys et al. | |

FOREIGN PATENT DOCUMENTS

| | | |
|---|---|---|
| CN | 102016407 A | 4/2011 |
| CN | 201811100 U | 4/2011 |
| CN | 102287711 A | 12/2011 |
| CN | 102421281 A | 4/2012 |
| CN | 202955670 U | 5/2013 |
| CN | 203628582 U | 6/2014 |
| CN | 203656872 U | 6/2014 |
| CN | 203686764 U | 7/2014 |
| CN | 203872684 U | 10/2014 |
| CN | 104520636 A | 4/2015 |
| CN | 104981147 A | 10/2015 |
| CN | 204929810 U | 1/2016 |
| CN | 105423198 A | 3/2016 |
| CN | 106151982 A | 11/2016 |
| CN | 205896799 U | 1/2017 |
| CN | 106402746 A | 2/2017 |
| CN | 206181943 U | 5/2017 |
| CN | 107091467 A | 8/2017 |
| CN | 107208871 A | 9/2017 |
| CN | 207369705 U | 5/2018 |
| DE | 202014105523 U1 | 2/2016 |
| DK | 2129212 T3 | 3/2016 |
| EP | 3123823 A1 | 2/2017 |
| EP | 3269231 A1 | 1/2018 |
| EP | 3281514 A1 | 2/2018 |
| EP | 3324099 A1 | 5/2018 |
| EP | 3326452 A1 | 5/2018 |
| EP | 3065535 B1 | 7/2020 |
| FR | 2173912 A1 | 10/1973 |
| JP | 2000207933 A | 7/2000 |
| JP | 2010192152 A | 9/2010 |
| JP | 2011054529 A | 3/2011 |
| JP | 2016214153 A | 12/2016 |
| KR | 10-0941000 B1 | 2/2010 |
| KR | 101020063 B1 | 3/2011 |
| KR | 101068315 B1 | 9/2011 |
| KR | 201125871 A | 9/2011 |
| KR | 101234587 B1 | 2/2013 |
| KR | 20150033363 A | 4/2015 |
| KR | 20150035102 A | 4/2015 |
| KR | 20170021662 A | 2/2017 |
| KR | 10-1730069 B1 | 4/2017 |
| KR | 20170085194 A | 7/2017 |
| KR | 20170115987 A | 10/2017 |
| KR | 20170127406 A | 11/2017 |
| RU | 2010150292 A | 6/2012 |
| TW | M 471005 U | 1/2014 |
| TW | 201501570 A | 1/2015 |
| WO | WO 2008/112822 | 9/2008 |
| WO | WO 2009/074602 A3 | 6/2009 |
| WO | WO 2012/067499 A1 | 5/2012 |
| WO | WO-2014/011444 A3 | 3/2014 |
| WO | WO-2014/064893 A1 | 5/2014 |
| WO | WO 2014/098735 A1 | 6/2014 |
| WO | WO 2015/004179 A1 | 1/2015 |
| WO | WO 2015/144660 A1 | 10/2015 |
| WO | WO-2016/115314 A1 | 7/2016 |
| WO | WO-2016/166311 | 10/2016 |
| WO | WO-2017/024079 A2 | 2/2017 |
| WO | WO-2017/044177 A1 | 3/2017 |
| WO | WO-2017087644 A1 | 5/2017 |
| WO | WO-2017/134623 A1 | 8/2017 |
| WO | WO 2017/184448 A1 | 10/2017 |
| WO | WO-2017/192566 A1 | 11/2017 |
| WO | WO 2018/010946 A1 | 1/2018 |
| WO | WO 2018/013161 A1 | 1/2018 |
| WO | WO 2018/017451 A1 | 1/2018 |
| WO | WO 2018/091560 A1 | 5/2018 |
| WO | WO 2019/014703 A1 | 1/2019 |
| WO | WO 2019/040944 A2 | 2/2019 |
| WO | WO 2019/204805 A1 | 10/2019 |
| WO | WO 2020/219832 | 10/2020 |

OTHER PUBLICATIONS

U.S. Appl. No. 16/390,501, filed Apr. 22, 2019, Lys et al.
U.S. Appl. No. 16/404,192, filed May 6, 2019, Lys et al.
U.S. Appl. No. 16/824,495, filed Mar. 19, 2020, Lys et al.
U.S. Appl. No. 16/828,521, filed Mar. 24, 2020, Lys et al.
U.S. Appl. No. 17/141,173, filed Jan. 4, 2021, Lys et al.
U.S. Appl. No. 17/083,461, filed Oct. 29, 2020, Lys et al.
U.S. Appl. No. 17/317,792, filed May 11, 2021, Lys et al.
U.S. Appl. No. 17/238,044, filed Apr. 22, 2021, Lys et al.
Corrected Notice of Allowance in U.S. Appl. No. 17/141,173 dated May 25, 2021, 2 pages.
International Search Report and Written Opinion in International Patent Application No. PCT/US2020/064382 dated May 27, 2021, 15 pages.
LED Application. Odtech 2014. Accessed at http://www.od-tech.com/eng/sub1/s42.php?PHPSESSID=64d5029f1b80d6df54ab87468d7f9172 on Apr. 23, 2018, 1 page.
PFLi Water-cooled LED Bar. NewLux Horticultural LED Lighting. Accessed at http://newlux.com/product/pfli-water-cooled-led-bar/ on Apr. 23, 2018, 8 pages.
Our Grow Light Models. GS Thermal Solutions 2018. Accessed at http://gsgrow.com/technology/liquid-cooled-led-models/ on Apr. 23, 2018.
GC-Plus Control System. Agrowtek Inc. Accessed at http://agrowtek.com/component/page,shop.product_details/flypage,flypage.tpl/product_id,53/category_id,14/option,com_virtuemart/Itemid,26/ on May 25, 2018, 4 pages.
Cooking Hacks. Accessed at https://www.cooking-hacks.com/documentation/tutorials/open-garden-hydroponics-irrigation-system-sensors-plant-monitoring on May 25, 2018, 11 pages.
LED Lighting for Horticulture, Aquabar LED Grow System brochure. Genesis Scientific. Accessed at www.gs.horti.com on Oct. 31, 2017, 4 pages.
Intravision Spectra R&D, Water-cooled 7-LED band Plant Research Rig., Accessed at <www.intravisiongroup.com> on Apr. 7, 2016, 1 page.
LED Grow World, Liquid Cooled LED Grow Light brochure, Model BLE-GL9015, 2017. Accessed at www.ledgrowworld.co, 3 pages.
JPFA Plant Factory Association. Accessed at http://npoplantfactory.org/english.html on May 18, 2018, 6 pages.
Harper, 2017: The OpenAG Ecosystem Expands Research, Non-Profit Ventrures. The Medium, Jan. 27, 2017. Accessed at https://medium.com/@calebgrowsfood/2017-the-openag-ecosystem-expands-research-non-profit-ventures-b5762beed64b, 10 pages.

(56) References Cited

OTHER PUBLICATIONS

Fenome. Vimeo. Accessed at https://vimeo.com/219601049, 3 pages, 2018.
Agnetix—The A3 Product Brochure, 2 pages, Aug. 24, 2017.
Agnetix—A3 Cables, 5 pages, Feb. 26, 2018.
Agnetix—Liquid-cooled, intelligent LED horticultural platform, 25 pages, Jan. 31, 2018.
Agnetix—A3 Horticulture LED, 6 pages, Jan. 31, 2018.
Agnetix—4' × 1 A3 Light Assembly, 1 page, Jan. 24, 2018.
Agnetix—8' × 2 A3 Light Assembly, 1 page, Jan. 24, 2018.
Agnetix—12' × 3 A3 Light Assembly, 1 page, Jan. 24, 2018.
Agnetix—16' × 3 A3 Light Assembly, 1 page, Jan. 23, 2018.
Agnetix—20'× 4 A3 Light Assembly, 1 page, Jan. 23, 2018.
Agnetix—20' × 5 A3 Light Assembly, 1 page, Mar. 8, 2018.
Agnetix—24' × 5 A3 Light Assembly, 1 page, Apr. 3, 2018.
Agnetix—24' × 6 A3 Light Assembly, 1 page, Jan. 16, 2018.
Agnetix—36' × 9 A3 Light Assembly, 1 page, Dec. 5, 2017.
Agnetix—32' × 8 A3 Light Assembly, 1 page, Feb. 12, 2017.
Agnetix—24'×12'×8' Growth Chamber, 1 page, Mar. 1, 2018.
Agnetix—42'×180'×12' Greenhouse, 1 page, Jan. 29, 2018.
Agnetix—20'×8'×9.5' 3-Light Isopod, 1 page, Mar. 17, 2018.
Agnetix—Hydronics Loop Diagram, 1 page, Mar. 9, 2018.
Bah, A. et al., "Sensor Technologies for Precision Soil Nutrient Management and Monitoring," American Journal of Agriculture and Biological Sciences 7(1): pp. 43-49, 2012.
Chandra, S. et al., "Photosynthetic response of Cannabis sativa L. to variations in Photosynthetic photon flux densities, temperature and $CO_2$ conditions," Physiol. Mol. Biol. Plants, vol. 14, No. 4, pp. 299-306, 2008.
Hamza, B. et al., "Distributed Polymer Optical Fibre Sensing of Moisture and pH in Soils: Feasibility for E-Agriculture," retrieved from https://www.research.manchester.ac.ukportal/files/38209074/FULL_TEXT.pdf, 7 pages, Nov. 3, 2017.
Nakano, A., "Plant Factories in Japan—An Integrated Approach," NARO Institute of Vegetable and Floriculture Science, National Agriculture and Food Research Organization (NARO), Tsukuba, Ibaraki, Japan, 11 pages. Sep. 11, 2017.
Nelson, J. A. et al., "Economic Analysis of Greenhouse Lighting: Light Emitting Diodes vs. High Intensity Discharge Features," PLoS One, vol. 9, Issue 6, e99010, 10 pages, 2014.
Photosynthetically Active Radiation (PAR) Units, 1 page, Aug. 16, 2000.
Sihombing, P. et al., "Automated hydroponics nutrition plants systems using arduino uno microcontroller based on android," 2nd International Conference on Computing and Applied Informatics, IPO Conf. Series: Journal of Physics 978 012014, 6 pages, 2018.
Vellidis, G., "The University of Georgia Smart Sensor Array," <http://scienceinhydroponics.com/2017/03/automating-a-hydroponic-system-sensors-and-monitoring.html>, 11 pages, 2018.
Vellidis, G. et al., "A real-time wireless smart sensor array for scheduling irrigation," Computers and Electronics in Agriculture 61, pp. 44-50, 2008.
Vijay, N., "Application of sensor networks in agriculture," https://ieeexplore.ieee.org/document/6719103/, Third International Conference on Sustainable Energy and Intelligent System, Dec. 27-29, 2012.
Products—Thrive Agritech. Accessed at http://www.thriveagritech.com/products/on May 16, 2019. 9 pages.
Intravision Products. Accessed at https://www.intravisiongroup.com/products on May 16, 2019. 2 pages.
Smart LED Grow Lights with Wireless Control LumiGrow. Accessed at https://www.lumigrow.com/ accessed on May 16, 2019. 8 pages.
PlantLab. Accessed at https://www.plantlab.com/ on May 16, 2019. 8 pages.
Aquabar. Genesis Scientific. Accessed at https://gs-horti.com/products/led-grow-lights/aquabar.html on May 16, 2019. 7 pages.
Viparspectra. Accessed at http://www.viparspectra.com/ on May 16, 2019. 10 pages.
Which regions of the electromagnetic spectrum do plants use to drive photosynthesis? Heliospectra. Accessed at www.heliospectra.com, Oct. 5, 2012.
International Search Report and Written Opinion in International Patent Application No. PCT/US2018/048190 dated Feb. 8, 2019, 100 pages.
Guidelines for Measuring and Reporting Environmental Parameters for Experiments in Greenhouses. International Committee for Controlled Environment Guidelines, Feb. 2016, 37 pages.
2JCIE-BU Environment Sensor (USB Type). Omron Electronic Components. Accessed at https://www.components.omron.com/product-detail?partNumber=2JCIE-BU on Apr. 13, 2019, 5 pages.
Environment Sensor Integrating various sensing capabilities into one single IoT sensor. Accessed at https://www.components.omron.com/solutions/mems-sensors/environment-sensor on Apr. 13, 2019, 6 pages.
Environment Sensor 2JCIE Series Catalog. Omron Electronic Components. Accessed at https://www.components.omron.com/solutions/mems-sensors/environment-sensor on May 16, 2019, 16 pages.
Schriber, Smart Agriculture Sensors: Helping Small Farmers and Positively Impacting Global Issues, Too. Mouser Electronics. Accessed at https://www.mouser.com/applications/smart-agriculture-sensors/ on Apr. 13, 2019, 4 pages.
Lakhiar et al., "Monitoring and Control Systems in Agriculture Using Intelligent Sensor Techniques: A Review of the Aeroponic System." Journal of Sensors 2018 (2018), 19 pages.
Hwang et al., "Study on an agricultural environment monitoring server system using wireless sensor networks." Sensors 10.12 (2010): 11189-11211.
Kerns et al., "Automated aeroponics system using IoT for smart farming." European Scientific Journal, ESJ 13.10 (2017), 7 pages.
Tsitsimpelis et al., "Development of a grow-cell test facility for research into sustainable controlled-environment agriculture." Biosystems Engineering 150 (2016): 40-53.
Keshtgary et al., "An efficient wireless sensor network for precision agriculture." Canadian Journal on Multimedia and Wireless Networks 3.1 (2012): 1-5.
Jawad et al., "Energy-efficient wireless sensor networks for precision agriculture: A review." Sensors 17.8 (2017): 1781, 45 pages.
Shamshiri et al., "Advances in greenhouse automation and controlled environment agriculture: A transition to plant factories and urban agriculture." (2018), 22 pages.
Ruiz-Garcia et al., "A review of wireless sensor technologies and applications in agriculture and food industry: state of the art and current trends." sensors 9.6 (2009): 4728-4750.
Dener et al., "Smart technologies with wireless sensor networks." Procedia-Social and Behavioral Sciences 195 (2015): 1915-1921.
Pahuja et al., "A wireless sensor network for greenhouse climate control." IEEE Pervasive Computing 12.2 (2013): 49-58.
Balendonck et al., "Monitoring spatial and temporal distribution of temperature and relative humidity in greenhouses based on wireless sensor technology." International Conference on Agricultural Engineering-AgEng. 2010, 10 pages.
Chaudhary et al., "Application of wireless sensor networks for greenhouse parameter control in precision agriculture." International Journal of Wireless & Mobile Networks (IJWMN) 3.1 (2011): 140-149.
Ferentinos et al., "Wireless sensor networks for greenhouse climate and plant condition assessment." Biosystems engineering 153 (2017): 70-81.
Vox et al., "A wireless telecommunications network for real-time monitoring of greenhouse microclimate." Journal of Agricultural Engineering 45.2 (2014): 70-79.
Sánchez-Álvarfz et al., "A Framework to Design the Computational Load Distribution of Wireless Sensor Networks in Power Consumption Constrained Environments." Sensors 18.4 (2018): 954, 20 pages.
Laamrani et al., "Using a Mobile Device "App" and Proximal Remote Sensing Technologies to Assess Soil Cover Fractions on Agricultural Fields." Sensors 18.3 (2018): 708, 16 pages.
Peng et al., "Comparative study of the detection of chromium content in rice leaves by 532 nm and 1064 nm laser-induced breakdown spectroscopy." Sensors 18.2 (2018): 621, 18 pages.

(56) References Cited

OTHER PUBLICATIONS

Pichorim et al., "Two solutions of soil moisture sensing with RFID for landslide monitoring." Sensors 18.2 (2018): 452, 11 pages.
Behmann et al., "Specim IQ: evaluation of a new, miniaturized handheld hyperspectral camera and its application for plant phenotyping and disease detection." Sensors 18.2 (2018): 441, 20 pages.
Nie et al., "Research on the effects of drying temperature on nitrogen detection of different soil types by near infrared sensors." Sensors 18.2 (2018): 391, 22 pages.
Cui et al., "Plant pest detection using an artificial nose system: a review." Sensors 18.2 (2018): 378, 18 pages.
Kafarski et al., "Evaluation of apple maturity with two types of dielectric probes." Sensors 18.1 (2018): 121, 13 pages.
Lim et al., "Application of near infrared reflectance spectroscopy for rapid and non-destructive discrimination of hulled barley, naked barley, and wheat contaminated with Fusarium." Sensors 18.1 (2018): 113, 16 pages.
Barriuso et al., "Combination of multi-agent systems and wireless sensor networks for the monitoring of cattle." Sensors 18.1 (2018): 108, 27 pages.
Meng et al., "A Compound Sensor for Simultaneous Measurement of Packing Density and Moisture Content of Silage." Sensors 18.1 (2018): 73, 10 pages.
Brinkhoff et al., "Multisensor capacitance probes for simultaneously monitoring rice field soil-water-crop-ambient conditions." Sensors 18.1 (2018): 53, 14 pages.
Bengochea-Guevara et al., "A low-cost approach to automatically obtain accurate 3D models of woody crops." Sensors 18.1 (2018): 30, 17 pages.
Skovsen et al., "Estimation of the Botanical Composition of Clover-Grass Leys from RGB Images Using Data Simulation and Fully Convolutional Neural Networks." Sensors 17.12 (2017): 2930, 18 pages.
Ravichandran et al., "In vivo non-destructive monitoring of capsicum annuum seed growth with diverse nacl concentrations using optical detection technique." Sensors 17.12 (2017): 2887, 12 pages.
Mao et al., "Contamination Event Detection with Multivariate Time-Series Data in Agricultural Water Monitoring." Sensors 17.12 (2017): 2806, 19 pages.
Castrignanò et al., "A combined approach of sensor data fusion and multivariate geostatistics for delineation of homogeneous zones in an agricultural field." Sensors 17.12 (2017): 2794, 20 pages.
Al-Saddik et al., "Development of spectral disease indices for 'Flavescence Dorée'grapevine disease identification." Sensors 17.12 (2017): 2772, 25 pages.
Wojnowski et al., "Portable electronic nose based on electrochemical sensors for food quality assessment." Sensors 17.12 (2017): 2715, 14 pages.
Dong et al., "Estimating crop area at county level on the North China Plain with an indirect sampling of segments and an adapted regression estimator." Sensors 17.11 (2017): 2638, 9 pages.
Kragh et al., "Fieldsafe: dataset for obstacle detection in agriculture." Sensors 17.11 (2017): 2579, 11 pages.
Zou et al., "A Real-Time Smooth Weighted Data Fusion Algorithm for Greenhouse Sensing Based on Wireless Sensor Networks." Sensors 17.11 (2017): 2555, 14 pages.
Fan et al., "Fast detection of striped stem-borer (Chilo suppressalis Walker) infested rice seedling based on visible/near-infrared hyperspectral imaging system." Sensors 17.11 (2017): 2470, 13 pages.
Nawar et al., "Comparison between random forests, artificial neural networks and gradient boosted machines methods of on-line Vis-NIR spectroscopy measurements of soil total nitrogen and total carbon." Sensors 17.10 (2017): 2428, 22 pages.
Moorhead et al., "Evaluation of sensible heat flux and evapotranspiration estimates using a surface layer scintillometer and a large weighing lysimeter." Sensors 17.10 (2017): 2350, 23 pages.
Corwin et al., "Evaluating Oilseed Biofuel Production Feasibility in California's San Joaquin Valley Using Geophysical and Remote Sensing Techniques." Sensors 17.10 (2017): 2343, 25 pages.
Nader et al., "Assessing white wine viscosity variation using polarized laser speckle: A promising alternative to wine sensory analysis." Sensors 17.10 (2017): 2340, 12 pages.
Tamouridou et al., "Application of multilayer perceptron with automatic relevance determination on weed mapping using UAV multispectral imagery." Sensors 17.10 (2017): 2307, 9 pages.
Lim et al., "Classification of Fusarium-Infected Korean Hulled Barley Using Near-Infrared Reflectance Spectroscopy and Partial Least Squares Discriminant Analysis." Sensors 17.10 (2017): 2258, 15 pages.
Jia et al., "Hyperspectral imaging analysis for the classification of soil types and the determination of soil total nitrogen." Sensors 17.10 (2017): 2252, 14 pages.
Fuentes et al., "A robust deep-learning-based detector for real-time tomato plant diseases and pests recognition." Sensors 17.9 (2017): 2022, 21 pages.
Alexandridis et al., "Novelty detection classifiers in weed mapping: Silybum marianum detection on UAV multispectral images." Sensors 17.9 (2017): 2007, 12 pages.
Feng et al., "Discrimination of transgenic maize kernel using NIR hyperspectral imaging and multivariate data analysis." Sensors 17.8 (2017): 1894, 14 pages.
Schmittmann et al., "A True-Color Sensor and Suitable Evaluation Algorithm for Plant Recognition." Sensors 17.8 (2017): 1823, 16 pages.
Villarrubia et al., "Combining multi-agent systems and wireless sensor networks for monitoring crop irrigation." Sensors 17.8 (2017): 1775, 23 pages.
Kicherer et al., "Phenoliner: A new field phenotyping platform for grapevine research." Sensors 17.7 (2017): 1625, 18 pages.
Wei et al., "Leaf area index estimation using Chinese GF-1 wide field view data in an agriculture region." Sensors 17.7 (2017): 1593, 14 pages.
Martinez-Guanter et al., "Optical sensing to determine tomato plant spacing for precise agrochemical application: Two scenarios." Sensors 17.5 (2017): 1096, 19 pages.
Shi et al., "Spectroscopic diagnosis of arsenic contamination in agricultural soils." Sensors 17.5 (2017): 1036, 15 pages.
Kameoka et al., "A wireless sensor network for growth environment measurement and multi-band optical sensing to diagnose tree vigor." Sensors 17.5 (2017): 966, 21 pages.
Shiffler, Smart Sensors in Farming: 10 Startups to Watch in 2018. Mar. 7, 2018. Accessed at https://www.disruptordaily.com/smart-sensors-farming-10-startups-watch-2018/ on May 17, 2019, 10 pages.
Danckwerts, A decentralized future for food: Indoor Farming, the Internet of Things and Blockchain Technology. Medium. Jun. 11, 2017. Accessed at https://medium.com/@forbesdanckwerts/a-decentralized-future-for-food-indoor-farming-the-internet-of-things-and-blockchain-technology-8d905b6dcb27 on May 17, 2019, 10 pages.
Agriculture Market 2018-2023: Focus on Systems (Sensing, Communication, Cloud Computing, Data), Applications (Precision Crop, Indoor, Livestock Monitoring, Aquaculture). Research and Markets Nov. 23, 2018. Accessed at https://www.prnewswire.com/news-releases/global-iot-in-agriculture-market-2018-2023-focus-on-systems-sensing-communication-cloud-computing-data-applications-precision-crop-indoor-livestock-monitoring-aquaculture-300754772.html on May 17, 2019, 8 pages.
Global IoT in Agriculture Market: Focus on Systems (Sensing, Communication, Cloud Computing, Data Management), Applications (Precision Crop Farming, Indoor Farming, Livestock Monitoring, Aquaculture)-Analysis and Forecast (2018-2023) Description. Nov. 2018 Research and Markets. Accessed at https://www.researchandmarkets.com/research/w5t7j8/global_iot_in?w=5 on May 21, 2019. 14 pages.
Environmental Monitoring & Aiflow for Climate Uniformity. The University of Arizona Controlled Environment Agriculture Center. Accessed at http://ceac.arizona.edu/environmental-monitoring on May 17, 2019, 6 pages.
Multi-Sensor Modules Ease Indoor Agriculture Design Challenges. Techmezine Feb. 19, 2019. Accessed at https://www.techmezine.com/internet-of-things/multi-sensor-modules-ease-indoor-agriculture-design-challenges/ on May 17, 2019, 8 pages.

(56) References Cited

OTHER PUBLICATIONS

Indoor Precision Farming in American medical marijuana plantations. Libelium Dec. 13, 2016. Accessed at http://www.libelium.com/indoor-precision-farming-in-american-medical-marijuana-plantations/ on May 17, 2019, 7 pages.
<https://sensorinsight.io/> Accessed on May 17, 2019, 7 pages.
Internet of Things Hardware Distributor. Accessed at https://sensorinsight.io/hardware/ on May 17, 2019, 4 pages.
Modular Farming Systems. Cityblooms. Accessed at https://cityblooms.com/modular-farms/ on May 17, 2019, 6 pages.
The Orchestra Conductor for Your Farm. The Cityblooms Commander. Accessed at https://cityblooms.com/commander/ on May 17, 2019, 12 pages.
New controlled-environment agriculture solution in Chile enables up to 50% energy saving. Advanticsys Feb. 3, 2018. Accessed at https://www.advanticsys.com/new-controlled-environment-agriculture-solution-in-chile-enables-up-to-50-energy-saving/ on May 17, 2019, 3 pages.
4-IN-1 Sensor. Growlink. Accessed at https://growlink.com/shop/4-in-1-sensor/ on May 17, 2019, 7 pages.
Growlink Climate Sensor. Growlink. Accessed at https://growlink.com/shop/environment-sensor-module/ on May 17, 2019, 7 pages.
Smart Sense Wireless Module. Growlink. Accessed at https://growlink.com/shop/remotesense/ on May 17, 2019, 7 pages.
Blink XP Plant Vision Cameras. Growlink. Accessed at https://growlink.com/shop/plant-vision-camera-system/ on May 17, 2019, 6 pages.
Advanced Soil Moisture Sensing. Growlink. Accessed at https://growlink.com/shop/terros12/ on May 17, 2019, 6 pages.
Small Soil Moisture Sensor. Growlink. Accessed at https://growlink.com/shop/ec-5-small-soil-moisture-sensor/ on May 17, 2019, 7 pages.
TE Connectivity AmbiMate Sensor Module MS4 Series. Mouser Electronics. Accessed at https://www.mouser.com/new/TE-Connectivity/te-connectivity-ambimate-sensor-module/ on May 17, 2019, 2 pages.
LED Grow Lights. Heliospectra. Accessed at https://www.heliospectra.com/led-grow-lights/ on May 17, 2019, 9 pages.
Oreon Grow Light 2.1 (GL 600 2.1 XXX) Installation Manual. Oreon. Jan. 22, 2018. Accessed at https://www.oreon-led.com/cache/InstallationManual20180122USCA.107/InstallationManual20180122USCA.pdf, 18 pages.
Oreon Grow Light 2.1. Oreon 2016. Accessed at https://hortinext.com/wp-content/uploads/2Q16/Q8/Lemnis-Oreon-Brochure_EN.pdf, 2 pages.
International Search Report and Written Opinion in International Patent Application No. PCT/US19/28493 dated Jul. 25, 2019, 15 pages.
Purwar, "In-situ Real-time Field Imaging and Monitoring of Leaf Stomata by High-resolution Portable Microscope." bioRxiv (2019): 677450. 24 pages.
Roots Corporate Presentation. Roots Sustainable Agricultural Technologies Ltd. Oct. 2018. 28 pages.
Model-W LED Grow Light. ThinkGrow 2019. Accessed at https://www.thinkgrowled.com/First/IndexW on Mar. 11, 2020. 3 pages.
Rosenthal, Light Dep vs Outdoor: Why Light Deprivation Greenhouses are a Good Investment. Ed Rosenthal.com May 3, 2019. Accessed at https://www.edrosenthal.com/the-guru-of-ganja-blog/light-dep-vs-outdoor on Mar. 11, 2020. 10 pages.
YellowScan Forestry. Accessed at https://www.yellowscan-lidar.com/applications/forestry/ on Mar. 16, 2020. 9 pages.
Bowen, GreenThumb IO Platform. GreenThumb.IO. Feb. 16, 2019. Accessed at https://medium.com/greenthumbio/greenthumb-io-platform-d6d09ca7fafb on Mar. 16, 2020. 4 pages.
Smarter Farming. TortugaAgTech. Accessed at https://www.tortugaagtech.com/ on Mar. 24, 2020. 10 pages.
PlantEye F500 multispectral 3D scanner for plants. Phenospec Smart Plant Analysis. Accessed at https://phenospex.com/products/plant-phenotyping/planteye-f500-multispectral-3d-laser-scanner/?gclid=Cj0KCQjwmdzzBRC7ARIsANdqRRn6QO5qmh0wwGnlkROEuysd8CaRKe94_kmoBIPuJzwlvcQGzgWGksMaAmt_EALw_wcB on Mar. 24, 2020.

Russo, "The case for the entourage effect and conventional breeding of clinical cannabis: no "strain," no gain." Frontiers in plant science 9 (2019): 1969. 8 pages.
US Energy Use Intensity by Property Type. Energy Star PortfolioManager Technical Reference. Aug. 2018. 6 pages.
International Search Report and Written Opinion in International Patent Application No. PCT/US2019/030889 dated Sep. 26, 2019, 22 pages.
Rodrigues, Agnetix—Most Powerful and Efficient LED Horticulture Lighting Platform. YouTube Jan. 8, 2018. Accessed at https://www.youtube.com/watch?v=y6rZeJ6V8Ug. 7 pages.
International Search Report and Written Opinion in International Patent Application No. PCT/US2019/061324 dated Mar. 18, 2020, 92 pages.
Spectranomics. Carnegie Airborne Observatory as of Dec. 5, 2019. Accessed at https://web.archive.org/web/20191205203624/https://cao.carnegiescience.edu/spectranomics on Apr. 17, 2020. 2 pages.
TerrAvion Product Info. Accessed at https://www.terravion.com/product-info/ on Apr. 17, 2020. 3 pages.
Story et al., "Design and implementation of a computer vision-guided greenhouse crop diagnostics system." Machine vision and applications 26.4 (2015): 495-506.
Canopy Scanalyzer. LemnaTec. Accessed at https://www.lemnatec.com/products/canopy-scanalyzer/ on Apr. 17, 2020. 2 pages.
PAM Chlorophyll Fluorescence Imaging. LemnaTec. Accessed at https://www.lemnatec.com/pam-chlorophyll-fluorescence-imaging/ on Apr. 17, 2020. 2 pages.
Cerna® Modular Microscopes. Thorlabs May 10, 2018. Accessed at https://www.thorlabs.com/images/Brochures/Thorlabs_Cerna_Brochure.pdf on Apr. 17, 2020. 6 pages.
Murphy et al., "OpenFluor-an online spectral library of autofluorescence by organic compounds in the environment." Analytical Methods 6.3 (2014): 658-661.
Ubbens et al., "Deep plant phenomics: a deep learning platform for complex plant phenotyping tasks." Frontiers in plant science 8 (2017): 1190. 11 pages.
YellowScan Reliable UAV LiDAR Mapping. Accessed at https://www.yellowscan-lidar.com/ on Apr. 17, 2020. 3 pages.
Earles et al., "Beyond porosity: 3D leaf intercellular airspace traits that impact mesophyll conductance." Plant physiology 178.1 (2018): 148-162.
LI-6400XT Portable Photosynthesis System. Li-Cor. Accessed at https://www.licor.com/env/products/photosynthesis/ on Apr. 17, 2020. 1 page.
Controlled Environment Agriculture. Cornell University college of Agriculture and Life Sciences Sep. 2, 2019. Accessed at https://web.archive.org/web/20190902094759/http://cea.cals.cornell.edu/bestPractices/lightControl.html on Apr. 17, 2020. 2 pages.
Sentera. Accessed at https://sentera.com/sensors/ on Apr. 17, 2020. 4 pages.
Accesssories: UV & NIR Illuminators, Filter Modules. Eigen Imaging. Accessed at https://www.eigenimaging.com/collections/uv-nir-illuminator on Apr. 17, 2020. 5 pages.
360 Soilscan. 360yieldcenter.com. Dec. 24, 2014. Accessed at http://nebula.wsimg.com/45a21444c39dcfb4b9ca43dedf13076e?AccessKeyId=42F03180740870DBA0EF&disposition=0&alloworigin=1 on Apr. 17, 2020. 2 pages.
TerrAvion + FluroSense: nitrogen management. TerrAvion Jun. 3, 2019. Accessed at https://blog.terravion.com/blog/terravion-flurosat-nitrogen-management on Apr. 17, 2020. 4 pages.
Osburn et al., "Predicting sources of dissolved organic nitrogen to an estuary from an agro-urban coastal watershed." Environmental science & technology 50.16 (2016): 8473-8484.
Excitation-Emission Matrix (EEM) Fluorescence Spectroscopy for Analysis of Dissolved Organic Matter (DOM) in Natural Water and Wastewaters. Application News No. AD-0133 Shimadzu Nov. 15, 2016. Accessed at https://solutions.shimadzu.co.jp/an/n/en/rf/apa417010.pdf?_ga=2.70350806.735204626.1575945001-871956823.1575945001 on Apr. 16, 2020.
Abramowitz et al., Overview of Fluorescence Excitation and Emission Fundamentals. Olympus. Accessed at https://www.olympus-lifescience.com/en/microscope-resource/primer/lightandcolor/fluoroexcitation/ on Apr. 17, 2020. 4 pages.

(56) References Cited

OTHER PUBLICATIONS

Fluorescence Imaging Filters. ThorLabs. Accessed at https://www.thorlabs.com/newgrouppage9.cfm?objectgroup_id=2990 on Apr. 17, 2020. 4 pages.

Shortwave Infrared Camera Core Tau™ SWIR. FLIR. Accessed at https://www.flir.com/products/tau-swir/?model=Tau-Vis-SWIR on Apr. 17, 2020. 2 pages.

Natali et al., "Light-harvesting complexes (LHCs) cluster spontaneously in membrane environment leading to shortening of their excited state lifetimes." Journal of Biological Chemistry 291.32 (2016): 16730-16739.

Ghassemi et al., "Evaluation of mobile phone performance for near-infrared fluorescence imaging." IEEE Transactions on Biomedical Engineering 64.7 (2016): 1650-1653.

310nm UV LED Fluorescence using iPhone 6s. Youtube Jul. 15, 2018. Accessed at https://www.youtube.com/watch?v=hA6VPmJWE_8 on Apr. 17, 2020. 3 pages.

Tran et al., Smartphone Multi-Spectral Imaging. Eigen Imaging Inc., Apr. 2013. Accessed at https://sites.google.com/a/eigenimaging.com/eigen/learn-more/smartphone-multi-spectral-imaging on Apr. 17, 2020. 5 pages.

The Greencube. Youtube Nov. 5, 2015. Accessed at https://www.youtube.com/watch?v=IqoENjkruMc on Apr. 17, 2020. 3 pages.

Executive Summary EDEN ISS. Apr. 2019. Accessed at https://eden-iss.net/wp-content/uploads/EDEN-ISS-Complete-Brochure_ONLINE_small.pdf on Apr. 17, 2020.

Non Final Office Action in U.S. Appl. No. 16/824,495 dated May 22, 2020, 47 pages.

Non Final Office Action in U.S. Appl. No. 16/114,088 dated May 5, 2020, 38 pages.

Notice of Allowance in U.S. Appl. No. 16/114,088 dated Jul. 24, 2020, 20 pages.

Notice of Allowance in U.S. Appl. No. 16/824,495 dated Jul. 29, 2020, 21 pages.

Notice of Allowance in U.S. Appl. No. 16/390,501 dated Aug. 24, 2020, 10 pages.

Lai—theory and practice. Accessed at https://www.metergroup.com/environment/articles/lai-theory-practice/ on Sep. 2, 2020. 35 pages.

Nynomic—The Photonics Group. Company Presentation Nynomic AG Dec. 10, 2019. Accessed at https://www.nynomic.com/wp-content/uploads/2019/12/Nynomic_28.MKK_2019.pdf. 34 pages.

Apogee Instruments. Accessed at https://www.apogeeinstruments.com/ on Sep. 2, 2020. 6 pages.

OCO-3 Instrument. NASA Jet Propulsion Laboratory California Institute of Technology. Accessed at https://ocov3.jpl.nasa.gov/instrument/ on Sep. 2, 2020. 3 pages.

Sensors, Sonars, and Cameras. BlueRobotics. Accessed at https://bluerobotics.com/product-category/sensors-sonars-cameras/ on Sep. 2, 2020. 6 pages.

Aidukas et al., "Low-cost, sub-micron resolution, wide-field computational microscopy using opensource hardware." Scientific reports 9.1 (2019): 1-12.

Koyama et al., "High-image quality, high-resolution camera with high sensitivity up to 1,100 nm." Ultra-High-Definition Imaging Systems. vol. 10557. International Society for Optics and Photonics, 2018. 32 pages.

About LCI. BLIPORTAL. Accessed at https://www.bli.eu/about-multi-light/about-lci/ on Sep. 2, 2020. 5 pages.

Prairie et al., "An accurate, precise, and affordable light emitting diode spectrophotometer for drinking water and other testing with limited resources." Plos one 15.1 (2020): e0226761. 32 pages.

Spectral Indices. L3Harris Geospatial. Accessed at https://www.harrisgeospatial.com/docs/spectralindices.html on Sep. 2, 2020. 12 pages.

Wünsch et al., "Fluorescence quantum yields of natural organic matter and organic compounds: Implications for the fluorescence-based interpretation of organic matter composition." Frontiers in Marine Science 2 (2015): 98. 15 pages.

Terra Mepp. Accessed at https://terra-mepp.illinois.edu/ on Sep. 2, 2020. 9 pages.

Valle et al., "PYM: a new, affordable, image-based method using a Raspberry Pi to phenotype plant leaf area in a wide diversity of environments." Plant methods 13.1 (2017): 98. 17 pages.

Mudhar, Using near IR to look for photosynthesis and plant health with NDVI. Richard Mudhar Blog. Jul. 21, 2015. Accessed at https://www.richardmudhar.com/blog/2015/07/using-near-ir-to-look-for-photosynthesis-and-plant-health-with-ndvi/. 7 pages.

LAPA, Raspberry + NoIR cam + Sensors to detect water stress of the plants during their growing. Public Lab Mar. 31, 2016. Accessed at https://publiclab.org/notes/LaPa/03-31-2016/raspberry-noir-cam-sensors-to-detect-water-stress-of-the-plants-during-their-growing. 11 pages.

Blonquist, Using Infrared Thermometers for Plant Science Research. Apogee Insturments Inc. Youtube Jul. 31, 2017. Accessed at https://www.youtube.com/watch?time_continue=120&v=U_azOSSvBW8&feature=emb_logo. 3 pages.

Non Final Office Action in U.S. Appl. No. 16/828,521 dated Jul. 28, 2020, 30 pages.

Notice of Allowance in U.S. Appl. No. 16/114,088 dated Sep. 30, 2020, 5 pages.

Notice of Allowance in U.S. Appl. No. 16/390,501 dated Oct. 15, 2020, 7 pages.

Notice of Allowance in U.S. Appl. No. 16/824,495 dated Oct. 23, 2020, 5 pages.

Notice of Allowance in U.S. Appl. No. 16/828,521 dated Nov. 9, 2020, 5 pages.

Notice of Allowance in U.S. Appl. No. 16/390,501 dated Feb. 10, 2021, 10 pages.

Notice of Allowance in U.S. Appl. No. 17/083,461 dated Feb. 26, 2021, 9 pages.

Extended European Search Report in European Patent Application No. 18848610.4 dated Mar. 2, 2021, 11 pages.

Notice of Allowance in U.S. Appl. No. 16/404,192 dated Mar. 30, 2021, 9 pages.

Notice of Allowance in U.S. Appl. No. 17/141,173 dated Mar. 30, 2021, 24 pages.

International Search Report and Written Opinion in International Patent Application No. PCT/US2020/064837 dated Mar. 31, 2021, 13 pages.

Corrected Notice of Allowance in U.S. Appl. No. 16/390,501 dated Apr. 8, 2021, 2 pages.

First Office Action in Chinese Patent Application 201880069341.0 and English Translation Thereof dated Mar. 31, 2021, 17 pages.

Notice of Allowance in U.S. Appl. No. 17/083,461 dated May 3, 2021, 8 pages.

U.S. Appl. No. 17/362,938, filed Jun. 29, 2021, Lys et al.

U.S. Appl. No. 17/323,822, filed May 18, 2021, Lys et al.

Yang et al., Application of Integrated Sensing and Automation Technology, and Preventive Bio-Control Agent for Greenhouse Precision Cultivation. Mardi Regional Workshop FFTC Sep. 21, 2017, 67 pages.

Non Final Office Action in U.S. Appl. No. 17/323,822 dated Jul. 14, 2021, 8 pages.

Notice of Allowance in U.S. Appl. No. 17/317,792 dated Sep. 16, 2021, 7 pages.

Non Final Office Action in U.S. Appl. No. 17/238,044 dated Sep. 30, 2021, 17 pages.

Final Office Action in U.S. Appl. No. 17/323,822 dated Nov. 3, 2021, 10 pages.

Chinese Office Action and English Translation Thereof in Chinese Application No. 201980044374.4 dated Dec. 3, 2021, 21 pages.

Chinese Office Action and English Translation Thereof in Chinese Application No. 201880069341.0 dated Dec. 24, 2021, 21 pages.

Extended European Search Report in European Patent Application No. 19796862.1 dated Jan. 3, 2022, 9 pages.

\* cited by examiner

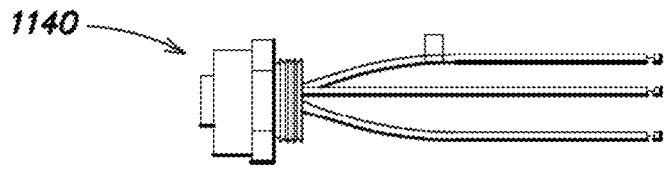
FIG. 8Q-1
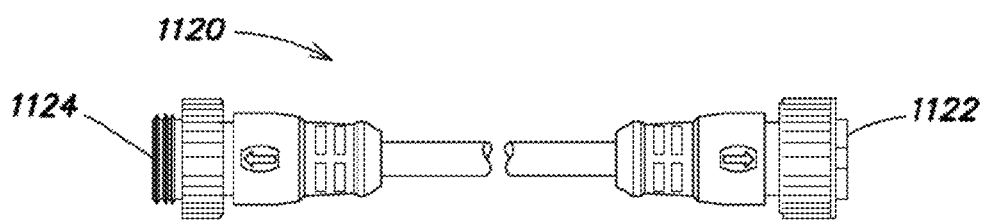
FIG. 8Q-2
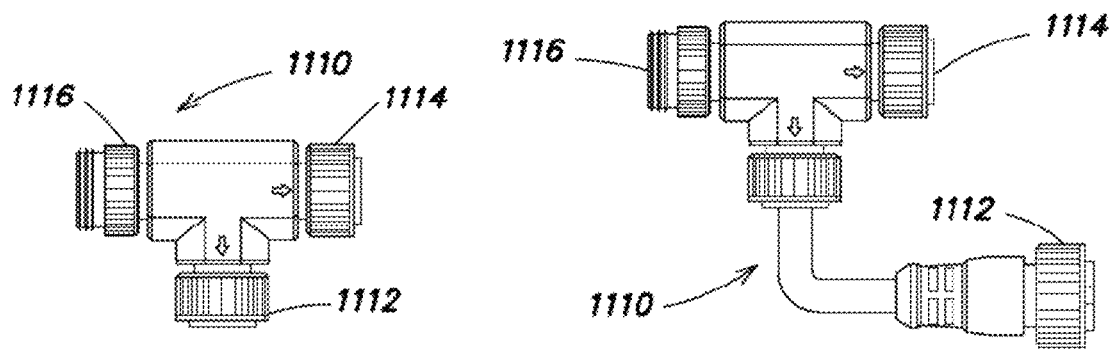
FIG. 8Q-3
FIG. 8Q-4
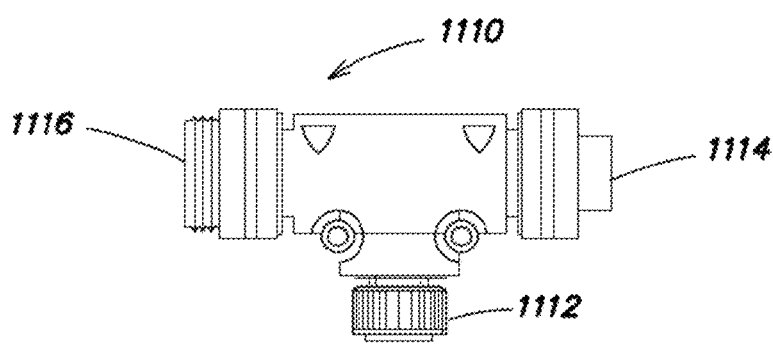
FIG. 8Q-5

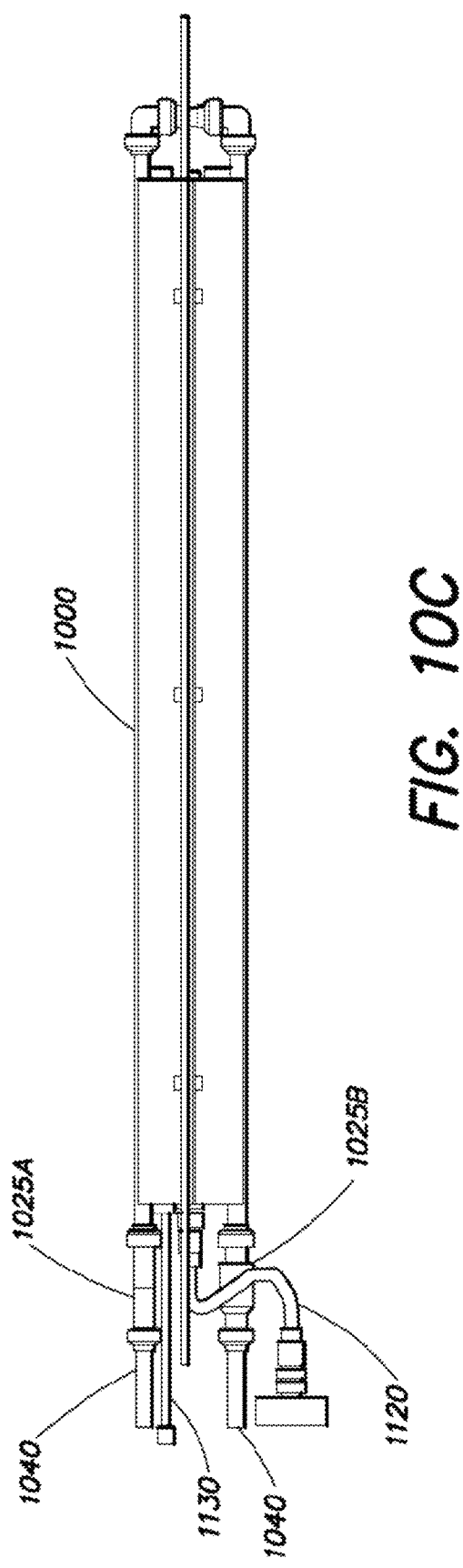

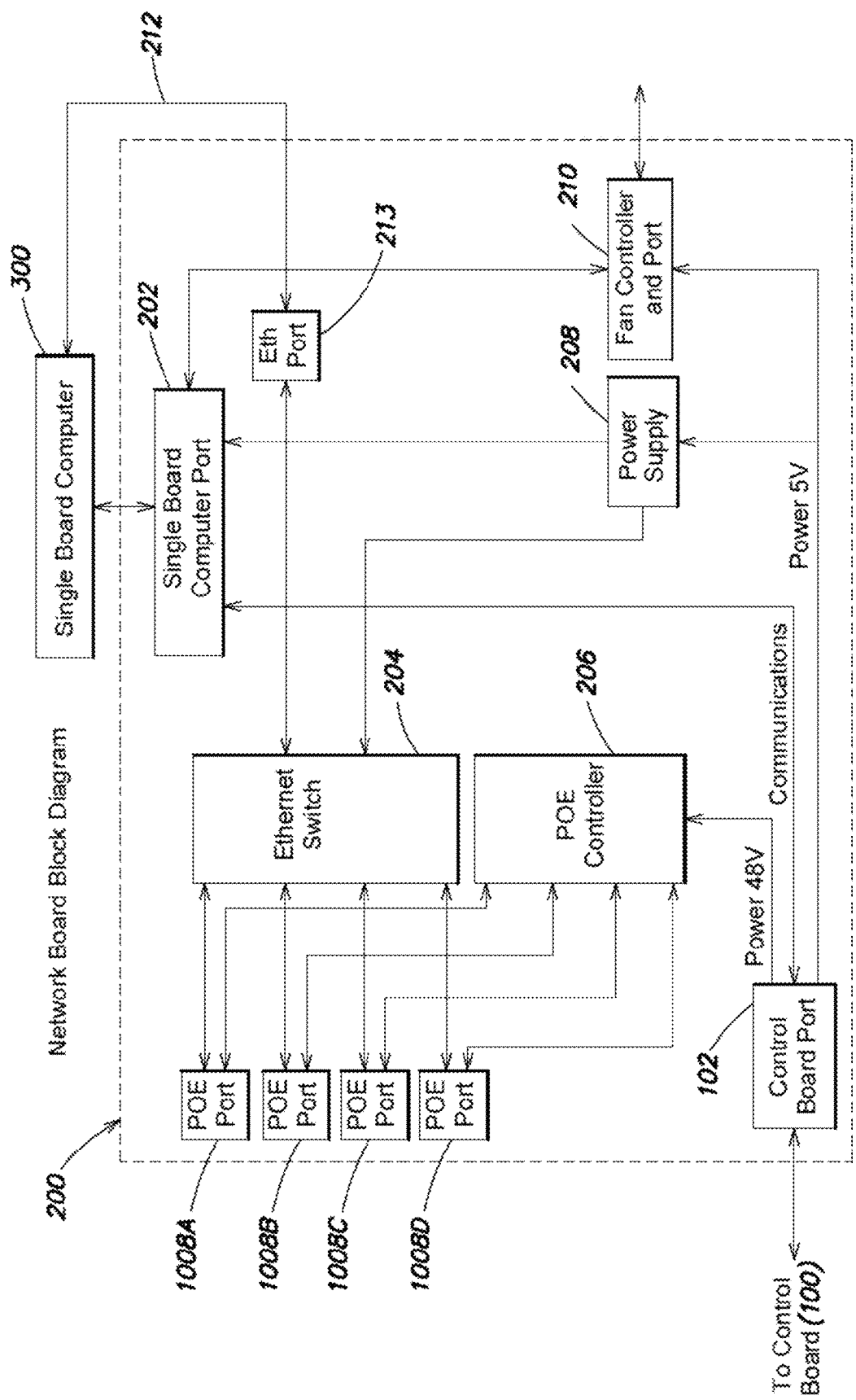

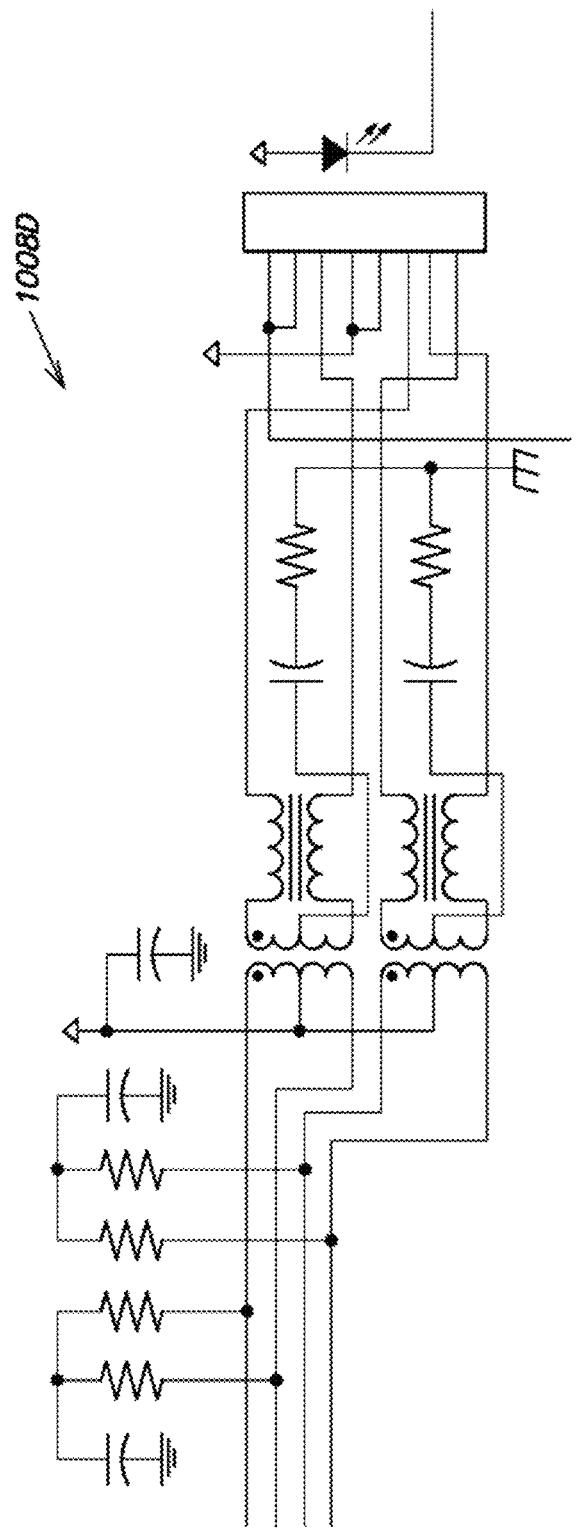

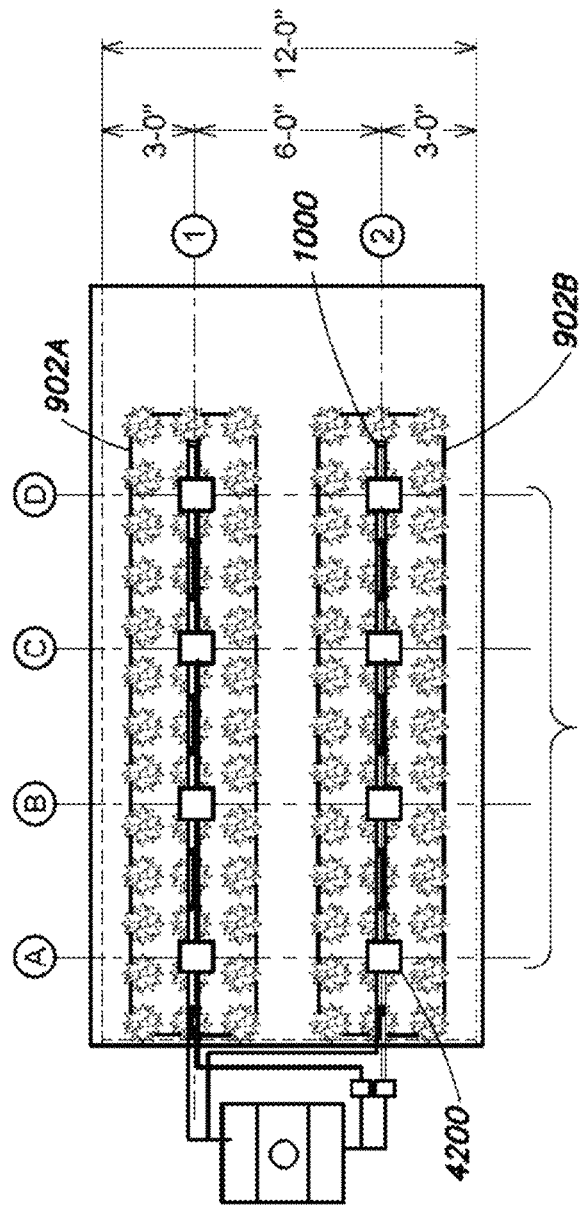
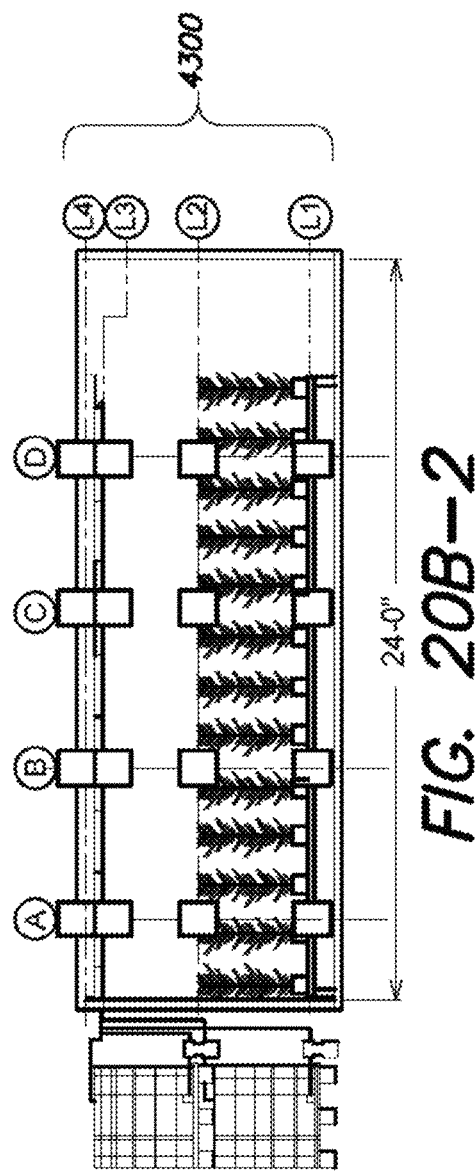
FIG. 20B-1
FIG. 20B-2

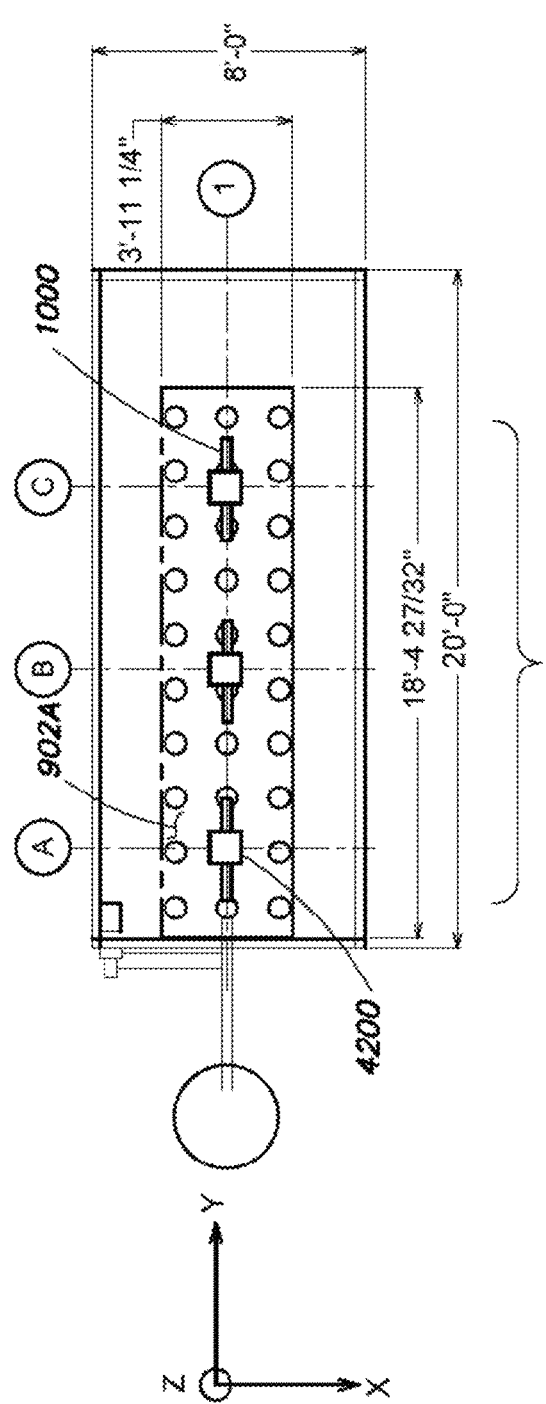
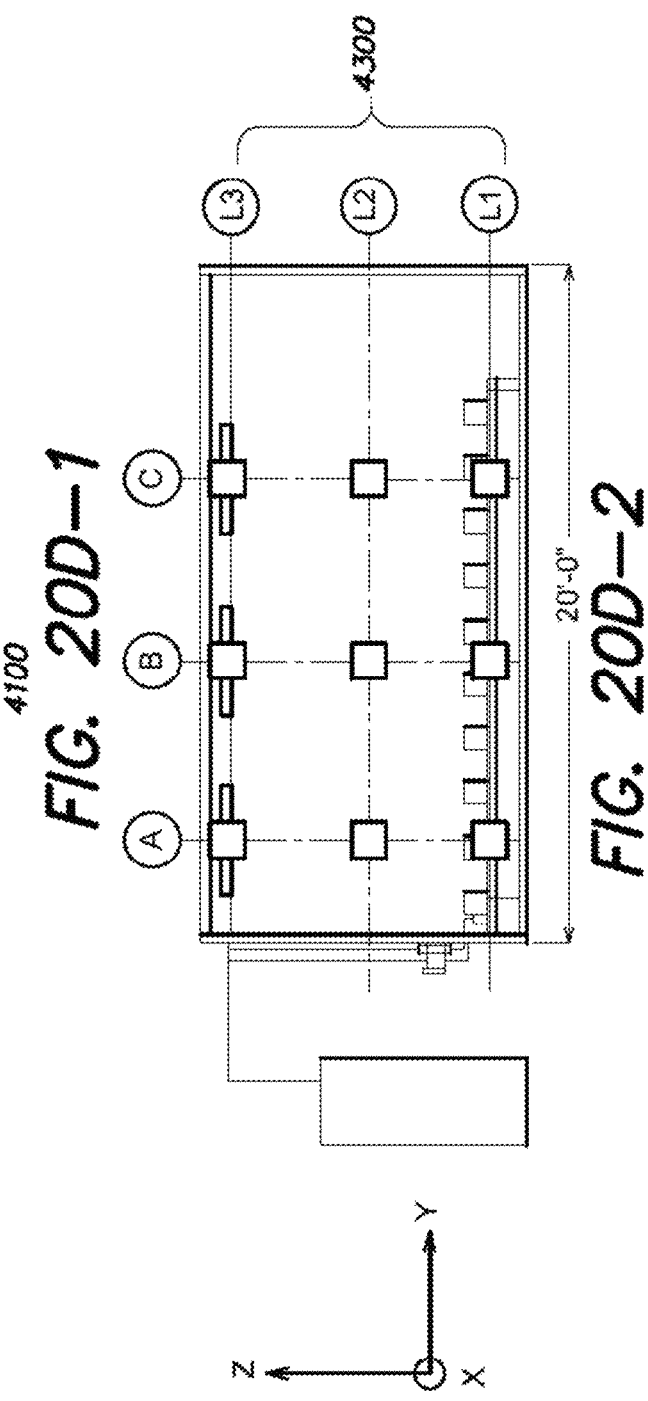

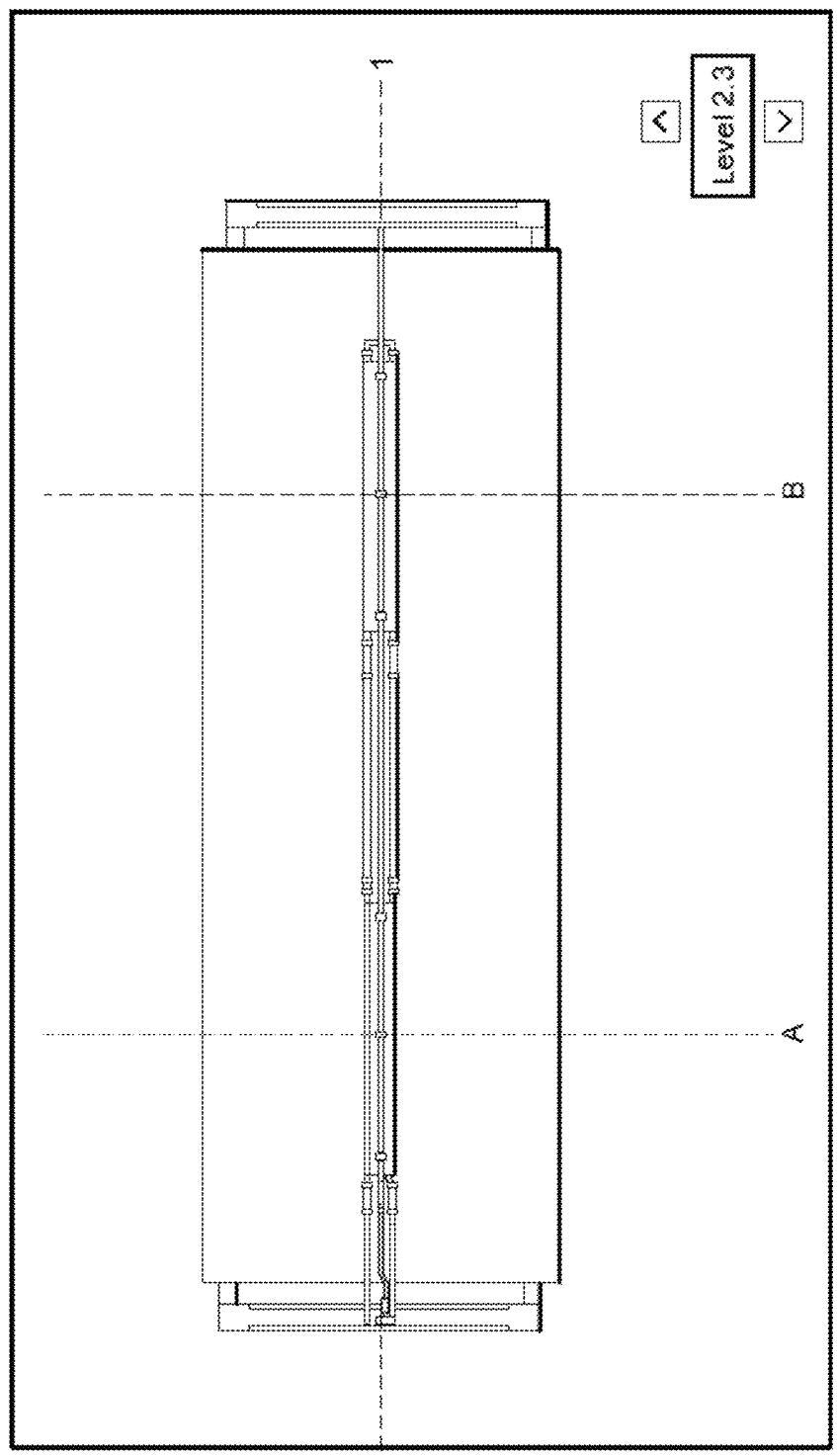

METHODS, APPARATUS, AND SYSTEMS FOR LIGHTING AND DISTRIBUTED SENSING IN CONTROLLED AGRICULTURAL ENVIRONMENTS

CROSS-REFERENCE TO RELATED PATENT APPLICATIONS

This application is a continuation of, and claims priority to, U.S. application Ser. No. 16/828,521, filed Mar. 24, 2020, entitled "METHODS, APPARATUS, AND SYSTEMS FOR LIGHTING AND DISTRIBUTED SENSING IN CONTROLLED AGRICULTURAL ENVIRONMENTS," which, in turn, is a Bypass Continuation Application of International PCT Application PCT/US2019/030889, filed on May 6, 2019, entitled "METHODS, APPARATUS, AND SYSTEMS FOR LIGHTING AND DISTRIBUTED SENSING IN CONTROLLED AGRICULTURAL ENVIRONMENTS," which, in turn, claims priority to U.S. Provisional Application No. 62/667,217, filed on May 4, 2018, entitled "METHODS, APPARATUS, AND SYSTEMS FOR DISTRIBUTED SENSING IN CONTROLLED AGRICULTURAL ENVIRONMENTS," and U.S. Provisional Application No. 62/684,641, filed on Jun. 13, 2018, entitled "METHODS, APPARATUS, AND SYSTEMS FOR DISTRIBUTED SENSING IN CONTROLLED AGRICULTURAL ENVIRONMENTS." Each of the above-identified applications is incorporated herein by reference in its entirety.

BACKGROUND

Controlled Environment Agriculture (CEA) is the process of growing plants in a controlled environment where various environmental parameters are monitored and adjusted to improve the quality and yield of the plants grown. Compared to conventional approaches of plant cultivation, CEA may enable year-round production of plants, insensitivity to variable weather conditions, reduce pests and diseases, and reduce the amount of resources consumed on a per plant basis. A controlled agricultural environment is typically enclosed, at least in part, by a building structure such as a greenhouse, a grow room, or a covered portion of a field in order to provide some degree of control over environmental conditions. Additional control systems may be deployed to adjust various environmental parameters including lighting, temperature, humidity, nutrient levels, and carbon dioxide ($CO_2$) concentrations. For example, one or more artificial lighting systems are often used in such controlled agricultural environments to supplement and/or replace natural sunlight that may be obstructed by the building structure or insufficient during certain periods of the year (e.g., winter months).

SUMMARY

In conventional CEA, multiple sensors are often deployed and utilized to monitor growth conditions in a growing area. The integration of sensors in various agricultural settings is typically based on two general design approaches: (1) a wireless sensor network (WSN) system and (2) an Internet of Things (IoT) system. For both WSN systems and IoT systems, each sensor deployed in the environment typically communicates wirelessly and relies upon a battery for power.

WSN and IoT sensor systems may in some instances provide for ease of installation and flexible deployment, particularly over larger growing environments. The Inventors have recognized and appreciated, however, that wireless sensor systems for agricultural applications may be significantly limited by (1) the reliance on a portable power source (e.g., a battery), which needs to be periodically replenished or replaced and (2) reliability issues that arise due to shadowing effects of plants in the environments (e.g., a sufficient density of leaves may obstruct and, in some instances, block wireless communication).

In view of the foregoing, the Inventors have contemplated sensor configurations for CEA to provide for more robust and reliable operation of sensors. For example, in one aspect, providing wired rather than wireless power and network communication resources to sensors in an agricultural setting arguably would increase their robustness and reliability; at the same time, providing sufficient cabling to power and/or communicate with each sensor in the environment may impose certain burdens to installers in, or operators of, the agricultural environment.

The Inventors have recognized and appreciated, however, that lighting systems employed in CEA may serve as a platform for distributing wired power and providing a wired network communications infrastructure for multiple other devices deployed and utilized in a controlled agricultural environment. By leveraging the lighting system to support the operation of various sensors and other devices, these sensors and devices may be easily positioned to cover regions of the environment relevant to the growth of plants (e.g., since the lighting fixtures are deployed in areas where plants are located).

More specifically, a lighting system for CEA is often deployed in a growing area in a substantially regular arrangement (e.g., of rows and columns of lighting fixtures above shelves of plants) to ensure a substantially even distribution of light in the environment (photosynthetically active radiation, or PAR). The Inventors have recognized and appreciated that the arrangement of lighting fixtures in a given growing area may be employed to divide the space of the growing area into a multidimensional grid of nodes, for which the lighting system may provide one or both of operating power and network communication access points in respective nodes of the grid.

For example, the space of a given growing area may be defined by three orthogonal axes (e.g., an x-axis along the width of the space, a y-axis along the length of the space, and a z-axis along the height of the space). Respective lighting fixtures of a lighting system may be positioned at a certain height ($z_{lights}$) in the space and at corresponding positions ($x_1$, $y_1$) along the width and length of the space. The respective positions of the lighting fixtures may in turn be used to define a multidimensional grid of nodes in the space for which the lighting system may provide one or both of operating power and network communications connections (e.g., Ethernet transmit/receive access) to one or more devices (e.g., a sensor or actuator) situated at or near one or more of the nodes. In such an exemplary framework, at a given lighting fixture position ($x_1$, $y_1$) along the width and length of the space, multiple sensors may be deployed at different heights along the z-axis (e.g., different vertical levels of the agricultural environment, such as a soil level, a plant level, a light canopy level, and an ambient environment level).

Thus, the Inventors have recognized and appreciated the practical advantages of an industrial horticultural lighting system for CEA that serves as a power and network communications "backbone" in a growing area to provide for significant flexibility, reliability and robustness in the deployment of other apparatus useful for CEA (e.g., sensors and actuators). The Inventors further have recognized and appreciated the practical advantages of designing respective components of such a lighting system to significantly facilitate safe, efficient and relatively inexpensive assembly and installation of the lighting system in a given growing area.

To this end, industrial horticultural lighting systems are described herein in which respective lighting fixtures of the system include industrial-type AC power connectors, and respective cables of the system are industrial type cables (e.g., multi-point interconnection power cable assemblies for industrial machinery according to the Underwriters Laboratory (UL®) product category PVVA and compliant with the UL® standard 2237). The use of industrial type connectors and cables to provide operating power to respective lighting fixtures of the system significantly facilitates an essentially "tool-less" lighting system assembly and installation process in a growing area (e.g., in which no conduit is required for running electrical wires). In one example implementation, multiple lighting fixtures may be daisy-chained together via industrial power cables (e.g., that ultimately connect directly to a breaker panel in the controlled agricultural environment).

In another aspect, respective lighting fixtures of an industrial horticultural lighting system are equipped with one or more network communication ports (e.g., RJ45 ports for Ethernet or Power over Ethernet), and waterproof network communication cables (e.g., Cat-5 or other categories of Ethernet cables) are employed to interconnect the network communication ports of respective lighting fixtures. In this manner, the lighting system may be washed down from time to time once deployed in the controlled agricultural environment. In yet another aspect, integrated sensor assemblies comprising multiple sensors may be readily coupled via a variety of cabling and wired connection assemblies (gooseneck flexible conductors, angled connectors, variable length cables) to one or more power and communication ports of a given lighting fixture (e.g., PoE ports or USB ports on the lighting fixtures) to provide for a multidimensional distributed sensing network in the growing area. In yet another aspect, respective lighting fixtures of the lighting system may be fluid-cooled fixtures, and pipes carrying fluid-coolant through respective lighting fixtures may be coupled together readily using a variety of push-to-connect plumbing fittings, thereby further facilitating system assembly and installation.

Distributed sensing techniques according to the present disclosure may be used to systematically monitor growth conditions for plants across an agricultural environment. Data collected by multiple sensors deployed in the controlled agricultural environment can be analyzed and displayed according to a variety of modalities, for example, via a sophisticated human-machine interface (HMI). Distributed sensors in the controlled agricultural environment may also be coupled to one or more control systems in a feedback loop where data acquired by one or more of the distributed sensors may be used to adjust the one or more control systems (e.g., to improve or maintain growth conditions in the agricultural environment).

In one exemplary implementation, multiple sensors are deployed in a controlled agricultural environment as a distributed sensor grid. The distributed sensor grid includes one or more node arrays, where each node array divides at least a portion of the controlled agricultural environment into nodes, e.g., discrete points in space which have a known location (e.g., absolute or relative) in the environment. In various aspects, a given node array of a distributed sensor grid may be one dimensional, two dimensional, or three dimensional (e.g., based at least in part on the distribution of growing areas and/or crops in the controlled agricultural environment). For example, in some implementations, a given node array may include multiple nodes arranged in a substantially linear or curvilinear fashion spaced along a row of plants to provide a one-dimensional node array. Another type of node array may include multiple nodes arranged in a horizontal plane substantially parallel to a floor or a ceiling in the controlled agricultural environment to provide a two-dimensional node array. Yet another type of node array may include multiple nodes arranged in multiple horizontal planes substantially parallel to the floor or ceiling in the controlled agricultural environment, wherein the respective horizontal planes of nodes constitute multiple vertical levels corresponding to different zones of interest in the controlled growing environment (e.g., the soil, the plant, the lighting canopy, and the ambient environment).

In another aspect of such node arrays, one or more sensors are deployed at a given node to monitor various environmental conditions near the node. Examples of sensors that may be included in the distributed sensor grid at a given node of a node array include, but are not limited to, a visible light sensor, a UV light sensor, an air temperature sensor, a relative humidity sensor, an airflow sensor, a $CO_2$ sensor, an IR temperature sensor, a chemical sensor, a pH sensor, and cameras configured to capture still images or videos of the agricultural environment with various spectral qualities. Thus, the distributed sensor grid including one or more node arrays in the controlled agricultural environment may be employed to systematically monitor a variety of environmental conditions relevant to the growth of plants as a function of location in the agricultural environment. In another aspect, common power and network connections may also be employed to facilitate connectivity between various nodes in the distributed sensor grid.

In some implementations, the controlled agricultural environment includes multiple fluid-cooled LED-based lighting fixtures, as described herein. In these implementations, the distributed sensor grid, at least in part, may be integrated with the LED-based lighting fixtures such that the fixtures provide a platform for the distribution of sensors disposed at one or more nodes of the distributed sensor grid. For example, the LED-based lighting fixtures can include network, electrical power, and plumbing connections to facilitate an assembly of multiple lighting fixtures in the controlled agricultural environment, and the lighting fixtures in turn provide networking and electrical connectivity to and between one or more sensors disposed at respective nodes of the sensor grid. In some implementations, each lighting fixture includes one or more ports (e.g., Power over Ethernet, USB) to which an integrated sensor assembly may be coupled, wherein the integrated sensor assembly includes multiple sensors to monitor growth conditions. Thus, the placement of such lighting fixtures in the controlled agricultural environment may in part define different nodes of the distributed sensor grid at which one or more integrated sensor assemblies may be deployed. By leveraging the power and network connections provided by the lighting fixtures, the integrated sensor assemblies can be connected to one another, thus forming a distributed sensor grid.

In some implementations, the distributed sensor grid can be coupled to a processor, e.g., a computer or a server, which stores and processes various data obtained by respective sensors in the distributed sensor grid. The processor (e.g., computer or server) also may provide for a graphical user interface, referred to herein as a "human machine interface"

(HMI), to allow curators/operators of the controlled agricultural environment ("users") to monitor and control various aspects of the agricultural environment (e.g., access various data obtained by the sensors, view and display various results relating to analysis of data obtained by respective sensors, control one or more of lighting, temperature, humidity, air flow, and air quality in the controlled agricultural environment). In one aspect, the HMI can enable users to display data and analytical results pertaining to one or more nodes of the distributed sensor grid on a node-by-node basis or on the basis of particular groups of nodes. Sensor data may be viewed in real-time, and historical data may be viewed as a function time in a wide variety of manners. Additionally, the HMI provides an interface to permit users to automate, at least in part, various controllable conditions in the agricultural environment based on data obtained by one or more sensors of the distributed sensor grid.

By way of example, the distributed sensor grid can incorporate integrated sensor assemblies and fluid-cooled LED-based lighting fixtures described in U.S. patent application Ser. No. 62/660,720 entitled, "Integrated sensor assembly for water-cooled LED-based controlled environment agricultural (CEA) lighting," filed on Apr. 20, 2018, the disclosure of which is incorporated herein by reference in its entirety. It should be appreciated that all combinations of the foregoing concepts and additional concepts discussed in greater detail below (provided such concepts are not mutually inconsistent) are contemplated as being part of the inventive subject matter disclosed herein.

In sum, one implementation is directed to an industrial horticultural lighting system for controlled environment agriculture (CEA), the lighting system comprising: A) a first lighting fixture comprising: a first housing; at least one first light source mechanically supported by the first housing; at least one first pipe thermally coupled to the first housing to carry a fluid coolant, wherein during operation of the first lighting fixture the fluid coolant flowing through the at least one first pipe extracts heat generated by the first lighting fixture; and a first AC power port comprising a first industrial type connector; B) a second lighting fixture comprising: a second housing; at least one second light source mechanically supported by the second housing; at least one second pipe thermally coupled to the second housing to carry the fluid coolant, wherein during operation of the second lighting fixture the fluid coolant flowing through the at least one second pipe extracts heat generated by the second lighting fixture; and a second AC power port comprising a second industrial type connector; C) a first industrial power cable coupled to the first industrial type connector constituting the first AC power port of the first lighting fixture, the first power cable having a first connector (P1) and a second connector (P2); D) an industrial drop tee cable, coupled to the first power cable and the second industrial type connector constituting the second AC power port of the second lighting fixture, the drop tee cable having a first connector (P1), a second connector (P2), and a third connector (P3); and E) a second industrial power cable coupled to the drop tee cable, the second power cable having a first connector (P1) and a second connector (P2).

Another example implementation is directed to a lighting system kit, comprising: A) X lighting fixtures, wherein X is an integer having a value of at least two, each lighting fixture of the X lighting fixtures comprising: a housing; at least one light source mechanically supported by the housing; at least one pipe thermally coupled to the housing to carry a fluid coolant, wherein during operation of the lighting fixture the fluid coolant flowing through the at least one pipe extracts heat generated by the lighting fixture; and an AC power port comprising an industrial type connector; B) X industrial power cables, each industrial power cable having a first connector and a second connector; and C) Y industrial drop tee cables, wherein Y is an integer having a value less than X, each drop tee cable having a first connector, a second connector, and a third connector.

Another example implementation is directed to a method of installing a lighting system comprising at least two lighting fixtures, each lighting fixture of the at least two lighting fixtures comprising a housing, at least one light source mechanically supported by the housing, at least one pipe thermally coupled to the housing to carry a fluid coolant, an AC power port, and at least one network communications port, the method comprising: A) coupling together the AC power port of respective lighting fixtures of the at least two lighting fixtures with a plurality of industrial power cables without using one or more conduits for the plurality of industrial power cables; and B) coupling together the at least one network communications port of the respective lighting fixtures of the at least two lighting fixtures with a plurality of waterproof network communications cables.

Another example implementation is directed to a distributed sensor system comprising: a first plurality of integrated sensor assemblies distributed along (1) a first horizontal axis at approximately or substantially regular intervals defined by a first pitch and (2) a vertical axis at intervals corresponding to a first set of vertical levels of an agricultural environment, wherein: the first horizontal axis is substantially orthogonal to the vertical axis; and the first pitch of the first plurality of integrated sensor assemblies along the first horizontal axis substantially corresponds to respective positions of a first plurality of lighting fixtures disposed in the agricultural environment substantially along the first horizontal axis.

Another example implementation is directed to a distributed sensor system comprising: a first plurality of integrated sensor assemblies distributed along (1) a first horizontal axis at approximately or substantially regular intervals defined by a first pitch and (2) a vertical axis at intervals corresponding to a first set of levels of an agricultural environment, wherein: the first horizontal axis is substantially orthogonal to the vertical axis; and each integrated sensor assembly in the first plurality of integrated sensor assemblies is mechanically coupled to one of a cable or a port that supplies at least one of power or network communication access to the integrated sensor assembly.

Another example implementation is directed to a distributed lighting and sensing system for controlled environment agriculture (CEA) in a growing area space defined by three orthogonal axes including a first axis (x) along a width of the growing area space, a second axis (y) along a length of the growing area space, and third axis (z) along a height of the growing area space, the system comprising: a lighting system, comprising: a first lighting fixture at a first position ($x_1$, $y_1$) in a plane defined by the first axis and the second axis of the growing area space and at a first height ($z_{light}$) along the third axis of the growing area space and; and a second lighting fixture at a second position ($x_2$, $y_2$) in the plane defined by the first axis and the second axis of the growing area space and at the first height ($z_{light}$) along the third axis of the growing area space, wherein the first position ($x_1$, $y_1$) of the first lighting fixture at the first height ($z_{light}$) and the second position ($x_2$, $y_2$) of the second lighting fixture at the first height ($z_{light}$) define a multidimensional grid of nodes in the growing area space at which the lighting system provides at least one of operating power or network communications access to respective nodes of the multidimensional grid of nodes; and a sensing system, comprising: a first sensor situated at or near a first node $(x_1, y_1, z_1)$ of the multidimensional grid of nodes, the first sensor coupled to the first lighting fixture to receive the at least one of operating power or network communication access from the first lighting fixture; and a second sensor situated at or near a second node $(x_2, y_2, z_2)$ of the multidimensional grid of nodes, the second sensor coupled to the second lighting fixture to receive the at least one of operating power or network communication access from the second lighting fixture, wherein $z_1$ and $z_2$ are different. In one aspect, $x_1=x_2$ or $y_1=y_2$ such that the multidimensional grid of nodes is a two-dimensional array of nodes. In another aspect, $x_1$ and $x_2$ are different, and $y_1$ and $y_2$ are different, such that the multidimensional grid of nodes is a three-dimensional array of nodes.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

FIG. 8H-1 shows a wiring diagram for the drop tee cable of FIG. 8C.

FIG. 8H-2 shows a right-side view of the drop tee cable of FIG. 8C based on the wiring diagram of FIG. 8H-1.

FIG. 8H-3 shows a left-side view of the drop tee cable of FIG. 8C based on the wiring diagram of FIG. 8H-1.

FIG. 8I shows a perspective view of the power cable of FIG. 8C.

FIG. 8O shows a top view of the waterproof Ethernet cable of FIG. 8N.

FIG. 8Q-1 shows an exemplary outlet.

FIG. 8Q-2 shows an exemplary power cable.

FIG. 8Q-3 shows a portion of an exemplary drop tee cable.

FIG. 8Q-4 shows another exemplary drop tee cable.

FIG. 8Q-5 shows yet another exemplary drop tee cable.

FIG. 10C shows a top view of the lighting system of FIG. 10B.

FIG. 11C is a block diagram providing additional detail of the network board of FIG. 11A.

FIG. 12C is an expanded view of the PoE port of FIG. 12A.

FIG. 20B-1 shows a top view of an exemplary node array in a distributed sensor system with two plant shelves, according to some implementations of the disclosure.

FIG. 20B-2 shows a front view of the node array of FIG. 20B-1.

FIG. 20B-3 shows a side view of the node array of FIG. 20B-1.

FIG. 20B-4 shows a perspective view of the node array of FIG. 20B-1.

FIG. 20D-1 shows a top view of another exemplary node array in a distributed sensor system with one shelf, according to some implementations of the disclosure.

FIG. 20D-2 shows a front view of the node array of FIG. 20D-1.

FIG. 20D-3 shows a perspective view of the node array of FIG. 20D-1.

FIG. 20D-4 shows a side view of the node array of FIG. 20D-1.

FIG. 20E-1 shows a front view of another exemplary node array in a distributed sensor system with numerous plant shelves, according to some implementations of the disclosure.

FIG. 20E-2 shows a top view of the node array of FIG. 20E-1.

FIG. 20E-3 shows a side view of the node array of FIG. 20E-1.

FIG. 20E-4 shows a perspective view of the node array of FIG. 20E-1.

FIG. 20E-5 shows another perspective view of the node array of FIG. 20E-1.

FIG. 21A-1 shows an expanded view of a portion of the HMI of FIG. 21A labeled "See FIG. 21A-1."

FIG. 21B shows a top view of a plant shelf as displayed in the HMI of FIG. 21A.

FIG. 21I-1 shows an expanded view of a portion of the chart of FIG. 21I labeled as "See FIG. 21I-1."

FIG. 21J-1 shows an expanded view of a portion of the chart of FIG. 21J labeled as "See FIG. 21J-1."

FIG. 21J-2 shows an expanded view of a portion of the chart of FIG. 21J labeled as "See FIG. 21J-2."

DETAILED DESCRIPTION

Figure 1:
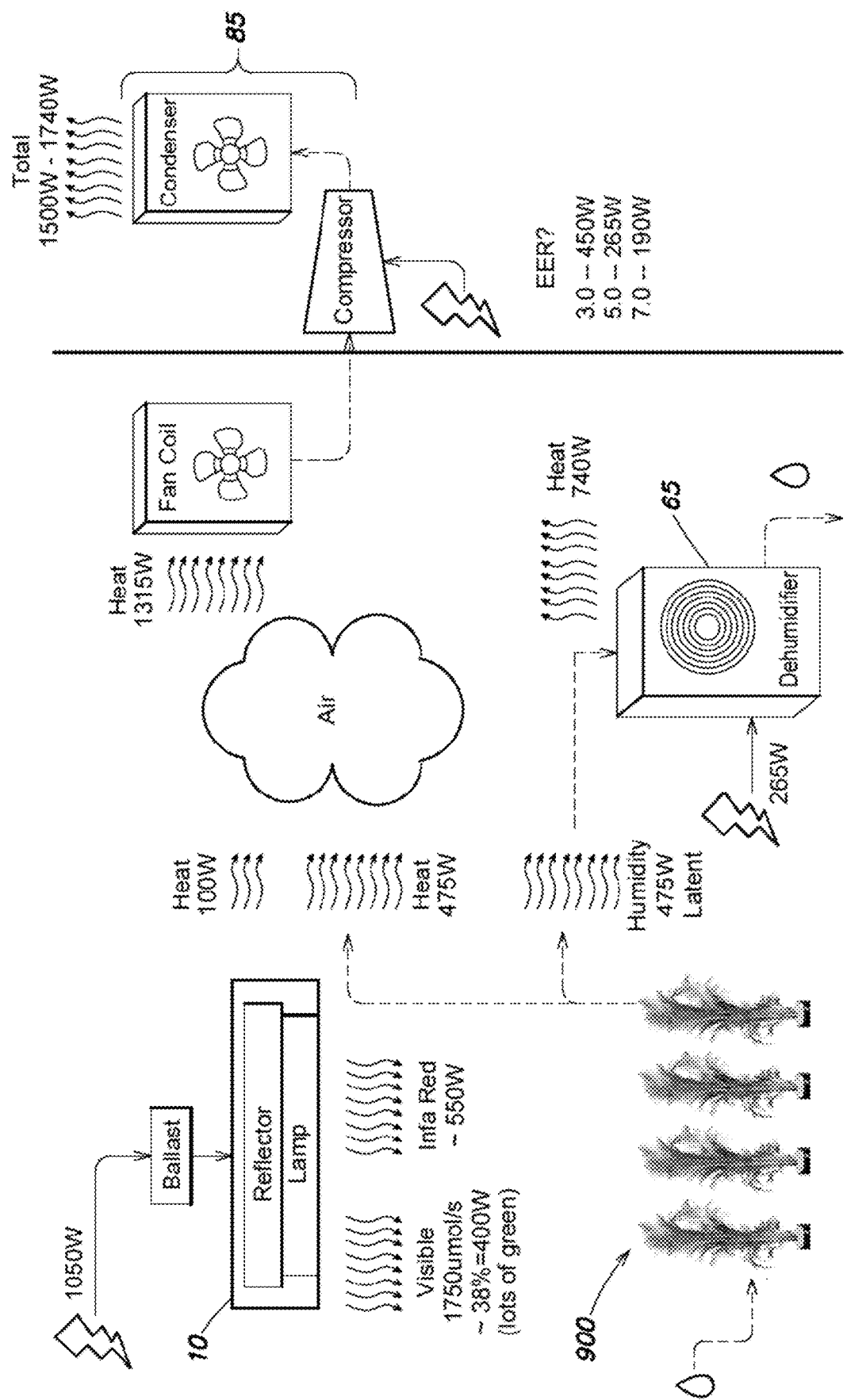
FIG. 1 is an illustration of a conventional controlled agricultural environment where one or more HPS lamps are used.

Following below are more detailed descriptions of various concepts related to, and implementations of, methods, apparatus and systems for lighting and distributed sensing in a controlled agricultural environment. It should be appreciated that various concepts introduced above and discussed in greater detail below may be implemented in multiple ways. Examples of specific implementations and applications are provided primarily for illustrative purposes so as to enable those skilled in the art to practice the implementations and alternatives apparent to those skilled in the art.

The figures and example implementations described below are not meant to limit the scope of the present implementations to a single embodiment. Other implementations are possible by way of interchange of some or all of the described or illustrated elements. Moreover, where certain elements of the disclosed example implementations may be partially or fully implemented using known components, in some instances only those portions of such known components that are necessary for an understanding of the present implementations are described, and detailed descriptions of other portions of such known components are omitted so as not to obscure the present implementations.

Controlled Environment Agriculture (CEA) is the process of growing plants in a controlled environment where various environmental parameters, such as lighting, temperature, humidity, nutrient levels, and carbon dioxide ($CO_2$) concentrations are monitored and adjusted to improve the quality and yield of the plants. Compared to conventional approaches of plant cultivation, CEA may enable year-round production of plants, insensitivity to variable weather conditions, reduce pests and diseases, and reduce the amount of resources consumed on a per plant basis. Additionally, CEA may support various types of growing systems including, but not limited to soil-based systems and hydroponics systems.

For an environment utilizing CEA, sensors should preferably be deployed throughout the environment to monitor various environmental parameters pertinent to the growth of different plant species contained within the environment. Various types of sensors may be deployed to monitor various environmental parameters including, but limited to, air temperature, leaf temperature, air flow, relative humidity, lighting conditions (e.g., spectral intensity, radiant intensity such as the photosynthetic flux density), $CO_2$ concentrations, pH levels in the soil, and air pollution. These environmental parameters may also vary as a function of location within the environment. For example, the air flow rate above a lighting fixture may differ substantially from the air flow rate just above the plants.

The data recorded by the sensors may be used to provide insight on various aspects of plant development including, but not limited to the health of the plants, yield rates, and projected harvest dates. The data may also be used to provide feedback to various control systems deployed in the environment in order to adjust the environmental parameters described above. These control systems may include, but are not limited to, lighting systems, heating/cooling systems (e.g., hydronics, air conditioning), air flow systems, and humidity conditioning systems.

Conventional sensors in CEA systems, however, are typically designed and deployed irrespective of other sensors disposed in the environment and the control systems to which they may be coupled to. For example, different types of sensors may each have to be installed separately even if the sensors are monitoring the same region of the environment. In some instances, a separate platform or support structure may be installed (e.g., a frame, a rafter) to enable the sensors to monitor an otherwise inaccessible region of the environment (e.g., right above the plants). In another example, each type of sensor deployed in the environment may be connected to a power source and/or a control system (e.g., a computer) using a proprietary connection mechanism (e.g., different types of cables). In an environment where numerous sensors may be deployed, the integration of the sensors into the CEA system may be hindered by practical limitations related to separately connecting each sensor to the power source/control system. In yet another example, each sensor may be communicatively coupled to a control system using a separate system (e.g. a different interface on a computer, different communication channels), which further increase the difficulty in leveraging multiple sensors to monitor and control the environment.

In order to overcome these challenges, conventional CEA systems and other agricultural applications have relied upon wireless sensors used in a wireless sensor network (WSN) system or an Internet of Things (IoT) system. The WSN and IoT systems have enabled deployment of sensors over large agricultural spaces. However, the sensors are typically powered by a battery, which should be periodically replaced or recharged in the field. For a CEA system comprising hundreds or thousands of sensors, the added cost for batteries and time for labor is undesirable. Additionally, wireless communication may be hindered by obstructions in the environment. For example, sensors deployed to monitor soil conditions may be blocked by plant leaves.

The present disclosure is thus directed to various implementations of a distributed sensor grid for controlled agricultural environments, respective components of such distributed sensor grids, and methods of assembling and using the distributed sensor grid. In one aspect, the sensors deployed in the distributed sensing systems may be wired (as opposed to being wireless) in order to provide a persistent source of power. In order to overcome the challenge of connecting each sensor to a common power source and/or network node for communication, a plurality of lighting fixtures disposed in the environment may be configured to supply power and/or communication to each sensor. The lighting fixture(s), which may be electrically and communicatively coupled to one another, may thus serve as a platform to support the sensors in the distributed sensing systems. Each sensor may be coupled to a lighting fixture rather than having to be routed to a common power source or communication node, thus simplifying installation and integration.

By leveraging the lighting fixtures to support the operation of various sensors, the distributed sensing system naturally covers regions of the environment relevant to the growth of plants (i.e., the lighting fixtures are deployed in areas where plants are located). In another aspect, the sensors used in the distributed sensing system may thus be deployed at locations in the environment where lighting fixtures are located.

The distributed sensor grid may include one or more node arrays that divide an agricultural environment into nodes, e.g., discrete points in space, with known locations in the environment. Each node can include one or more sensors to monitor the environmental conditions proximate to the node. The nodes may be further differentiated according to levels that correspond to various parts of a plant system. The nodes in the node array may also share power and network connections to simplify the integration of various sensor modalities in the distributed sensor grid and to improve ease of use in storing, accessing, and processing data from said sensor modalities. A processor may also be coupled to the distributed sensor grid to facilitate user interaction via a human machine interface.

Exemplary implementations of a distributed sensor grid are based, in part, on concepts related to fluid-cooled LED-based lighting fixtures and integrated sensor assemblies deployed in controlled agricultural environments. Accordingly, example implementations of a fluid-cooled LED-based lighting fixture and an integrated sensor assembly are described below in the first instance to provide illustrative context for inventive implementations of the distributed sensor grid described in the present disclosure.

An Exemplary Lighting Fixture and Lighting System for CEA

A controlled agricultural environment is typically enclosed, at least in part, by a building structure such as a greenhouse, a grow room, or a covered portion of a field in order to provide some degree of control over environmental conditions. One or more artificial lighting systems are often used in such controlled agricultural environments to supplement and/or replace natural sunlight that may be obstructed by the building structure or insufficient during certain periods of the year (e.g., winter months). The use of an artificial lighting system may also provide yet another measure of control where the intensity and spectral characteristics of the lighting system may be tailored to improve the photosynthetic rates of plants. Various types of artificial lighting systems may be used including, but not limited to, a high intensity discharge lamp, a light emitting diode (LED), and a fluorescent lamp.

Artificial lighting systems, however, generate heat, which when dissipated into the environment may contribute significantly to the cooling load of the controlled agricultural environment. In order to accommodate the higher cooling load and thus maintain the controlled agricultural environment within a desired temperature envelope, the cooling capacity of a cooling system may need to be increased resulting in greater energy consumption. For a controlled agricultural environment on a variable energy budget, greater energy consumption may lead to higher energy costs. Alternatively, for a controlled environment on a fixed energy budget, a larger portion of the energy budget may be consumed by the cooling system, thus reducing the energy and capacity available to support a larger crop size and yield.

To illustrate the impact excess heat generated by an artificial lighting system may have on energy consumption, FIG. 1 shows a conventional controlled agricultural environment with one or more high pressure sodium (HPS) lamps 10, a particular type of high intensity discharge lamp, which irradiates a plurality of plants 900. The exemplary controlled agricultural environment shown in FIG. 1 further includes a dehumidifier 65 to manage the relative humidity of the environment and an air conditioner 85, which may include a fan coil, compressor, and condenser. Energy consumption by the air conditioner 85 generally depends on (1) the total cooling load of the environment and (2) the energy efficiency ratio (EER) of the air conditioner 85. The EER of an air conditioner is defined as the ratio of the cooling capacity (in Watts) to the input power (in Watts) at a given operating point. The EER was calculated with a 35° C. (95° F.) outside temperature and an inside (return air) temperature of 26.7° C. (80° F.) and 50% relative humidity. A higher EER indicates the air conditioner 85 is more efficient.

As shown in FIG. 1, the HPS lamps 10 may increase the cooling load of the environment by (1) dissipating heat convectively and/or radiatively directly into the environment and (2) increasing the relative humidity of the environment and thus, the power input and resultant heat generated by the dehumidifier 65. The cooling load in this exemplary controlled agricultural environment is about 1315 W. For an EER ranging from 3 to 7, the input power for the air conditioner thus ranges from 450 to 190 W, respectively. Based on the input power to the HPS lamps 10 of 1009 W and the dehumidifier 65 of 265 W, the air conditioner 85 thus consumes about 13% and 26% of the total energy budget, corresponding to an EER of 7 and 3, respectively.

Figure 2:
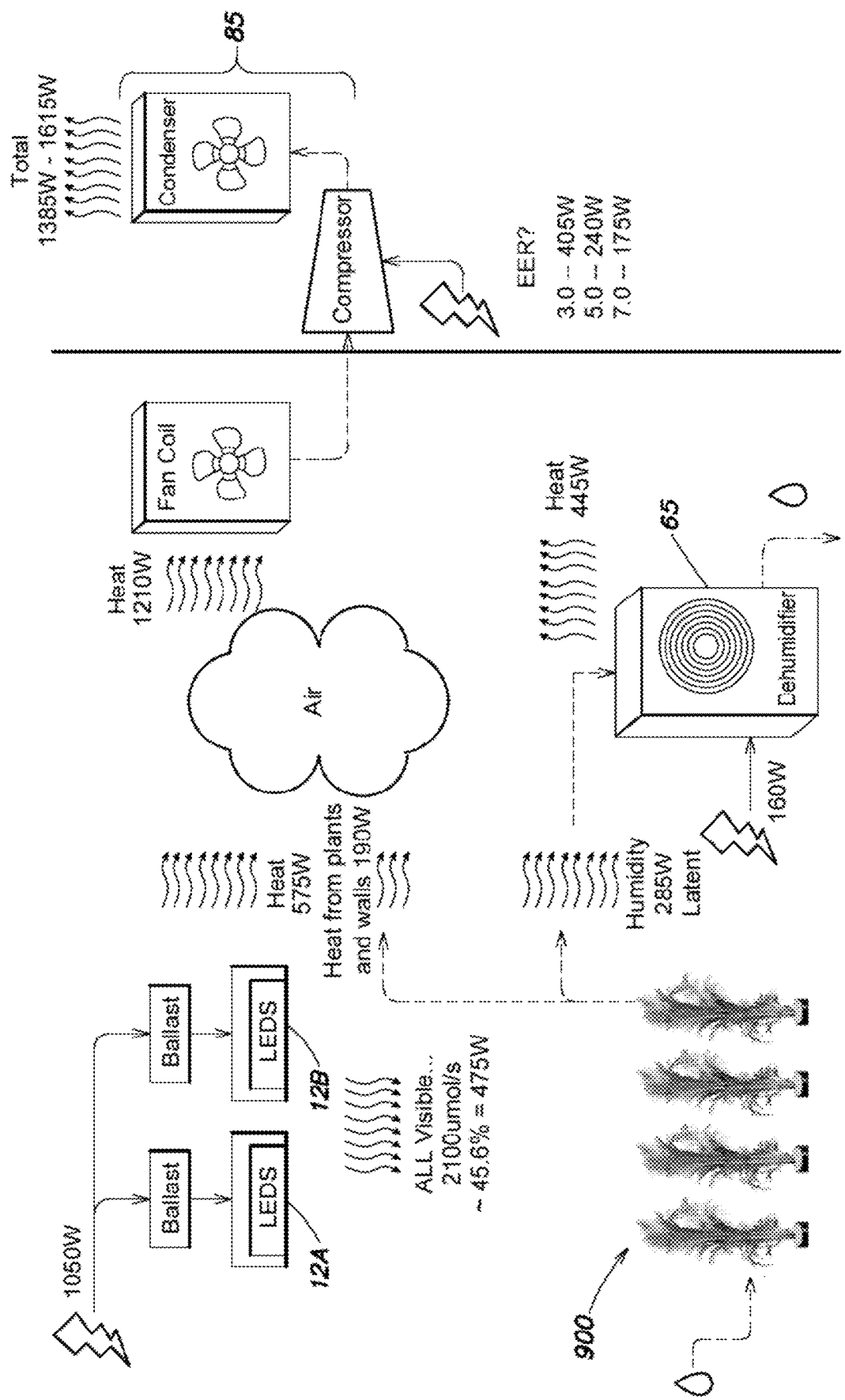
FIG. 2 is an illustration of a conventional controlled agricultural environment where one or more conventional LED-based lighting fixtures are used.

The amount of heat generated may vary depending on the type of lighting system used. However, artificial lighting systems for controlled agricultural environments generally have large power inputs (e.g., greater than 1000 W) in order to sustain a sufficient level of photosynthetically active radiation (PAR). Thus, the heat generated by various types of lighting systems may still constitute a large portion of heat produced within the environment. In another example, FIG. 2 illustrates a conventional controlled agricultural environment where one or more conventional LED-based lighting fixtures 12A and 12B irradiate a plurality of plants 900. In this exemplary controlled agricultural environment, the LED-based lighting fixtures 12A and 12B dissipates heat primarily via convection, which may reduce the power input and heat generated by the dehumidifier 65. In this example, the total cooling load is about 1210 W. For an EER ratio ranging from 3 to 7, the input power for the air conditioner 85 ranges from 405 W to 175 W. Compared to the first example, the use of LED-based lighting fixtures 12A and 12B decreases the total energy budget of the controlled agricultural environment. However, the proportion of energy used by the air conditioner 85 remains similar to the first example at about 13% and 25% for an EER ratio of 7 and 3, respectively. As shown in the two exemplary controlled agricultural environments, artificial lighting systems may generate a substantial amount of heat, which may result in air conditioning systems consuming a significant portion of the total energy budget in a controlled agricultural environment.

Figure 3:
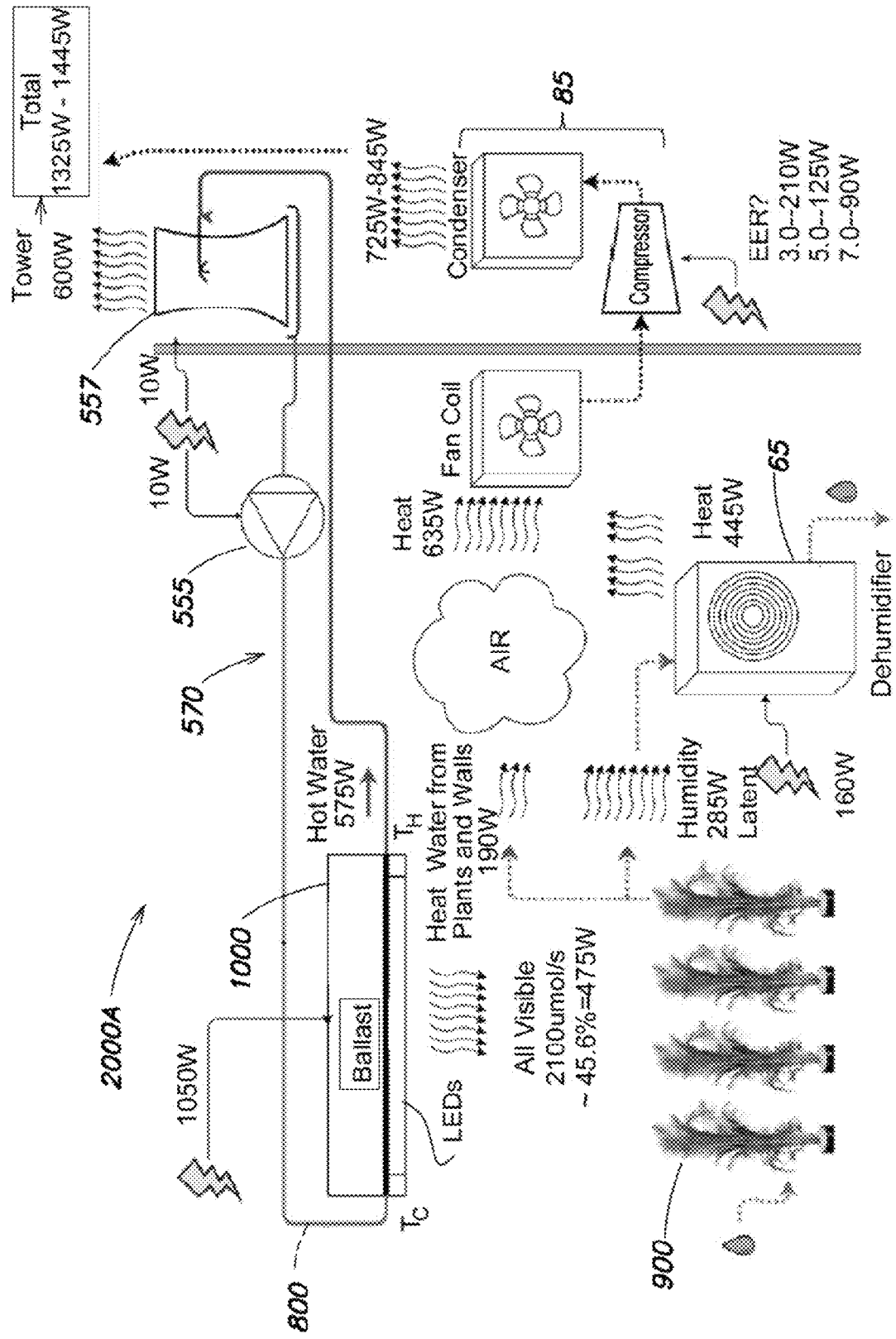
FIG. 3 is an illustration of a controlled agricultural environment where one or more fluid-cooled LED-based lighting fixtures are retrofit into a pre-existing environment, according to some implementations of the disclosure.

A fluid-cooled LED-based lighting fixture may provide several benefits to a controlled agricultural environment. As an example, FIG. 3 shows an exemplary implementation of a controlled agricultural environment 2000A where a lighting fixture 1000 is retrofit into a preexisting environment that includes a dehumidifier 65 and an air conditioner 85. While not shown explicitly in FIG. 3, the environment may be constituted, at least in part, by a building structure to house a plurality of plants 900, one or more lighting fixtures 1000, and other equipment. The lighting fixture 1000 is cooled by a fluid coolant 800 that circulates through a coolant circuit 570. Heat carried by the fluid coolant 800 is removed by a cooling tower 557 located outside of the controlled agricultural environment 2000A. The coolant circuit 570 may include one or more pumps, regulators and/or valves 555 to control the flow of the fluid coolant 800 in the coolant circuit 570.

As shown in FIG. 3, the one or more pumps, regulators, and/or valves 555 may produce a flow of fluid coolant 800 that exhibits a relatively colder temperature TC upon entry into the lighting fixture 1000 and a relatively hotter temperature TH upon exit from the lighting fixture 1000. The rise in temperature of the fluid coolant 800 is due, in part, to convective heating of the fluid as it passes through the lighting fixture 1000 due to heat generated from one or more LED modules within the lighting fixture 1000. The fluid coolant 800 may thus be used to capture and transport heat generated by the lighting fixture 1000, which may substantially reduce the cooling load of the environment and the power inputs to the air conditioner 85 and/or the dehumidifier 65. As shown in FIG. 3, the cooling load for the exemplary controlled agricultural environment 2000A is about 635 W, which is approximately 50% the cooling load in the exemplary controlled agricultural environments shown in FIGS. 1 and 2. For an EER ranging from 3 to 7, the input power for the air conditioner thus ranges from 210 W to 90 W, respectively. Based on the input power to the lighting fixture 1000 of 1009 W and the dehumidifier 65 of 160 W, the air conditioner 85 thus consumes about 7% and 15% of the total energy budget, corresponding to an EER of 7 and 3, respectively.

Although a cooling tower 557 is shown in FIG. 3 to facilitate evaporative cooling of the heated fluid coolant exiting the lighting fixture 1000, it should be appreciated that various types of heat rejection devices may be employed in the coolant circuit 570 to remove heat from the fluid coolant 800. Some examples of heat rejection devices include, but are not limited to, various types of evaporative coolers, "free" coolers, chillers, dry coolers, air source coolers, ground source heat exchangers, water source heat exchangers, or any combinations of the foregoing.

Figure 4:
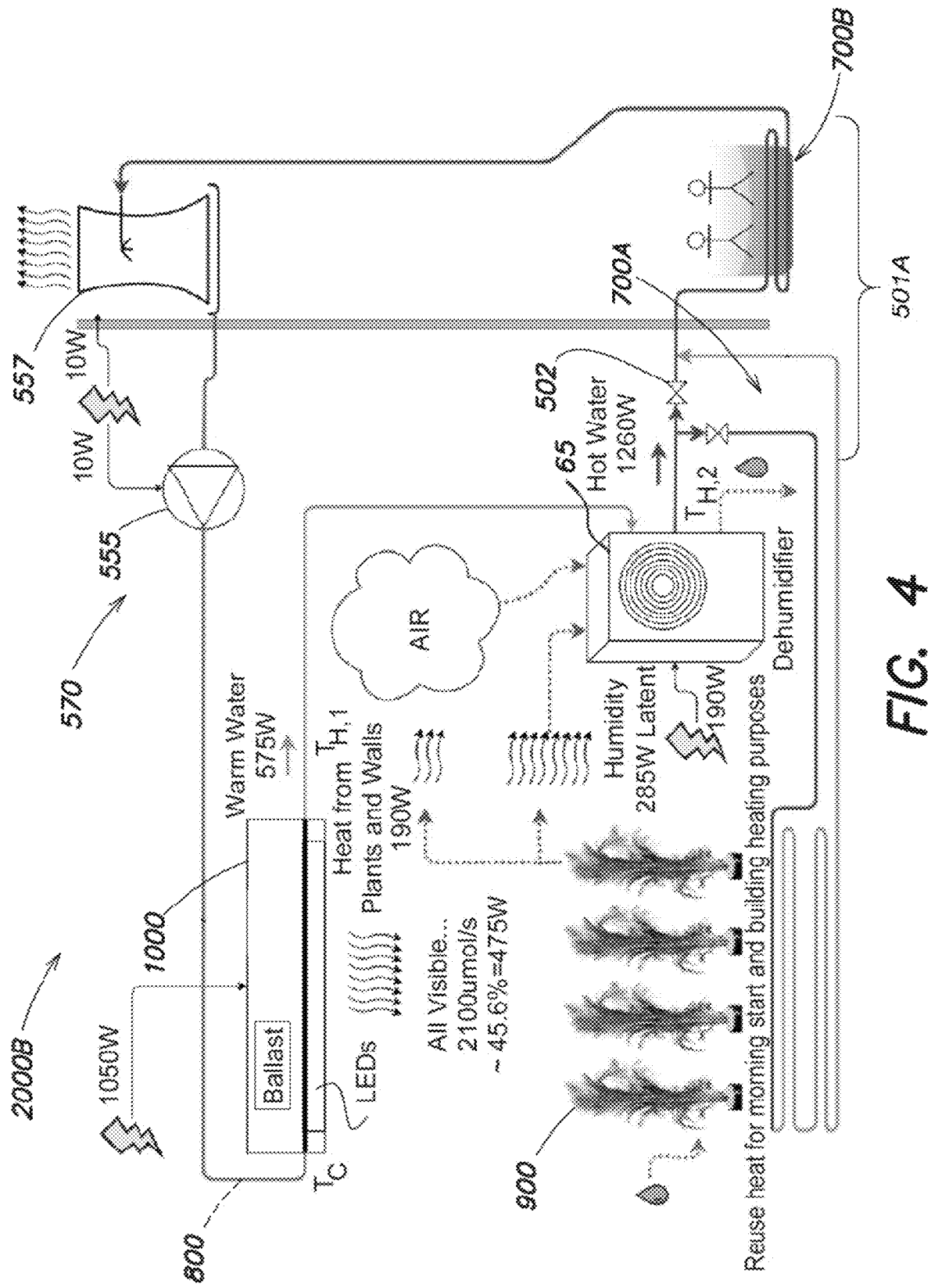
FIG. 4 is an illustration of a controlled agricultural environment where one or more fluid-cooled LED-based lighting fixtures are coupled to a hydronics system, according to some implementations of the disclosure.

In another example, FIG. 4 shows an exemplary controlled agricultural environment 2000B where a lighting fixture 1000 is coupled to a coolant circuit 570 that directs the fluid coolant 800 to a hydronics system 501A having multiple plumbing subsystems 700A and 700B (also referred to herein as "hydronics loops"), which regulate and/or maintain the temperature of various portions of the controlled agricultural environment 2000B and/or space near the controlled agricultural environment 2000B (e.g., a hot pool, the growing area) by utilizing the waste heat generated by the lighting fixture 1000 as a heat source. The coolant circuit 570 may receive heat from the lighting fixture 1000 and other environment sources (e.g., a dehumidifier 65, the ambient air) such that excess heat generated in the environment may be substantially removed, thus further improving the energy savings to operate the controlled agricultural environment 2000B. In some implementations, the cooling load may be sufficiently reduced so as to eliminate the need for any air conditioning systems (i.e., there is no air conditioner fan coil, compressor or condenser).

As shown in FIG. 4, the controlled agricultural environment 2000B may include a dehumidifier 65 to regulate the relative humidity of the environment. The coolant circuit 570 may direct fluid coolant 800 heated by the lighting fixture 1000 into the dehumidifier 65 to further remove heat generated by the dehumidifier 65 in a convective manner similar to the removal of heat from the lighting fixture 1000. The coolant circuit 570 may then direct the fluid coolant 800 to the hydronics loops 700A and 700B, which may be used to heat the plurality of plants 900 and a hot pool, respectively. The coolant circuit 570 may distribute and direct heated fluid coolant 800 in a controlled manner by one or valves 502 before dissipating the remaining heat by the cooling tower 557.

In some implementations, the hydronics system 501A may also be used to regulate the temperature of the ambient environment itself. For example, the hydronics system 501A may be used to heat the controlled agricultural environment 2000B convectively and/or radiatively as the fluid coolant 800 flows through the hydronics system 501A. Furthermore, while FIG. 4 shows a coolant circuit 570 passing through the dehumidifier 65, it should be appreciated that in other implementations the coolant circuit 570 need not include the dehumidifier 65, e.g. the coolant need not flow through the humidifier 65.

Figure 5:
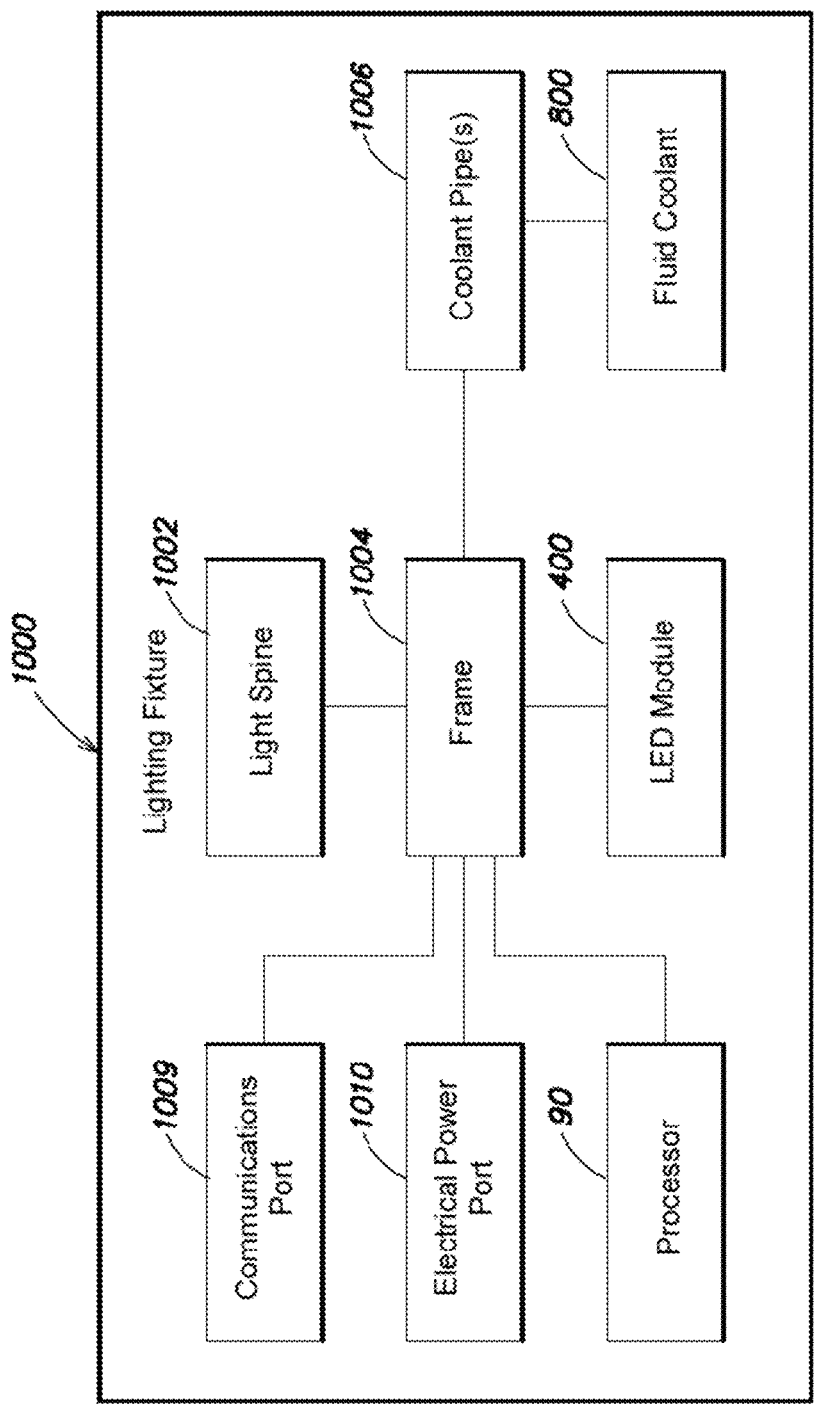
FIG. 5 is a block diagram of a lighting fixture, according to some implementations of the disclosure.

An exemplary implementation of a fluid-cooled LED-based lighting fixture 1000 is shown in FIG. 5. The lighting fixture 1000 may include a frame 1004 to mechanically support and house various components of the lighting fixture 1000. A light spine 1002 may be incorporated onto one or more sides of the frame 1004 with features to mechanically couple and secure the lighting fixture 1000 to a support structure disposed within a controlled agricultural environment. One or more coolant pipes 1006 may be coupled to the frame 1004, where each coolant pipe 1006 may be used to flow a fluid coolant 800 to cool the lighting fixture 1000. One or more LED modules 400 may be disposed on the frame 1004 to emit PAR towards a plurality of plants. A processor 90 may be coupled to the frame 1004 to facilitate the operation of the lighting fixture 1000 including, but not limited to power conversion, network connectivity, and data processing. One or more electrical power ports 1010 may be disposed on the frame 1004 to supply electrical power to various components of the lighting fixture 1000, including, but not limited to the LED modules 400, the processor 90, and other sensors that may be coupled to the lighting fixture 1000. One or more communication ports 1009 may be disposed on the frame 1004 to facilitate electrical communication and data transmission.

The frame 1004 may be a mechanically rigid, hollow structure that forms a substantially enclosed housing. The interior cavity of the frame 1004 may be dimensioned to house a plurality of components in the lighting fixture 1000, such as various electronics in the processor 90. The frame 1004 may include one or more mounting features within the interior cavity to securely couple the plurality components to the frame 1004. For example, the frame 1004 may include one or more slots disposed within the interior cavity of the frame 1004 and arranged so as to mechanically support at least two opposing edges of a printed circuit board. Other mounting features may include, but are not limited to mounting posts and mounting stubs.

One or more removable panels may be included in the frame 1004 to provide access to the interior space. The one or more removable panels may be coupled to a portion of the frame 1004 using various types of coupling mechanisms including, but not limited to screw fasteners, bolt fasteners, clips, and clamps. In some implementations, the frame 1004 may form a sufficiently airtight enclosure or cavity to protect components, e.g., electronics, that may be sensitive to the environmental conditions of the controlled agricultural environment. For example, the controlled agricultural environment may operate at a relative humidity that may cause moisture to condense onto various surfaces of the lighting fixture 1000, causing damage to components including exposed electronics. In instances where the frame 1004 is an airtight enclosure, moisture may be substantially restricted from infiltrating the interior space of the frame 1004 to reduce the likelihood of condensation forming onto components disposed within the frame 1004.

The frame 1004 may also include a recessed portion disposed along at least one side of the frame 1004, e.g., the bottom side, with sidewalls that at least partially surround one or more LED modules 400. The recessed portion may be used to direct light emitted by the one or more LED modules 400 along a preferred direction and angular distribution. For example, the recessed portion may be used to substantially illuminate a growing area containing one or more plants located below the frame 1004. In some implementations, the surface quality and orientation of the interior surfaces of the sidewalls forming the recessed portion may form an integrated reflector to reflect light emitted by the one or more LED modules 400. For example, the interior surfaces of the sidewalls may be polished to reflect light in a substantially specular manner and oriented such that light is reflected towards a preferred direction, e.g., the growing area.

The frame 1004 may also include one or more channels formed along one or more sides of the frame 1004 where each channel may be used to secure a corresponding coolant pipe 1006 to the frame 1004. The cross-sectional shape of the channel may be substantially similar to the cross-sectional shape of the coolant pipe 1006 to facilitate insertion of the coolant pipe 1006 into the channel. The coolant pipe 1006 may be secured to the channel of the frame 1004 using several approaches. For example, the cross-section dimensions of the channel may be equal to or smaller than the cross-sectional dimensions of the coolant pipe 1006 to facilitate a press fit where the coolant pipe 1006 is secured to the channel via friction. In other examples, the coolant pipe 1006 may be clamped to the frame 1004 using one or more clamps, which may include, but are not limited to zip ties and clamps with a worm drive fastener. The clamps may be removable to allow replacement of the coolant pipes 1006. The surface of the one or more channels may also be polished to improve thermal contact with the coolant pipe 1006, thus enabling greater heat dissipation into the fluid coolant 800. In yet other examples, the coolant pipes 1006 may be adhered or bonded to the frame 1004 using various methods including, but not limited to adhesive bonding, welding, and brazing. Thermal interface material may also be disposed between the channel and the coolant pipe to improve thermal contact.

The frame 1004 may also be, at least in part, thermally conducting to transfer heat from the one or more LED modules 400 to the coolant pipe 1006. In particular, a first portion of the frame 1004 disposed between the LED module 400 and the coolant pipe 1006 may be formed from a thermally conducting material with dimensions to (1) reduce the distance between the LED module 400 and the coolant pipe 1006 and (2) increase the lateral cross-sectional area between the LED module 400 and the coolant pipe 1006. In this manner, the thermal resistance between the LED module 400 and the coolant pipe 1006 may be reduced. In some implementations, the frame 1004 may be formed entirely from the thermally conducting material to simplify manufacture and assembly. In some implementations, the first portion of the frame 1004 may be formed from a thermally conducting material while the remainder of the frame 1004 is formed from another material, such as a polymer in order to reduce material costs.

The frame 1004 may be formed from various metals, ceramics, polymers, or composites including, but not limited to, copper, aluminum, stainless steel, carbon steel, polyethylene, acrylic, and porcelain. Depending on the materials used to form the frame 1004, various method of manufacture may be utilized including, but not limited to, extrusion, sandcasting, milling, injection molding, and manual molding. For instances where the frame 1004 is assembled form multiple parts, various coupling mechanisms may be used for assembly including, but not limited to snap fits, screw fasteners, bolt fasteners, adhesives, brazing, and welding.

The light spine 1002 may be used to secure the lighting fixture 1000 to a support structure in the controlled agricultural environment. The support structure may be various types of structures including, but not limited to a railing, a suspended platform, a ceiling, and a wall. The light spine 1002 may be a protruding fin formed onto the frame 1004 that includes one or more holes of varying size to accommodate different sizes and types of coupling mechanisms used to secure the lighting fixture 1000 to the support structure. The coupling mechanisms may include, but are not limited to bolt fasteners, screw fasteners, hooks, and shackles. The light spine 1002 may be dimensioned to span the length of the frame 1004, thus providing multiple locations along the frame 1004 to couple the lighting fixture 1000 to the support structure in a stable manner. For example, the light spine 1002 may be disposed on the top side of the frame 1004 with a length that spans the length of the frame 1004. The light spine 1002 may include a plurality of holes where the center axis of each hole is parallel to the top side of the frame 1004. Multiple bolt fasteners may be installed at each end and the center of the light spine 1002 to secure the lighting fixture 1000 to a sidewall of a support structure. Multiple light spines 1002 may also be distributed along the length of the frame 1004 or on multiple sides of the frame 1004 to allow the lighting fixture 1000 to be coupled to different support structures.

As described above, the coolant pipe 1006 may be used to flow fluid coolant 800 to capture heat generated by the LED module 400. The coolant pipe 1006 may be dimensioned to have a length longer than the frame 1004 such that a portion of the coolant pipe 1006 may extend beyond the sides of the frame 1004 to facilitate coupling of the coolant pipe 1006 to a pipe from a coolant circuit, a hydronics system, or another lighting fixture 1000. Various types of coupling mechanisms may be used to couple the coolant pipe 1006 to another pipe including, but not limited to threaded fittings, where the ends of the coolant pipe 1006 have corresponding threads, and bolt fasteners, where the end of the coolant pipe 1006 have a flange that mates to a corresponding flange on another pipe. In a preferred implementation, push-to-connect plumbing fittings may be used as a coupling mechanism where the ends of the coolant pipe 1006 are left bare. In this manner, internal seals and O-rings do not need to be used.

Multiple coolant pipes 1006 may be incorporated into the frame 1004 where each coolant pipe 1006 may be used to flow fluid coolant 800 along the same or opposing directions. For example, the lighting fixture 1000 may include two coolant pipes 1006 disposed on opposing sides of the frame 1004. For a lighting fixture 1000 that supports multiple LED modules 400, an opposing flow configuration (e.g., fluid coolant 800 flows in opposing directions between the two coolant pipes 1006) may more uniformly remove heat from the multiple LED modules 400. In comparison, a same flow configuration will result in more heat removed from the LED module 400 closest to the fluid coolant 800 input and less heat removed from the LED module 400 furthest from the fluid coolant 800 input. Additionally, the opposing flow configuration may more readily facilitate implementation of a closed coolant circuit. For example, the two coolant pipes 1006 may be connected at one end by a plumbing fitting such that fluid coolant 800 entering the lighting fixture 1000 flows through a first coolant pipe 1006 and then a second coolant pipe 1006 serially before exiting the lighting fixture 1000 on the same side.

The coolant pipe 1006 may be formed from various materials including copper, aluminum, and stainless steel. In a preferred implementation, the coolant pipes 1006 may be formed from copper to reduce algae growth, fouling, and corrosion. Thus, by coupling copper coolant pipes 1006 using the push-to-connect plumbing fittings described above, the fluid coolant 800 may pass through a coolant circuit made up of only copper without contacting other materials in the lighting fixture (e.g., an aluminum frame 1004).

The cross-sectional dimensions of the coolant pipe 1006 may vary depending on multiple factors including, but not limited to a desired flow rate, fluid coolant properties (e.g., dynamic viscosity, density), and a desired type of flow. For example, it may be desirable for the fluid coolant to be in a turbulent flow regime, which engenders a higher heat transfer coefficient, thus dissipating more heat from the lighting fixture 1000. In some implementations, the cross-sectional dimensions of the coolant pipe 1006 may be chosen such that a particular Reynold's number, Re, is greater than a desired threshold (e.g., Re>4000 for turbulent flow) for a given pump power and coolant circuit geometry. The interior surface of the coolant pipe 1006 may also be roughened to increase the surface area and the convective heat transfer coefficient. The effective depth and pitch of the interior surface roughness may be chosen so as to not substantially increase pumping requirements (e.g., due to a larger pressure drop) and maintains wettability of the interior surface to the fluid coolant 800 (e.g., remains hydrophilic, oleophilic).

The fluid coolant 800 used to capture and carry heat from the lighting fixture 1000 may be chosen based on several factors. First, it is preferable for the fluid coolant 800 to exhibit a high thermal conductivity and a high specific heat in order to increase heat dissipation from the LED module 400 to the fluid coolant 800. Second, the fluid coolant 800 should remain in a liquid phase within the operating temperature and pressure range of the controlled agricultural environment. For example, the fluid coolant 800 should not freeze or boil as it passes through the lighting fixture 1000, the coolant circuit, the hydronics system, or a cooling tower. Third, the fluid coolant 800 should also be chosen so as not to substantially corrode the coolant pipe 1006. For controlled agricultural environments, the fluid coolant 800 may be various fluids including, but not limited to water, mineral oil, glycol, and mixtures.

The lighting fixture 1000 also may include one or more communication and/or auxiliary power ports, for example, to provide auxiliary DC power to one or more auxiliary devices coupled to the port(s), and/or facilitate communications between the lighting fixture and the one or more auxiliary devices. Example of such ports include, but are not limited to, one or more Power over Ethernet (PoE) ports and/or one or more Universal Serial Bus (USB) ports.

For example, the lighting fixture 1000 may include at least one electrical power port 1010 to supply electrical power to various components in the lighting fixture 1000 (e.g., the LED module 400) and/or various components electrically coupled to the lighting fixture 1000 (e.g., other lighting fixtures 1000 or auxiliary sensors). The electrical power port 1010 may receive as input alternating current (AC) power, such as from a building electrical supply system, which may be converted into direct current (DC) power via the processor 90. The processor 90 may include electronics to facilitate conversion between DC and AC power, as will be discussed in greater detail below.

One or more communication ports 1009 may also be used in the lighting fixture 1000 to facilitate data transmission to and from the lighting fixture 1000. For example, the communication port 1009 may be used to remotely control various aspects of the lighting fixture 1000 including, but not limited to adjustments to electrical power (e.g., high voltage and low voltage modes), adjustments to the spectral content of the light emission (e.g., directing more power to blue or red LED elements), and commands to operate auxiliary sensor devices (e.g., frequency of data recording). In another example, the communication port 1009 may be used to send various status and monitoring data to a remote user including, but not limited to electrical power consumption, temperature, and data measured by auxiliary sensor devices. The data received and transmitted by the communication port 1009 may be managed, in part, by the processor 90, as will be discussed in more detail below.

The communication port 1009 may accommodate various types of electrical cabling including, but not limited to universal serial bus (USB) cables and Power over Ethernet (PoE) cables. In some implementations, multiple communication ports 1009 including both USB and PoE ports may be used to enable greater flexibility and compatibility with more types of cabling and auxiliary devices. One or more communication ports 1009 may be disposed on one or more sides of the frame 1004. For example, a set of communication ports 1009 may be disposed on opposite sides of the frame 1004 (e.g., left and right sides or front and rear sides) to facilitate connectivity between a plurality of lighting fixtures 1000 in a daisy-chain configuration. Communication ports 1009 may also be disposed on the frame 1004 where auxiliary sensors are likely to be deployed. For example, communication ports 1009 may be disposed on the bottom side of the frame 1004 to provide electrical connection to auxiliary sensors that are used to monitor ambient conditions near the plants located below the lighting fixture 1000. In some implementations, the communication port 1009 may also supply DC power. For example, the lighting fixture 1000 may include a USB port that may electrically power an auxiliary sensor device and receive data measured by the auxiliary sensor device through the same communication port 1009.

Figure 6A:
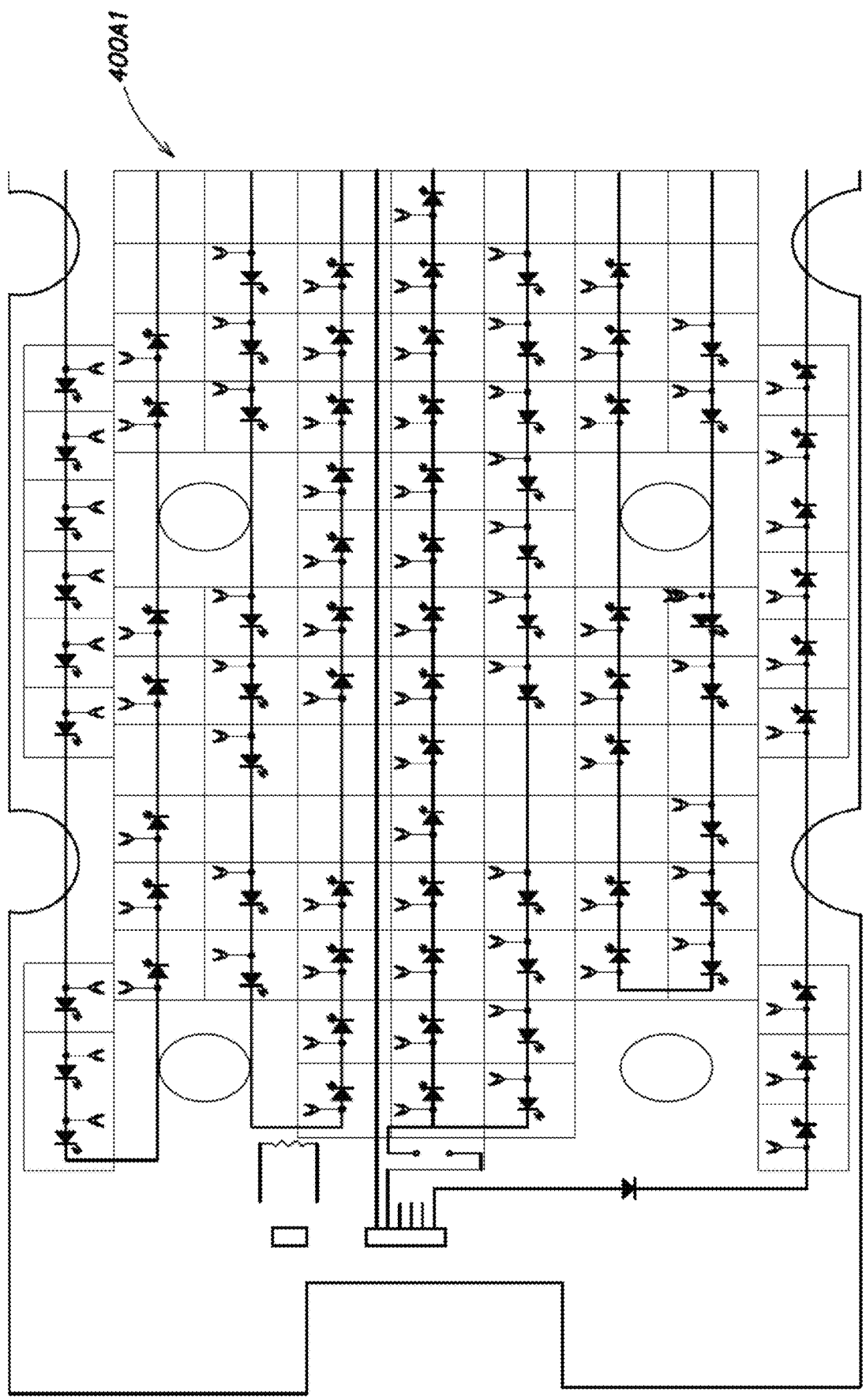
FIG. 6A is a circuit diagram detailing a first half of an exemplary LED module of a lighting fixture, according to some implementations of the disclosure.
Figure 6B:
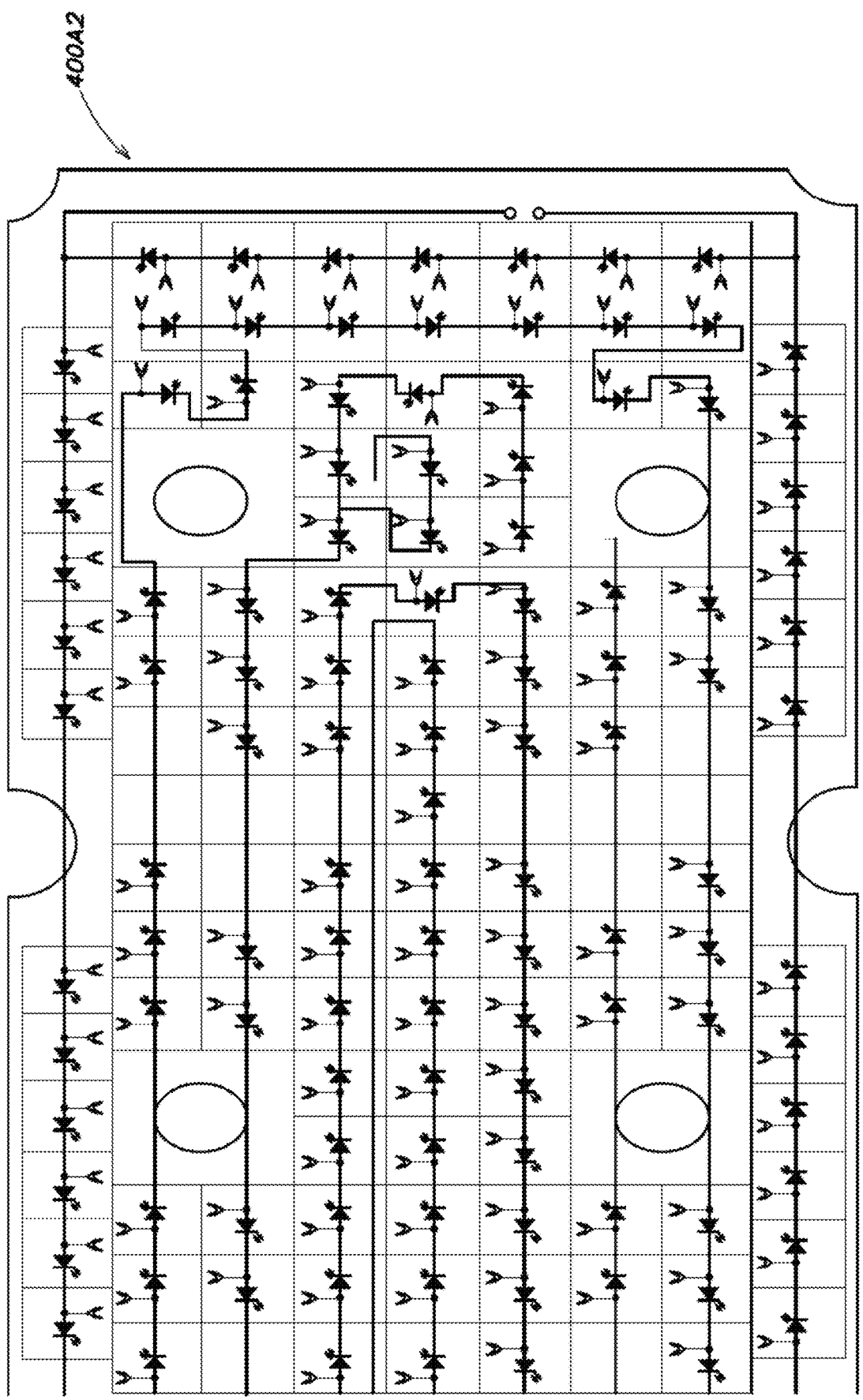
FIG. 6B is a circuit diagram detailing the second half of the exemplary LED module of FIG. 6B.

The LED module 400 may include one or more LED elements arranged into an array. The one or more LED elements of the LED module 400 may each emit light at a particular wavelength such that in combination, the LED module 400 irradiates plants with light at multiple wavelengths tailored to improve various aspects related to the growth of plants and operation of the controlled agricultural environment including, but not limited to improving photosynthetic rates of the plants, growth modification, and ultraviolet (UV) sterilization. The one or more LED elements may be assembled onto the frontside of a printed circuit board. An exemplary circuit layout of an LED module 400 according to one inventive implementation is shown in FIGS. 6A and 6B, which illustrates the respective halves 400A1 and 400A2 of the LED module 400A. As shown, the LED module 400A may include multiple LED elements that are distributed across the printed circuit board.

The printed circuit board may be a metal core printed circuit board (MCPCB) to facilitate heat dissipation generated by the one or more LED elements. The LED module 400 may be coupled to the frame 1004 such that the backside of the printed circuit board is in contact with the bottom side of the frame 1004 located in the recessed portion as described above. The LED module 400 may be coupled to the frame 1004 using various coupling mechanisms including, but not limited to screw fasteners, bolt fasteners, clips, and clamps. The coupling mechanism may be adjusted such that a clamping force is applied to the LED module 400, thus improving the thermal contact between the LED module 400 and the frame 1004. Additionally, thermal interface material may also be placed between the LED module 400 and the frame 1004 to improve thermal contact.

In some implementations, the lighting fixture 1000 may also include an optic located on the recessed portion of the frame 1004, which covers the LED module 400. The optic may be used to modify the direction and angular distribution of the light emitted by the LED module 400. For example, a portion of the optic may have a convex surface to focus light emitted from the LED module 400 onto plants located directly below the lighting fixture 1000. The optic may be coupled to the frame 1004 using various coupling mechanisms including, but not limited to screw fasteners, bolt fasteners, clips, and clamps. In some implementations, the optic may form a substantially airtight enclosure around the LED module 400, thus substantially isolating the LED module 400 from the ambient environment in the controlled agricultural environment. Similar to the airtight enclosure that may be formed by the frame 1004, the optic may reduce moisture infiltration, thus reducing the risk of condensation damaging the LED module 400.

Figure 7A:
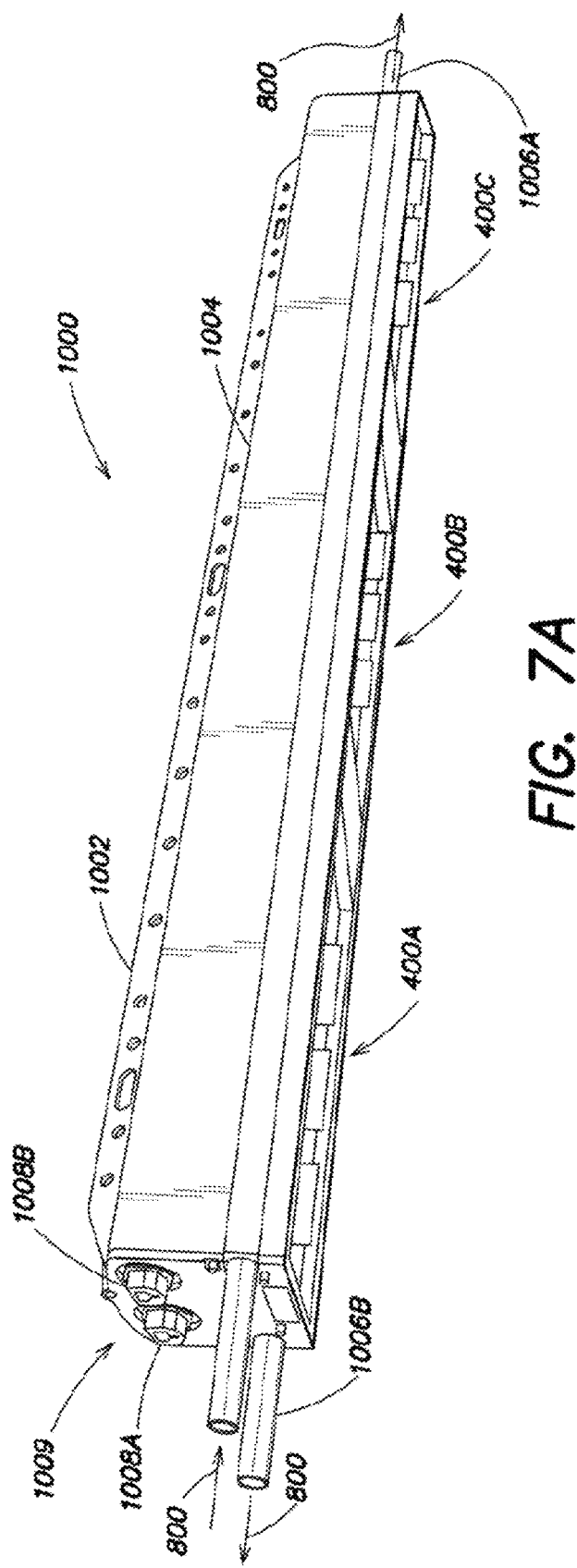
FIG. 7A shows a bottom, front perspective view of a lighting fixture, according to some implementations of the disclosure.
Figure 7B:
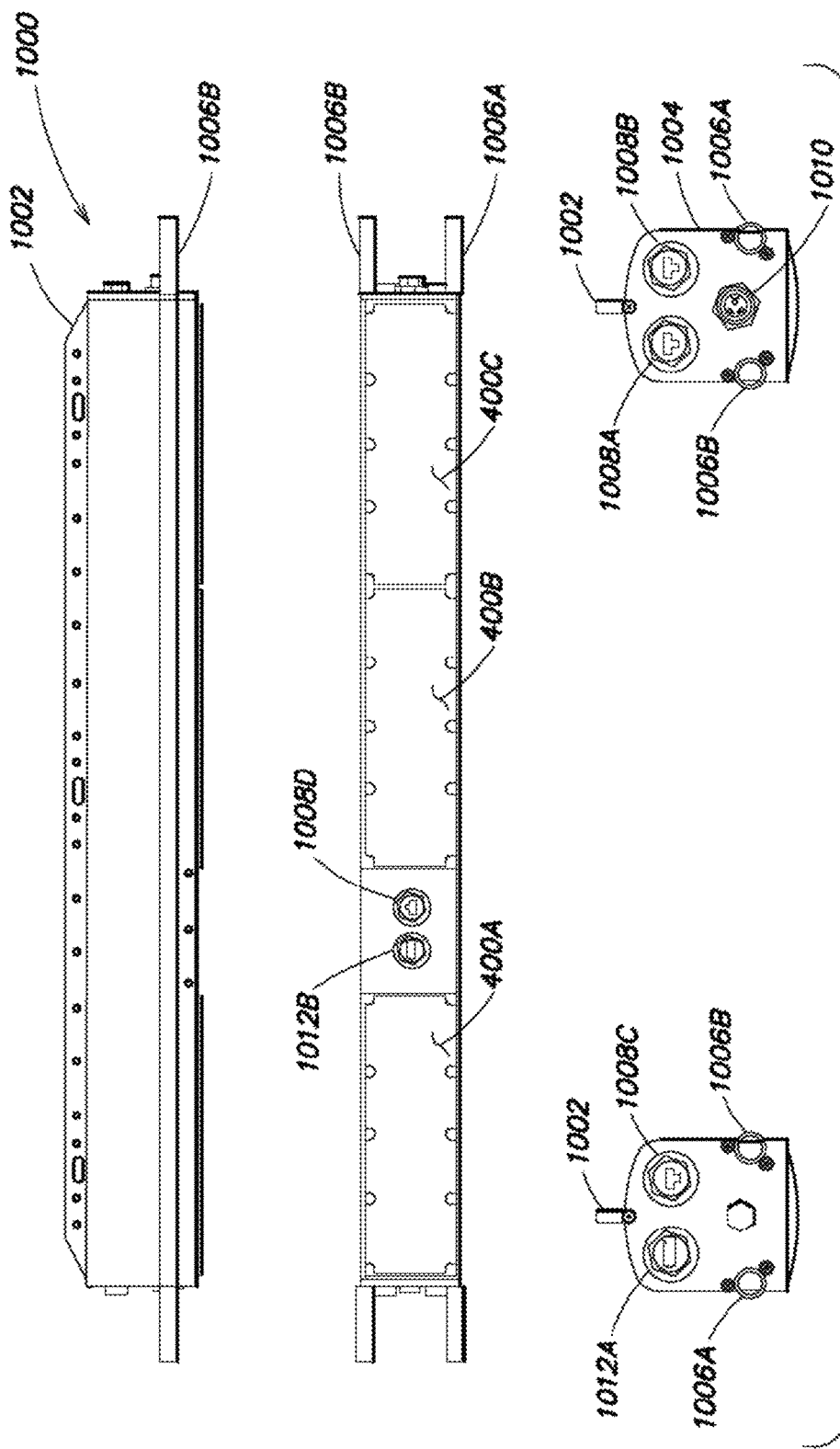
FIG. 7B shows front, bottom, left side, and right side views of the lighting fixture of FIG. 7A.
Figure 7C:
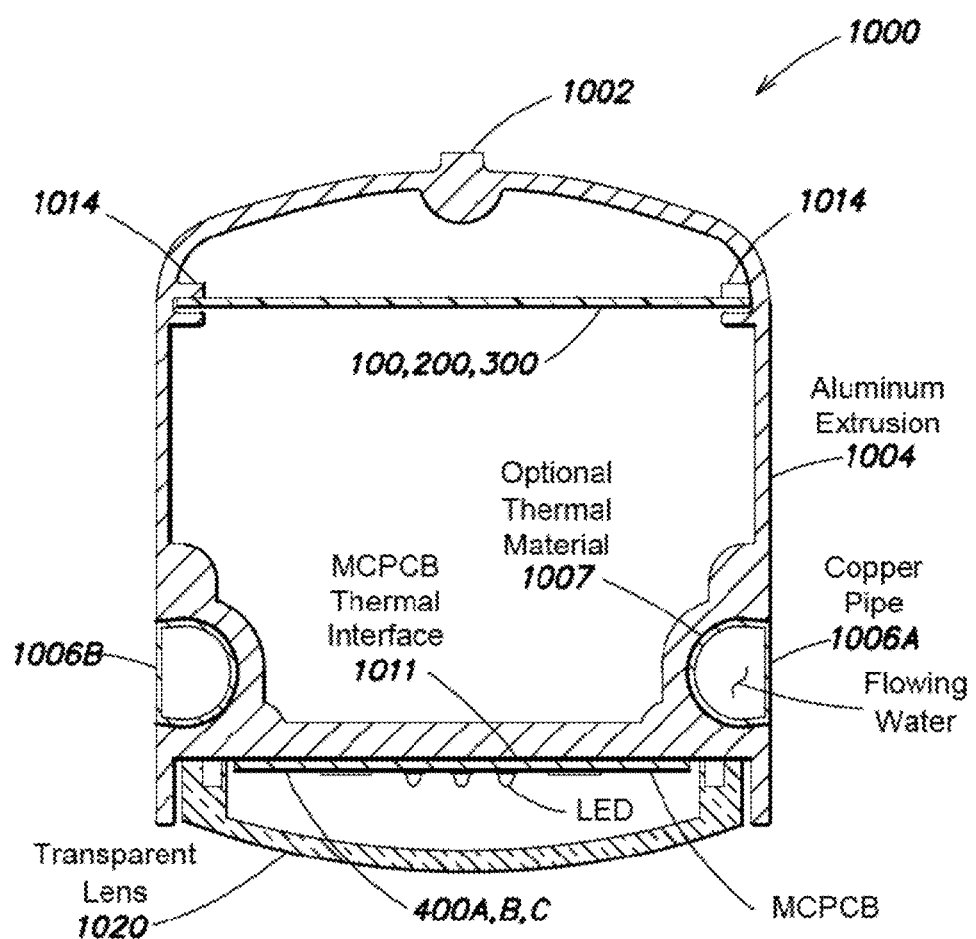
FIG. 7C shows a cross-sectional view of the lighting fixture of FIG. 7B along the plane AA.

An exemplary lighting fixture 1000 according to one inventive implementation is shown in FIGS. 7A-7C. FIG. 7A shows a bottom perspective view of the lighting fixture 1000 and FIG. 7B shows a front, bottom, left and right side view of the lighting fixture 1000. As shown, the lighting fixture 1000 includes a frame 1004 dimensioned to support three LED modules 400A, 400B, and 400C positioned in a row and disposed on the bottom side of the frame 1004. A light spine 1002 may be formed on the top of the frame 1004 that substantially spans the entire length of the frame 1004. The light spine 1002 may include a plurality of different sized holes to facilitate coupling of the lighting fixture 1000 to a support structure in the controlled agricultural environment. The left and right-side panels of the frame 1004 may be secured by a plurality of screw fasteners and hence, may be removed to allow access into the interior cavity of the frame 1004. The left side panel of the frame 1004 may include two communication ports 1009, e.g., a USB port 1012A and a PoE port 1008C. The right-side panel of the frame 1004 may also include two communication ports 1009, e.g., two PoE ports 1008A and 1008B, as well as an electrical power port 1010. Two communication ports, e.g., a USB port 1012B and a PoE port 1008D, may be disposed on the bottom side of the frame 1004 to facilitate connectivity to auxiliary senor devices that may be used to monitor ambient conditions near the plants. The lighting fixture 1000 also includes two coolant pipes 1006A and 1006B disposed along the front and rear sides of the frame 1004. The frame 1004 may be formed from an aluminum extrusion to include a corresponding pair of channels. The coolant pipes 1006A and 1006B, which may be formed form copper, may be press-fit or crush-fit into the corresponding channels. In this manner, the likelihood that fluid coolant flowing through the coolant pipes 1006A and 1006B contacts the frame 1004 is substantially reduced.

FIG. 7C shows a cross-sectional view of the lighting fixture 1000 where the coolant pipes 1006A and 1006B are shown to be press-fit into the channels of the frame 1004. Thermal interface material 1007 may be disposed between the channels and the coolant pipes 1006A and 1006B to improve thermal contact. The LED modules 400A-400C are disposed substantially in a recessed portion of the bottom side of the frame 1004 and in close proximity to the coolant pipes 1006A and 1006B to facilitate heat dissipation. As shown, a small portion of the frame 1004, which is formed from a thermally conducting material, is present between the coolant pipes 1006A and 1006B and the LED modules 400A-400C. FIG. 7C also shows mounting features 1014 used to support various control circuitry boards 100, 200, and 300, which are collectively referred to hereafter as a processor 90. The mounting features 1014 are a pair of protruding slots disposed along the front and rear sides of the frame 1004, which are dimensioned to support the opposing edges of the processor 90. The processor 90 is positioned above the coolant pipes 1006A and 1006B and LED modules 400A-400C in order to reduce thermal effects due to heat generated by the LED modules 400A-400C. An optic 1020 is also included, which may be coupled to the frame 1004 via a plurality of screw fasteners. The optic 1020 may be a transparent lens with a convex surface used to redirect light emitted by the LED modules 400A-400C along a desired direction and angular distribution. The optic 1020 may also substantially enclose and isolate the LED modules 400A-400C from the surrounding ambient environment.

Figure 8A:
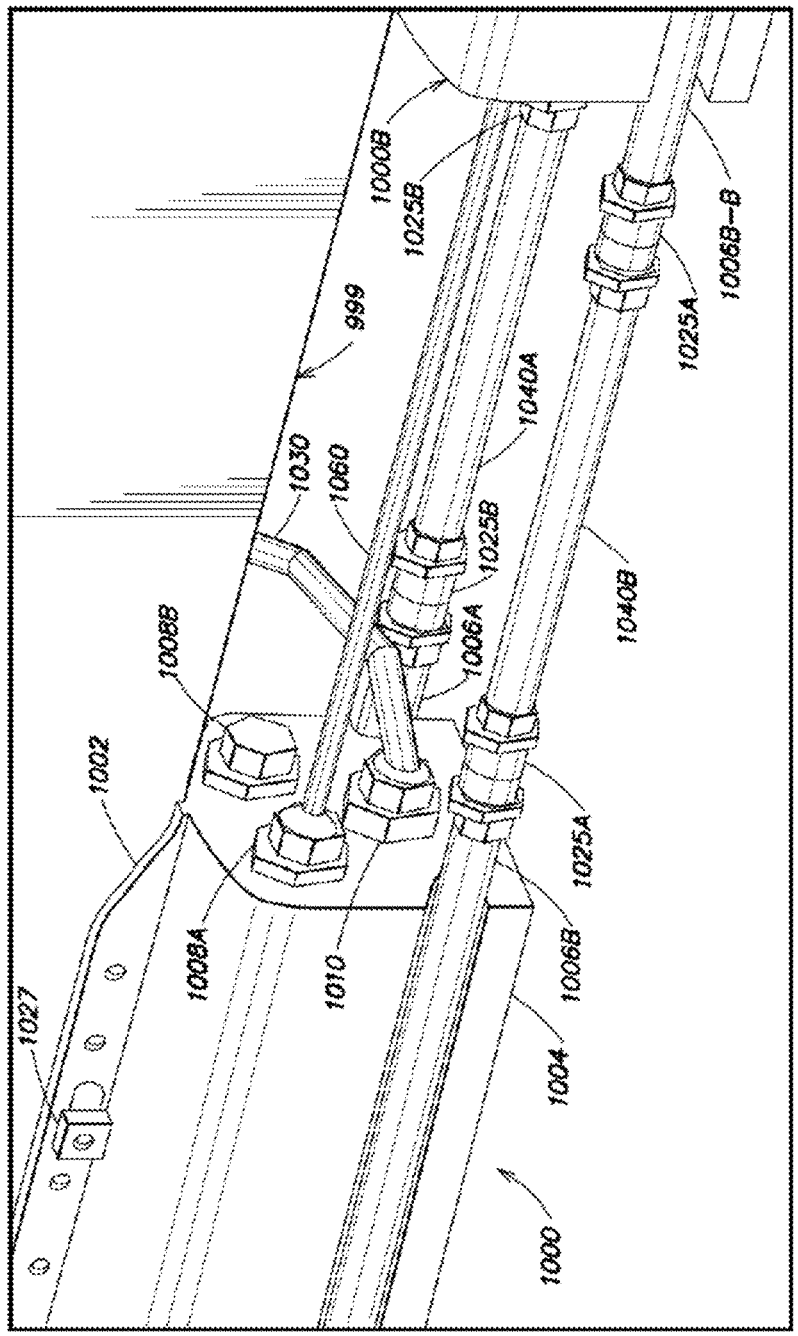
FIG. 8A shows a top perspective view of a first lighting fixture coupled to a second lighting fixture and a support structure, according to some implementations of the disclosure.

As described above, the lighting fixture 1000 may be coupled to other lighting fixtures 1000 in a daisy-chain configuration where electrical and piping connections are shared to facilitate assembly of a continuous electrical circuit and coolant circuit. For the coolant circuit, the daisy-chain configuration may be in series where the fluid coolant 800 exiting from one lighting fixture 1000 flows into a subsequent lighting fixture 1000 within the daisy-chain. The temperature of the fluid coolant 800 may increase further due to heat generated from the LED modules 400 of the subsequent lighting fixture 1000. It should be appreciated that so long as the temperature of the coolant fluid 800 is less than the temperature of the LED modules 400 in the lighting fixture 1000, the fluid coolant 800 may still capture heat from the lighting fixture 1000. Furthermore, in some implementations, heat rejection devices may be interspersed along the coolant circuit to reduce the temperature of the fluid coolant 800 and maintain sufficient heat dissipation as the fluid coolant 800 passes through multiple lighting fixtures 1000. An exemplary implementation detailing the manner in which two lighting fixtures 1000 and 1000-B may be coupled in a daisy-chain configuration is shown in FIG. 8A. In some implementations, the lighting fixture 1000 may be coupled to a support structure 999 using a bolt fastener 1027 placed through a hole in the light spine 1002 and secured to the side of the support structure 999 as shown in FIG. 8A.

The coolant pipes 1006A and 1006B of the lighting fixture 1000 may be coupled to a corresponding set of coolant pipes 1006A-B and 1006B-B from the other lighting fixture 1000-B using one or more intermediate pipes. As shown in FIG. 8A, the pair of coolant pipes 1006B and 1006B-B (1006A and 1006A-B) may be connected via a single intermediate pipe 1040B (1040A). Each intermediate pipe 1040B (1040A) may have push-to-connect fittings 1025A (1025B) disposed on both ends to facilitate connection to the coolant pipes 1006B and 1006B-B (1006A and 1006A-B). The shape of the intermediate pipe may vary depending on the desired distance and orientation between lighting fixtures 1000 and 1000-B. For example, the length of the intermediate pipe may be longer in order to space the lighting fixtures 1000 and 1000-B further apart to provide greater areal coverage or to traverse a gap separating two separate growing areas. In another example, the intermediate pipe may be curved such that the lighting fixtures 1000 and 1000-B are oriented at an angle relative to one another, e.g., 90 degrees, to accommodate variable shaped growing areas. In yet another example, the intermediate pipe may be substantially U-shaped to couple two parallel rows of lighting fixtures 1000 where the lighting fixtures 1000 and 1000-B are the last lighting fixtures 1000 in each respective row. In this manner, the coolant circuit may be continuous for multiple rows of lighting fixtures 1000.

Electrical power may be supplied to multiple lighting fixtures 1000 through a single power cable. An exemplary power cable 1030 coupled to the lighting fixture 1000 is shown in FIG. 8A. In some implementations, the power cable 1030 may be rated to support a particular electrical power and current input. For example, the power cable 1030 may be rated to supply at least 1000 W of electrical power and up to 15 A of current. Depending on the power and current requirements of the lighting fixture 1000, the power cable 1030 may be used to power multiple lighting fixtures 1000, thus reducing the amount of cabling and the number of electrical terminals (e.g., electrical outlets) that need to be installed in the controlled agricultural environment.

The lighting fixture 1000 may also be communicatively coupled to another lighting fixture 1000 to facilitate transmission of data and control signals to multiple lighting fixtures 1000. As shown in FIG. 8A, an Ethernet cable 1060 may be used to couple the PoE port 1008A of lighting fixture 1000 to the PoE port 1008C-B of lighting fixture 1000-B. Each of the lighting fixtures 1000 and 1000-B may include a processor to manage the flow of data and/or control signals. In some implementations, the lighting fixture 1000 may be used as a piggyback to facilitate the transfer of data and/or control signals to another lighting fixture 1000 located further along the daisy-chain. In this manner, multiple lighting fixtures 1000 spanning a large area may be communicatively coupled to a fewer number of network nodes (e.g., hubs, switches, routers) and without using excessive amounts of network cabling.

Figure 8B:
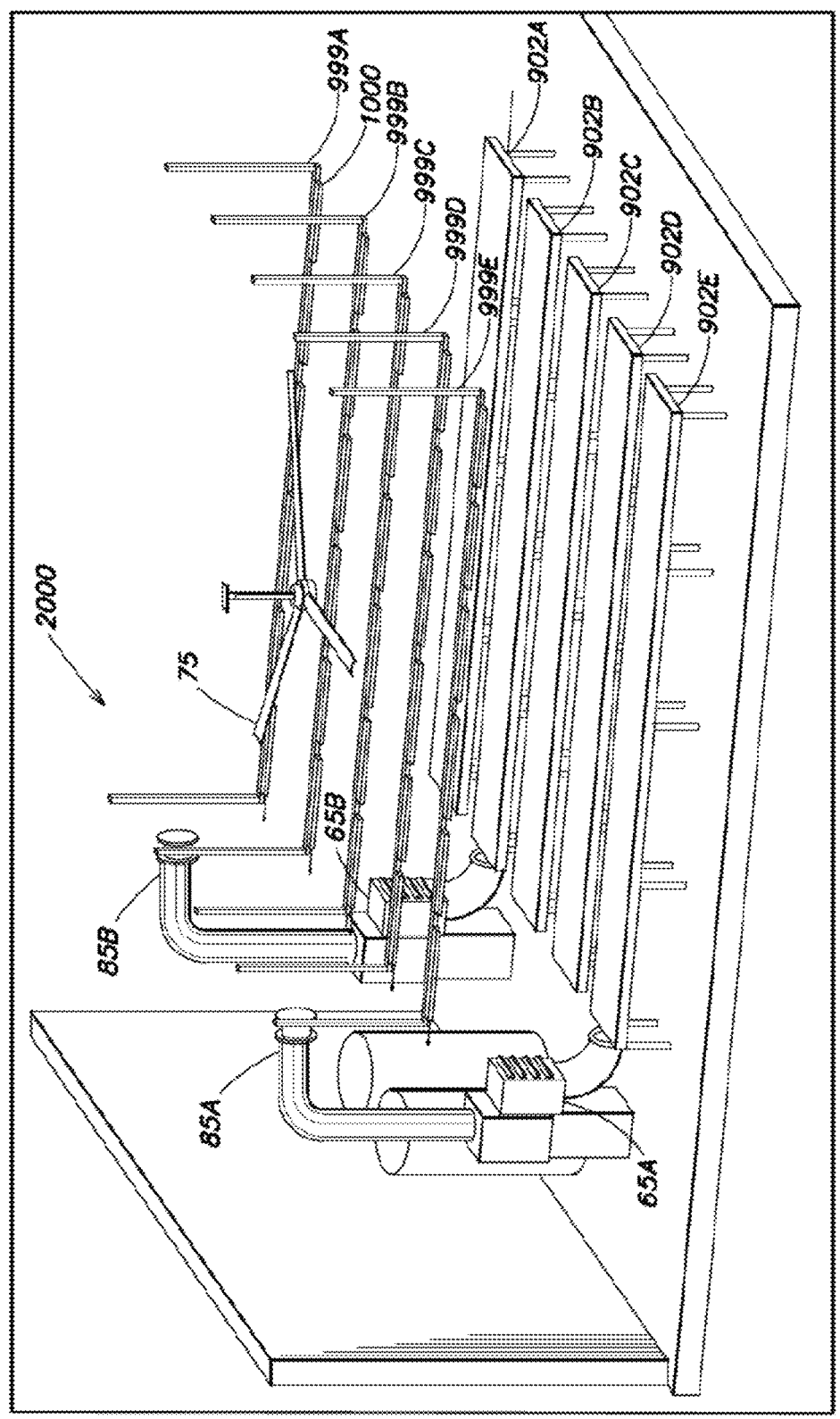
FIG. 8B shows a perspective view of a controlled agricultural environment showing multiple rows of fluid-cooled LED-based lighting fixtures coupled together forming a continuous electrical and coolant circuit, according to some implementations of the disclosure.

An exemplary arrangement of lighting fixtures 1000 in a controlled agricultural environment 2000 is shown in FIG. 8B. Multiple lighting fixtures 1000 may be arranged along a row spanning a growing area defined by the dimensions of a shelf 902A. Each lighting fixture 1000 in the row may be coupled to a support structure 999A disposed above the shelf 902A. The lighting fixtures 1000 in the row may be coupled together in a daisy chain configuration, as described above. Intermediate piping may be used to couple adjacent lighting fixtures 1000 such that fluid coolant 800 may circulate through the multiple lighting fixtures 1000 in a continuous manner from a single inlet and outlet for the row. One or more power cables may be used to supply electrical power to the lighting fixtures 1000. Ethernet cabling may be used to communicatively couple the lighting fixtures 1000 in a serial manner and to a common network node. As shown in FIG. 8B, the controlled agricultural environment 2000 may include multiple rows of lighting fixtures 1000 supported by support structures 999A-999E arranged above corresponding rows of shelves 902A-902E. The controlled agricultural environment 2000 may further include a fan 75, dehumidifiers 65A and 65B, and air conditioning ducts 85A and 85B for one or more air conditioners.

As previously shown in the exemplary controlled agricultural environments 2000A and 2000B in FIGS. 3 and 4, respectively, the lighting fixture 1000 may be incorporated into a coolant circuit 570 to facilitate the flow of fluid coolant 800 such that heat may be continuously removed from the lighting fixture 1000. In some implementations, the coolant circuit 570 may be designed to substantially remove heat from only the lighting fixture 1000 and is not intended to thermally interact with other components or regions of the controlled agricultural environment 2000A, as shown in the coolant circuit 570 in FIG. 3 for a retrofit application. In some implementations, however, the coolant circuit 570 may include additional piping subsystems designed to redistribute heat to a space near or within the controlled agricultural environment, such as the hydronics loops 700A and 700B shown in FIG. 4 for a hydronics application, and/or to store heat captured by the lighting fixture 1000 for later use.

A piping subsystem may be branched from the coolant circuit 570 such that the flow of fluid coolant 800 may be controllably adjusted (e.g., by a valve and a separate pump) without affecting the flow of fluid coolant 800 through the coolant circuit 570 and hence, without affecting the removal of heat from the lighting fixture 1000. However, in some instances, a piping subsystem may be placed in series with the coolant circuit 570 where the piping subsystem is also used on a continual basis. Some exemplary instances of a piping subsystem being used in series with the coolant circuit 570 includes, but is not limited to a heating system for a hot water system in a residential space, storing heat from the fluid coolant 800 in a thermal energy storage system, and charging a battery by converting heat from the fluid coolant 800 into electricity (e.g., using a thermoelectric device).

In some example implementations, particularly in connection with power cabling code compliance, the lighting fixture 1000 may be considered as an industrial horticultural lamp and a component of an "industrial machine" (rather than a general lighting fixture). For purposes of the present disclosure, an "industrial machine" is a power-driven machine, not portable by hand while working, that is used to process material by cutting; forming; pressure; electrical, thermal, or optical techniques; lamination; or a combination of these processes. The associated electrical equipment, including the logic controller(s) and associated software or logic together with the machine actuators and sensors, are considered as part of the industrial machine (the foregoing definition is consistent with that provided in chapter 3, section 3.3.54 of the U.S. National Fire Protection Association (NFPA) 79 Electrical Standard for Industrial Machinery). As such, the lighting fixture 1000 may be equipped with and used with industrial type connectors and industrial cable systems.

For example, industrial power cables and connectors may be employed in a lighting system comprising multiple lighting fixtures 1000, wherein the industrial cables and connectors are multipoint interconnection power cable assemblies for industrial machinery according to the Underwriters Laboratory (UL®) product category PVVA and compliant with the UL® standard 2237. According to UL® PVVA, multi-point interconnection power cable assemblies are intended for use in an industrial environment to distribute power to branch circuits, including motor branch circuits, of industrial machinery. The assemblies may consist of power cable assemblies, male and female power cable fittings, panel-mounted power cable/conductor fittings and feeder-tap power cable fittings used with industrial machinery in accordance with ANSI/NFPA 79, Electrical Standard for Industrial Machinery.

The PVVA UL Product Spec UL 2237 states that devices covered under this standard are only intended for indoor use, unless otherwise identified. Devices covered under this standard are rated 1,000 V or less. Each device is rated in volts and amperes. The electrical ratings are marked, on each device or on a flag label affixed to each individual power cable assembly. The cable assembly fittings are intended to be assembled or molded on flexible cord. The power cable assemblies and mating fittings are not intended to be used as a substitute for the fixed wiring of the building or structure. The power cable assemblies and mating fittings may be connected to the fixed wiring of the building or structure; using a feeder tap fitting or male/female cable fitting. Power cable assemblies and fittings covered under this standard are not intended to make or interrupt current under load conditions. These power cable assemblies and fittings have been investigated to their marked short-circuit current rating. Power cable assemblies and fittings may specify a maximum ampere rating, type of overcurrent protective device, or both. Unless otherwise marked, the power cable assemblies and fittings are intended to be supplied from an overcurrent protective device of the maximum ampere rating permitted by the Relationship Between Conductor Size and Maximum Rating or Setting of Short-Circuit Protective Device for Power Circuits Table, Table 7.2.10.4, of the National Fire Protection Association Electrical Standard for Industrial Machinery, NFPA 79, reproduced below:

TABLE 7.2.10.4

Relationship Between Conductor Size and Maximum Rating or Setting of Short-Circuit Protective Device for Power Circuits

| Conductor Size (AWG) | Maximum Rating | |
|---|---|---|
| | Non-Time-Delay Fuse or Inverse Time Circuit Breaker (amperes) | Time Delay or Dual Element Fuse (amperes) |
| 14 | 60 | 30 |
| 12 | 80 | 40 |
| 10 | 100 | 50 |
| 8 | 150 | 80 |
| 6 | 200 | 100 |
| 4 | 250 | 125 |
| 3 | 300 | 150 |
| 2 | 350 | 175 |
| 1 | 400 | 200 |
| 0 | 500 | 250 |
| 2/0 | 600 | 300 |
| 3/0 | 700 | 350 |
| 4/0 | 800 | 400 |

It is acceptable under UL 2237 and NFPA 79 to specify a 40 A circuit breaker for a continuous 30 A load in mixed 10 AWG and 14 AWG assemblies. For assemblies containing only 14 AWG a 20 A circuit breaker may be used for a continuous 15 A load.

Figure 8C:
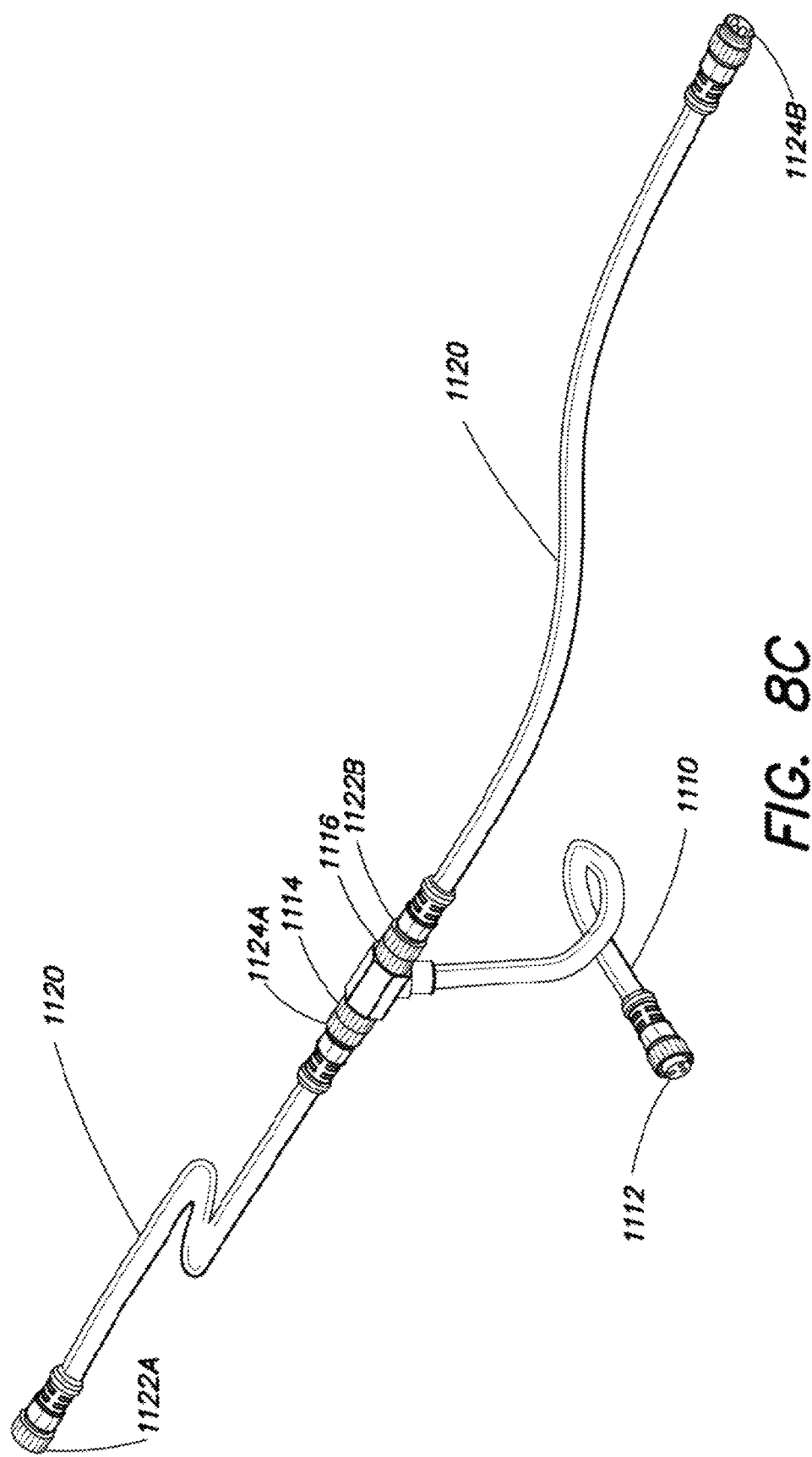
FIG. 8C shows an exemplary assembly of power cables and a drop tee cable.
Figure 8D:
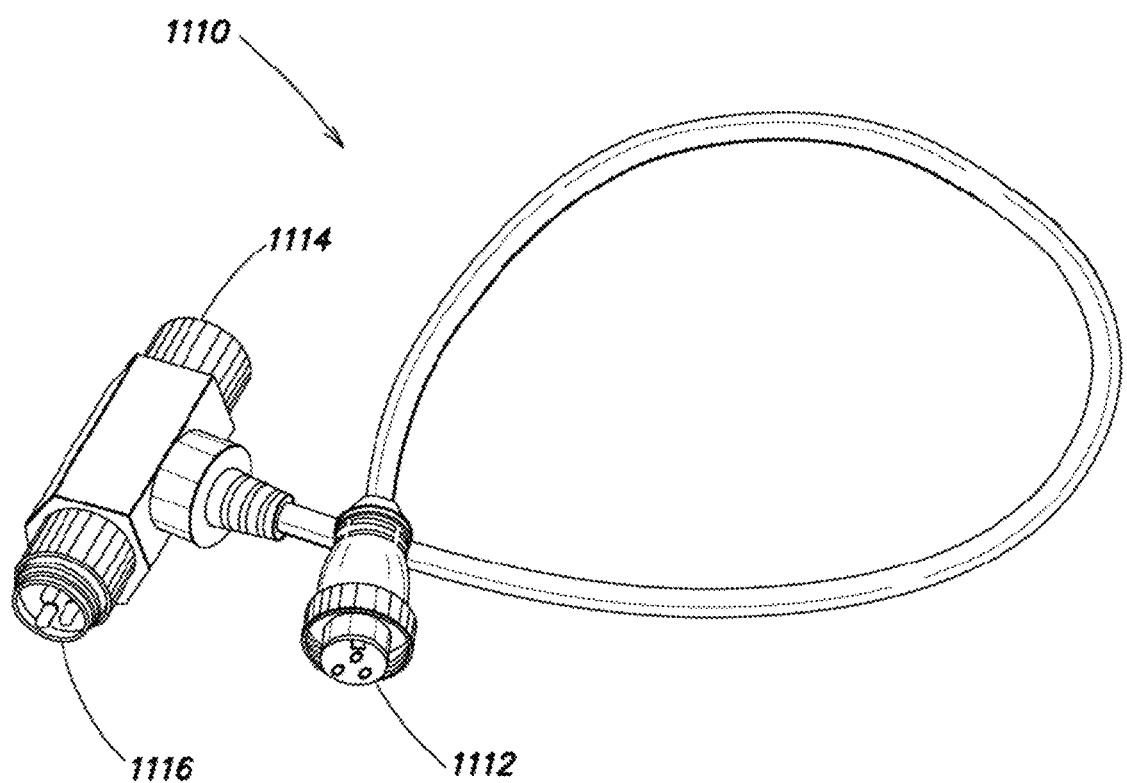
FIG. 8D shows a perspective view of the drop tee cable of FIG. 8C.
Figure 8E:
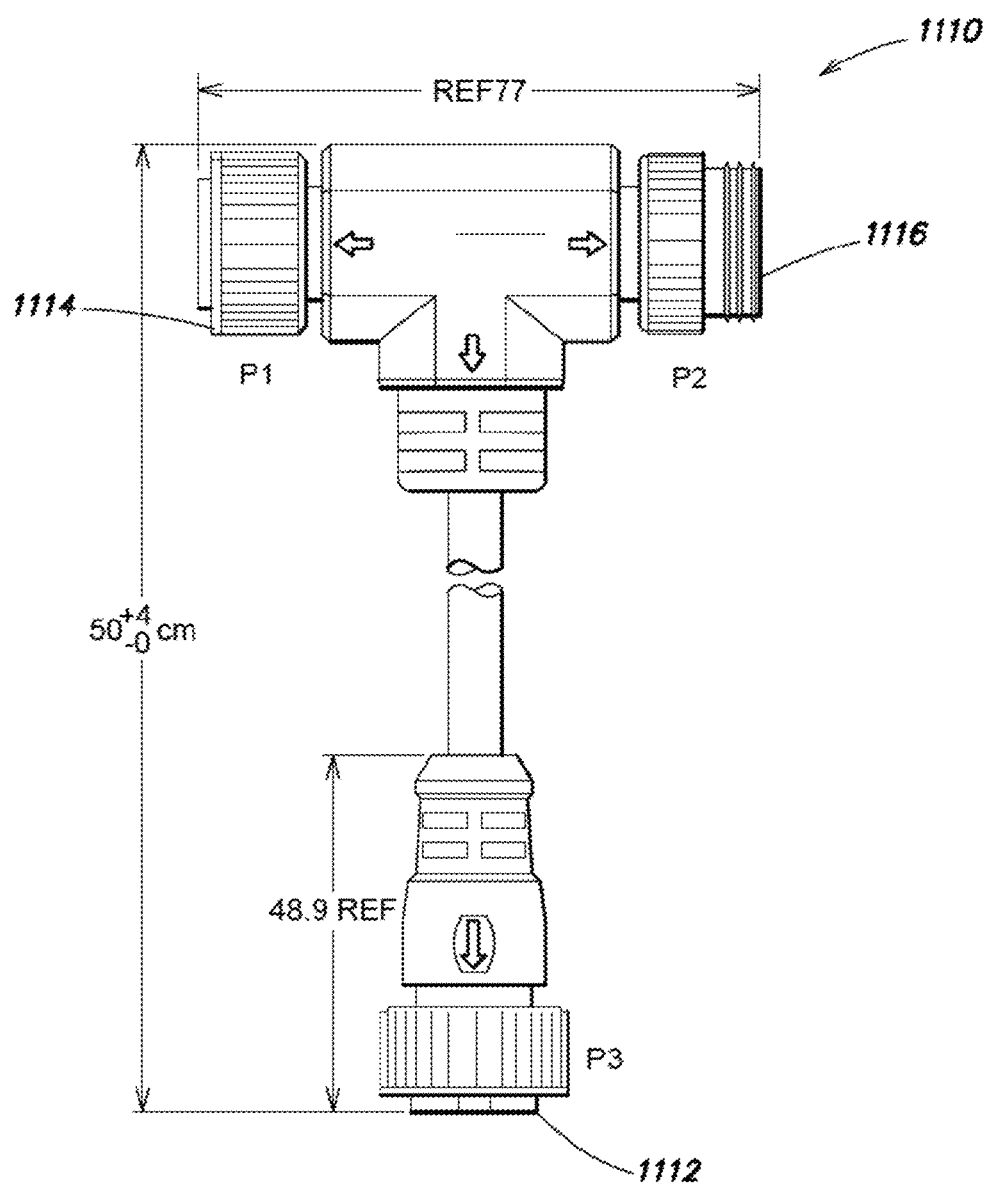
FIG. 8E shows a front view of the drop tee cable of FIG. 8C.
Figure 8F:
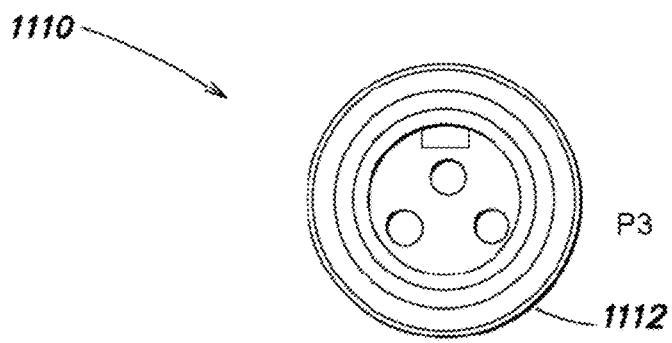
FIG. 8F shows a bottom view of the drop tee cable of FIG. 8C.
Figure 8G:
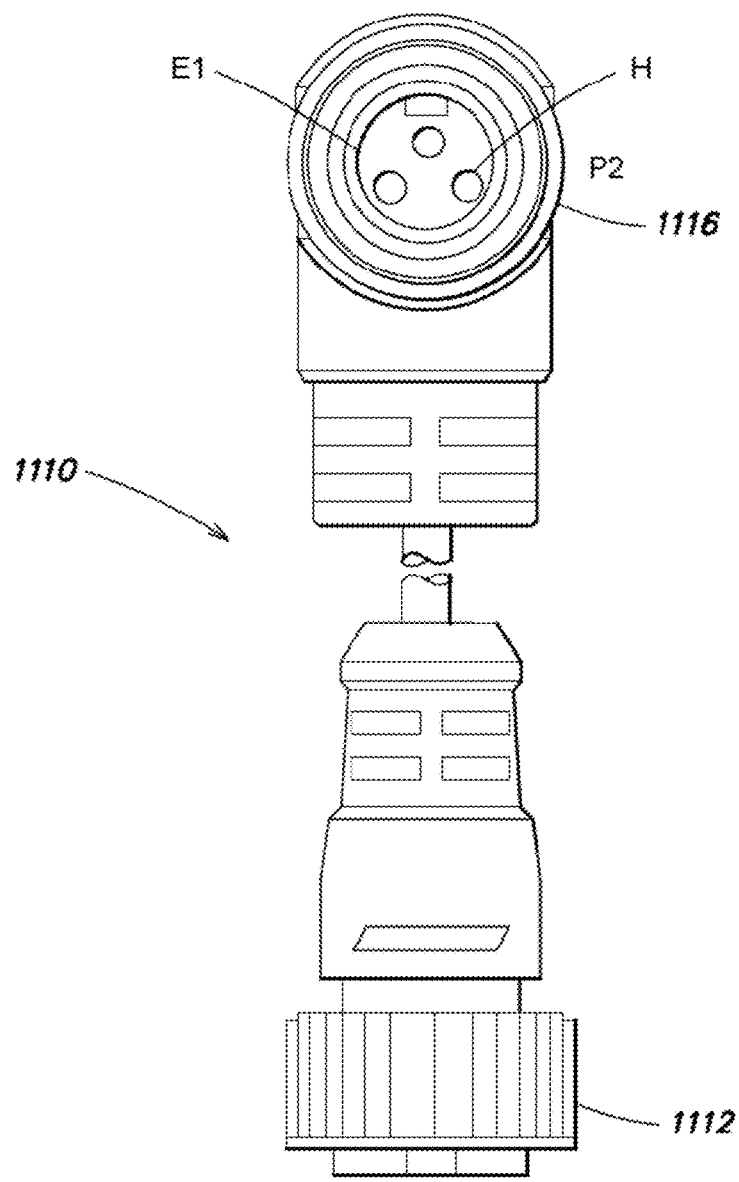
FIG. 8G shows a left-side view of the drop tee cable of FIG. 8C.

FIG. 8C shows one exemplary assembly of cabling used to electrically power multiple lighting fixtures. As shown, the assembly may include a drop tee cable 1110 coupled to two power cables 1120 (1120A and 1120B in FIG. 8C). The power cables 1120 may be used, in part, as extension cables to extend cabling to lighting fixtures 1000 located at a greater distance from a power source. The drop tee cables 1110 may be used to generate branches in the cabling to distribute power to multiple lighting fixtures 1000. For example, the exemplary cabling assembly shown in FIG. 8C may be connected to an electrical power supply system via the power cable 1120A at the port 1122A, the power cable 1120B may be connected to one lighting fixture 1000 via the port 1124B, and the drop tee cable 110 may be connected to another lighting fixture 1000 via the port 1112. It should be appreciated that the cabling assembly in FIG. 8C is one example and that multiple drop tee cables 1110 and power cables 1120 may be coupled together to provide power to multiple lighting fixtures 1000. In some implementations, the assembly may be limited, in part, by the power rating of each cable and/or the amount of power that should be supplied to each lighting fixture 1000.

Figures 1, 8H:
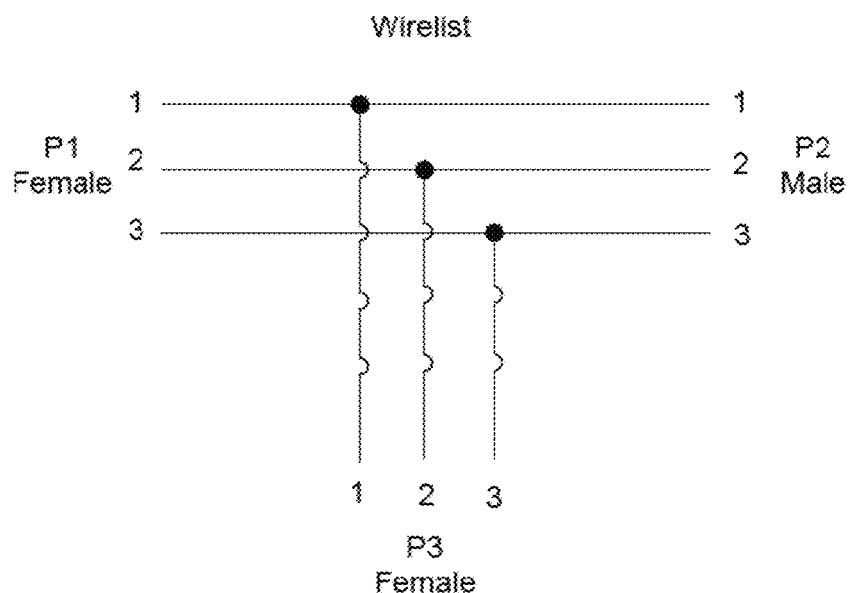
Figures 2, 8H:
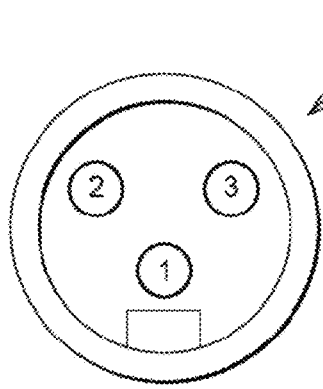
Figures 3, 8H:
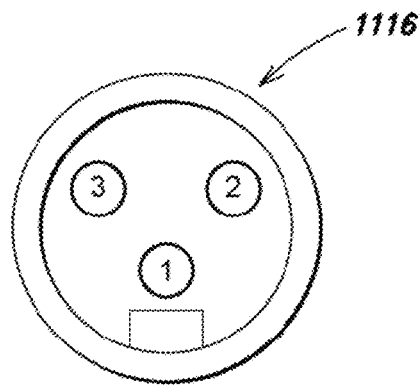
Figure 81:
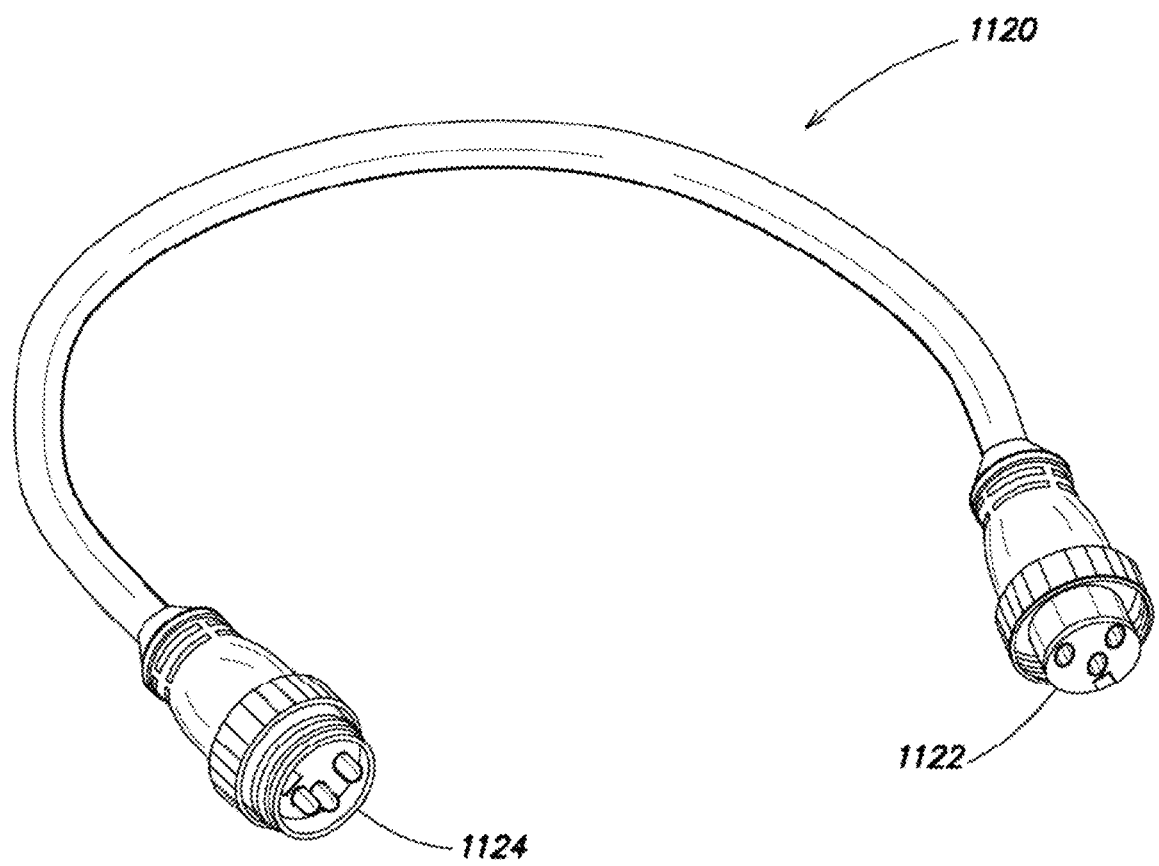
Figure 8J:
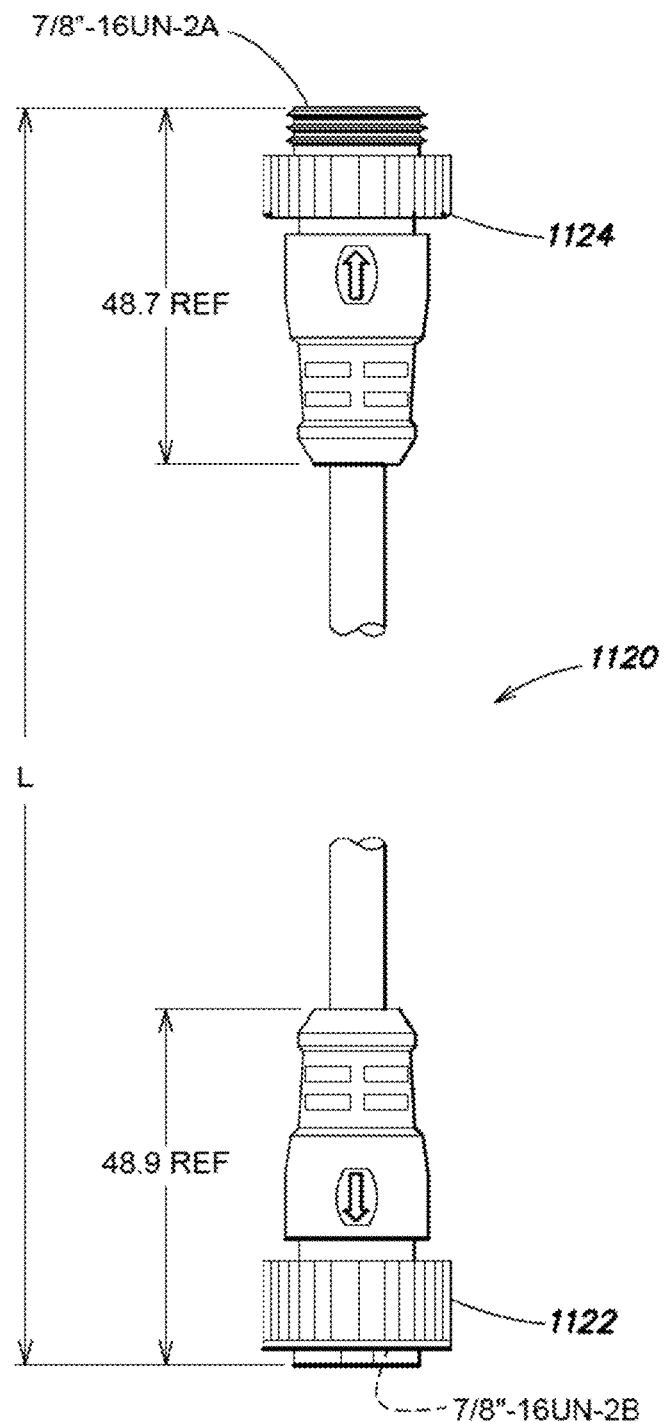
FIG. 8J shows a top view of the power cable of FIG. 8C.
Figure 8K:
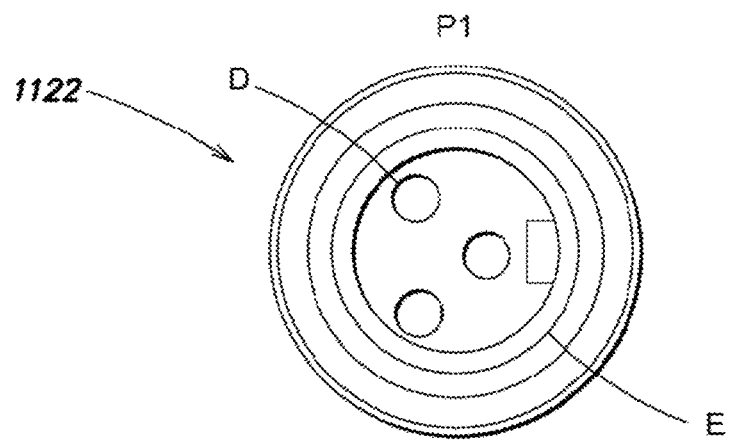
FIG. 8K shows a right-side view of the power cable of FIG. 8C.
Figure 8L:
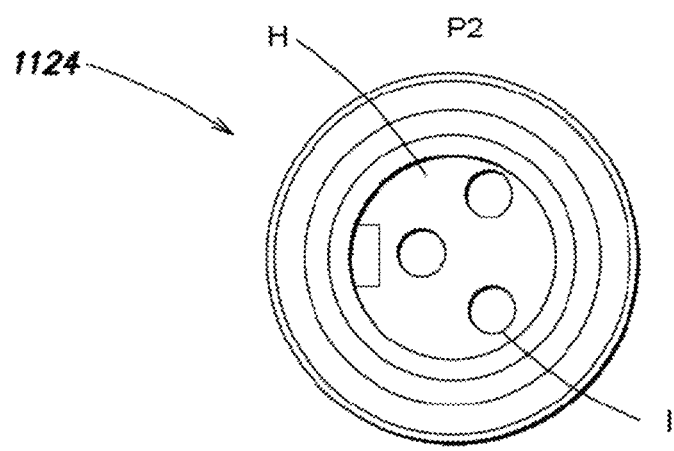
FIG. 8L shows a left-side view of the power cable of FIG. 8C.

FIGS. 8D-8G show several views of the drop tee cable 1110. As shown, the drop tee cable 1110 may include two female ports 1112 and 1114 and one male port 1116. Each port may be designed in accordance to a standard size and/or connector type. For example, the ports shown in FIGS. 8D-8G correspond to a ⅞ inches threaded connector (male and female). The threaded connector may further be a Unified National 16 pitch (16UN) threaded connector. The size and type of ports used may depend, in part, on the electrical power port 1110 on the lighting fixture 1000 (e.g., a ⅞ inches AC or DC power port). The length of the respective cabling for the port 1112 may also vary based on typical distances between neighboring lighting fixtures 1000. The drop tee cable 1110 may also be rated to support a current up to 15 A. The drop tee cable 1110 may also be designed to be multi-point interconnection power cables for industrial machinery according to the Underwriters Laboratory (UL®) product category PVVA and compliant with the UL® standard 2237. The drop tee cable 1110 may include three electrical pins (e.g., a positive terminal, a negative terminal, and/or ground). For example, FIGS. 8H-1-8H-3 shows an exemplary wiring diagram of how the pins at each port in the drop tee cable 1110 are electrically coupled to one another.

Figure 8M:
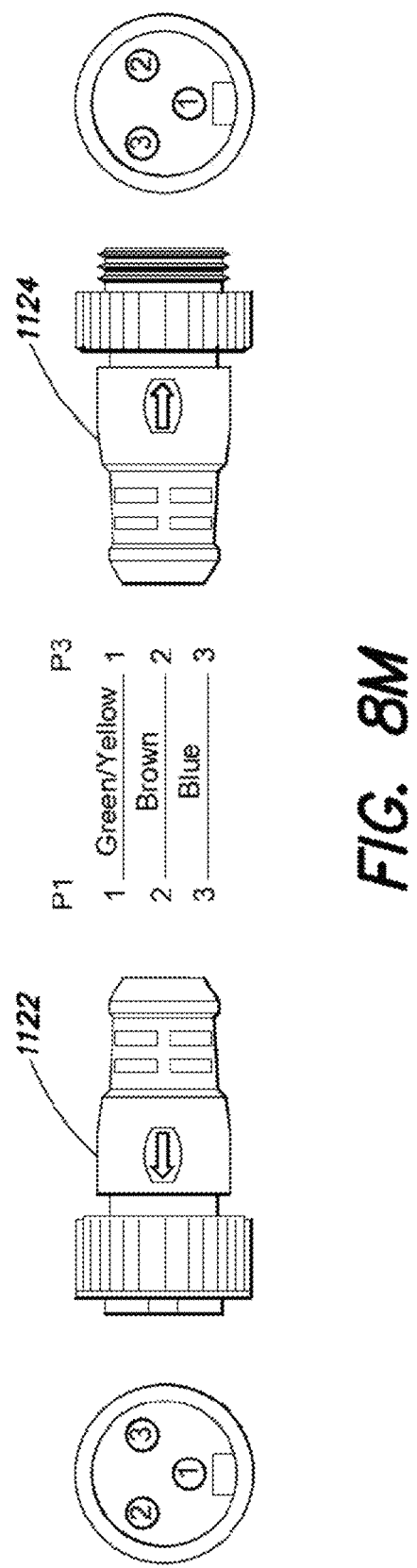
FIG. 8M shows a wiring diagram for the power cable of FIG. 8C.

FIGS. 8I-8L show several views of the power cable 1120. As shown, the power cable 1120 may include a male port 1124 and a female port 1122. Similar to the drop tee cable 1110, the ports of the power cable 1120 may also conform to a standard size and connector type, such as a 7/8 inches threaded connector (male and female) where the threaded connector is a Unified National 16 pitch (16UN) threaded connector. The power cable 1120 may also be rated to support a current up to 15 A. The power cable 1120 may also be designed to be multi-point interconnection power cables for industrial machinery according to the Underwriters Laboratory (UL®) product category PVVA and compliant with the UL® standard 2237. The power cable 1120 may also include three electrical pins (e.g., a positive terminal, a negative terminal, and/or ground). FIG. 8M shows an exemplary wiring diagram describing how the pins of the ports 1122 and 1124 are connected.

Figure 8N:
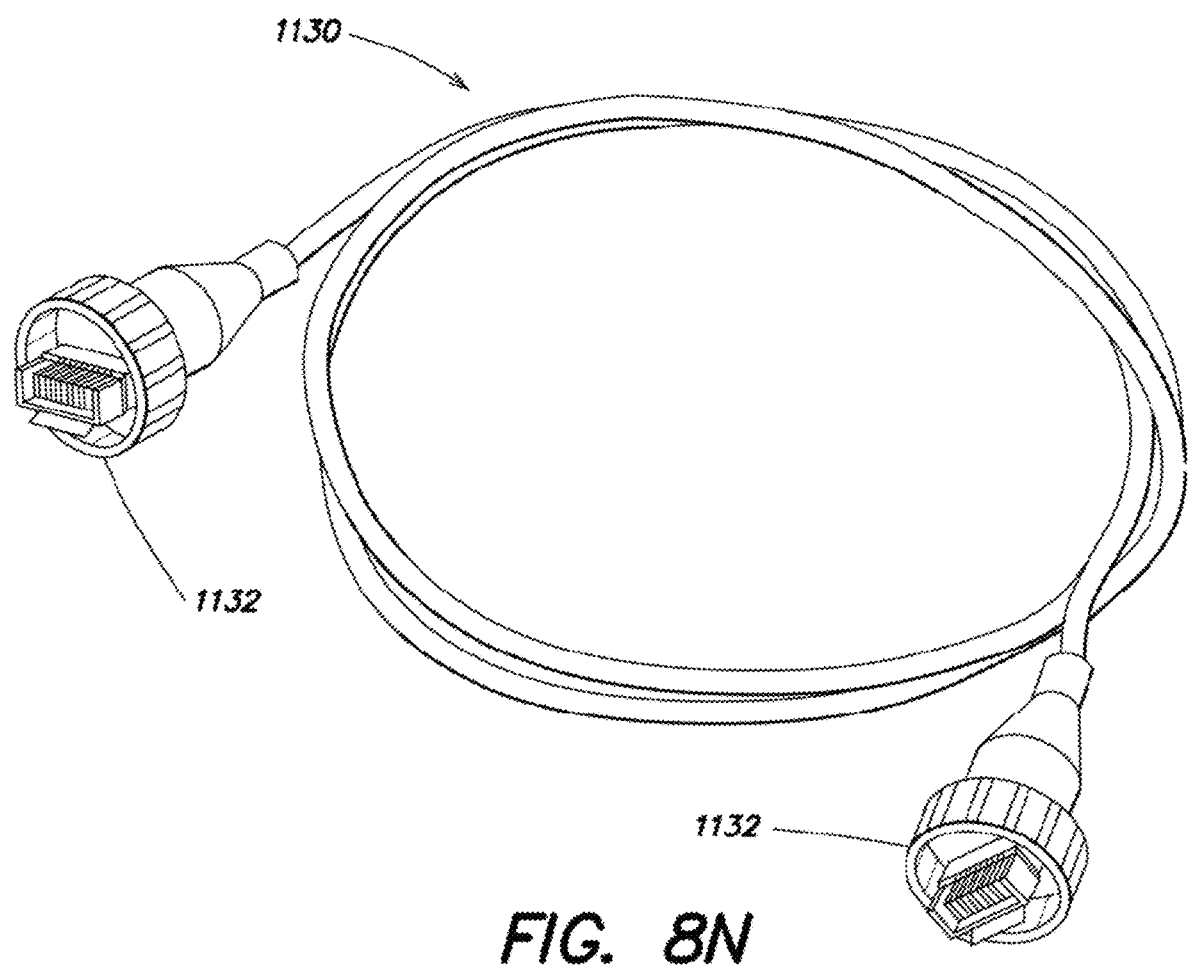
FIG. 8N shows a perspective view of an exemplary waterproof Ethernet cable.
Figure 80:
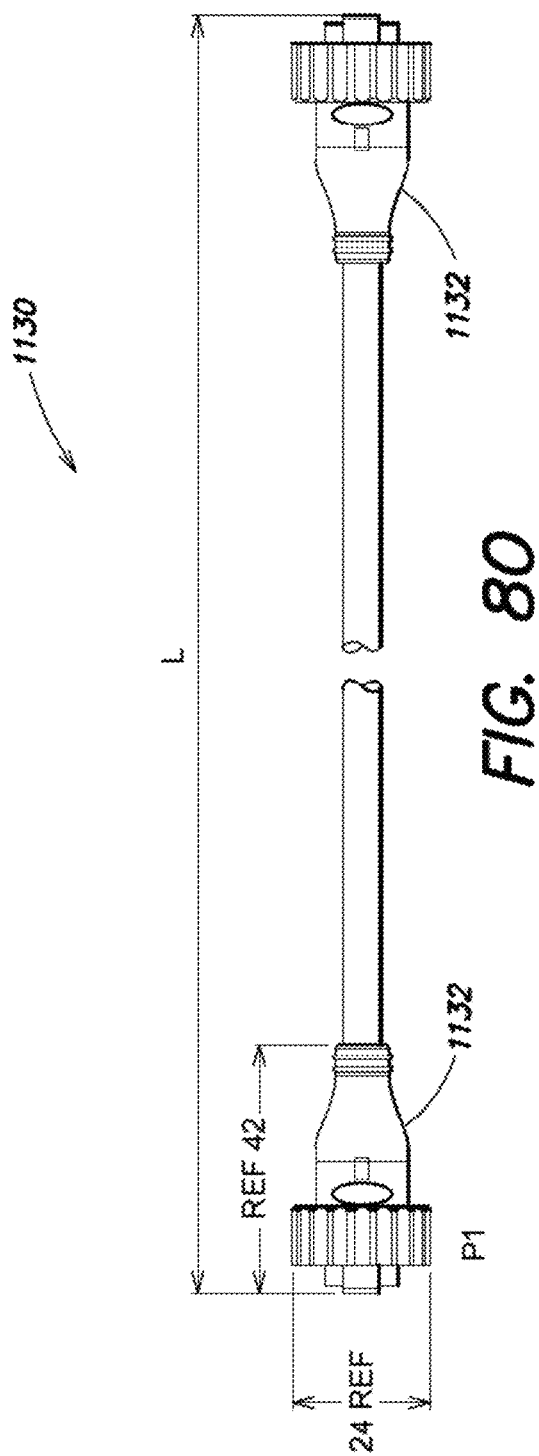
Figure 8P:
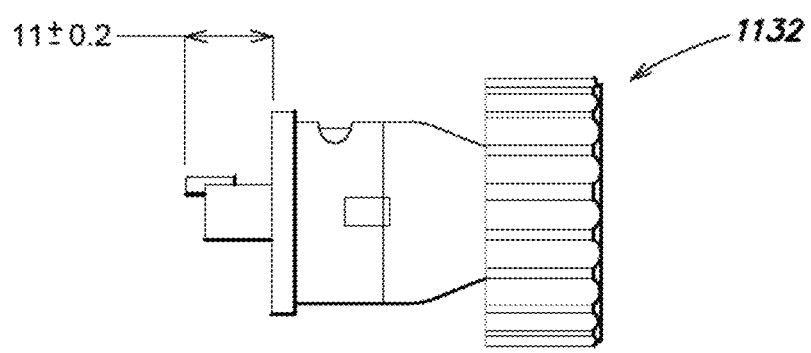
FIG. 8P shows an expanded front view one portion of the waterproof Ethernet cable of FIG. 8N.

FIGS. 8N-8P shows several views of a network cable 1130 used to communicatively couple multiple lighting fixtures 1000 to one another via the PoE ports 1008A and/or 1008B on the lighting fixture 1000. The lighting fixture 1000 may also be used as a platform to provide communication (e.g., data transfer, control) between multiple lighting fixtures 1000 and the sensors that may be coupled to each lighting fixture 1000, thus simplifying the manner in which a plurality of lighting fixtures 1000 and sensors are communicatively coupled. In some implementations, the network cable 1130 may be an Ethernet cable, as depicted in FIGS. 8N-8P though it should be appreciated other connector types may be used in other implementations. In some implementations, the network cable 1130 may be waterproof (e.g., a waterproof Ethernet cable) to provide a longer lifetime use, particularly in an agricultural environment with potentially high ambient moisture content. One examples of an Ethernet cable is a Cat-5 cable, as well as other categories of Ethernet cables (e.g., Cat-5e, Cat-6, Cat-7).

Figure 8R:
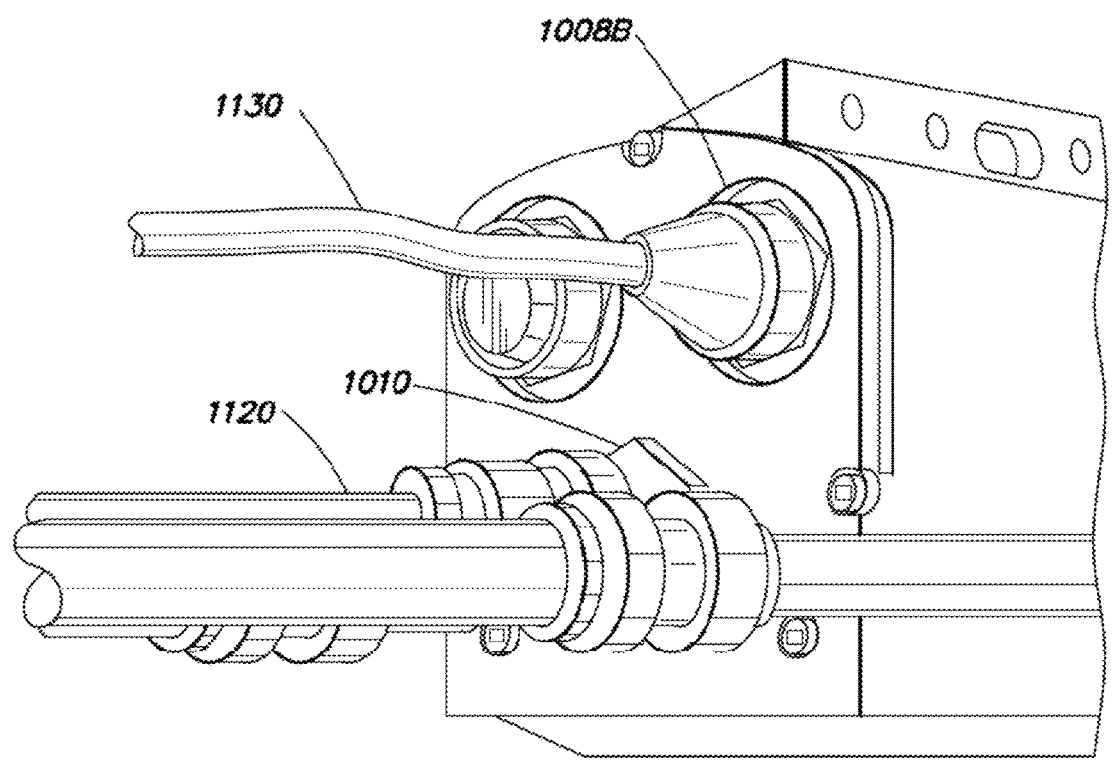
FIG. 8R shows an exemplary assembly of a waterproof Ethernet cable and a power cable coupled to the lighting fixture of FIGS. 7A-7C.

FIGS. 8Q-1-8Q-5 shows additional designs for the drop tee cable 1110 and the power cable 1120. Additionally, FIG. 8Q-1 also shows an outlet 1140 that supports connectivity to the drop tee cable 1110 and/or the power cable 1120. The outlet 1140 may be integrated into the power source to facilitate connectivity. FIG. 8R shows an exemplary lighting fixture 1000 where a power cable 1120 is connected to the power port 1010 and a network cable 1130 is connected to the PoE port 1008B.

Figure 9A:
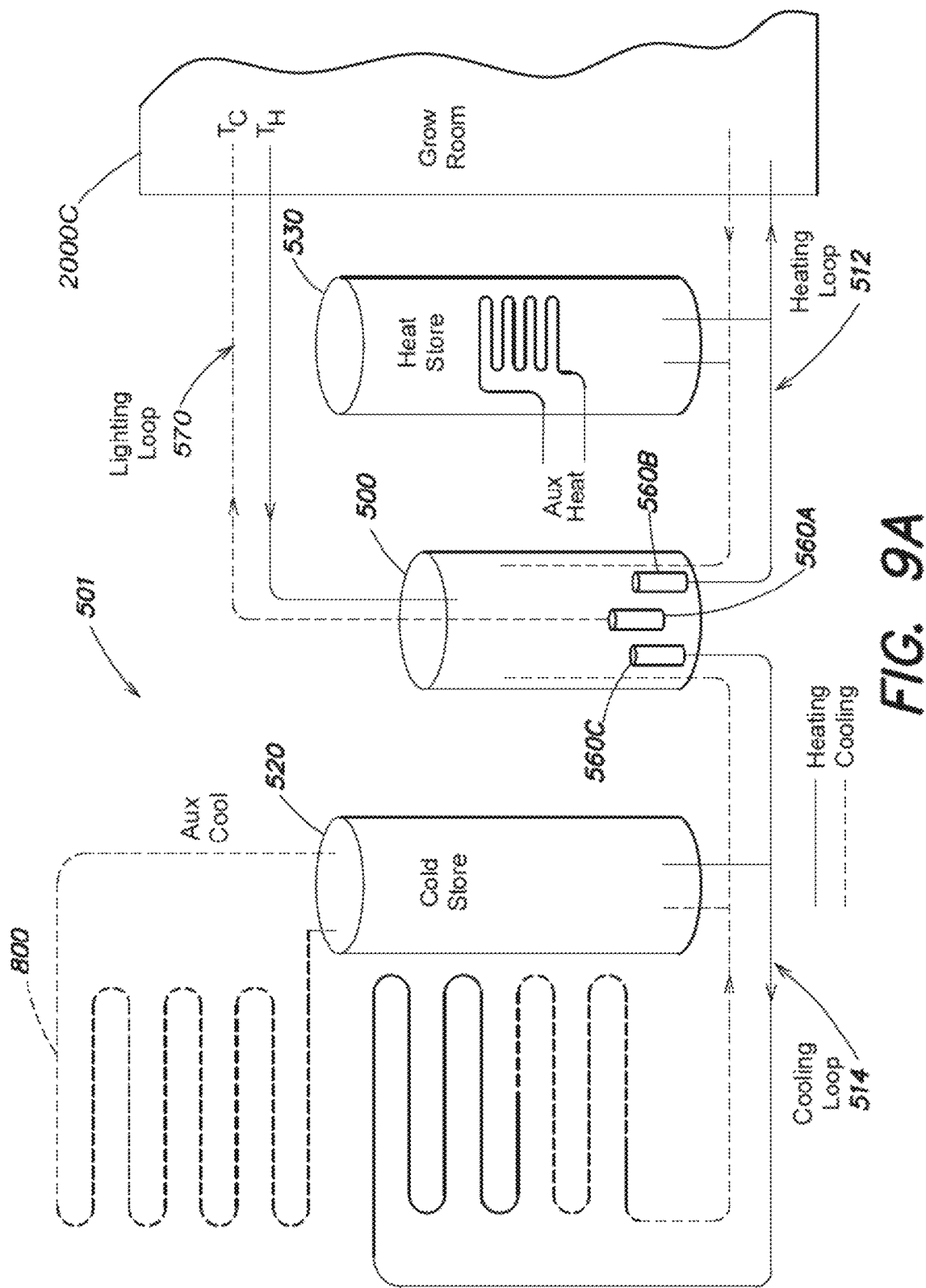
FIG. 9A shows an exemplary hydronics system including a fluid storage tank and multiple piping subsystems such as a lighting loop, a heating loop, and a cooling loop, according to some implementations of the disclosure.

FIG. 9A shows an exemplary hydronics system 501 that may be used in connection with a coolant circuit 570 as well as in other implementations of a controlled agricultural environment where one or more lighting fixtures 1000 are used. As shown, the hydronics system 501 may include a fluid storage tank 500 to store fluid coolant 800, which may be disposed internally or externally to the controlled agricultural environment. In some implementations, the fluid storage tank 500 may include separate compartments for relatively cooler fluid coolant 800 and relatively hotter fluid coolant 800 with sufficient thermal insulation to substantially thermally isolate the compartments from one another and the surrounding environment. The fluid storage tank 500 may also be dimensioned to have a sufficiently large storage capacity such that the thermal time constant of the fluid storage tank 500 meets a desired rate of change in temperature during operation. For example, it may be desirable for the temperature of the fluid coolant 800 stored in the fluid storage tank 500 to remain substantially unchanged (e.g., 1° C. per hour) throughout the day to reduce fluctuations in the amount of heat supplied to various piping subsystems. However, if adjustments to the fluid coolant 800 temperature are desired, the amount of time needed for the adjustments to occur may be prohibitive due to the long thermal time constant. In such instances, multiple fluid storage tanks 500, each having a smaller capacity and thus a shorter thermal time constant, may be used instead.

Three submersible pumps 560A, 560B, and 560C may be disposed within the fluid storage tank 500 to pump fluid coolant 800 through three corresponding piping subsystems, namely, the coolant circuit 570 (also referred to in FIG. 9A as a "lighting loop"), a heating loop 512, and a cooling loop 514. The lighting loop 570 associated with the pump 560A is responsible for providing relatively cooler fluid coolant from the fluid storage tank 500 to one or more lighting fixtures 1000 (e.g., via the coolant circuit 570 as shown in FIGS. 3 and 4) and returning relatively hotter fluid coolant 800 from the one or more lighting fixtures 1000 to the fluid storage tank 500. In this manner, the lighting loop 570 may function as a heat source to heat fluid coolant 800 stored in the fluid storage tank 500 with heat being subsequently distributed to other piping subsystems. In some implementations, the lighting loop 570 may be used to heat at least a portion of the controlled agricultural environment 2000C via natural convection or thermal radiation to regulate and maintain temperature of the portion within a desired temperature envelope.

In some implementations, a secondary heating loop may be incorporated into the lighting loop 570 to more directly and controllably heat a portion of the controlled agricultural environment 2000C that may not be proximate to the lighting loop 570 (e.g., a growing area, as shown in FIG. 4). For example, the secondary heating loop may include a pump, a fan, and a fan coil. The pump may generate a flow of relatively hotter fluid coolant 800 through the fan coil, thus heating the fan coil. The fan may then generate a flow of hot air, thus heating the portion of the controlled agricultural environment 2000C via forced convection. In another example, the secondary heating loop may be routed through the root zone of the growing area to heat the soil or nutrient solution to a desired temperature via a combination of convection and conduction (e.g., see the hydronics loop 700A in FIG. 4). The secondary heating loop may include a flow controlling device (e.g., a valve) to control the amount of heat added to the portion of the controlled agricultural environment. For example, the secondary heating loop may be coupled to a thermostat that adjusts the heat added according to a day/night cycle.

The heating loop 512 associated with the pump 560B may also be used to heat a portion of the controlled agricultural environment 2000C or another space located separately to the controlled agricultural environment 2000C. For example, the heating loop 512 may be coupled to a heating, ventilation, and air conditioning (HVAC) system in a building to regulate the interior climate of the building, a heating system in a manufacturing plant to offset gas or electricity consumption, or a cogeneration plant to produce electricity and high-grade heat. In some implementations, the heating loop 512 may also be coupled to a heat store 530, which may provide additional capacity to store heat for future use by the controlled agricultural environment 2000C or another space.

The cooling loop 514 associated with the pump 560C may be used to cool the fluid coolant 800 stored in the fluid storage tank 500. In this manner, the temperature of the relatively cooler fluid coolant 800 entering the lighting loop 570 may be regulated and maintained, which may reduce the effects of thermal drift over time where the temperature of the relatively cooler fluid coolant 800 increases, thus reducing the amount of heat removed from the one or more lighting fixtures 1000. In some implementations, the cooling loop 514 may be a piping subsystem that captures heat to an exterior environment via natural convection and radiation along the length of the cooling loop 514. In some implementations, a heat rejection device may be incorporated into the cooling loop 514 to facilitate cooling of the fluid coolant 800. Various types of heat rejection devices may be used including, but not limited to cooling towers (e.g., see the cooling tower 557 in FIG. 3 or FIG. 4), evaporative coolers, "free" coolers, chillers, dry coolers, air source coolers, ground source heat exchangers, water source heat exchangers, or any combinations of the foregoing. In some implementations, the cooling loop 514 may also be coupled to a cold store 520, which may provide additional capacity to store relatively cooler fluid coolant 800 for future use by the controlled agricultural environment 2000C or another space.

In various implementations described herein, the temperature of the fluid coolant 800 stored in the fluid storage tank 500 and flowing through the lighting loop 570, heating loop 512, cooling loop 514, and one or more secondary loops coupled to any of the lighting loop 570, heating loop 512, cooling loop 514 may vary within an appreciable temperature range. In some implementations, the temperature of the fluid coolant 800 may range from about 20° C. to about 50° C. The flow rate of the fluid coolant 800 may range from about 1 gallon per minute to about 3 gallons per minute through the lighting loop 570. Similar or significantly different (e.g., higher) flow rates may be used by the heating loop 512 and the cooling loop 514. Furthermore, the various piping subsystems (e.g., the lighting loop 570, the heating loop 512, and the coolant loop 514) may be controlled via at least one of a pump, regulator, and/or valves. The at least one of a pump, regulator, and/or valves may be operated on various time cycles (e.g., daily, weekly, monthly, seasonal, other periodicities, or any combination thereof) to regulate and maintain desired thermal conditions, which may be dynamic as a function of time, in the controlled agricultural environment 2000C.

Additionally, while three piping subsystems are shown in FIG. 9A, it should be appreciated that any number and combination of piping subsystems may be used with the coolant circuit 570. For example, one or both of the heating loop 512 and the cooling loop 514 may be used in conjunction with the lighting loop 570. It should also be appreciated that while three submersible pumps 560A-560C are shown in FIG. 9A, any number of pumps may be used for a particular piping subsystem and the pumps 560A-560C may also be disposed externally to the fluid storage tank 500. The pumps may be various types of pumps including, but not limited to piston pumps, end-suction pumps, diaphragm pumps, gear pumps, lobed pumps, flexible-vane pumps, nutating pumps, peristaltic pumps, centrifugal pumps, diffuser pumps, propeller pumps, and peripheral pumps.

Figure 9B:
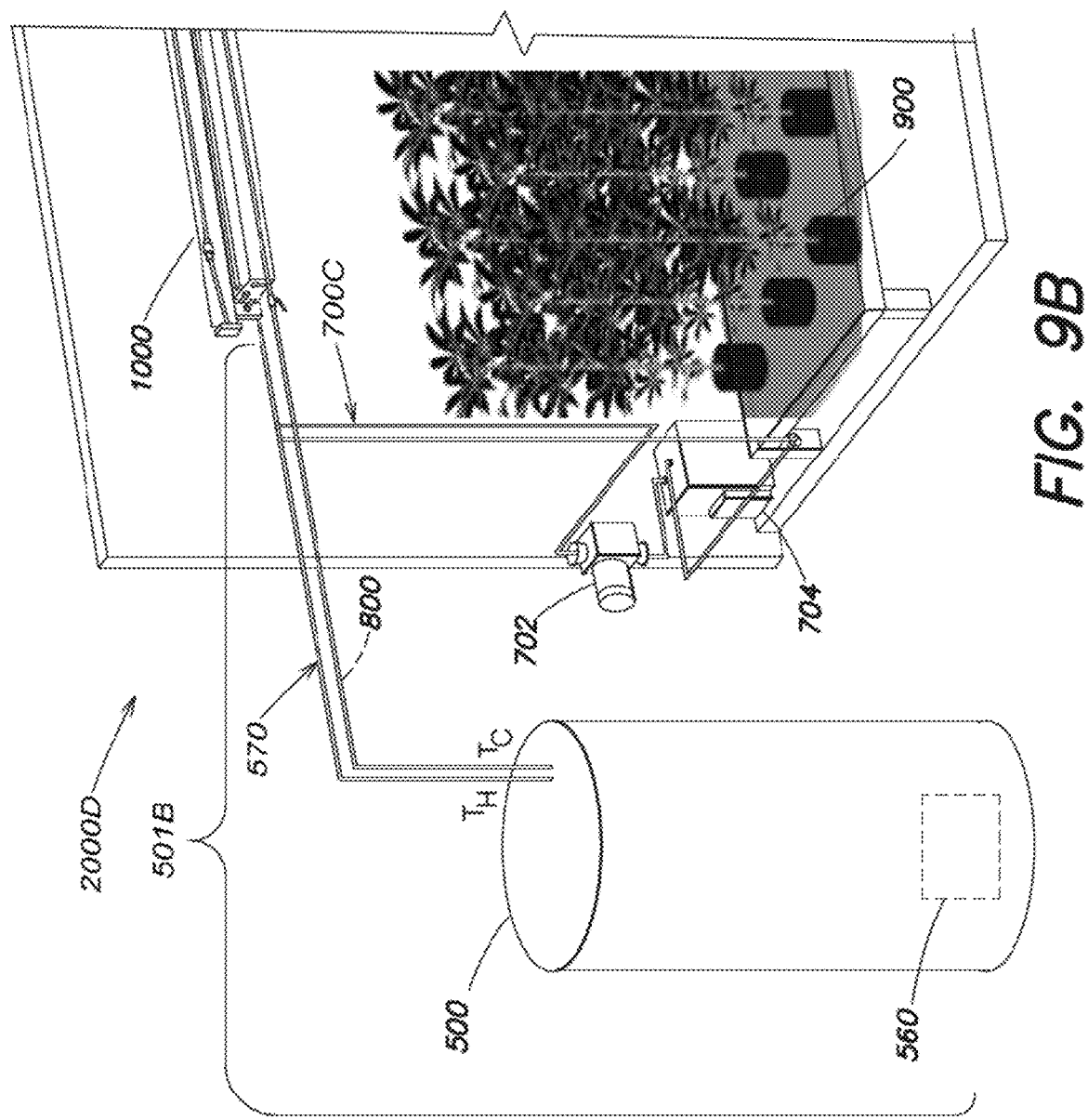
FIG. 9B shows a portion of an exemplary hydronics system coupled to a lighting fixture and a growing area, according to some implementations of the disclosure.

An exemplary implementation of a hydronics system 501B coupled to a lighting fixture 1000 and a coolant circuit ("lighting loop") 570 in a controlled agricultural environment 2000D is shown in FIG. 9B. The hydronics system 501B may include a fluid storage tank 500 having contained therein a submersible pump 560. The submersible pump 560 is used to pump relatively cooler fluid coolant 800 into a lighting loop 570, where the fluid coolant 800 is then heated as it passes through the lighting fixture 1000. Subsequently, the relatively hotter fluid coolant 800 exits the lighting loop 570 and enters the fluid storage tank 500 for storage. It should be appreciated that so long as the temperature of the fluid coolant 800 stored in the fluid storage tank 500 is less than the temperature of the fluid coolant 800 entering the fluid storage tank 500 from the lighting loop 570, heat generated by the lighting fixture 1000 may be removed. Over time, if the temperature of the fluid coolant 800 increases, the amount of heat that may be removed may decrease due to a smaller temperature difference. Thus, a heat rejection device may need to be incorporated into the hydronics system 501B to regulate the temperature of the fluid coolant 800 stored in the fluid storage tank 500.

The hydronics system 501B shown in FIG. 9B may also include a secondary heating loop 700C coupled to the portion of the lighting loop 570 where relatively hotter fluid coolant 800 heated by the lighting fixture 1000 flows through (e.g., similar to the hydronics loops 700A and 700B shown in FIG. 4). As shown, the secondary heating loop 700C may include a pump 704 and an electric fan with a fan coil 702. The pump 704 generates a flow of the relatively hotter fluid coolant 800 through the fan coil, thus heating the fan coil. The electric fan 702 may then blow heated air towards a plurality of plants 900 located below the lighting fixture 1000 to increase the temperature of the growing area as desired. The second heating loop 700C may be controlled using one or more controllable valves to toggle the secondary heating loop 700C and to adjust the temperature of the air blown by the electric fan 702.

Figure 9C:
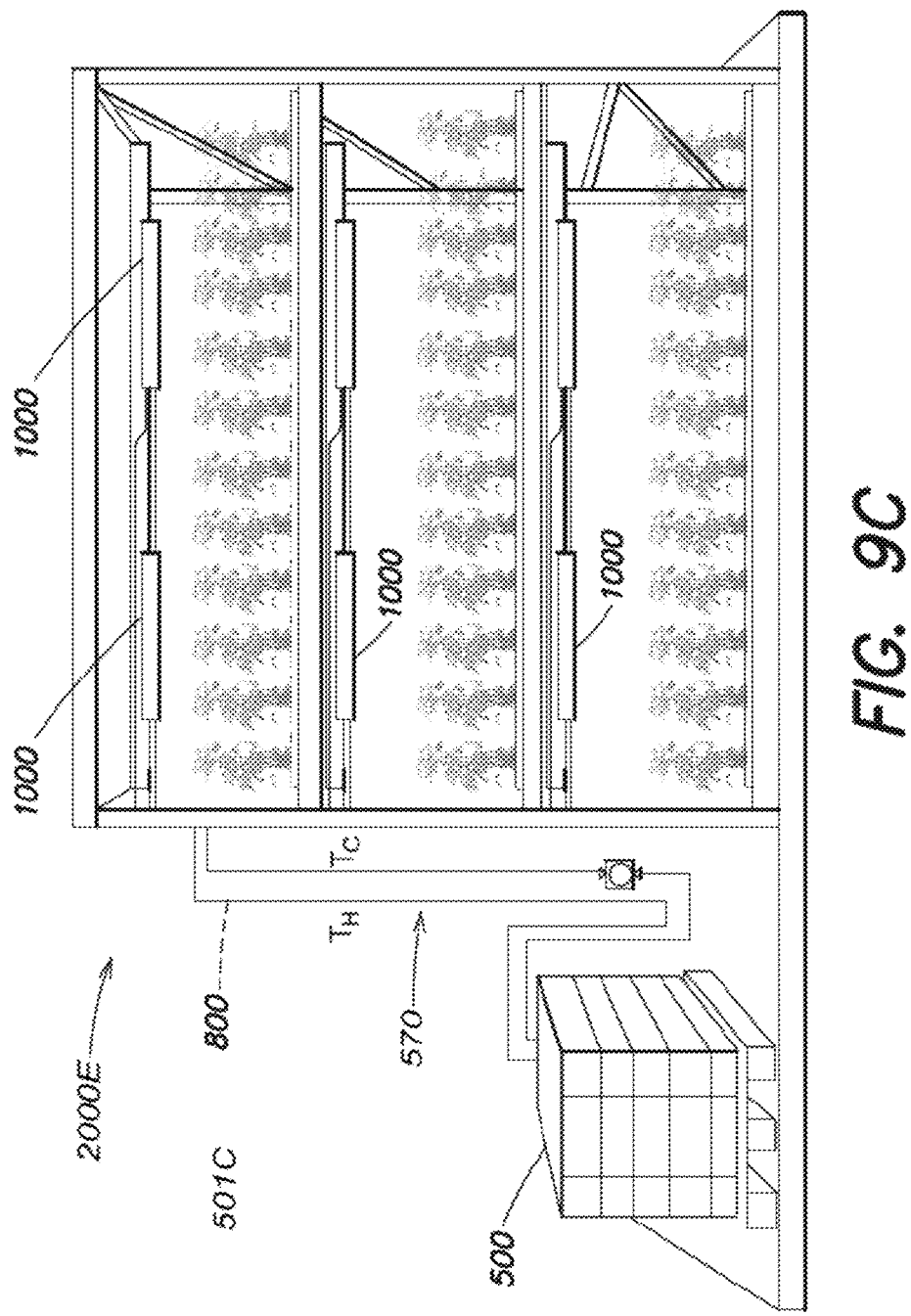
FIG. 9C shows a controlled agricultural environment where one or more fluid-cooled LED-based lighting fixtures are disposed in a vertically-stacked multiple-level growing area and coupled to a hydronics system, according to some implementations of the disclosure.

Another exemplary implementation of a hydronics system 501C disposed in a controlled agricultural environment 2000E is shown in FIG. 9C. As shown, the controlled agricultural environment 2000E may have a vertically-stacked multiple-level growing area. Each level of the growing area may include one or more lighting fixtures 1000 coupled to a lighting loop 570. The lighting loop 570 may be coupled to a fluid storage tank 500, which may again contain therein a submersible pump. Similar to the controlled agricultural environment 2000D of FIG. 9B, the hydronics system 501C may include secondary heating loops to separately heat each growing area in each level. The portions of the lighting loop 570 corresponding to each level may be coupled using a plumbing fitting with multiple inlets and outlets. Additionally, the portion of the lighting loop 570 coupled to the fluid storage tank 500 may support a higher flow rate to account for a reduction in flow rate once the fluid coolant 800 flows into each respective level of the growing area.

In some implementations, the lighting fixture 1000 may also function as a sensor platform supporting one or more sensors used to monitor environmental conditions in the controlled agricultural environment. The processor 90 in the lighting fixture 1000 may supply and regulate electrical power to the sensor through the communication ports 1009 (e.g., a USB port and a PoE port). The processor 90 may also include electronics to convert AC power to DC power, as will be described below, thus obviating the need for a separate AC to DC converter in each sensor deployed in the controlled agricultural environment. The processor 90 may also be used to manage data communications, including sending control signals to the sensor and receiving sensory data measured by the sensor for processing and/or transmission to a remote device (e.g., a remote computer or server). In this manner, the lighting fixture 1000 may provide integration of one or more sensors of various types, supplementing the need for separate power and data communications systems. Furthermore, the data measured by the one or more sensors may be used to adjust and control operation of one or more lighting fixtures 1000 (e.g., adjusting the PAR output from the lighting fixture 1000), one or more coolant circuits or other fluid coolant loops (e.g., adjusting the fluid flow through the coolant circuit/lighting loop, heating loop, and cooling loops shown in FIG. 9A), one or more fans, one or more dehumidifiers, or one or more air conditioners in the controlled agricultural environment. In some implementations, various environmental conditions are measured and controlled to provide target vapor pressure deficits in the environment.

Figure 10A:
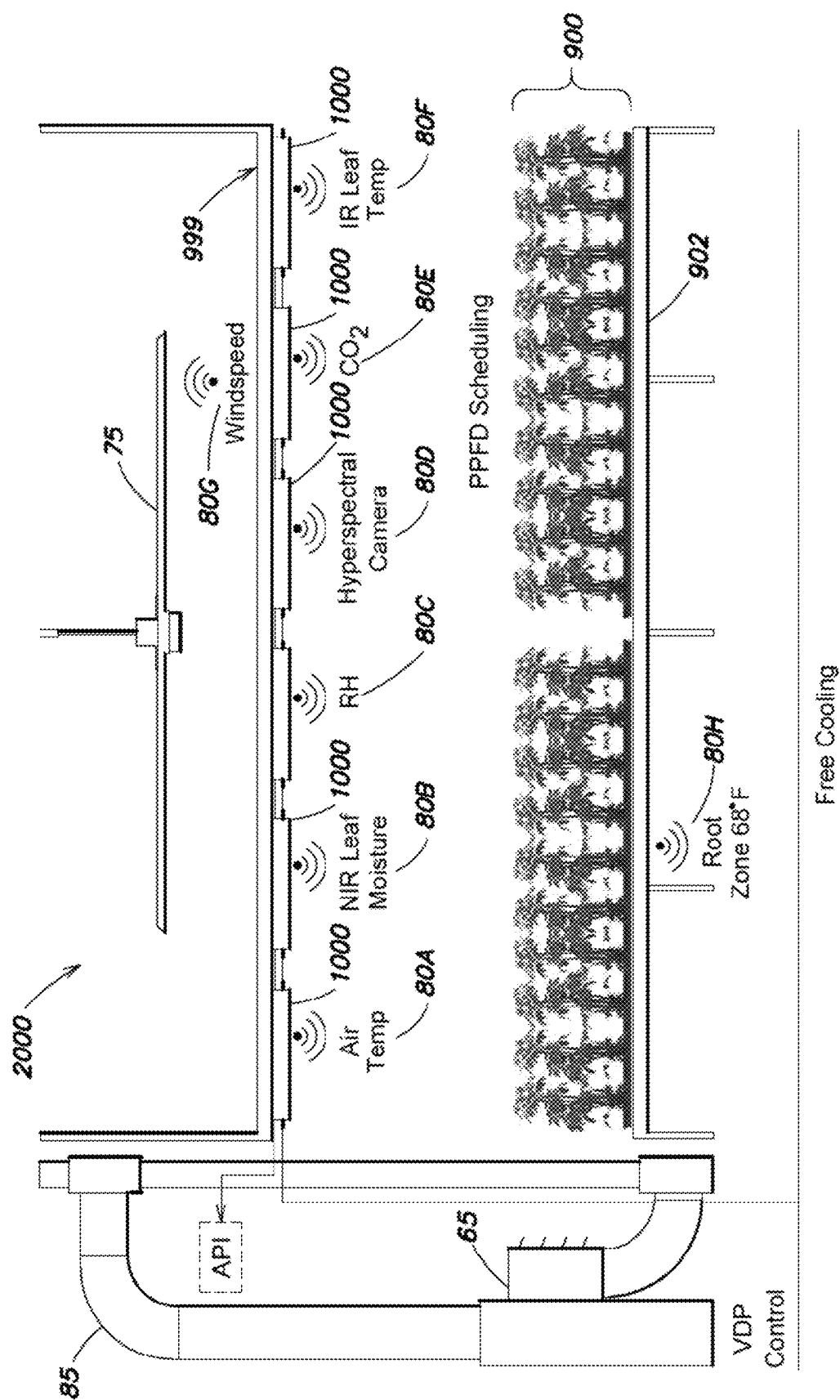
FIG. 10A shows a side view of a controlled agricultural environment with a plurality of fluid-cooled LED-based lighting fixtures and a plurality of sensors to facilitate monitoring of environmental conditions, according to some implementation of the disclosure.

An exemplary implementation of a controlled agricultural environment 2000 detailing the integration of various sensors via multiple lighting fixtures 1000 is shown in FIG. 10A. Similar to FIG. 8B, multiple lighting fixtures 1000 may be mounted to a support structure 999 disposed above a plurality of plants 900 arranged on a shelf 902. The controlled agricultural environment 2000 may include one or more dehumidifiers 65, one or more air conditioners 85, and one or more fans 75. A variety of sensors may be supported by the lighting fixture 1000 including, but not limited to an air temperature sensor 80A, a near infrared (NIR) leaf moisture sensor 80B, a relative humidity sensor 80C, a hyperspectral camera 80D, a carbon dioxide sensor 80E, an infrared (IR) leaf temperature sensor 80F, an airflow sensor 80G, and a root zone temperature sensor 80H. The hyperspectral camera 80D refers to a type of camera that measures light within numerous energy bands (e.g., hundreds) where each band is narrower (e.g., 10 nm) than conventional imaging systems. Finite spectral cameras (also referred to as multispectral cameras) may also be used in the controlled agricultural environment 2000 to measure light using a fewer number of energy bands (e.g. 3 to 10) where each band is broader (e.g., greater than 20 nm). The cameras utilized in the controlled agricultural environment 2000 may measure light across various portions of the electromagnetic spectrum including, but not limited to ultraviolet, visible, near-infrared, midinfrared, and far-infrared wavelengths. The lighting fixture 1000 may also be used to support other auxiliary devices including, but not limited to one or more fans, security cameras, smart phones, and multi-spectral cameras (e.g., to analyze soil moisture and nutrient content). In this manner, various auxiliary devices may be distributed in the controlled agricultural environment due to the flexible placement of communication ports 1009 on the respective lighting fixtures 1000.

Figure 10B:
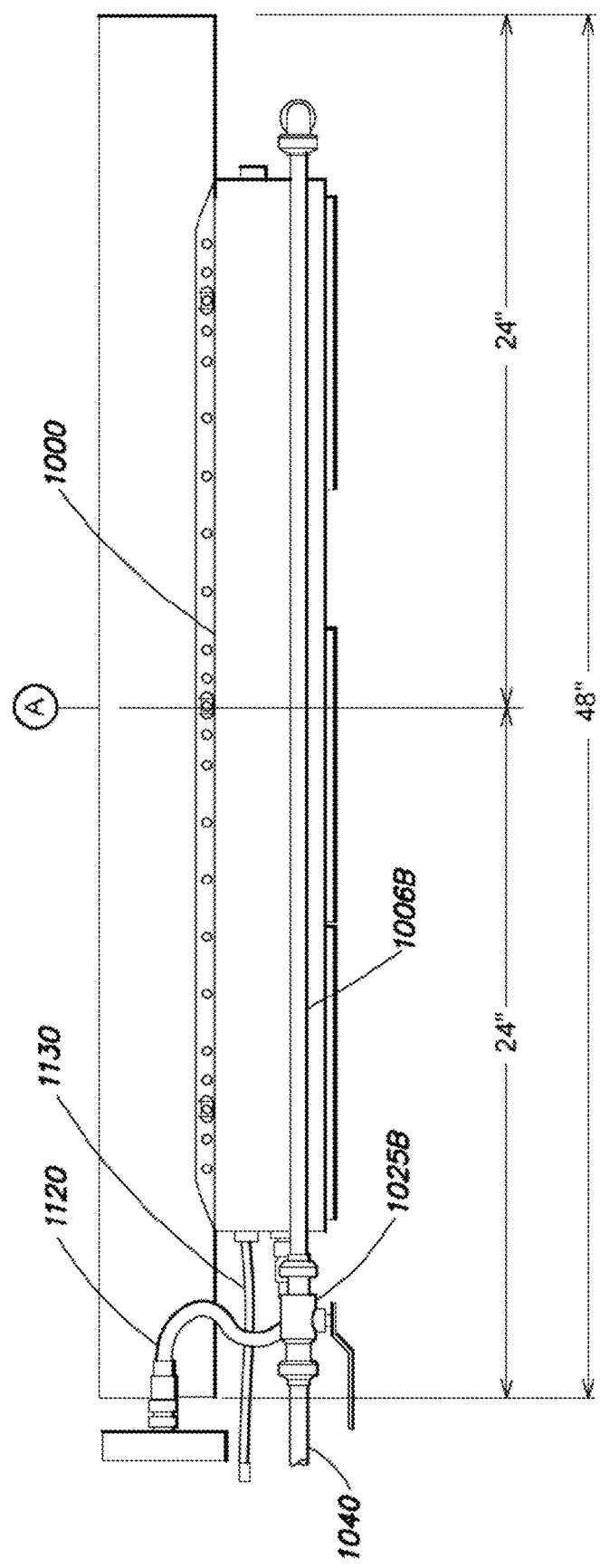
FIG. 10B shows a side view of an exemplary lighting system with a single lighting fixture.
Figure 10D:
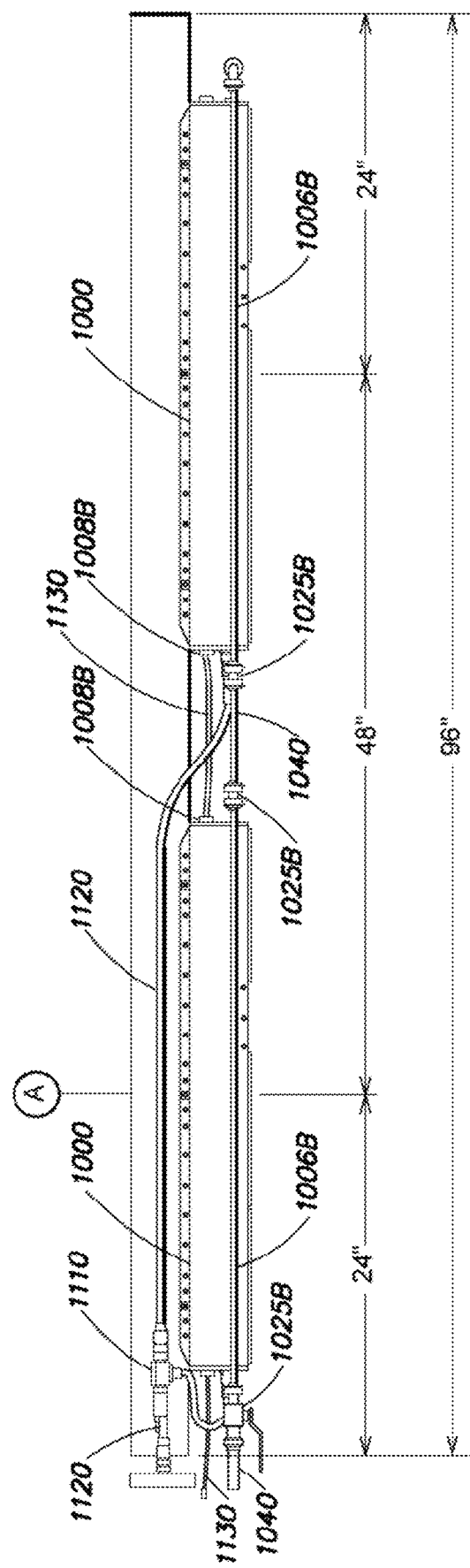
FIG. 10D shows a side view of an exemplary lighting system with two coupled lighting fixtures.
Figure 10E:
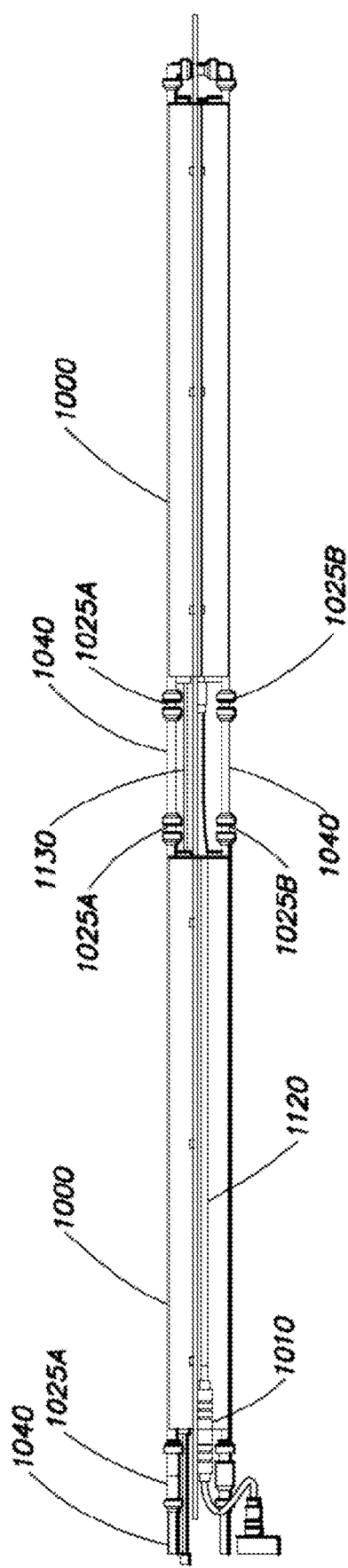
FIG. 10E shows a top view of the lighting system of FIG. 10D.
Figure 10F:
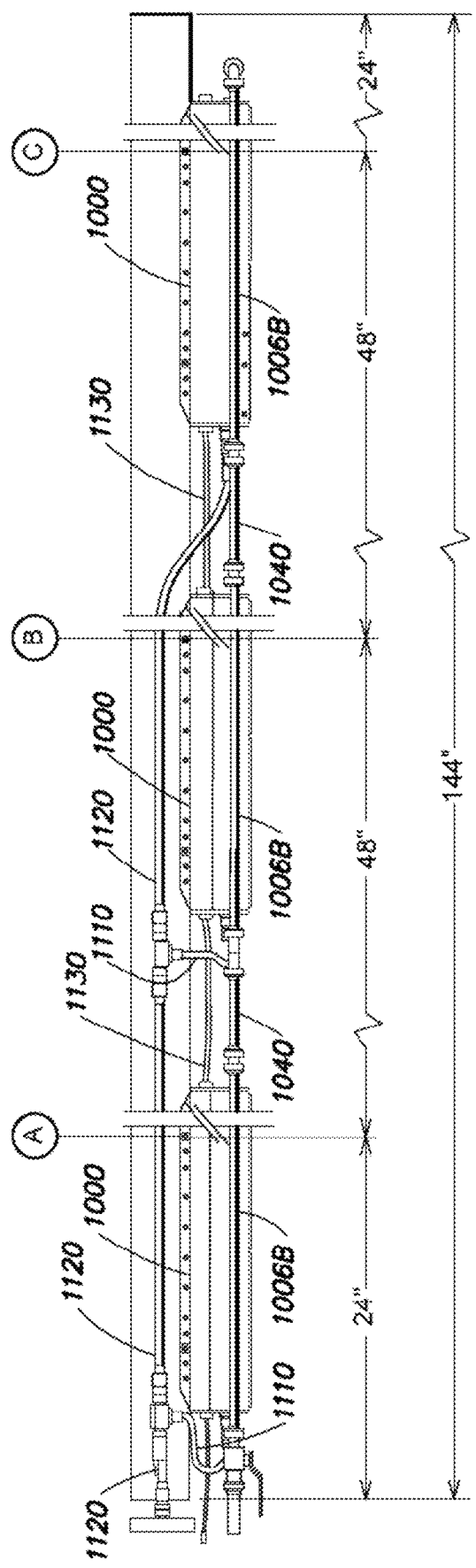
FIG. 10F shows a side view of an exemplary lighting system with three coupled lighting fixtures.
Figure 10G:
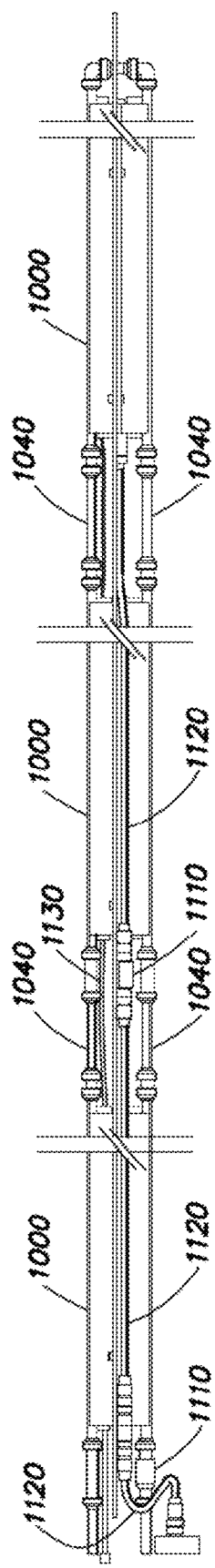
FIG. 10G shows a top view of the lighting system of FIG. 10F.

FIGS. 10B-10G show multiple exemplary lighting systems that incorporate a varying number of lighting fixtures 1000 joined together in terms of electrical power transfer, networking, and plumbing. Specifically, FIGS. 10B and 10C show a lighting system with a single lighting fixture 1000. As shown, a single power cable 1120, network cable 1130, and intermediate piping 1040 for each coolant pipe 1006 may be used to couple the lighting fixture 1000 for operation. FIGS. 10D and 10E show another lighting system that uses two lighting fixtures 1000. As shown, an assembly of power cabling (e.g., the two power cables 1120 and the drop tee cable 1110 in FIG. 8C) may be used to supply power to the two lighting fixtures 1000. Additionally, a network cable 1130 may be couple one lighting fixture 1000 to the other lighting fixture 1000 to communicatively couple the lighting fixtures 1000 to a common node. Additionally, intermediate pipes 1140 may be used to join the two lighting fixtures 1000 via the plumbing fittings 1025A and 1025B. FIGS. 10F and 10G show another lighting system that uses three lighting fixtures 1000. As shown, the power cabling may include an additional drop tee cable 1110 and power cable 1120 compared to FIGS. 10D and 10E. Additional network cable 1130 and intermediate pipes 1040 may be used to connect the additional lighting fixture 1000.

It should be appreciated this approach of assembling multiple lighting fixtures 1000 may be used to build lighting systems that include even more lighting fixtures 1000 (e.g., tens of lighting fixtures 1000, hundreds of lighting fixtures 1000). The extent to which the number of lighting fixtures 1000 may be coupled in this manner may depend on external factors such as the pumps used to drive coolant through the coolant pipes 1006 (e.g., a longer coolant circuit exhibits a greater pressure drop and hence a higher pumping specification to sufficiently flow coolant through the coolant circuit) and/or the power that should be supplied to each lighting fixtures 1000 (e.g., the cabling rating of up to 15 A may limit how many lighting fixtures 1000 are powered simultaneously).

Regarding fluid coolant flowing through the pipes of respective lighting fixtures 1000, as noted above the fluid coolant prevents heat generated by the lighting fixture from entering the controlled agricultural environment and keeps the lighting fixture at reasonable operating temperatures. In some implementations, the temperature of the fluid coolant flowing through the lighting fixtures is above the dew point within the controlled agricultural environment (e.g., to prevent condensation on the lighting fixture), and below 120° F. (or 48° C.) at the last fixture through which the fluid coolant flows in a fluid coolant circuit. In one aspect, the LED light sources of each lighting fixture generally operate about 15° F. (or 7° C.) higher than the temperature of the fluid coolant flowing through the fixture. In some implementations, a recommended temperature for the fluid coolant is approximately 100-110° F.

Regarding the pipes 1006A and 1006B of a given lighting fixture, fluid coolant may flow in either direction through each pipe, and both parallel and U-shaped end return configurations are acceptable. When respective pipes of multiple lighting fixtures are connected in series to form a coolant circuit, in some implementations a fluid flow rate of between 0.33 gallons per minute (GPM) to 0.5 GPM per light is acceptable; in one aspect, at least 0.5 GPM per pipe ensures sufficient turbulence. In one aspect, higher flow rates allow for smaller dry coolers and cooling towers.

The maximum flow rate per pipe is set by the tubing wear limit. The Copper Development Association's Copper Tube Handbook recommends maximum water velocities of between 5 and 8 feet per second for "Hot" and "Cold" water, respectively. For lighting fixtures 1000 in which the pipes 1006A and 1006B are ½ inch copper tubing, the flow velocity is 1.37 ft/s per GPM. Hence the recommended range of maximum flow rates is between 3.6 and 5.8 GPM per tube.

The temperature rise in the fluid coolant circuit can be estimated from the heat produced per lighting fixture (e.g., 600 W), the flow rate, and N the number of lights:

$$\Delta T \circ_{F.} = \frac{600 \text{ W}}{147 * GPM} \cdot N \text{ or}$$

$$\Delta T \circ_{C.} Q = \frac{600 \text{ W}}{70 * LPM} \cdot N$$

In one aspect, there is virtually no change in the amount of heat captured in the fluid coolant circuit as the temperature of a lighting fixture changes. The internal temperatures of lighting fixtures increase and decrease proportionally to the cooling loop temperature.

When choosing between a U-return configuration and a parallel flow design for the pipes 1006A and 1006B of multiple lighting fixtures of a lighting system, in some implementations the parallel flow setup is required over approximately 4 GPM, since higher flow rates will cause tubing degradation, as all of the flow is confined to the one tube.

In one example lighting system installation, the fluid coolant is water pumped from a small reservoir by a pump to a set of piping connecting the pipes of multiple lighting fixtures 1000 such that the water flows through all of the pipes 1006A and 1006B to a radiator placed outside of the controlled agricultural environment and finally back to the small reservoir. Such a system may be used in applications in which re-use of the heat absorbed by the water is not desired, impractical, etc. The systems design in this case involves selecting the dry cooler, and then choosing a suitable pump to achieve the water flow needed.

For a system of six lighting fixtures and a flow rate of 3 GPM (i.e., 0.5 GPM per light), the temperature rise across the series of lights is approximately 8 degrees. A U-return configuration may be employed for the fluid coolant circuit (as 3 GPM is below the wear limit which begins above 4 GPM). The minimum dry cooler must then be capable of a capacity of 3600 W of rejection at the maximum expected outside temperature, the maximum recommended water inlet temperature (e.g., 120 degrees F.), and 3 GPM. Once a suitable dry cooler is selected, its known water flow characteristics as well as those of the plumbing can be used to properly size the pump to achieve 3 GPM.

Additional components such as air separators, an expansion tank, and provisions for filling and draining the system are also needed, as with any hydronics system. A thermostat on the dry cooler inlet can operate the fan. Setting this at approximately 100 degrees F. to 120 degrees F. will generally achieve good thermal regulation. Multiple dry coolers can be placed in various configurations to expand capacity as is common. As noted above, it is important not to reduce the water temperature below the dewpoint in the room, to prevent condensation. In very cold climates it may be necessary to install a temperature controlled bypass valve to bypass the radiator completely to achieve this. Glycol may also be needed.

Figure 11A:
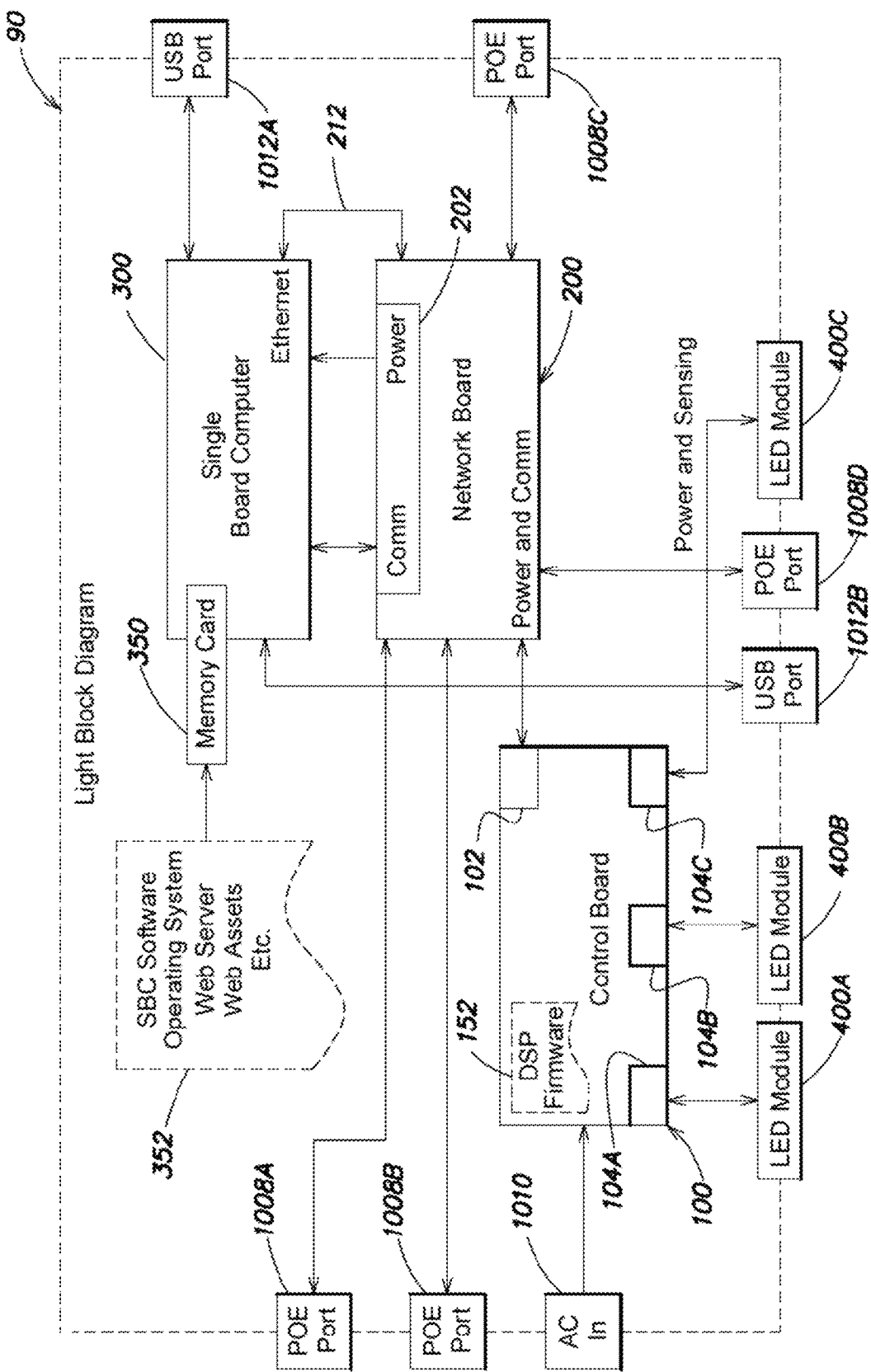
FIG. 11A is a block diagram detailing various electronics components of a processor including a control board, a network board, and a single board computer, according to some implementations of the disclosure.

Returning now to the functionality of the lighting fixture 1000, the processor 90 may be used to facilitate multiple functionalities pertinent to the operation of the lighting fixture 1000 including, but not limited to power conversion, network connectivity, and data processing in the operation of the lighting fixture 1000. In some implementations, the processor 90 may be comprised of discrete electronics assemblies that are electrically coupled together where each electronics assembly provides one or more distinct functionalities. For example, FIG. 11A shows a block diagram detailing various electronic components and circuitry in the processor 90 to meet these functionalities according to one inventive implementation. The processor 90 may include a control board 100, a network board 200, and a single board computer 300.

The control board 100 may be used to regulate and distribute electrical power to other components of the lighting fixture 1000. As shown in FIG. 11A, the control board 100 may receive AC power through an electrical power port 1010 and convert the AC power to DC power. The control board 100 may then supply DC power and other control signals to other electronics in the lighting fixture 400. For example, the control board 100 may be directly coupled to multiple LED modules 400A, 400B, and 400C via ports/connectors 104A, 104B, and 104C, respectively, on the control board 100. The control board 100 may also be coupled to the network board 200, providing both electrical power and control signals to the network board 200. The control board 100 may also include onboard memory, in which digital signal processing (DSP) firmware 152 is stored to facilitate generation of control signals as described below.

Figure 11B:
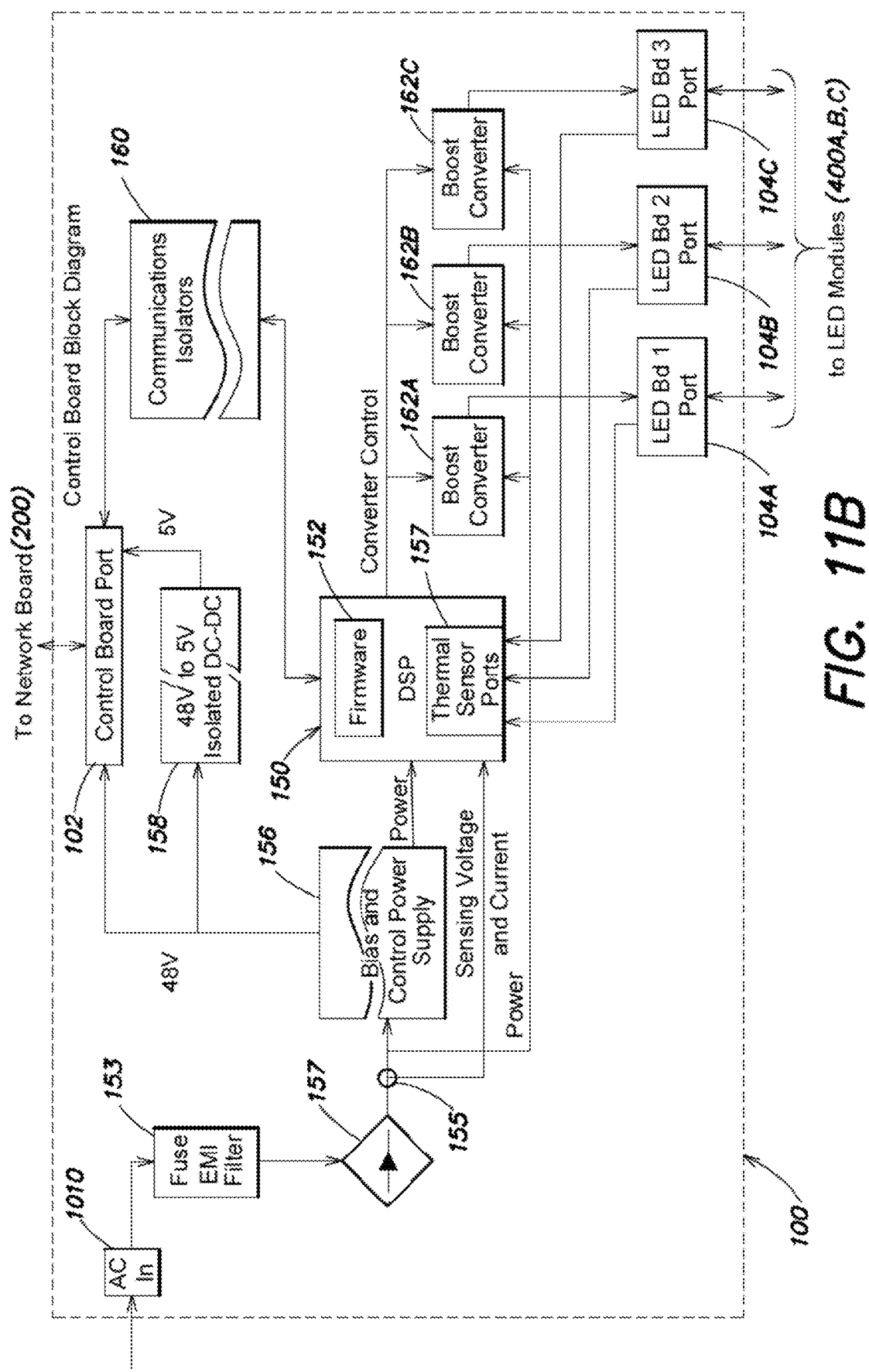
FIG. 11B is a block diagram providing additional detail of the control board of FIG. 11A.

A more detailed block diagram of the control board 100 in FIG. 11A is shown in FIG. 11B. The control board 100 may include a fuse/electromagnetic interference (EMI) filter 153 to provide safety and reduce noise input into the lighting fixture 1000. A rectifier 154 may be used to convert AC power to DC power. An AC line sensor 155 may be used to monitor the voltage and current of the DC power input. DC power may then be passed directly to a bias and control power supply 156, which may be used to distribute DC power to other components of the lighting fixture 1000 including the network board 200 and a digital signal processor (DSP) 150. A DC-DC converter 158 may also be included to supply different voltage inputs to the network board 200. For example, the bias and control power supply 156 may supply 48 V and 5 V to power different circuitry on the network board 200 and the single board computer 300. The 5 V input may be down converted from the 48 V line via the DC-DC converter 158. The DSP 150 may provide control signals by executing the firmware 152 described above to various components including the network board 200, via one or more communications isolators 160. The DSP 150 may also provide control signals to one or more boost converters 162A, 162B, and 162C, which may be used to regulate electricity supplied to the corresponding LED modules 400A-400C via ports 104A-104C. The boost converters 162A-162C may receive DC power directly once converted from AC power via the rectifier 154. The DSP 150 may receive power from the bias and control power supply 156, a voltage and current measurement from the AC line sensor 155, and thermal sensor inputs via the thermal sensor ports 154, which may be used to monitor the temperature of the LED modules 400A-400C.

The network board 200 may be used to manage data communication between the lighting fixture 1000 and various devices coupled to the lighting fixture 1000 including, but not limited to other lighting fixtures 1000 and one or more auxiliary sensors coupled to the lighting fixture 1000. As shown in FIG. 11A, in some implementations, the network board 200 may control one or more PoE ports 1008A, 1008B, 1008C, and 1008D of the lighting fixture 1000. The network board 200 may receive electrical power and control signals from the control board 100 via a control board port 102. The network board 200 may also supply electrical power and control signals to the single board computer 300 via a single board computer port 202. The network board 200 may also support a dedicated Ethernet cable connection 212 through an Ethernet port 213 between the network board 200 and the single board computer 300 to manage data transfer through the PoE ports 1008A-1008D.

A more detailed block diagram of the network board 200 in FIG. 11A is shown in FIG. 11C. The control board port 102 may be used to supply electrical power at different voltages, e.g., 48 V and 5 V, to a PoE controller 206, a power supply 208, and a fan controller and port 210. The control board port 102 may also directly relay control signals from the control board 100 to the single board computer 300 via the single board computer port 202. In some implementations, the control board port 102 may be arranged as a piggyback board to the network board 200. The PoE controller 206 may be used to regulate and supply electrical power to the PoE ports 1008A-1008D. The power supply 208 may supply electrical power to the single board computer 300, through the single board computer port 202, and to an Ethernet switch 204. The Ethernet switch 204 is communicatively coupled to the PoE ports 1008A-1008D and to the single board computer 300 via the Ethernet port 213, which supports the dedicated Ethernet cable connection 212. The Ethernet switch 204 may be used to facilitate receipt and transmission of data and/or control signals to and from the PoE ports 1008A-1008D.

The single board computer 300 may provide several functions to the processor 90 including, but not limited to managing the operation of the control board 100 and the network board 200 and data processing. As shown in FIG. 11A, the single board computer 300 may also be used to support the functionality of USB ports 1012A and 1012B on the lighting fixture 1000. The single board computer 300 may include a memory card 350 that contains (has stored thereon) various data and computer executable code 352 including, but not limited to, session border controller (SBC) software, an operating system, web server software and other web server assets.

The processor 90 may be used to manage the voltage and current supplied to various components of the lighting fixture 1000, e.g., a power cable, the LED modules 400A-400C, in order to reduce the likelihood of damage under different operating conditions. For example, the lighting fixture 1000 may be operated under low voltage conditions where 1200 W may be supplied to the LED modules 400A-400C and 65 W for auxiliary sensors. The power cable used to supply electricity to the lighting fixture 1000 from an external source, e.g., a building electrical supply system, may be rated to sustain a current up to 15 A. The processor 90 may be used to limit the current through the lighting fixture 1000 to 5 A such that three lighting fixtures 400A-400C may be powered by a single power cable 1030. If the current draw of the lighting fixture 1000 approaches 5 A, the processor 90 may reduce the power draw of the lighting fixture. In this manner, the three lighting fixtures 400A-400C may collectively avoid a total current draw that exceeds 15 A, thus reducing the likelihood of damaging the power cable.

In some implementations, the processor 90 may enforce a current draw limit using an active feedback control loop. For instance, the DSP 150 of the control board 100 may be used to actively measure the voltage and current supplied to the lighting fixture 1000 via the AC line sensor 155. Depending on the magnitude and/or rate of change of the measured voltage and current, the DSP 150 may then adjust the voltage and current supplied to each of the LED modules 400A-400C such that the current drawn by the lighting fixture 1000 is maintained below the current draw limit. This process may be conducted in an iterative manner where measurements of the voltage and current supplied to the lighting fixture 1000 and subsequent adjustments to the voltage and current supplied to the LED modules 400A-400C repeatedly occur at a preset timescale. The timescale may vary from about 1 ms to about 60 s. The amount the voltage and current are varied during each increment may also vary according to the rate of change of the voltage and current supplied to the lighting fixture 1000. In some implementations, the stability of the active feedback control loop may be controlled by incorporating a proportional integral differential (PID) controller into the processor 90.

Figure 12A:
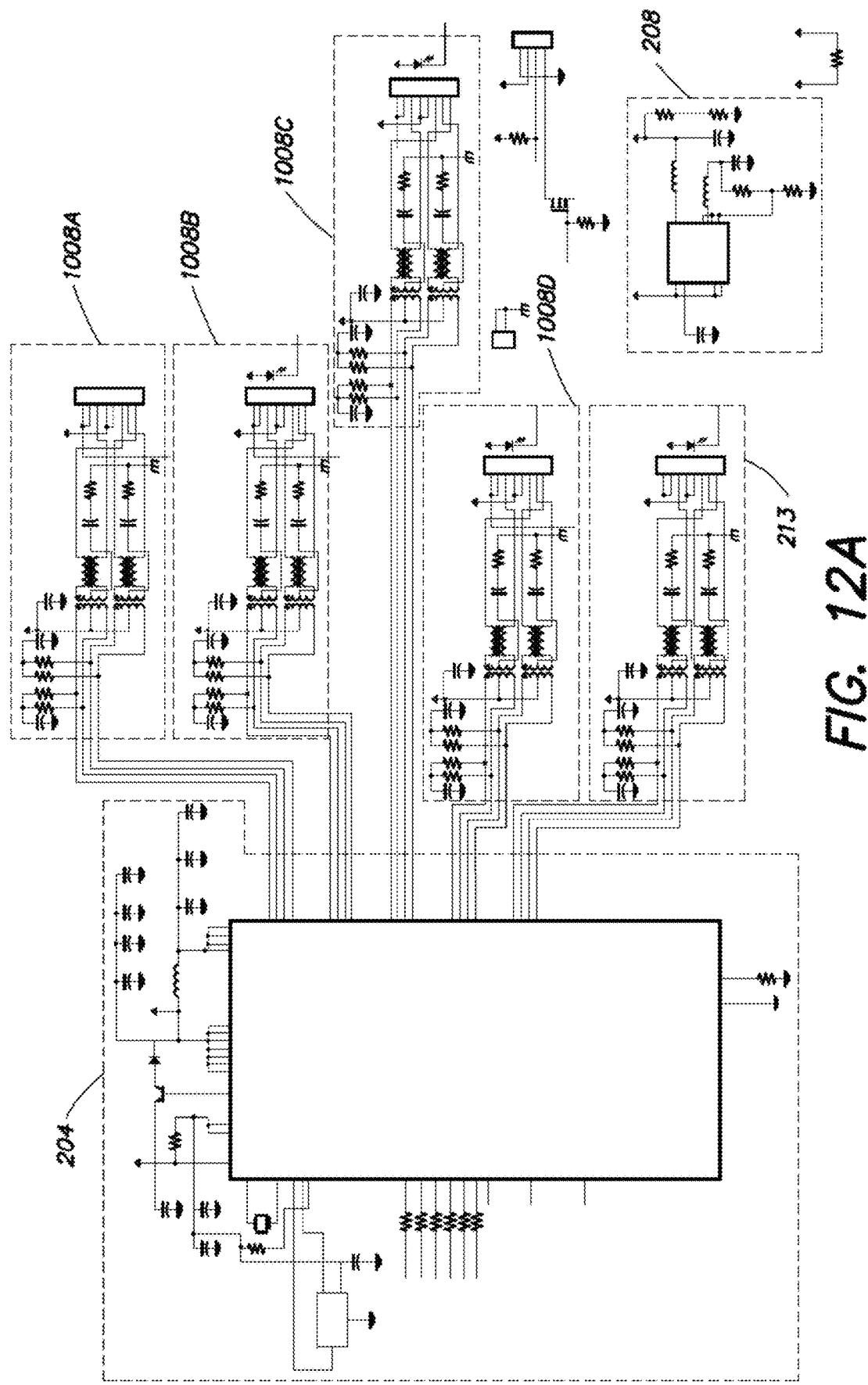
FIG. 12A is a circuit diagram detailing various electronic components of a network board, according to some implementations of the disclosure.
Figure 12B:
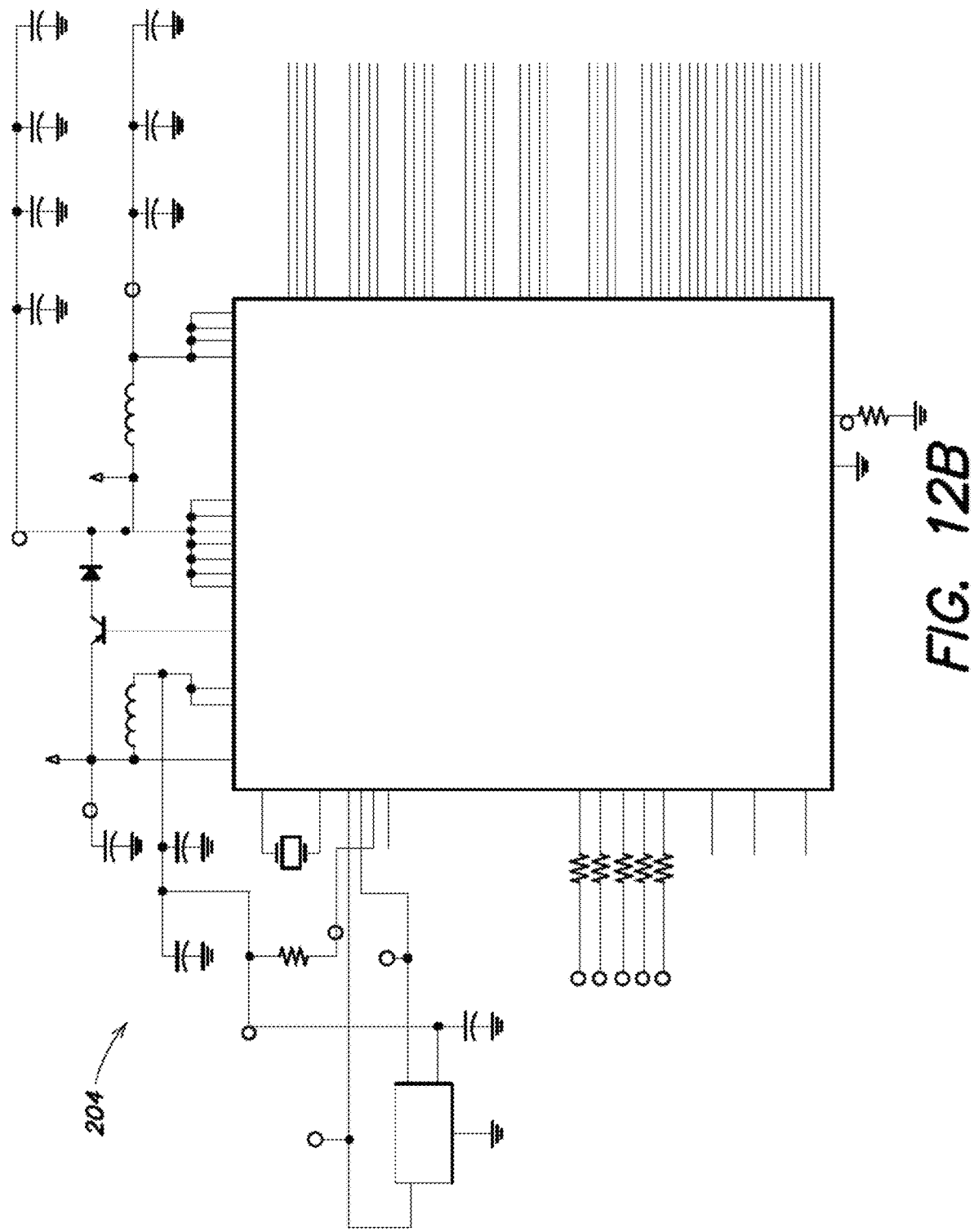
FIG. 12B is an expanded view of the Ethernet switch of FIG. 12A.
Figure 12D:
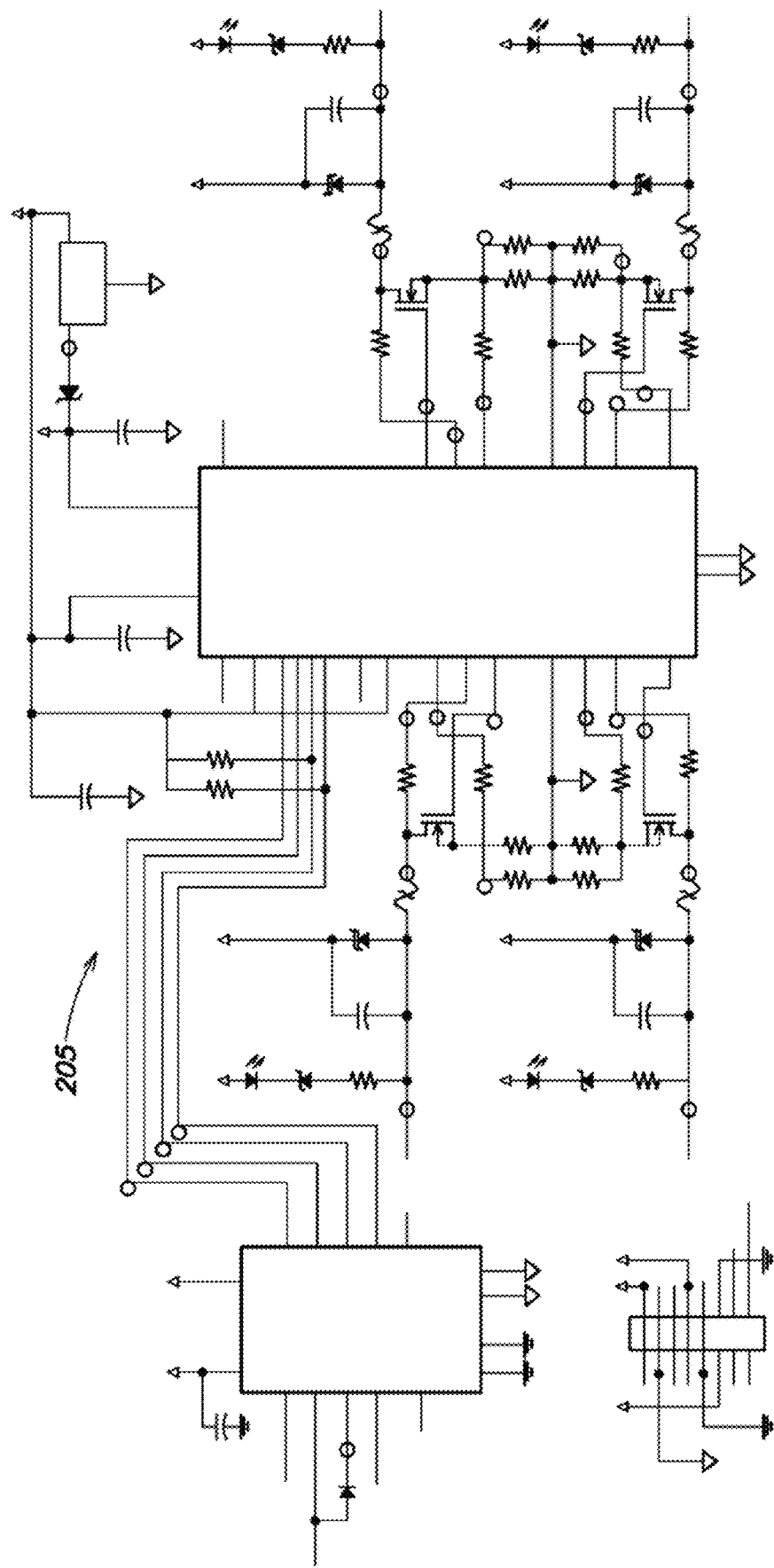
FIG. 12D is a circuit diagram of the PoE controller of FIG. 12A.
Figure 13:
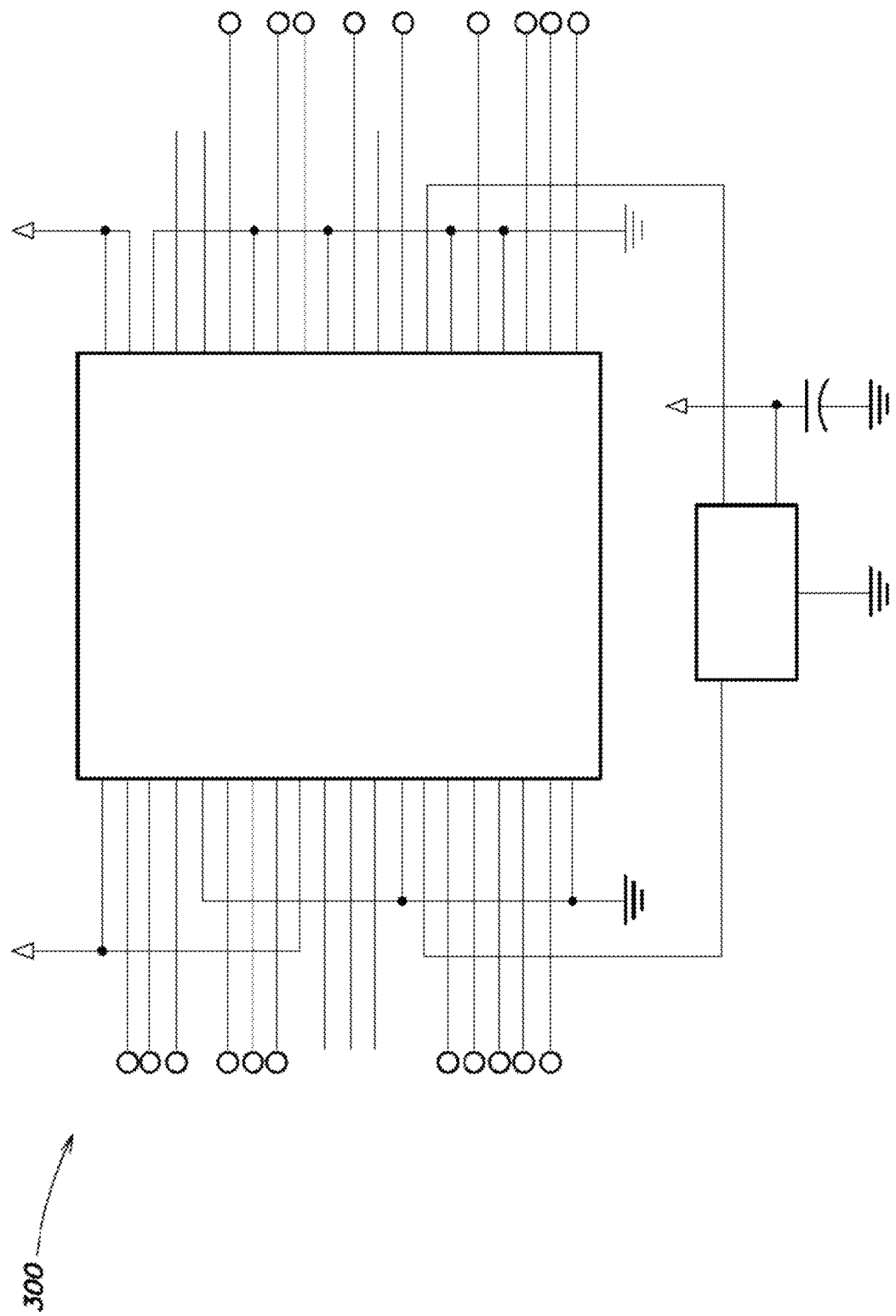
FIG. 13 is a circuit diagram of a single board computer, according to some implementations of the disclosure.
Figure 14A:
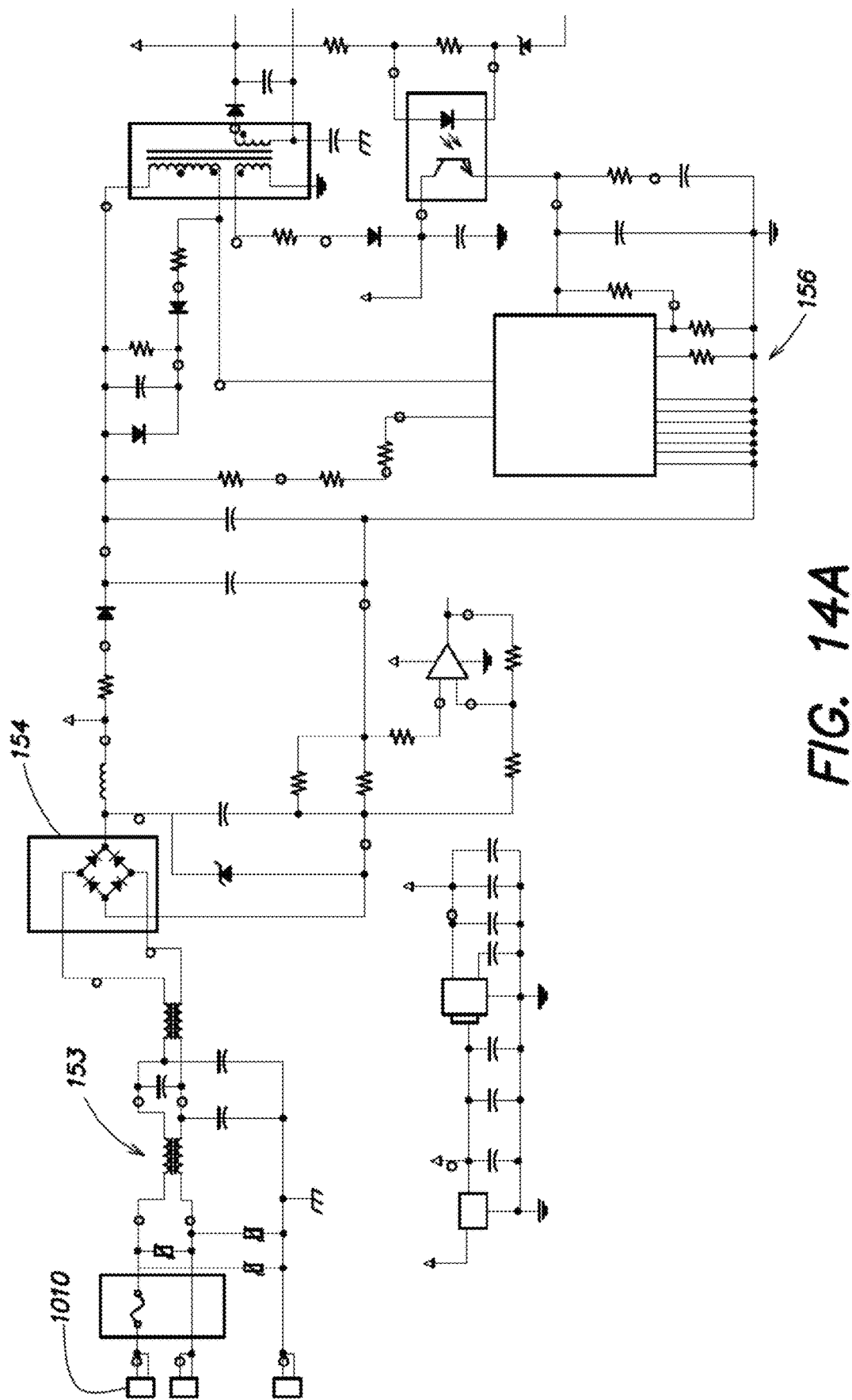
FIG. 14A is a circuit diagram detailing various electrical components of a control board, according to some implementations of the disclosure.
Figure 14B:
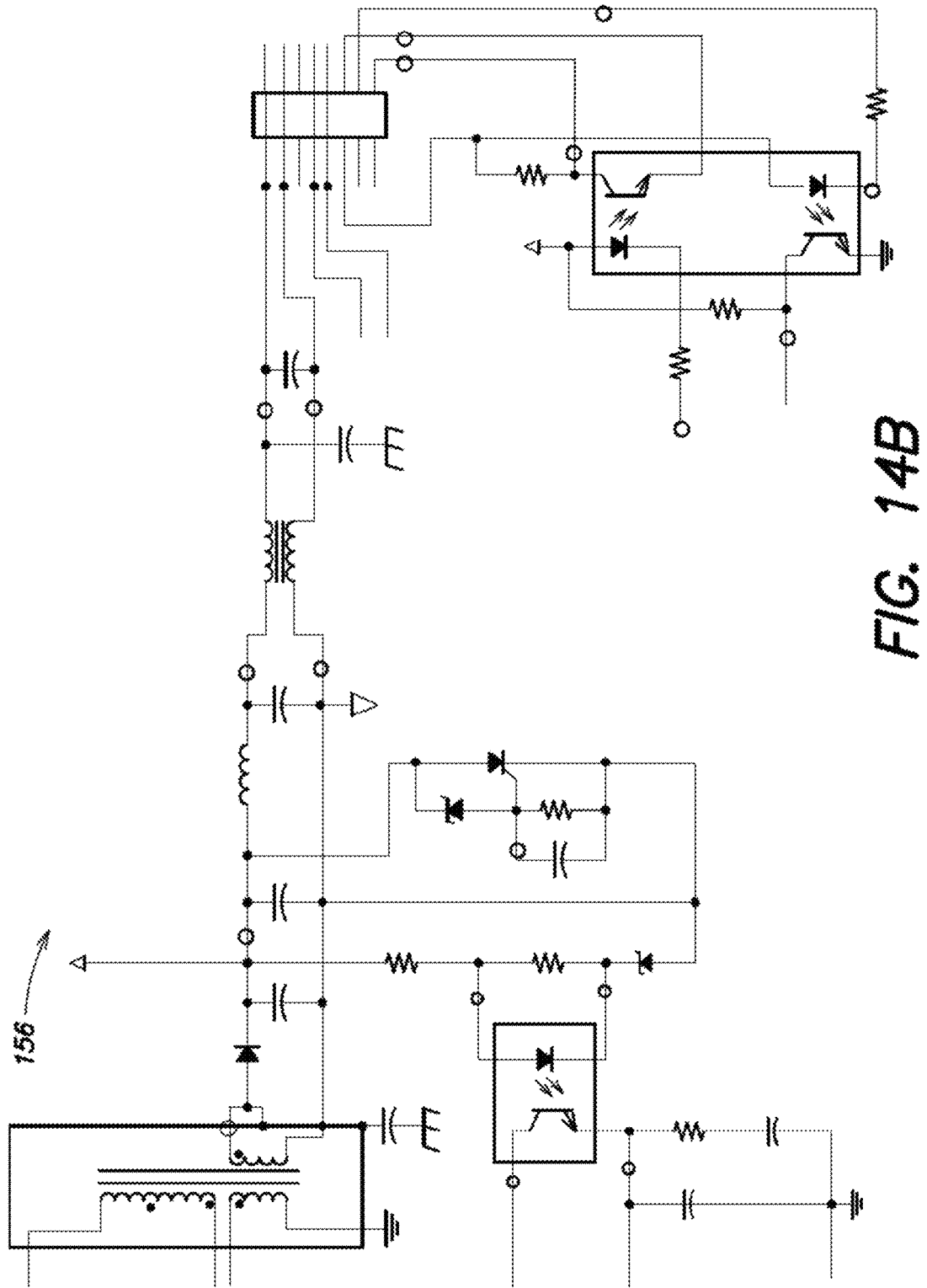
FIG. 14B is a circuit diagram detailing the bias and control power supply of the control board of FIG. 14A.
Figure 14C:
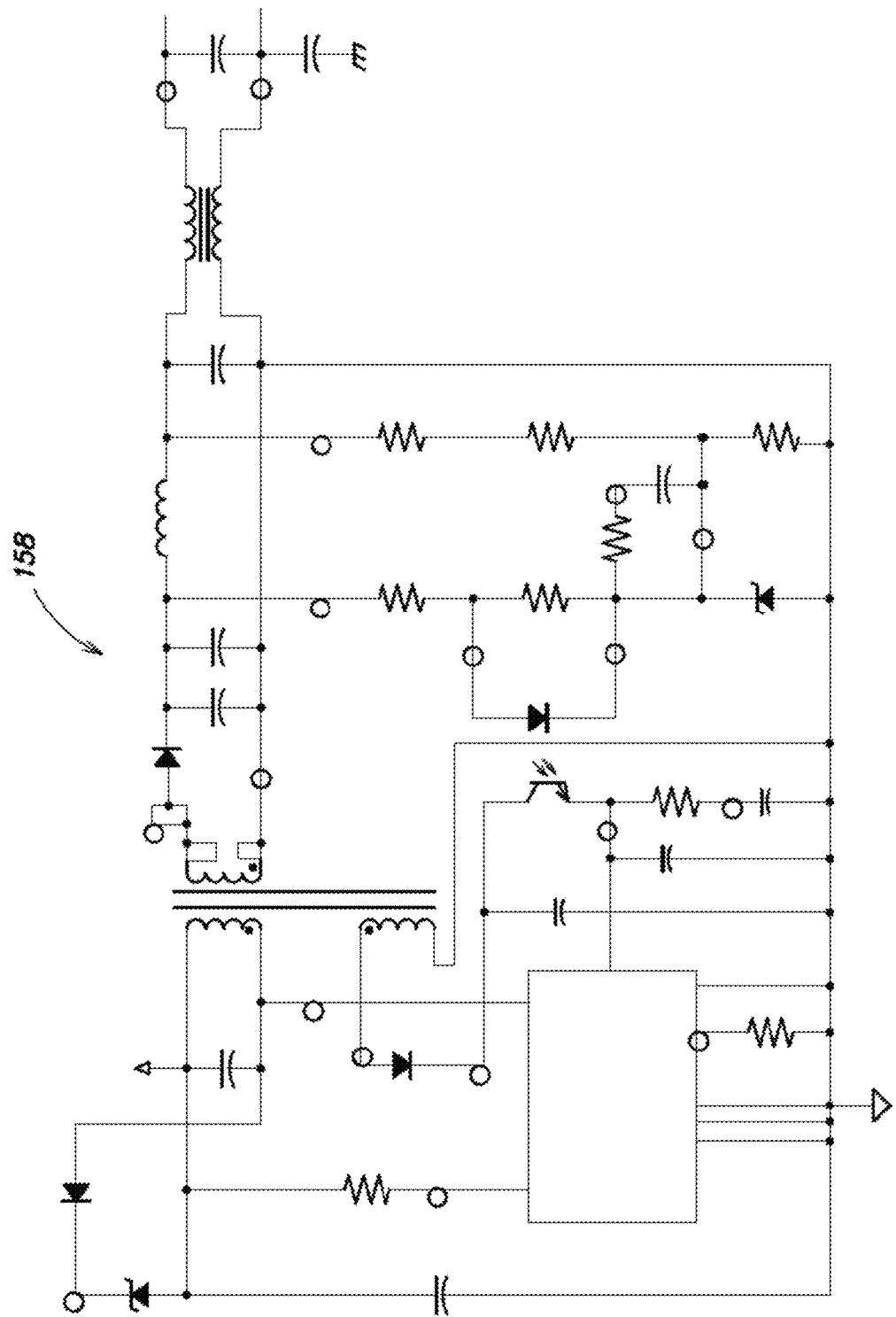
FIG. 14C is a circuit diagram detailing the DC-DC converter of the control board of FIG. 14A.
Figure 14D:
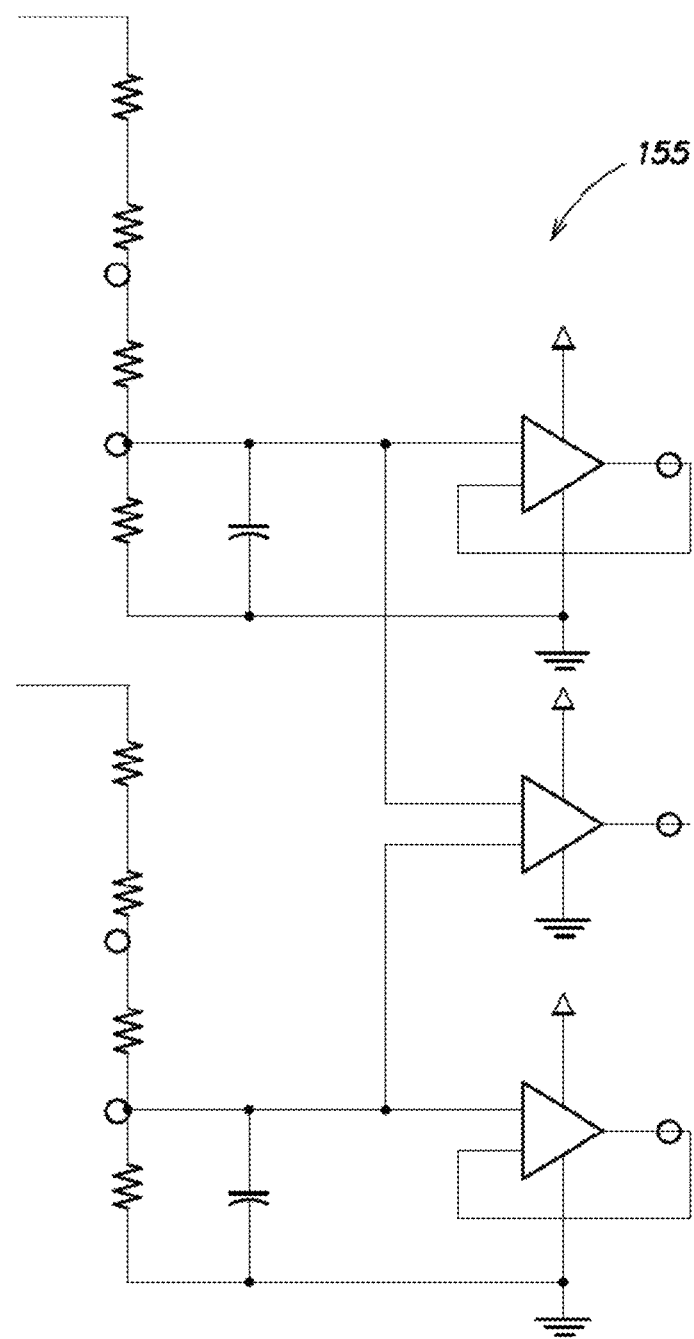
FIG. 14D is a circuit diagram detailing the AC line sensor of the control board of FIG. 14A.
Figure 14E:
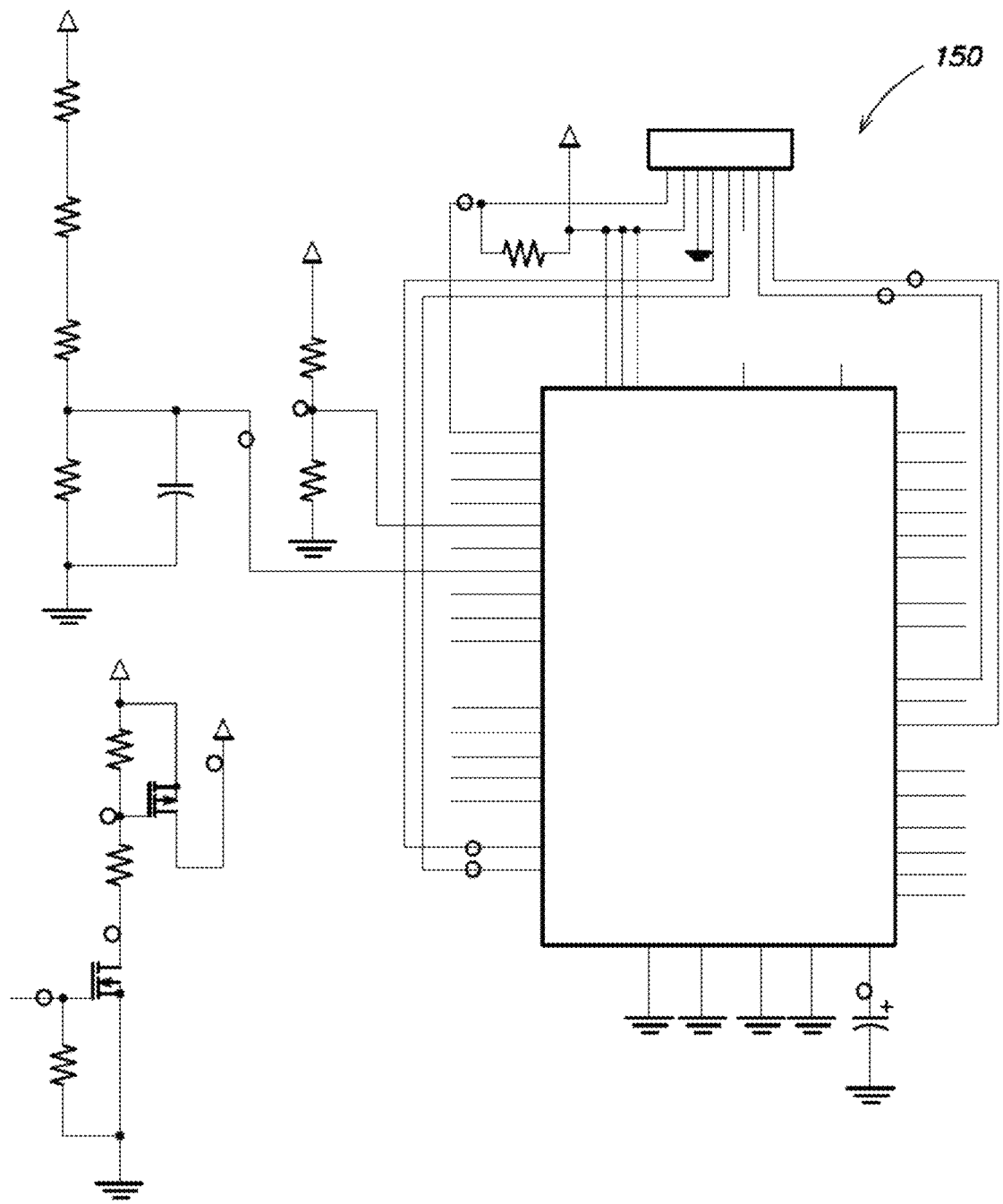
FIG. 14E is a circuit diagram detailing the DSP of the control board of FIG. 14A.
Figure 14F:
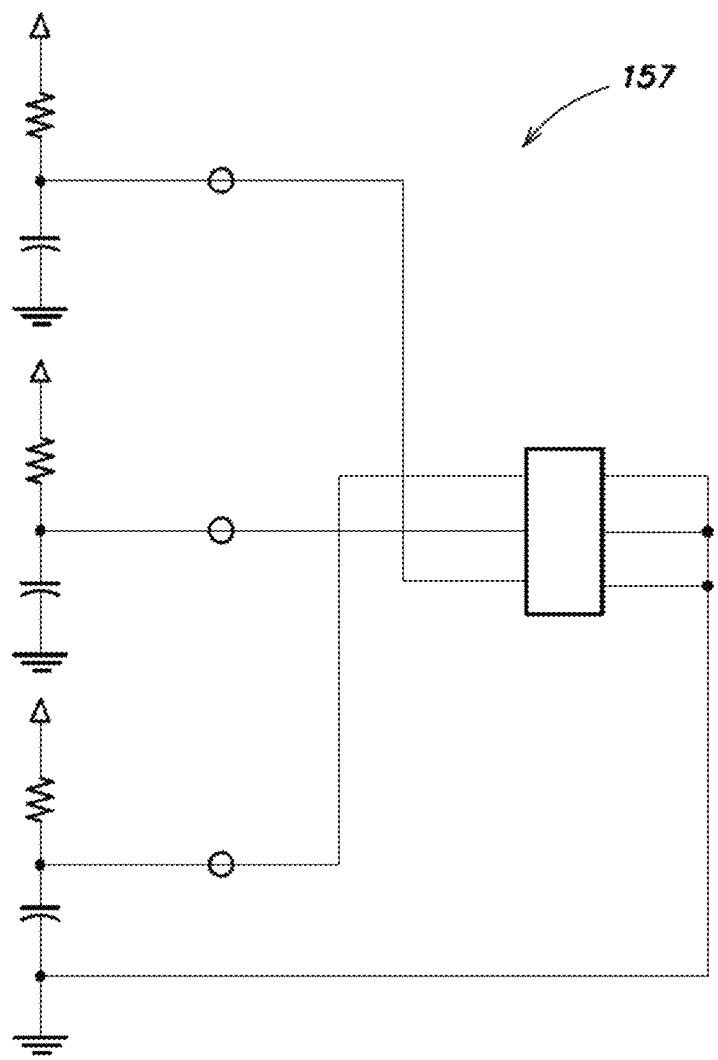
FIG. 14F is a circuit diagram detailing the temperature sensor circuitry of the control board of FIG. 14A.
Figure 14G:
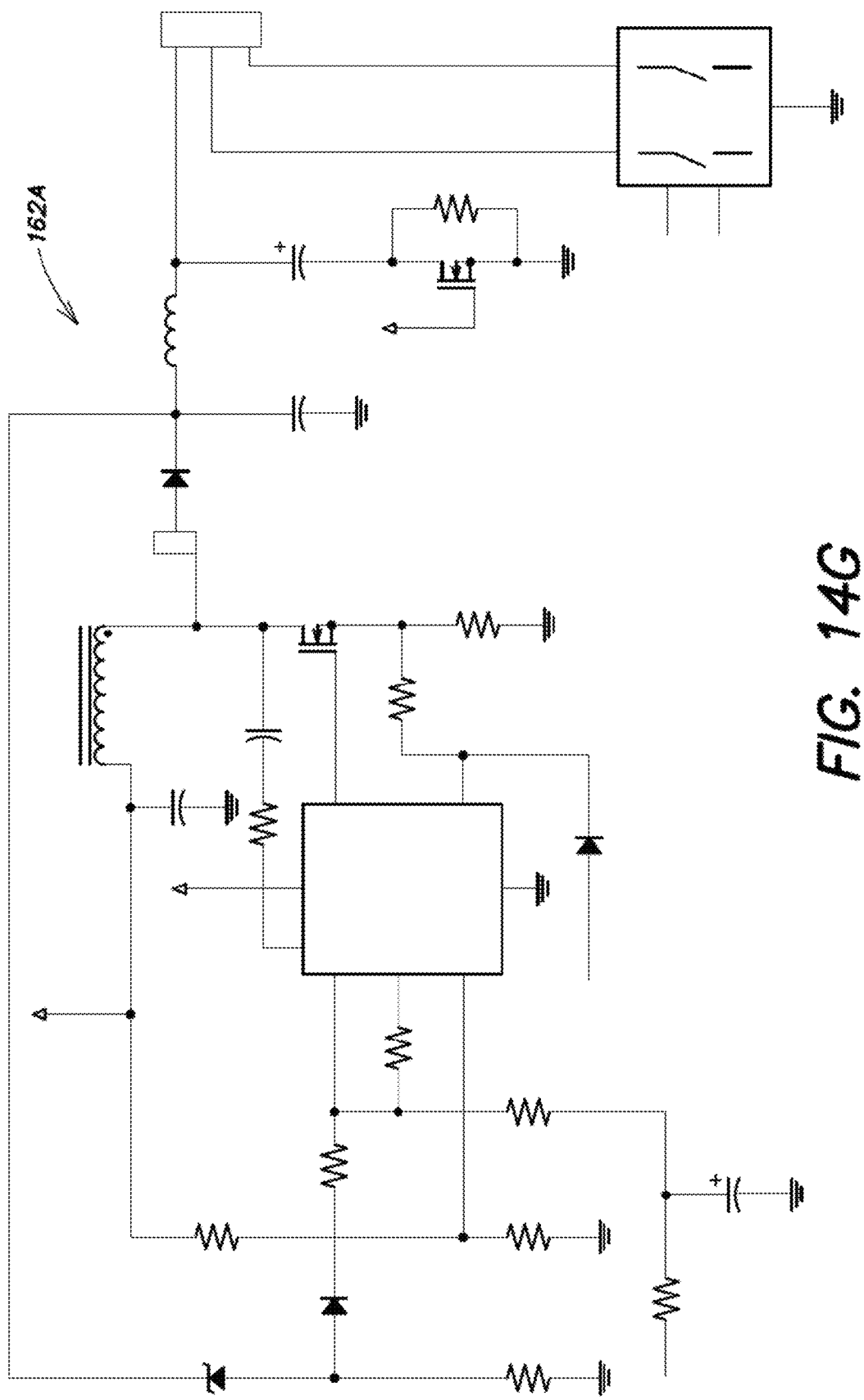
FIG. 14G is a circuit diagram detailing the boost circuit of the control board of FIG. 14A.
Figure 14H:
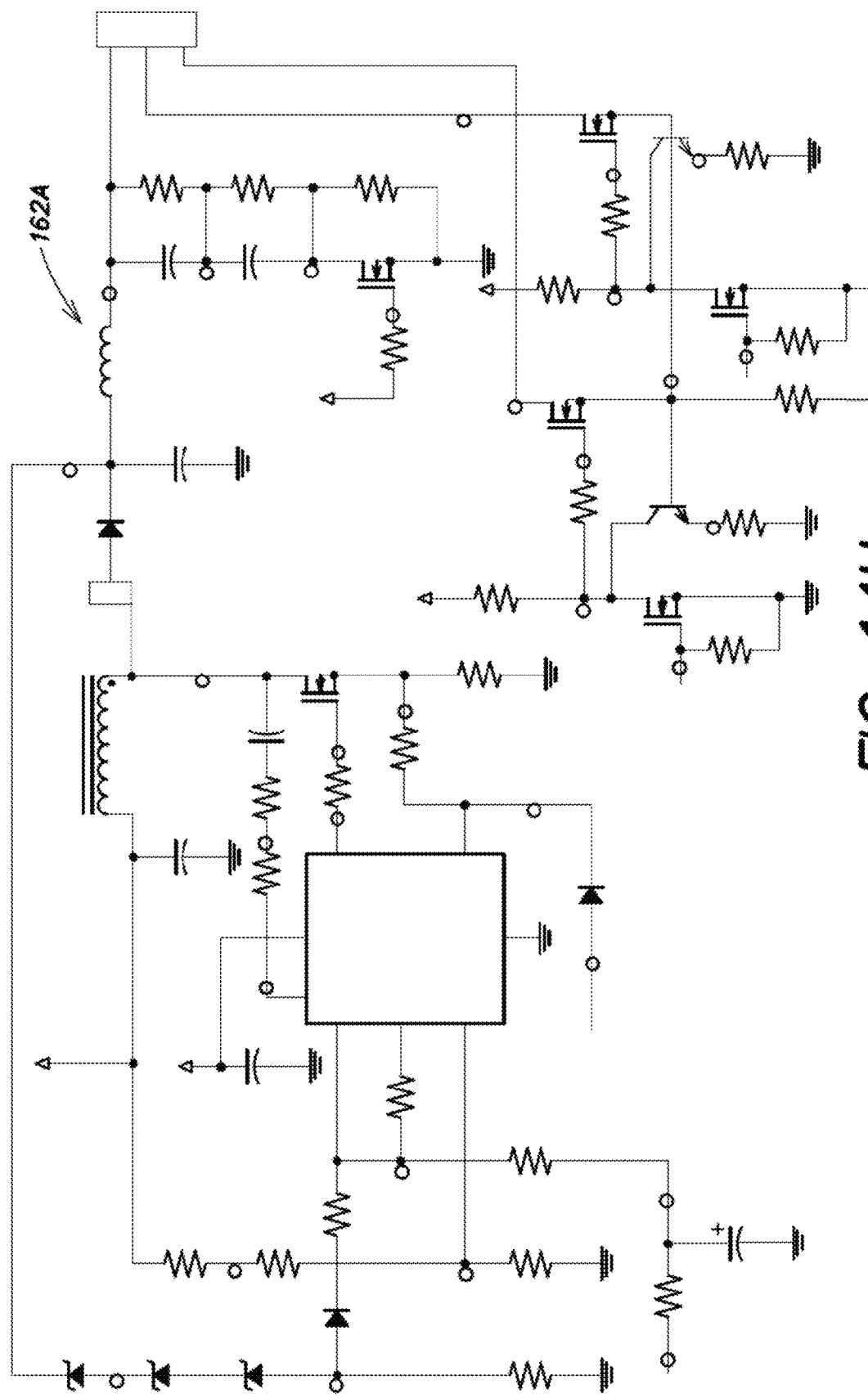
FIG. 14H is a circuit diagram further detailing the boost circuit of FIG. 14G.

FIGS. 12A-12D, 13, 14A-14H show circuit diagrams of various electrical components of a processor 90 according to one implementation. FIG. 12A shows a circuit diagram of an Ethernet switch 204 from a network board 200 and the electrical connections to PoE ports 1008A-1008D and an Ethernet port 213 for communication to a single board computer 300. FIG. 12A also shows a circuit diagram of a power supply 208 from the network board 200. For visual clarity, FIGS. 12B and 12C show expanded views of the Ethernet switch 204 and the PoE port 1008D from FIG. 12A, respectively. FIG. 12D shows a circuit diagram of a PoE controller 206 from the network board 200. FIG. 13 shows a circuit diagram of a single board computer 300 detailing various input and output connections. FIG. 14A shows circuit diagrams for an electrical power port 1010, fuse/EMI filter 153, a rectifier 154, and a first portion of a bias and control power supply 156 from a control board 100. FIG. 14B shows a second portion of the bias and control power supply 156 shown in FIG. 14A. FIGS. 14C-14F show a DC-DC converter 158, an AC line sensor 155, a DSP 150, and thermal sensor ports 154 from the control board 100. FIGS. 14G and 14H show circuit diagrams of an exemplary boost circuit 162A from the control board 100.

The lighting fixture 1000 disclosed herein may also be utilized in a leased lighting system where a customer pays a recurring fee to rent and operate the lighting fixture 1000 (e.g., provide lighting using the lighting fixture 1000). In this system, the costs typically associated with purchasing the lighting fixture 1000 hardware and installation may be substantially reduced, thus providing substantial savings to the customer. The manufacturer providing the operation of the lighting fixture 1000 may earn a profit over time through continuing payments by the customer. In some implementations, the leased lighting system may be based on payment of a fee to operate the lighting fixture 1000 for a preset period of time. The lighting fixture 1000 may be communicatively coupled to a server via the processor 90. The server may remotely regulate operation of the lighting fixture, enabling the lighting fixture 1000 to provide lighting so long as the customer provides necessary payment to maintain the lease.

Figure 15A:
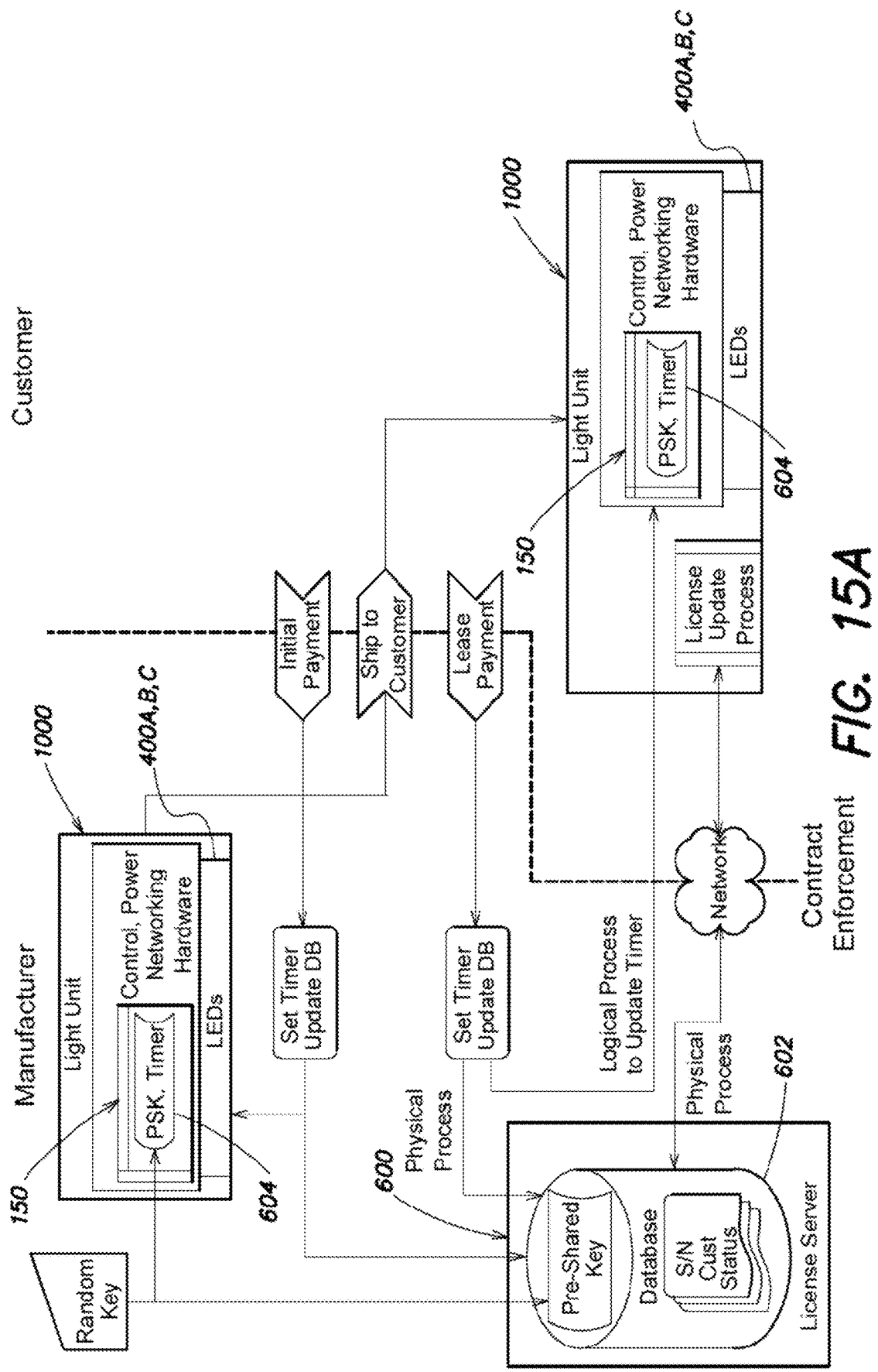
FIG. 15A is a flow diagram of a contract enforcement method, according to some implementations of the disclosure.

An exemplary implementation of a contract enforcement method where the lighting fixture 1000 is communicatively coupled to a license server 600 is shown in FIG. 15A. As shown, the license server 600 may include a database 602 containing information including, but not limited to a serial number for one or more lighting fixtures 1000 installed by a customer and a customer status (e.g., a payment status) for the customer to which the one or more lighting fixtures 1000 are leased. The database may also include a pre-shared key 604, which is also installed onto each lighting fixture 1000, e.g., such as in protected internal storage of the DSP 150 of the lighting fixture 1000, by the manufacturer, together with a timer, prior to shipment to the customer. Upon initial payment by the customer, the manufacturer may setup an initial timer update in the database 1000 to provide for some time period for initial lighting, after which an additional lease payment is required. Once the lighting fixture 1000 is deployed to the customer, the expiration of the timer may trigger a license update process. Once the additional lease payment is made, the manufacturer operating the license server 600 may update the database 602 with a new timer value, which is communicated to the lighting fixture 1000. Communication may occur via a proprietary communication protocol.

Figure 15B:
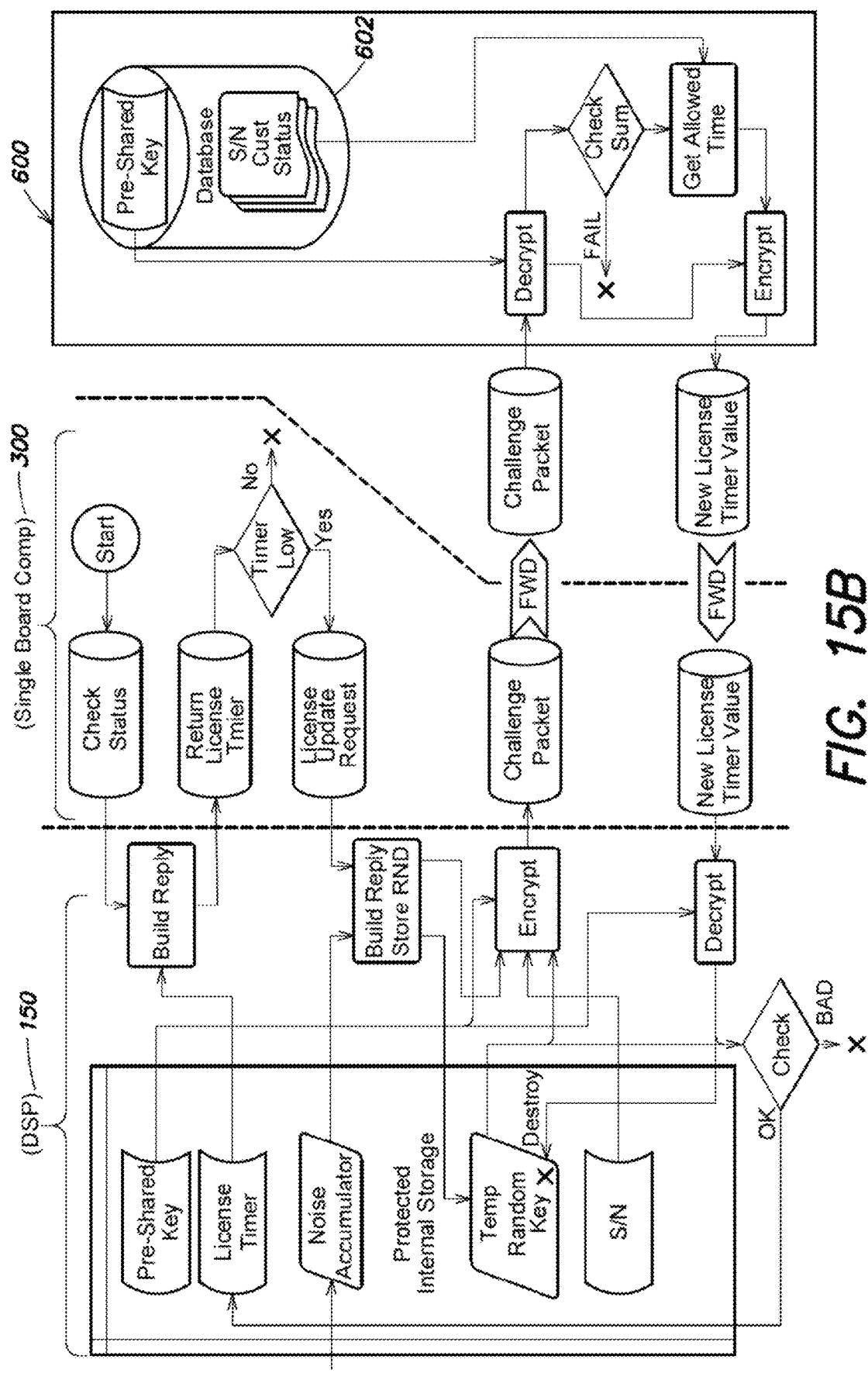
FIG. 15B is a flow diagram of a method to update a license in a leased lighting system, according to some implementations of the disclosure.

An exemplary implementation of a process to update a license for a leased lighting model with one or more lighting fixtures 1000 is shown in FIG. 15B. In this exemplary process, the DSP 150 and the single board computer 300 of the processor 90 may be coupled to the license server 600 and database 602 via the Internet to facilitate operation by the manufacturer of the one or more lighting fixtures 1000 or a leasing agent. As described above, the pre-shared key 604 and license timer may be stored in the protected internal storage of the DSP 150 by the manufacturer together with the serial number of the lighting fixture 1000. The single board computer 300 may periodically check the status of the license timer. Once the license timer is near expiration, the single board computer 300 may initiate with the DSP 150 a license update request. This request may include a "challenge packet" generated by the DSP 150, which is forwarded by the single board computer 300 to the license server 600. The challenge packet may include encrypted information based, at least in part, on the serial number of the lighting fixture 1000 and a temporary random key generated using a noise accumulator. The challenge packet may then be decrypted by the license server 600. If the challenge packet is found to be valid and payment is made for additional lighting, the license server 600 may then determine a new allowed timer value. The new allowed timer value may then be encrypted and sent back to the single board computer 300, which passes the encrypted timer value to the DSP 150. The DSP 150 may then decrypt the new timer value based on the pre-shared key 604. If the new timer value is found to be valid, the DSP 150 may update the license timer stored in the protected internal storage of the DSP 150.

An Exemplary Integrated Sensor Assembly

Based on the various concepts described above and illustrated in the accompanying drawings, various inventive implementations of an integrated sensor assembly for CEA systems will now be described. As described in the foregoing, sensors can be deployed in a controlled agricultural environment to monitor environmental conditions and to provide feedback to lighting, heating and/or cooling (e.g., via hydronics and/or other techniques), air flow, and humidity conditioning systems to facilitate control of growth conditions for plants. In some implementations, the sensors can be packaged as a single integrated assembly that utilizes a single port to receive electrical power and communicate data. In this manner, multiple sensing modalities can be added to CEA systems to augment monitoring of environmental conditions to improve the growth conditions of plants while simplifying installation and reducing maintenance. Furthermore, multiple integrated sensor assemblies can be deployed to cover larger areas of the agricultural environment to also monitor variations in growth conditions across the agricultural environment.

Figure 16A:
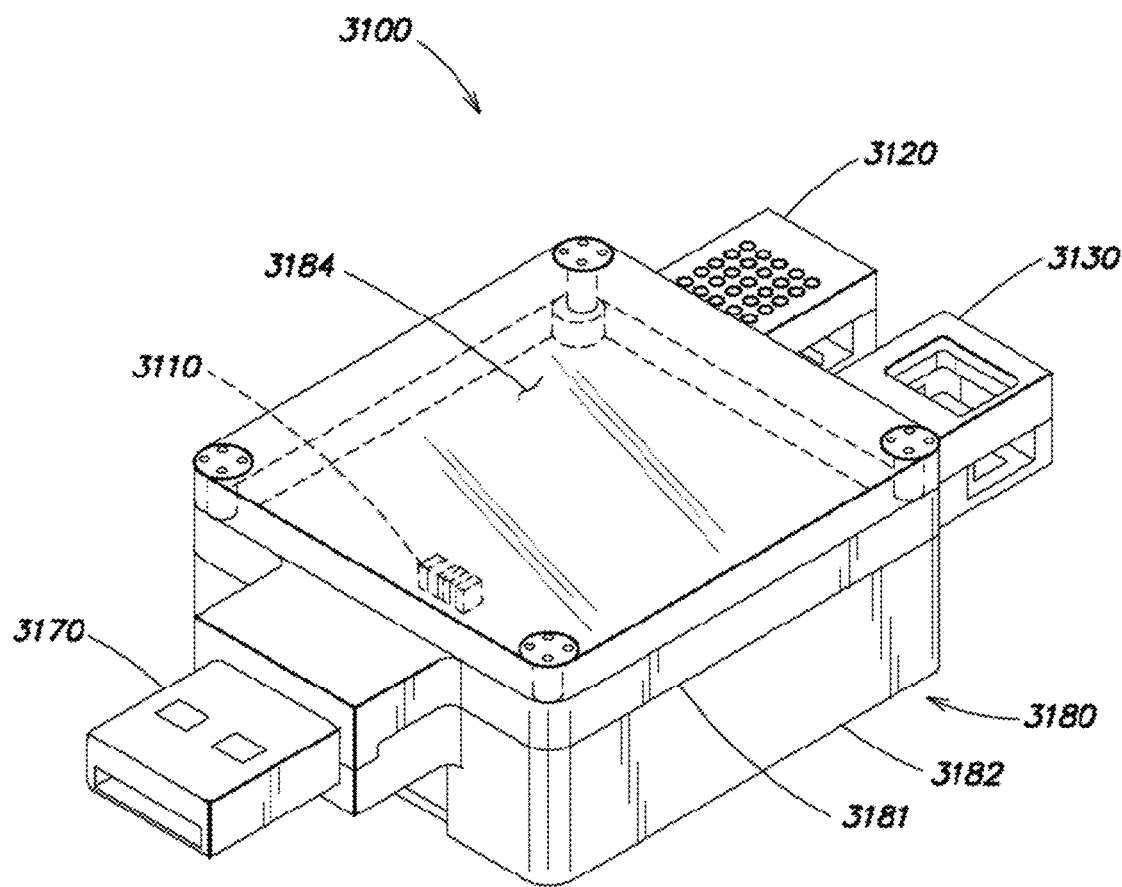
FIG. 16A is a top perspective view of an integrated sensor assembly according to some implementations of the disclosure.
Figure 16B:
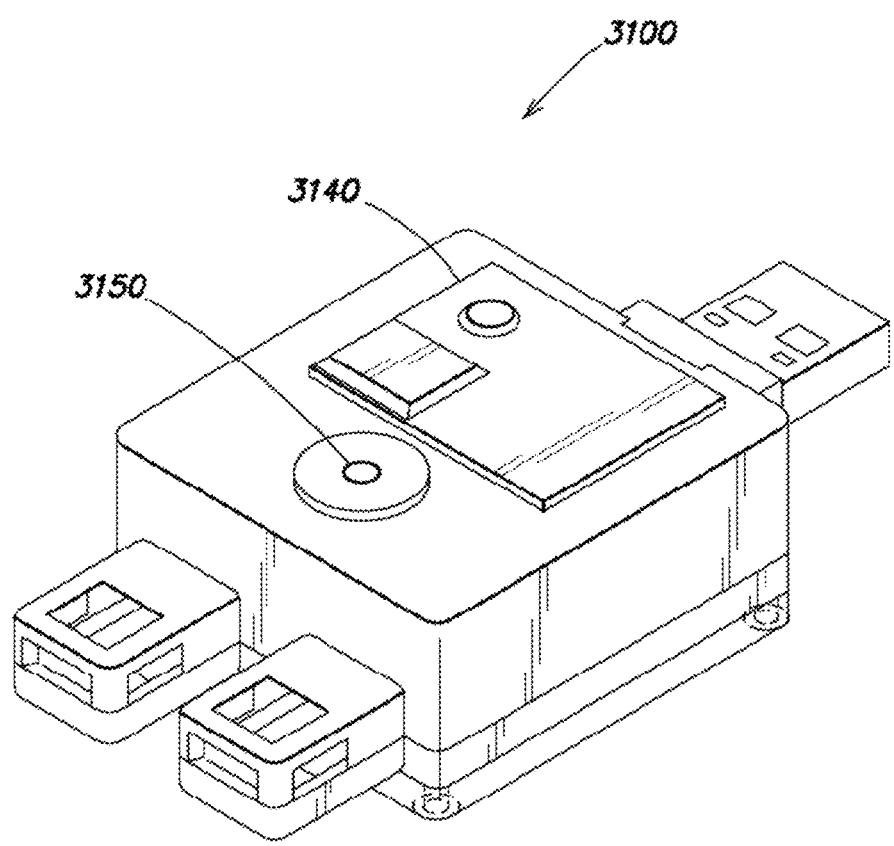
FIG. 16B is a bottom perspective view of the integrated sensor assembly shown in FIG. 16A according to some implementations of the disclosure.
Figure 16C:
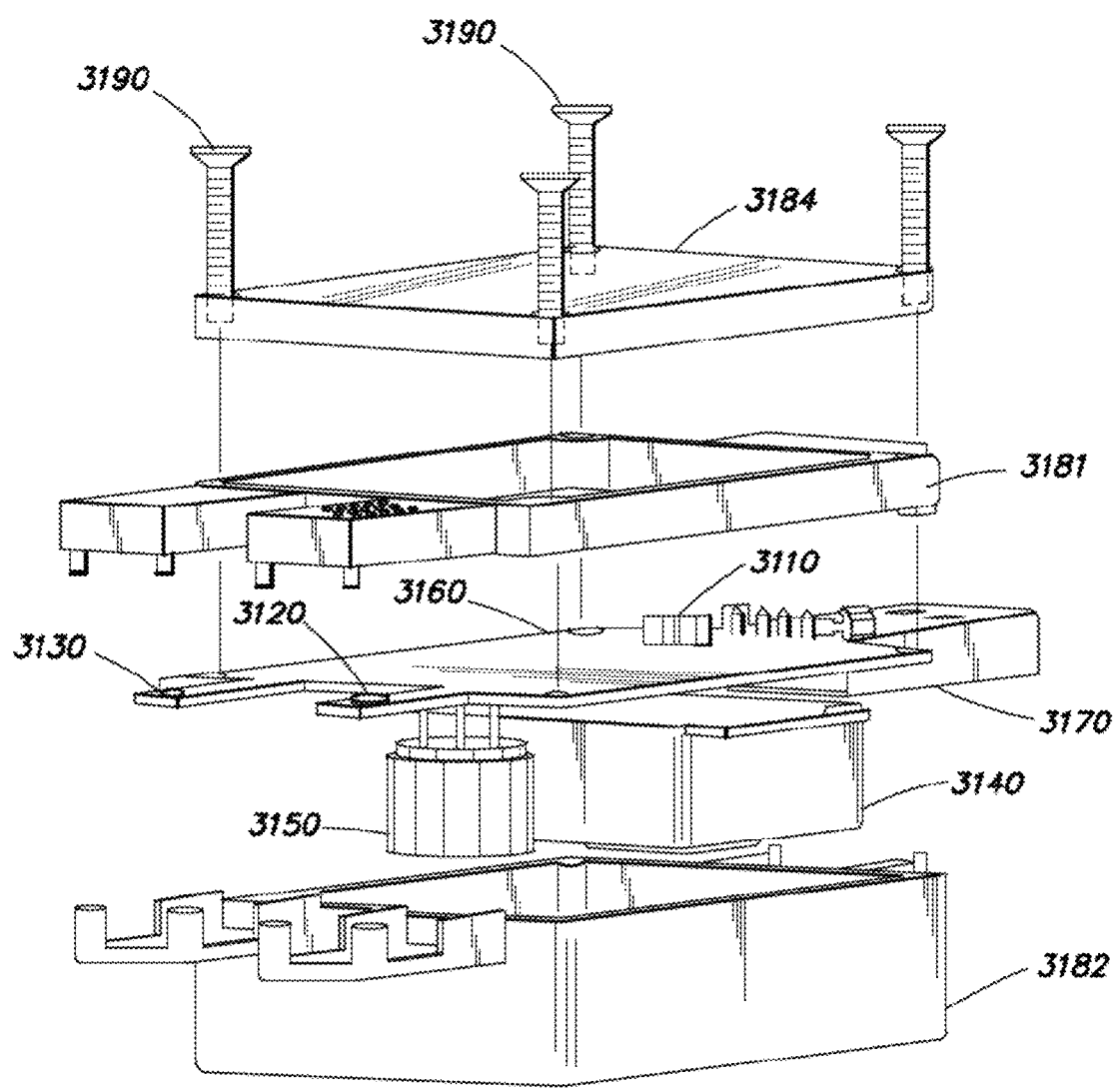
FIG. 16C is an exploded side view of the integrated sensor assembly shown in FIG. 16A according to some implementations of the disclosure.
Figure 16D:
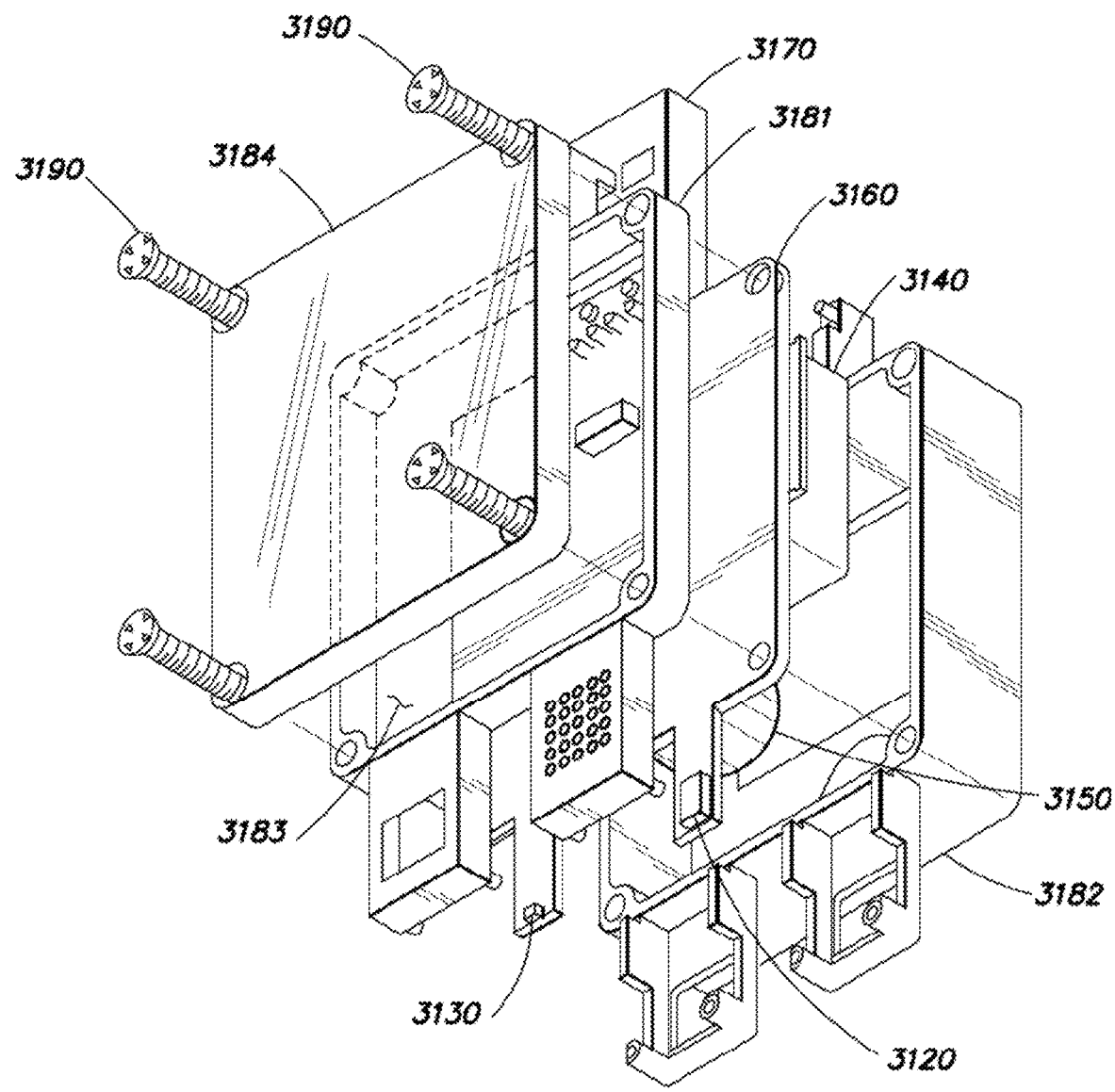
FIG. 16D is an exploded top perspective view the integrated sensor assembly shown in FIG. 16A according to some implementations of the disclosure.

An exemplary implementation of an integrated sensor assembly 3100 is shown in FIGS. 16A and 16B. The assembly 3100 includes multiple sensors to monitor various parameters relevant to the growth of plants, such as a visible light sensor 3110, a combined temperature and relative humidity sensor 3120, an air flow sensor 3130, a CO2 sensor 3140, and an IR temperature sensor 3150. The sensors can be mounted on a circuit board 3160, which can also include a USB port 3170 to provide electrical power and communication between the integrated sensor assembly 3100 and an external power and control system (e.g., a lighting fixture 1000 as described above). A housing 3180 can be used to protect the sensors and circuitry disposed on the circuit board 3160. As shown in FIG. 16C, the circuit board 3160 can be positioned inside a cavity defined by a housing top 3181 and a housing bottom 3182, which are assembled using a plurality of coupling members 3190. In some implementations, the housing top 3181 can include an open aperture 3183, as shown in FIG. 16D, which can be covered by a lens 3184 to allow light to transmit through the housing for detection by the visible light sensor 3110 while protecting the sensors and circuitry contained within the housing.

Figure 16E:
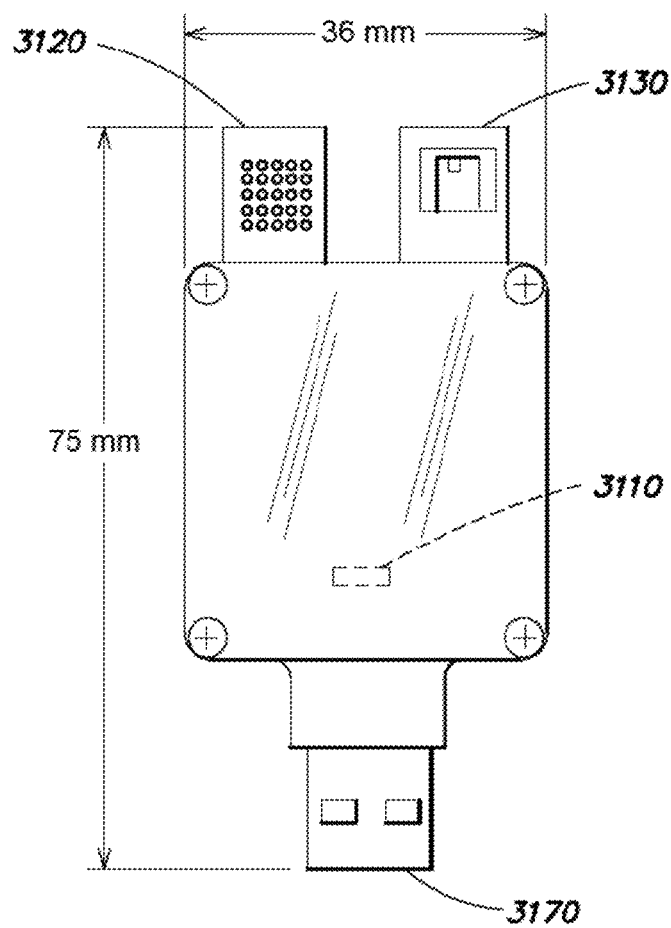
FIG. 16E is a top view the integrated sensor assembly shown in FIG. 16A according to some implementations of the disclosure.
Figure 16F:
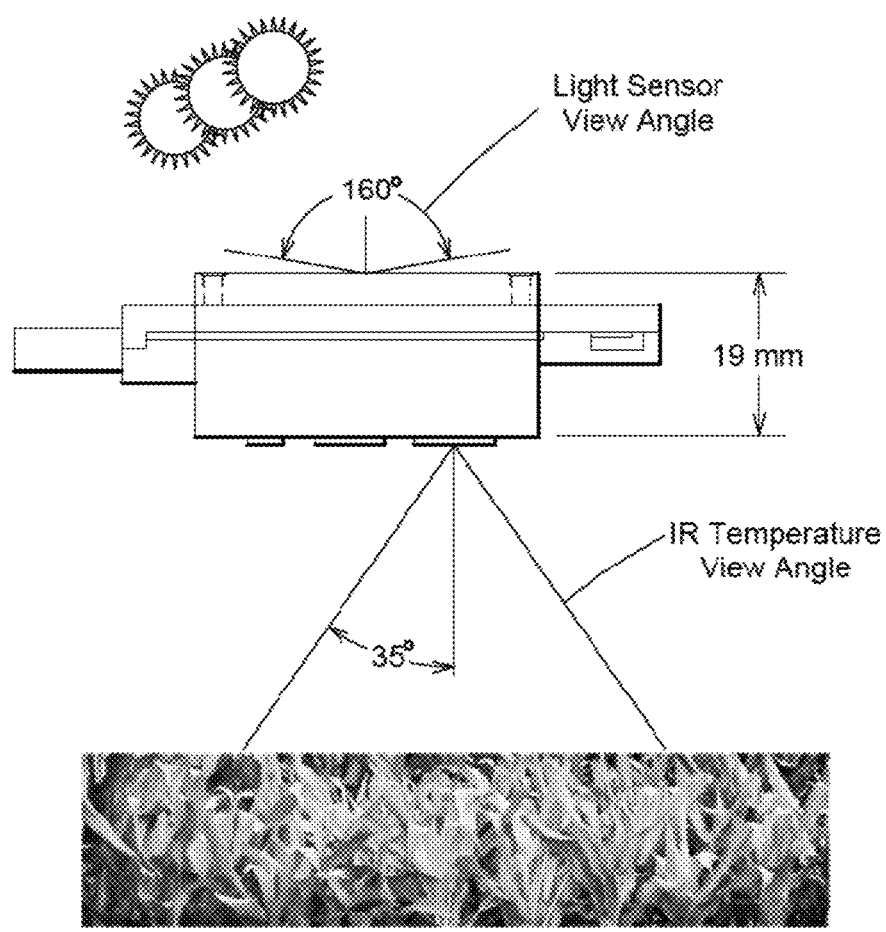
FIG. 16F is a side view of the integrated sensor assembly shown in FIG. 16A detailing the field of view of various sensors according to some implementations of the disclosure.

The visible light sensor 3110 can be used to monitor light emitted by natural or artificial light sources, e.g., sunlight or LED lighting, incident on plants in the agricultural environment. In particular, the visible light sensor 3110 can be configured to measure the photosynthetic photon flux density (PPFD), which is a measure of photon flux per unit area integrated over a wavelength spectrum. The visible light sensor 3110 can be various suitable types of light detectors including, but not limited to, photodiodes, thermopiles, and pyroelectric detectors. In some implementations, the visible light sensor 3110 can be configured to be spectrally sensitive to PAR light in the visible spectrum and ultraviolet radiation, e.g., UVA and UVB ranges, using filters, coatings, or different materials for detection. In other implementations, the visible light sensor 3110 can be configured to be a spectrometer to characterize the spectral components of the light source. As shown in FIG. 16E, the visible light sensor 3110 can be positioned near the top of the integrated sensor assembly 3100 and oriented to face a light source for detection. The visible light sensor 3110 can also be configured to detect light across a range of viewing angles, e.g., from normal incidence at 0 degrees to oblique incidence up to 80 degrees, as shown in FIG. 16F, in cases where the light source can illuminate plants at different angles of incidence, e.g., variations in sunlight during the day. Two examples of a light sensor 3110 is given by a Vishay VEML6075 and VEML7700.

The combined temperature and relative humidity sensor 3120 can be used to monitor the temperature and water vapor concentration in the growing environment. The temperature sensing element in the combined temperature and relative humidity sensor 3120 can be various suitable types of temperature sensors including, but not limited to, a thermocouple, a thermistor, and a resistance temperature detector (RTD). The relative humidity sensing element can be various suitable types of humidity sensor including, but not limited to, capacitive, resistive, or thermal sensors. Examples of a combined temperature and relative humidity sensor 3120 are given by a Texas Instruments HDC1010YPAR and a Sensiron SHT31. As shown in FIG. 16D, the combined temperature and relative humidity sensor 3120 can be positioned on a protruding member of the circuit board 3160 such that the sensing elements are exposed to air surrounding the integrated sensor assembly 3100. In some implementations, the housing near the combined temperature and relative humidity sensor 3120 and other sensing elements in the integrated sensor assembly 3100 can be configured such that measurements of the temperature and relative humidity are not significantly influenced by the integrated sensor assembly 3100. For example, the housing can include a plurality of openings to facilitate air flow and the combined temperature and relative humidity sensor 3120 can be positioned relatively far from heat sources near the integrated sensor assembly 3100, e.g., heat dissipated by a lighting fixture.

The air flow sensor 3130 can monitor air circulation, which can provide insight to the directionality of air flow, uniformity of temperature, detection of leaks, and the performance of air flow and ventilation systems deployed in the agricultural environment. The air flow sensor 3130 can be various suitable types of air flow sensors including, but not limited to, air flow meters, hot wire anemometers, and sonic anemometers. One example of an air flow sensor 3130 is given by a TDK Thermistor 470 NTC 0402 with accompanying resistors, capacitors, and operational amplifiers. As shown in FIG. 16D, the air flow sensor 3130 can be positioned on a protruding member of the circuit board 3160 such that the sensor is exposed to air surrounding the integrated sensor assembly 3100. In some implementations, the housing near the air flow sensor 3130 and other sensing elements in the integrated sensor assembly 3100 can be configured to reduce disruptions in air flow near the air flow sensor 3130 to enable more accurate measurements of air flow. For example, the housing can include a plurality of openings to allow air to freely flow across the air flow sensor 3130.

In agricultural environments, the concentration of $CO_2$ is an important parameter governing the growth of plants since plants absorb $CO_2$ during photosynthesis. Furthermore, the photosynthetic activity of plants can vary throughout the day; hence, the amount of absorbed $CO_2$ can also vary accordingly. The $CO_2$ sensor 3140 can thus be used to monitor the concentration of $CO_2$ near the plants in the agricultural environment. The $CO_2$ sensor 3140 can be various suitable types of $CO_2$ sensors including, but not limited to, non-dispersive infrared (NDIR) sensors and chemical $CO_2$ sensors. One example of a $CO_2$ sensor 3140 is given by a Winsensor MH-Z19. In some implementations, the $CO_2$ sensor 3140 can be an enclosed device electrically coupled to the circuit board 3160 for operation, as shown in FIG. 16C. Furthermore, the $CO_2$ sensor 3140 can be positioned on the bottom of the integrated sensor assembly 3100 such that the sensing elements of the $CO_2$ sensor 3140 are oriented towards the plants. Such configurations can be preferable to increase air flow across the $CO_2$ sensor 3140 since convective currents near the plants can drive air upwards towards the bottom of the integrated sensor assembly 3100. In some implementations, the $CO_2$ sensor 3140 can further protrude through the housing bottom 3182 to reduce obstructions to air flow and thus provide more accurate measurements of $CO_2$ concentrations.

As described above, the combined temperature and relative humidity sensor 3120 can monitor the air temperature near the plants, which is an important parameter governing plant growth. In addition, it is also instructive to monitor the surface temperature of the plants, as the surface temperature of the plants may differ due to irradiation by light and convective heat transfer from the plant to the surrounding air. The IR temperature sensor 3150 can thus be used to remotely monitor the temperature of plants near the integrated sensor assembly 3100 by measuring IR radiation emitted from the plants. In some implementations, the IR temperature sensor 3150 can be a single pixel sensor that measures an average temperature within a particular field of view. In other implementations, the IR temperature sensor 3150 can be a multi-pixel camera capable of recording IR images to discern temperature gradients within a single plant or between neighboring plants. The IR temperature sensor 3150 can be various suitable types of IR sensors including, but not limited to, pyroelectric detectors and bolometers. Furthermore, the IR temperature sensor 3150 can be configured to be spectrally sensitive to long wavelength infrared (LWIR) radiation, midinfrared (MIR) radiation, or near-infrared (NIR) radiation. In some implementations, the IR temperature sensor 3150 can be configured to be a spectrometer, e.g., a Fourier transform infrared (FTIR) spectrometer, to characterize the spectral components of the radiation emitted by the plants. The IR temperature sensor 3150 can be configured to have a wide field of view to cover a larger area of plants. For implementations where the IR temperature sensor 3150 is a multi-pixel camera, the IR temperature sensor 3150 can also be configured to record images at sufficient spatial resolution to discern the temperature of individual leaves on a plant. One example of an IR temperature sensor 3150 is given by Melexis MLX90614.

Figure 17A:
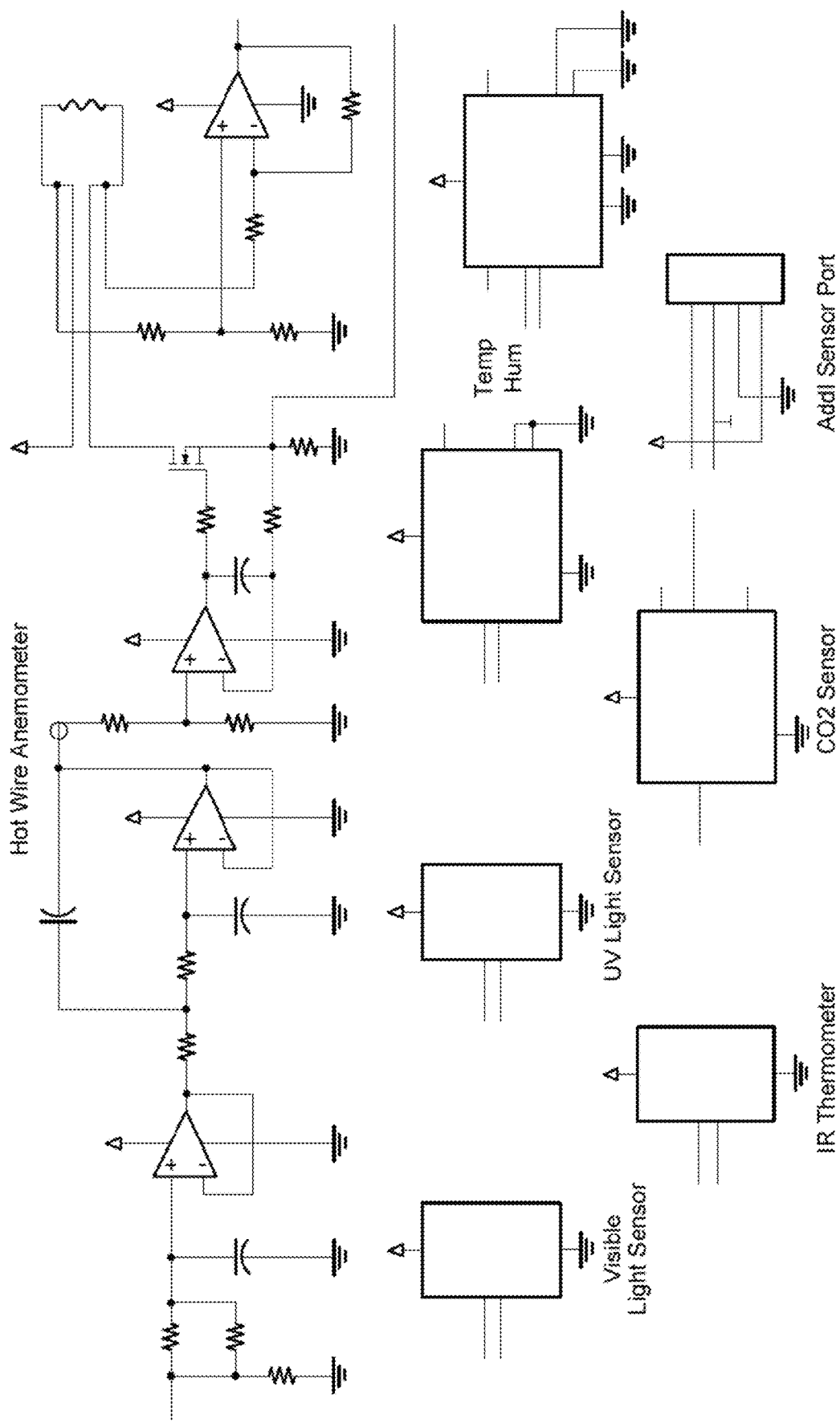
FIG. 17A shows a circuit diagram of the various sensors incorporated into an integrated sensor assembly according to some implementations of the disclosure.
Figure 17B:
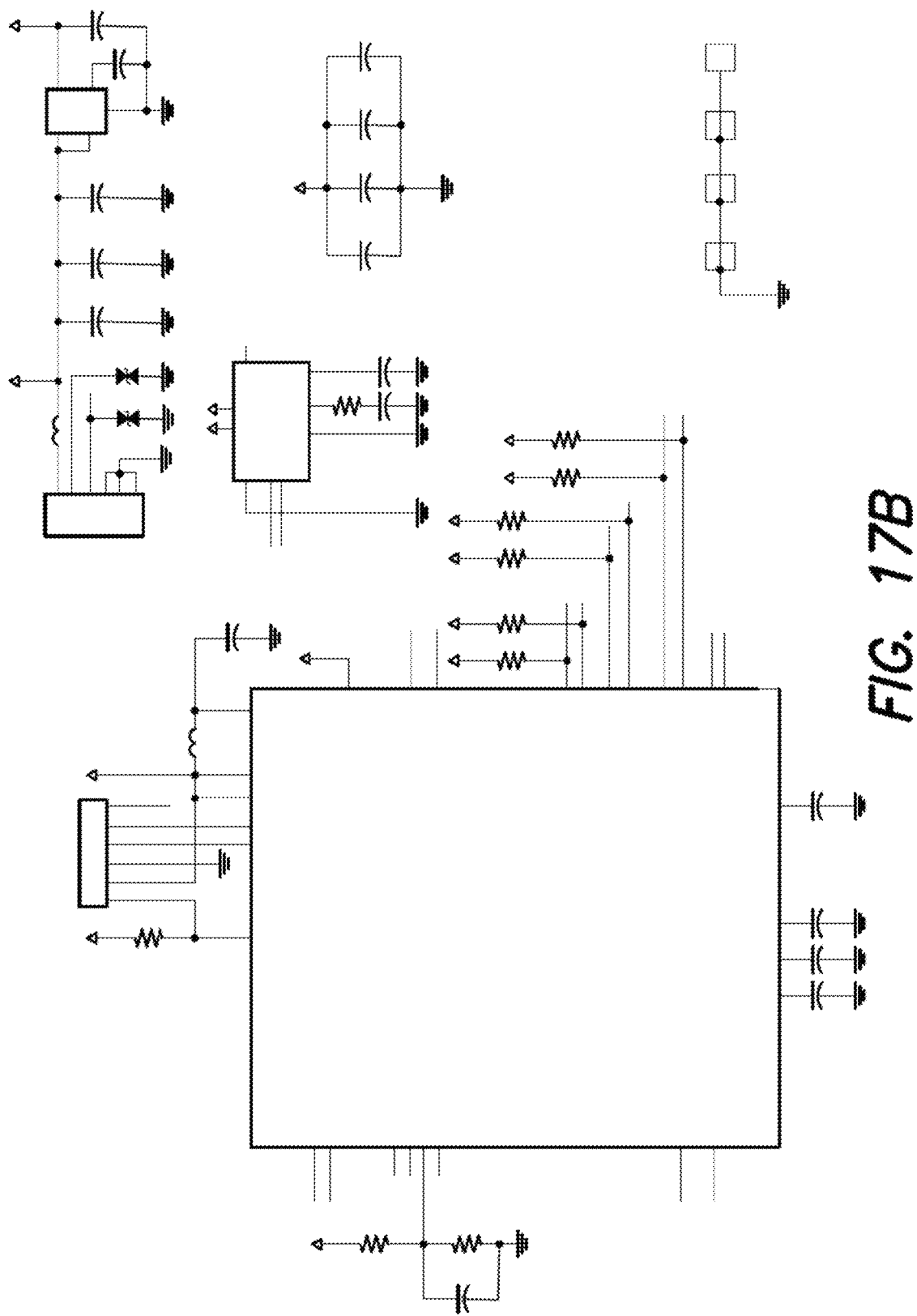
FIG. 17B shows a circuit diagram of electrical components and circuitry that support the operation of various sensors incorporated into an integrated sensor assembly according to some implementations of the disclosure.

The circuit board 3160 can include one or more printed circuit boards supporting circuitry and electrical components used in the operation of the respective sensor components discussed above. One inventive implementation of the circuitry supported by the circuit board 3160 is shown in FIGS. 17A and 17B. In some implementations, the circuit board 3160 can include multiple single sided circuit boards for sensors positioned on the top and the bottom of the integrated sensor assembly 3100, respectively. In other implementations, the circuit board 3160 can be a double sided circuit board. In some implementations, the circuit board 3160 can also include open ports for additional sensors, as shown in FIGS. 17A and 17B. Some examples of additional sensors can include gas sensors configured to detect pollutants in the air, pH sensors to monitor soil quality, and a hyperspectral camera.

As described above, the housing 3180 may be used to protect the sensors and circuitry disposed on the circuit board 3160 contained within the cavity defined by the housing 3180. In some implementations, the housing 3180 may be a two piece construction with a housing top 3181 and a housing bottom 3182 that forms an interior cavity where the circuit board 3160 can be positioned. The housing top 3181 and the housing bottom 3182 may be mated together with coupling members 3190, as shown in FIGS. 16C and 16D. The coupling members 3190 can be various suitable types of coupling components including, but not limited to, screw fasteners, clips, pins, snap-fits, and pegs with corresponding holes in the housing 3180. The housing 3180 can include one or more openings and apertures to allow various sensors to detect surrounding environmental conditions without significant obstruction. For example, the housing top 3181 can have a relatively large opening 3183 to allow passage of light at relatively large oblique angles of incidence for detection by the visible light sensor 3110. To ensure the visible light sensor 3110 and the circuit board 3160 are protected, a transparent lens 3184 can be coupled to the top of the housing top 3181, as shown in FIG. 16C. The lens can be made of material transparent to PAR light or UV radiation, such as polytetrafluoroethylene (PTFE), silica, magnesium fluoride, or calcium fluoride.

The housing 3180 may also include one or more protruding portions in both the housing top 3181 and the housing bottom 3182 to support and/or house the various connectors and sensors in the integrated sensor assembly 3100. As an example, FIGS. 16C and 16D show the housing top 3181 may include a first top protruding portion 3187A and the housing bottom 3182 may include a first bottom protruding portion 3187B that couple to one another to form a first protruding portion that partially surrounds the USB port 3170. The housing top 3181 may also include a second top protruding portion 3185A and the housing bottom 3182 may similarly include a second bottom protruding portion 3185B to form a second protruding portion on an opposite side of the housing 3180 from the first protruding portion with a cavity that contains therein the air flow sensor 3130. The housing top 3181 may also include a third top protruding portion 3186A and the housing bottom 3182 may also include a third bottom protruding portion 3186B to form a third protruding portion adjacent to the second protruding portion with a cavity that contains therein the combined temperature and relative humidity sensor 3120.

In some implementations, the housing 3180 can also be configured to be water tight or air tight to reduce potential failures caused by moisture accumulation in electronic components or circuitry. To ensure the cavity of the housing 3180 is tightly sealed, gaskets can be used to seal each opening or aperture in the housing 3180, particularly openings where sensors protrude from the housing 3180 to expose the sensors to air surrounding the integrated assembly 3100. The housing 3180 can be formed from metals, polymers, metal alloys, ceramics, and/or other materials. Depending on the materials used to form the housing 3180, various manufacturing methods can be used to fabricate the housing 3180 including injection molding, blow molding, casting, or milling. In some implementations, the housing can be coated with materials to reduce moisture infiltration, e.g., hydrophobic coatings, to increase the operating lifetime of the integrated sensor assembly 3100.

In some implementations, the integrated sensor assembly 3100 can also include a USB port 3170 to facilitate connection to an external system, such as a LED-based lighting fixture 1000 as described above. The USB port 3170 can both supply electrical power to the integrated sensor assembly 3100 and facilitate data communication between the integrated sensor assembly 3100 and a control system operably coupled to the external system, e.g., the lighting fixture 1000. In some implementations, the integrated sensor assembly 3100 can be configured to be a "plug and play" device for ease of installation. For example, the integrated sensor assembly 3100 can be plugged into a LED-based lighting fixture, wherein the integrated sensor assembly 3100 is automatically recognized by the control system for the LED-based lighting fixture. Once the integrated sensor assembly 3100 is identified, the control system can begin receiving data recorded by the integrated sensor assembly 3100, which can then be processed and used in a feedback loop to adjust one or more of lighting, heating and/or cooling (e.g., via hydronics and/or other techniques), air flow, and humidity conditioning systems in the agricultural environment.

Figure 18:
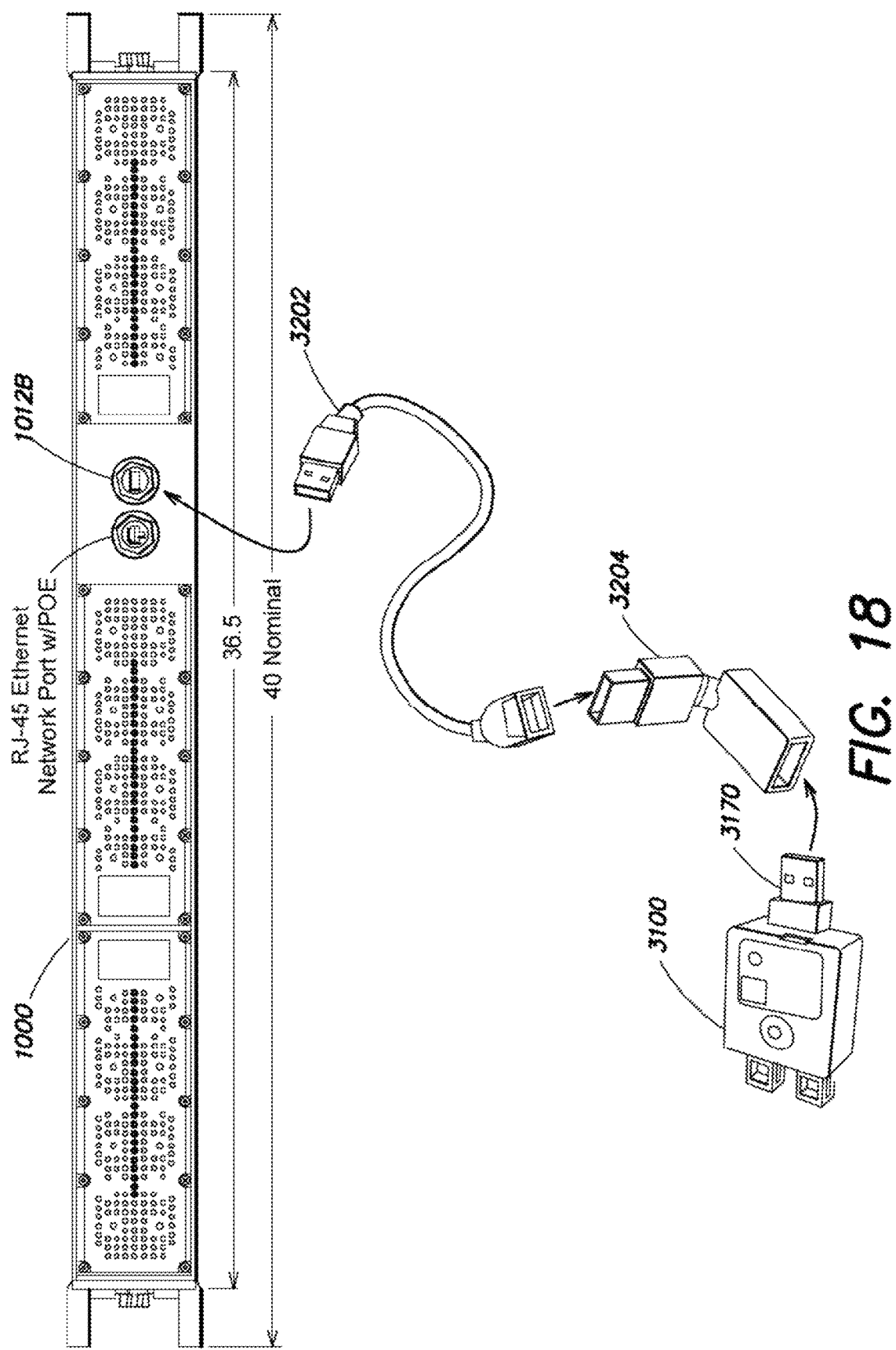
FIG. 18 illustrates an integrated sensor assembly coupled to a downward or bottom USB port of the lighting fixture shown in FIGS. 7A and 7B via one or more USB couplers/extenders, according to some implementations of the disclosure.

FIG. 18 illustrates an integrated sensor assembly coupled to a downward or bottom USB port 1012B of the lighting fixture 1000 shown in FIGS. 7A and 7B via one or more USB couplers/extenders, according to some implementations of the disclosure. In one implementation, the USB port 3170 of the sensor assembly 3100 may be plugged directly into the lighting fixture USB port 1012B. In other implementations, it may be desirable to position the sensor assembly 3100 essentially on the same level or proximate to a downward face of the lighting fixture 1000, but generally out of the path of illumination provided by the lighting fixture 1000. To this end, one or more "gooseneck-type" flexible USB extenders 3202, and/or one or more adjustable-angle USB extenders 3204, may be employed to communicatively couple and adjustably position the sensor assembly 3100 to the lighting fixture 1000. While a gooseneck-type and an adjustable angle-type USB extender are shown in FIG. 18, it should be appreciated that various other types of USB extenders, including cables, may be employed alone or together with other types of USB extenders to couple the sensor assembly to the lighting fixture 1000.

Figure 19:
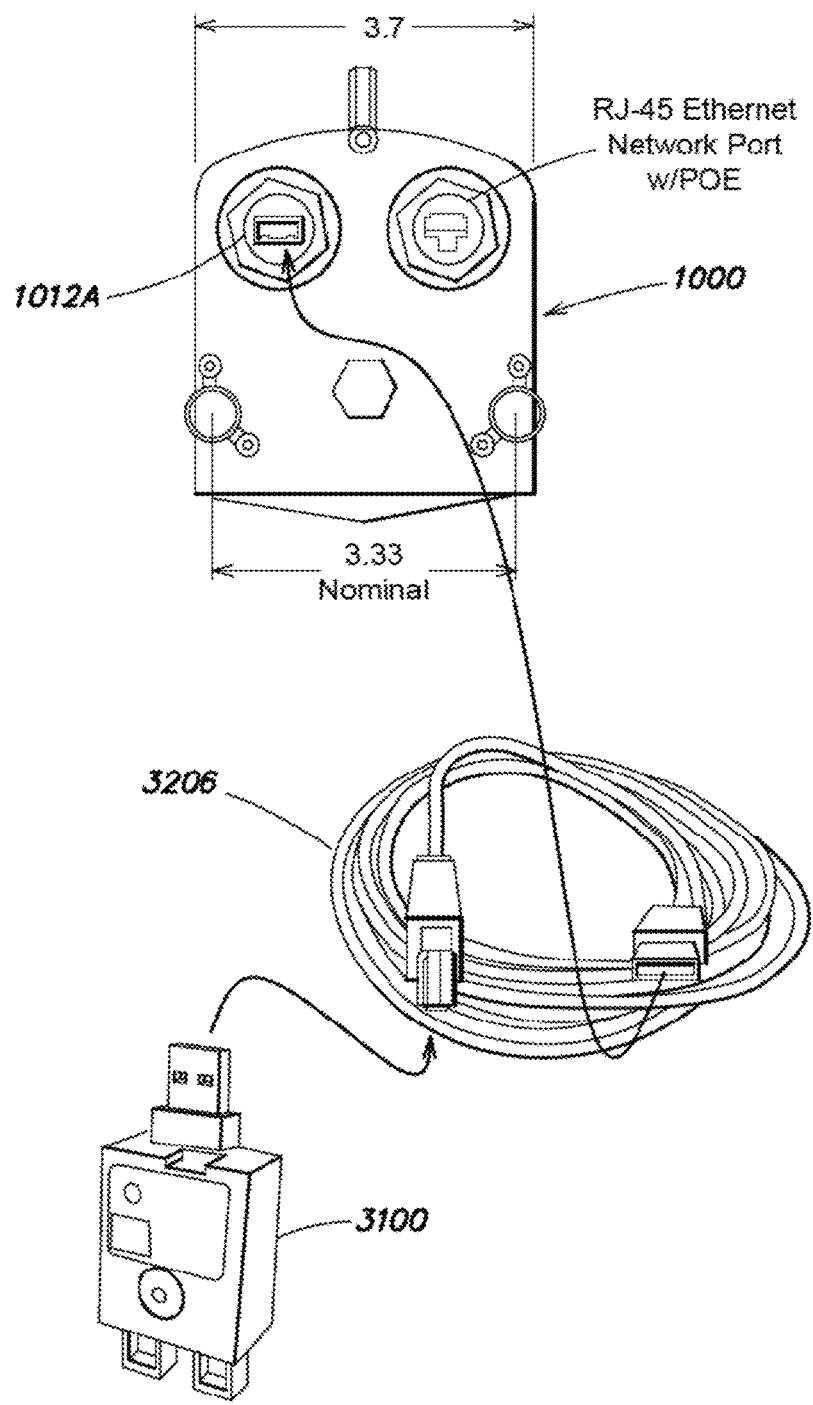
FIG. 19 illustrates an integrated sensor assembly coupled to a side or end USB port of the lighting fixture shown in FIGS. 7A and 7B via one or more USB couplers/extenders, according to some implementations of the disclosure.

To this end, FIG. 19 illustrates an integrated sensor assembly 3100 coupled to a side or end USB port 1012A of the lighting fixture 1000 shown in FIGS. 7A and 7B via one or more cable-type USB couplers/extenders, according to some implementations of the disclosure. In FIG. 19, the sensor assembly may be coupled to one end of a USB cable extender 3206, and the other end of the cable extender 3206 may be coupled to the USB port 1012A of the lighting fixture. Various lengths of cable extenders may be employed for the extender 3206 so as to position the sensor assembly 3100 at different distances below the lighting fixture 1000. The cable extender 3206 may be used alone, or together with one or more other cable extenders, one or more gooseneck-type extenders 3202, one or more adjustable angle-type extenders 3204, one or more other types of extenders, or combinations of the foregoing. As noted above in connection with FIG. 18, different lengths of cable extenders 3206 may be employed to couple the sensor assembly 3100 to the downward or bottom USB port 1012B as well; likewise, one or both of the gooseneck-type extender 3202, the adjustable angle-type extender 3204, or yet another type of USB extender, without a cable-type extended 3206, may be employed to couple the sensor assembly 3100 to the side or end USB port 1012A of the lighting fixture 1000.

In some implementations, once the integrated sensor assembly 3100 interfaces with an external system, the external system can control how frequently measurements are taken by each sensor in the integrated sensor assembly 3100. Sensor measurements can be recorded simultaneously or at different time intervals. For example, the integrated sensor assembly 3100 can be configured to measure the air flow every second, the PPFD every minute, and the CO2 concentration every hour.

In some implementations, multiple integrated sensor assemblies 3100 can be installed as an array to monitor larger areas of the controlled agricultural environment. For example, controlled agricultural environments can include multiple LED-based lighting fixtures where each lighting fixture supports multiple integrated sensor assemblies 3100. Each integrated sensor assembly 3100 in the array can be used to locally monitor growth conditions for a single or small group of plants, as described above in connection with FIG. 10A. Additionally, analysis of sensor data from multiple integrated sensor assemblies 3100 can be used to determine variations in growth conditions, such as temperature, air flow, or lighting, across an entire agricultural environment. Based on this aggregate data, adjustments can be made to one or more of the lighting, heating and/or cooling (e.g., via hydronics and/or other techniques), air flow, and humidity conditioning systems to foster improved growth conditions over larger areas in the agricultural environment. In some implementations, each integrated sensor assembly 3100 can include an identification number, e.g., vendor identification (VID) or product identification (PID), which can be used to determine the location of each sensor assembly in the array.

Distributed Sensor Grid

Based on the various concepts described above and illustrated in the accompanying drawings, various inventive implementations of a distributed sensor grid for a controlled agriculture environment will now be described. A controlled agricultural environment can include one or more control systems, including, but not limited to, lighting, heating, air flow, hydronics, and humidity conditioning systems, configured to work in concert with one or more sensors, e.g., temperature, relative humidity, air flow, soil quality, the integrated assembly 3100 described above. The sensors can measure various environmental conditions in an agricultural environment, and data from the sensors can then be used to adjust one or more control systems to improve or maintain growth conditions for plants.

The Inventors have recognized and appreciated that conventional controlled agricultural environments may have appreciably large growing areas for multiple plants or crops over which growing conditions may vary as a function of space and/or time. In particular, growing conditions in a given environment (for relatively larger or smaller growing areas alike) may significantly differ in one or more respects in different portions of a given growing area at different times (e.g., amongst different rows or groupings of plants, as well as at different elevations in the environment). Inconsistent growing conditions across a growing area in turn may result in unpredictable and undesirable variations in plant growth that similarly may be difficult to discern as the plants are growing initially, but become evident at later stages of growth when remediation measures may be difficult or impossible to implement.

In general, varying space-dependent and/or time-dependent growing conditions over different portions of a growing area in conventional controlled agricultural environments remain substantially undetected. If a curator of the environment observes variations in plant growth in different portions of a growing area, the curator may attempt to compensate for such variations based on "experience," e.g., adjusting one or more conditions in the environment using empirically-derived manual techniques (based on working with a given crop in a given environment over several growing cycles) so as to improve growth conditions for sluggish or distressed crops. In some instances, one or more sensors are employed in the environment to measure various conditions relevant to plant growth; however, in those conventional controlled agricultural environments in which one or more sensors may be deployed, such sensors typically do not provide sufficient coverage for all of the plants in the growing area, nor are they deployed with sufficient spatial resolution to adequately observe significant variations in growth conditions throughout a given growing area. Furthermore, different types of sensors (for measuring different types of environmental conditions) are often deployed and/or operated independently of one another, making it challenging to comprehensively monitor multiple conditions in the environment relevant to plant growth.

In view of the foregoing challenges with conventional approaches to controlled agricultural environments, the present disclosure is directed to distributed sensing techniques in which multiple sensors are arranged in the environment to provide sufficient coverage over a given growing area. In one aspect, sensors are disposed in the growing area at an appropriate spatial resolution to effectively monitor growth conditions of plants in the growing area, in some instances on a plant-by-plant basis or for relatively small groups of plants. In another aspect, multiple sensors disposed in a growing area can be configured to utilize common power and network connections, thus simplifying the integration of various sensors in the environment and data collection from the sensors.

In one exemplary implementation, multiple sensors are deployed in a controlled agricultural environment as a distributed sensor grid. The distributed sensor grid includes one or more node arrays, where each node array divides at least a portion of the controlled agricultural environment into nodes, e.g., discrete points in space which have a known location (e.g., absolute or relative) in the environment. In various aspects, a given node array of a distributed sensor grid may be one dimensional, two dimensional, or three dimensional (e.g., based at least in part on the distribution of growing areas and/or crops in the controlled agricultural environment). For example, in some implementations, a given node array may include multiple nodes arranged in a substantially linear or curvilinear fashion spaced along a row of plants to provide a one-dimensional node array. Another type of node array may include multiple nodes arranged in horizontal plane substantially parallel to a floor or a ceiling in the controlled agricultural environment to provide a two-dimensional node array. Yet another type of node array may include multiple nodes arranged in multiple horizontal planes substantially parallel to the floor or ceiling in the controlled agricultural environment, wherein the respective horizontal planes of nodes constitute multiple vertical levels corresponding to different zones of interest in the controlled growing environment (e.g., the soil, the plant, the lighting canopy, and the ambient environment).

Figure 20A:
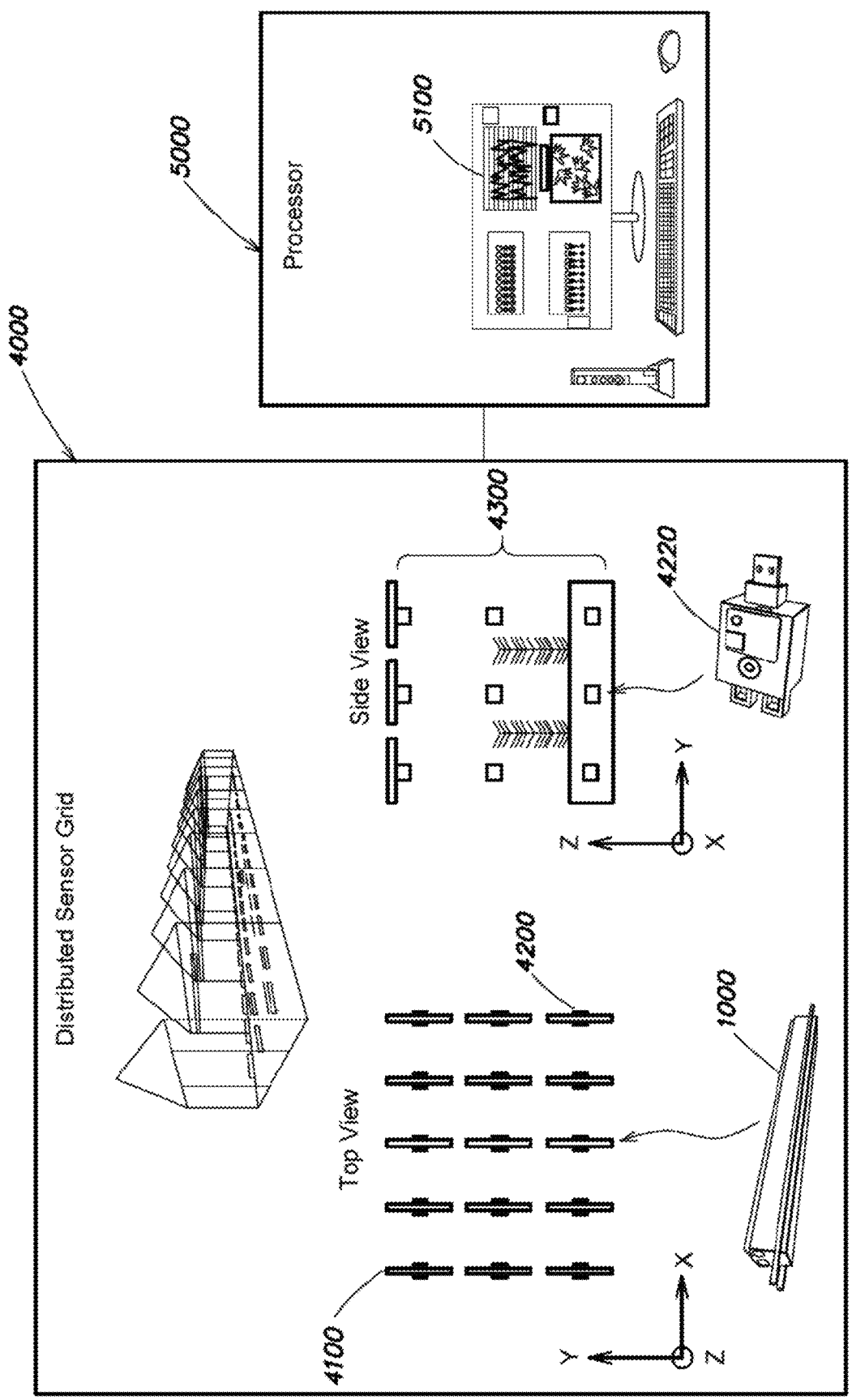
FIG. 20A shows an exemplary distributed sensor system, according to some implementations of the disclosure.

An exemplary implementation of a distributed sensor grid 4000 for a controlled agricultural environment is shown in FIG. 20A. The distributed sensor grid 4000 includes one or more node arrays 4100, and each node array contains multiple nodes 4200 respectively positioned at corresponding coordinate locations (e.g., X, Y, and Z coordinates) in the controlled agricultural environment. At a given node 4200, the distributed sensor grid further includes one or more sensors 4220 deployed at the node to monitor growth conditions in proximity to the node. In the example illustrated in FIG. 20A, the distributed sensor grid is arranged as a three-dimensional node array, in which an arrangement of lighting fixtures 1000 constitutes a horizontal plane of nodes defined by an X-axis and a Y-axis of the node array (see "Top View"), and the node array also includes multiple vertical levels 4300 along a Z-axis (e.g., respectively corresponding to a soil level, a plant level, and a light canopy level; see "Side View"). One or more sensors 4220 may be placed at multiple nodes or each node of the node array to comprehensively monitor growth conditions in the environment. In one example, the sensors 4220 deployed at the nodes may be the integrated sensor 3100 discussed above in connection with FIGS. 16A-19.

Node Array

Each node array 4100 covers at least a portion of an agricultural environment. In some controlled agricultural environments, one node array may be sufficient given a particular number and arrangement of plants in a growing area, while in other environments multiple node arrays may be employed to flexibly configure a distributed sensor grid (in some instances over multiple growing areas in the environment with different layouts and/or different crops). For example, in vertical farming (in which different growing areas are stacked one on top of another in a vertical arrangement), one or more node arrays 4100 can be used for each vertically-stacked growing area in the environment. In another example, an agricultural environment can be divided into separate climate-controlled rooms with each room having one or more node arrays 4100. Each node array 4100 divides the covered portion of the agricultural environment into a grid of nodes 4200, where each node 4200 is a discrete point with a known coordinate location within the node array 4100. As noted above, respective nodes 4200 can include one or more sensors 4220 to monitor growth conditions proximate to a given node (e.g., in a volume of space around the node, which may depend in part on the type(s) of sensor(s) deployed at the node). In some implementations, the number of nodes 4200 in a node array 4100 can depend upon the constraints imposed on or by the agricultural environment.

The coordinate location of each node 4200 can include one or more coordinate components to describe the location of a node 4200 in the agricultural environment. In some implementations, the coordinate location of a node 4200 can correspond to a physical location in the agricultural environment with reference to a spatial origin. For example, the corner of a growing area can be set as the origin of the coordinate system and nodes 4200 can be defined at known and/or defined distances from the origin along one or more axes (e.g., respective X, Y, and Z axes). In some implementations, the coordinate location can correspond to an indexed location related to one or more aspects of the physical arrangement of the agricultural environment (e.g., dimensions and/or shape of one or more growing areas, arrangement of plants in a given growing area, arrangement of control systems in a given growing area).

Figures 4, 20B:
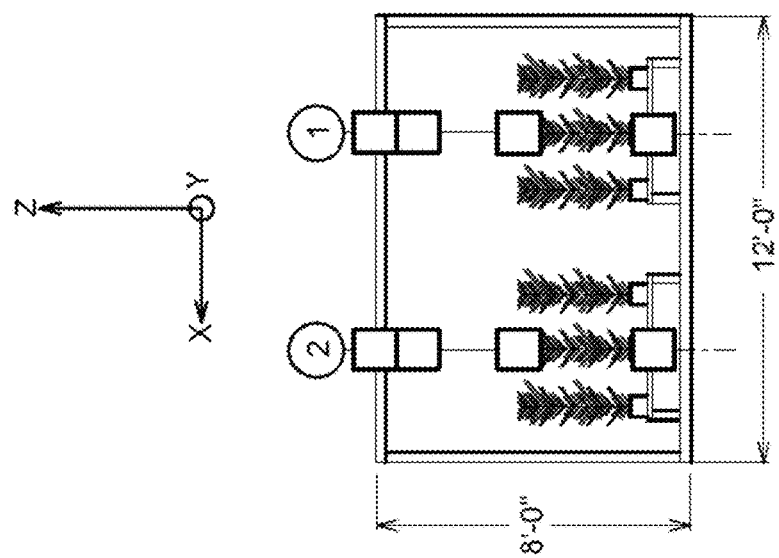
Figures 3, 20B:
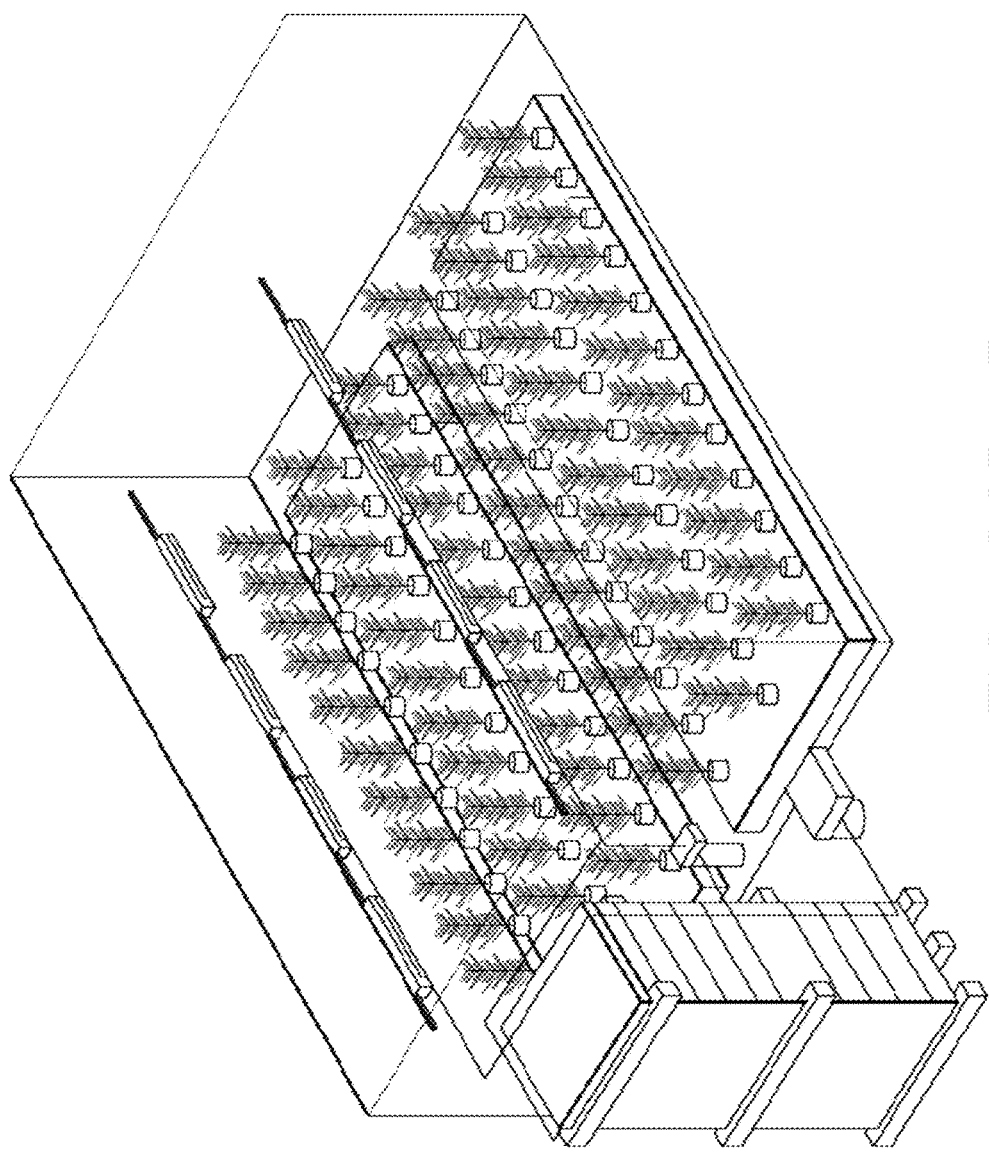

For example, FIGS. 20B-1-20B-4 illustrates an agricultural environment that includes two elongated shelves 902A and 902B disposed next to each other at some spacing in a growing area. Three rows of plants are positioned next to each other on each shelf along the long length of the shelf. Above each shelf, positioned generally over the middle row of the three rows of plants, are four lighting fixtures 1000. In this example, a Y-axis for the node array is chosen parallel to the long length of the shelves 902A and 902B (and, accordingly, the X-axis is parallel to the short width of the shelves). The center lines of the shelves themselves along the length (e.g., halfway across the width of a shelf) define indexed positions 1 and 2 along the X-axis, and the four lighting fixtures 1000 disposed above each of the shelves 902A and 902B respectively define indexed positions A, B, C, and D along the Y-axis (e.g., the centers of the lighting fixtures may correspond with the indexed positions A through D). The Z-axis for the node array is taken along the vertical height of the environment, and is divided in the example shown in FIGS. 20B-1-20B-4 into four indexed positions or "levels" 4300 (respectively labeled as L1, L2, L3 and L4). Thus, there are a total of 32 nodes 4200 in the node array 4100 of the distributed sensor grid.

As discussed in greater detail below, it should be appreciated that the example node array shown in FIGS. 20B-1-20B-4 based on two shelves of plants, four lighting fixtures per shelf, and four vertical levels is provided primarily for purposes of illustration, and that other node array configurations are contemplated according to the present disclosure.

For example, in some implementations in which the lighting fixtures 1000 serve as a connectivity platform for a distributed sensor grid, the number of nodes 4200 supported in a node array 4100 is based at least in part on the number of power and network ports available for connection with sensors 4220 deployed at respective nodes. For example, in the configuration shown in FIGS. 20B-1-20B-4, each lighting fixture 1000 includes USB ports 1012A and 1012B that may be employed to couple one or more integrated sensor assemblies 3100 to each fixture (wherein the assemblies 3100 serve as the sensors 4220 deployed at respective nodes; also, lighting fixtures 1000 may be equipped with one or more additional USB ports for this purpose). Each lighting fixture also includes PoE ports 1008A-D, any one or more of which ports may be employed to couple one or more sensors to each fixture.

In some implementations, the number of nodes 4200 can be determined by a user-defined density and/or coverage area in the agricultural environment. For example, the IR temperature sensor 3150 in the integrated sensor assembly 3100 can have a finite field of view, as described above. An array of integrated sensor assemblies 3100, each corresponding to a node 4200, can thus be installed and spaced apart such that the respective fields of view of the IR temperature sensors 3150 sufficiently overlap to effectively provide sensing coverage for the plants in the environment.

The distribution of nodes 4200 in the node array 4100 can also vary spatially and quantitatively. In some implementations, the nodes 4200 can be uniformly distributed. For example, a uniform array of lighting fixtures 1000 can be deployed with an integrated sensor assembly 3100 connected to USB ports 1012A and 1012B on each lighting fixture 1000, as described above. In some implementations, the nodes 4200 distributed in the node array 4100 can be non-uniform. For example, the number of nodes 4200 may vary according to each level 4300 of a plant system where, for example, more nodes 4200 can be used to monitor soil quality than the ambient environment conditions due to variations in coverage by each type of sensor. In another example, an agricultural environment can include different plant species of varying size. The nodes 4200 can be more closely spaced for smaller-sized plants and sparser for larger-sized plants. Additionally, a node 4200 may not include a sensor 4220. Such empty nodes 4200 can be used to define a non-uniform distribution of sensors 4220 with a uniform distribution of nodes 4200. For example, soil quality sensors can occupy every node 4200 at the bottom level 4300 and ambient environment sensors can occupy every other node 4200 at the top level 4300 with empty nodes 4200 in between.

Figure 20C:
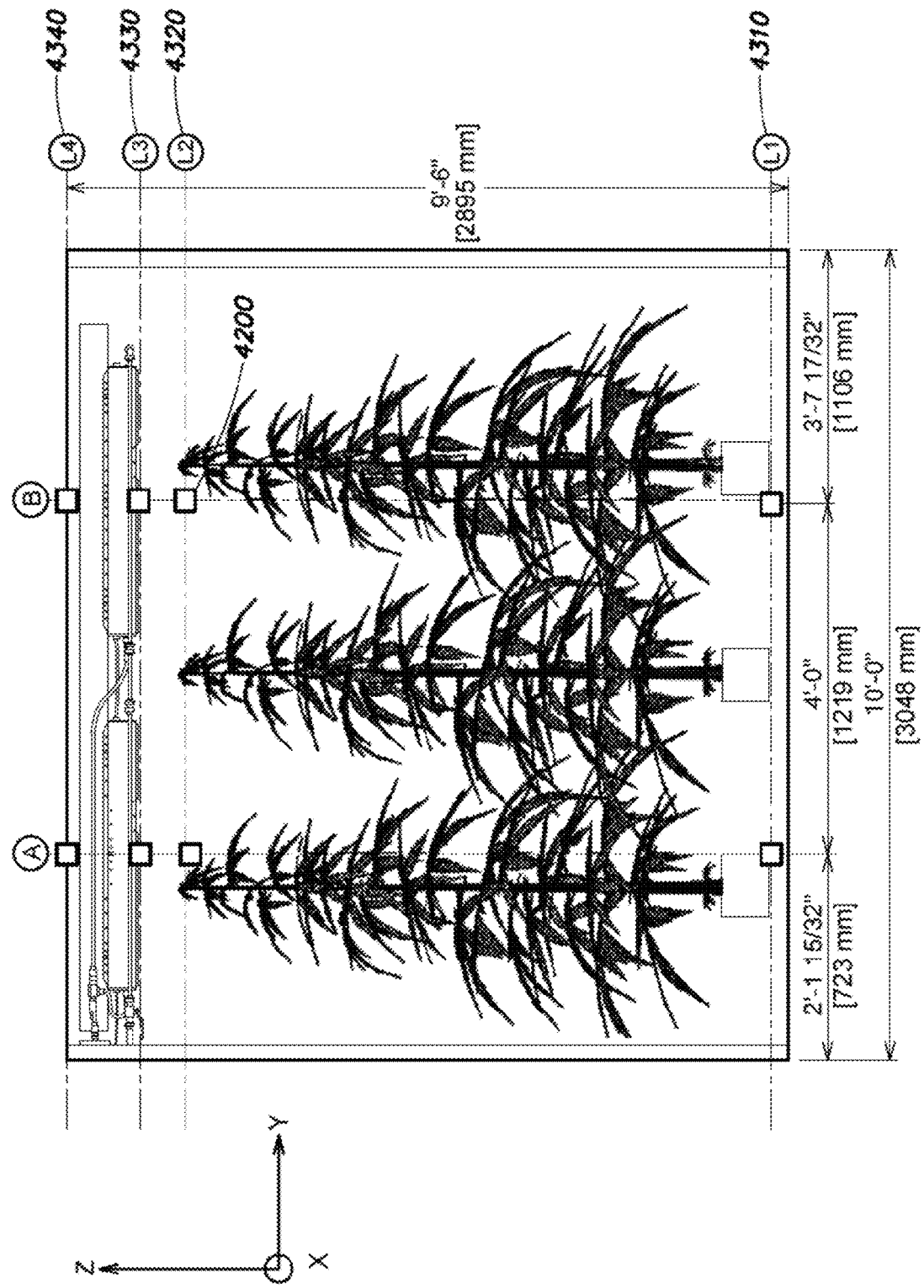
FIG. 20C shows a side view of an exemplary distributed sensor system subdivided along a vertical axis into levels corresponding to the agricultural environment.

As described above, the node array 4100 can include multiple levels 4300 (e.g., along a Z-axis) that correspond to various zones of interest in the controlled growing environment. An exemplary set of levels 4300 are shown in FIG. 20C. As shown, each level corresponds to a zone of interest in a plant system including a soil level 4310, a plant level 4320, a light canopy level 4330, and an ambient environment level 4340. The soil level 4310 can provide data on soil conditions, such as pH value and chemical composition. The plant level 4320 can provide data on the leaf temperature or $CO_2$ concentrations near the plant. The light canopy level 4330 can provide data on the illumination source, e.g., PPFD, air temperature, relative humidity, or heat dissipation or electrical power for the lighting fixture 1000. The ambient environment level 4340 can provide data on air circulation or the temperature of the walls or ceiling of the agricultural environment.

Figures 3, 20D:
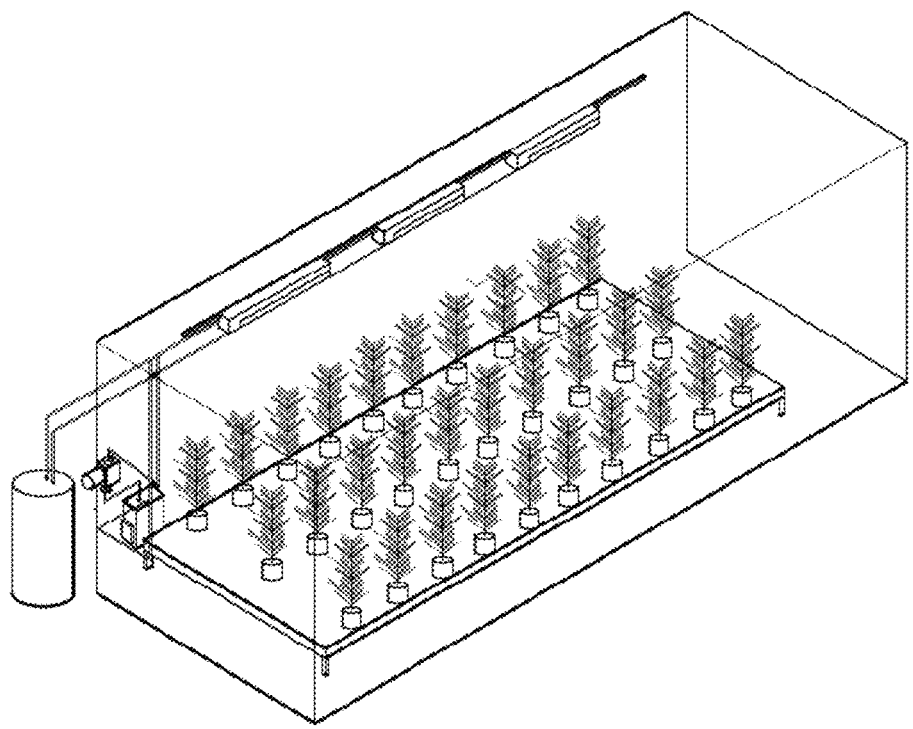
Figures 4, 20D:
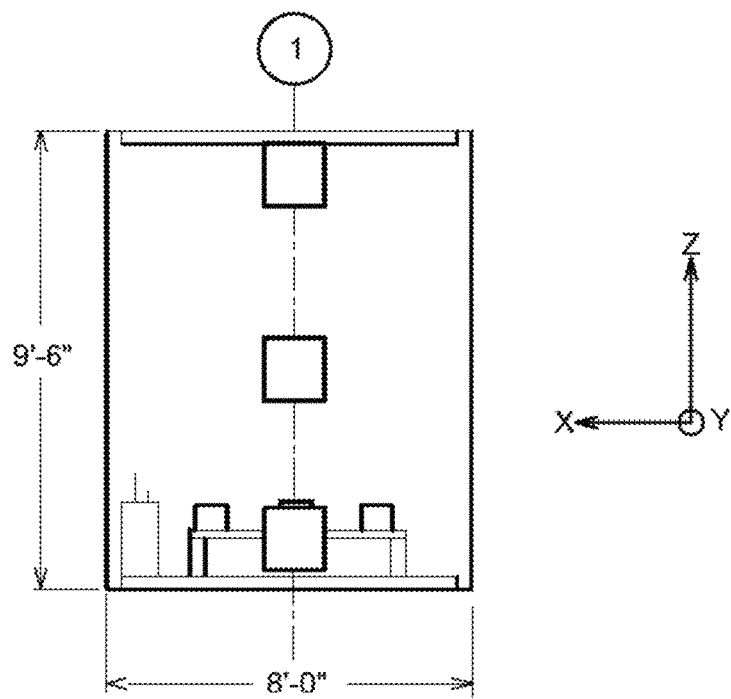
Figures 1, 20E:
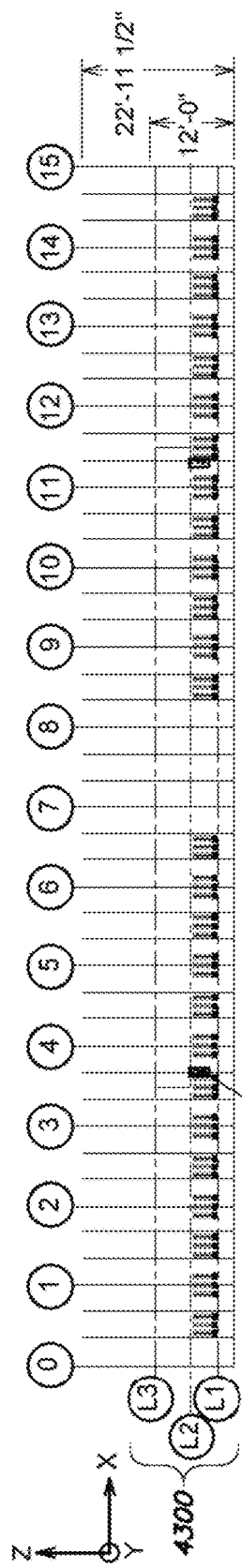
Figures 2, 20E:
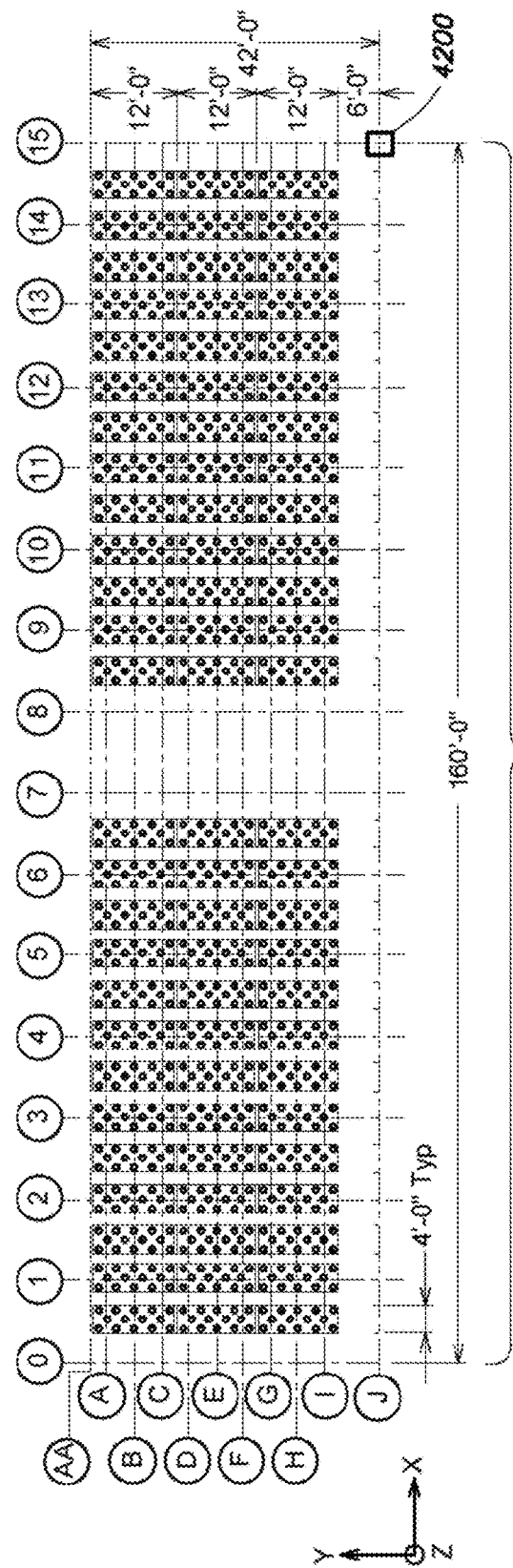
Figures 3, 20E:
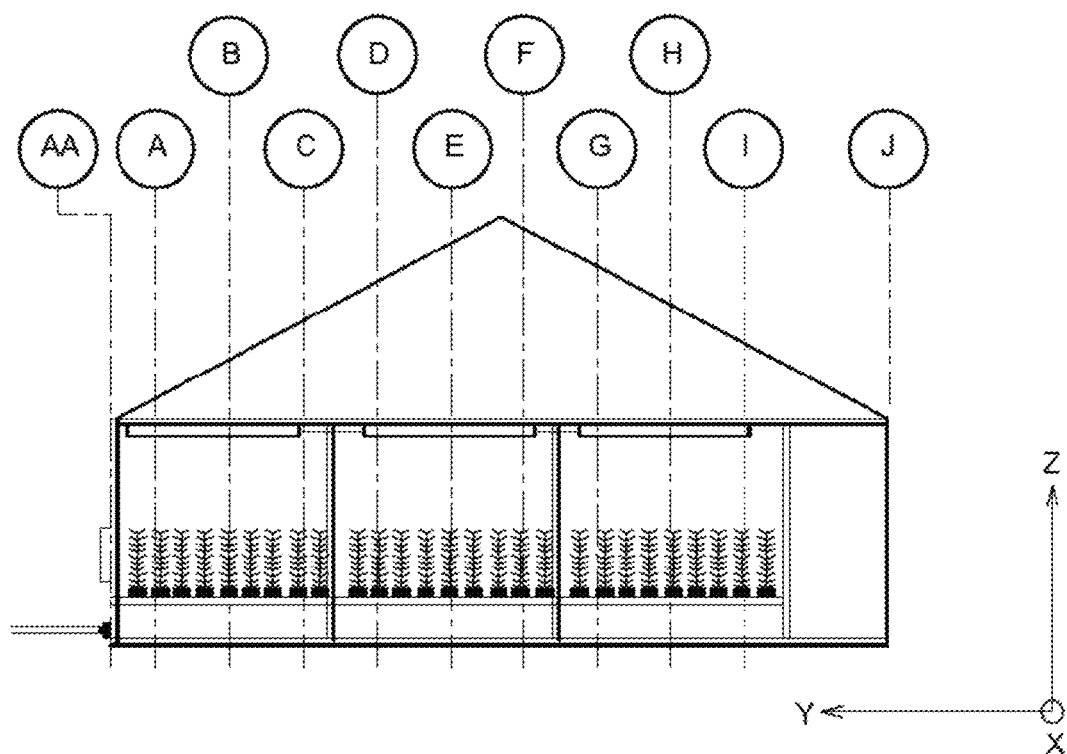
Figures 4, 20E:
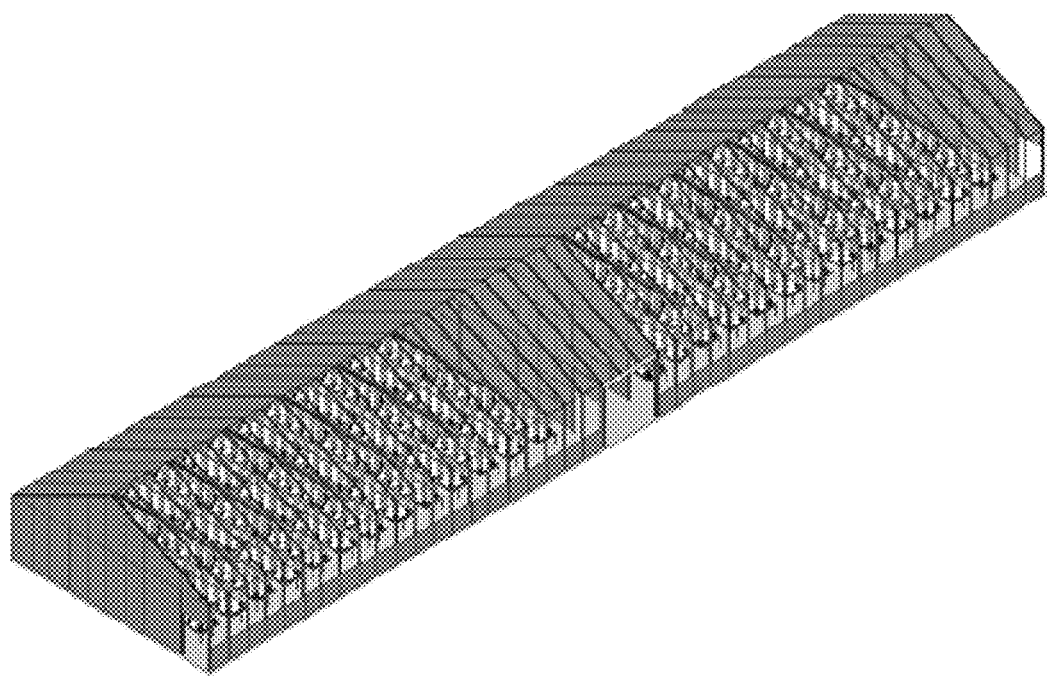
Figures 5, 20E:
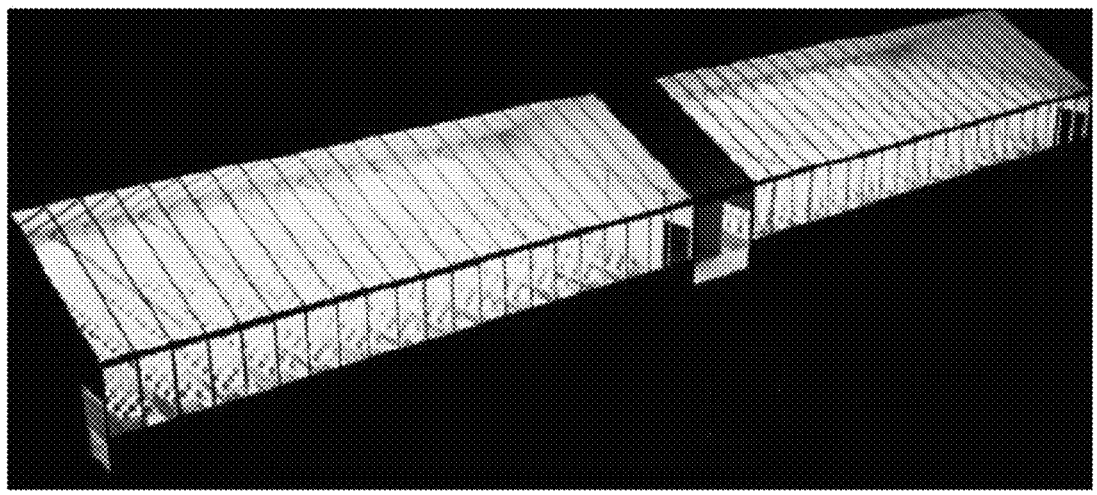

FIGS. 20D-1-20D-4 show another exemplary implementation of a distributed sensor grid 4000 for a single elongated plant shelf 902A. Similar to the example shown in FIGS. 20B-1-20B-4, the X-axis is parallel to the short width of the shelf 902A with an index position of 1 and the Y-axis is parallel to the long length of shelf 902A with index positions A, B, and C. The node array is divided into three nodes 4200 along the Z-axis corresponding to three levels 4300 with indices L1, L2, and L3. As shown in FIGS. 20D-1-20D-4, the location of the nodes 4200 can be defined, at least in part, by the respective locations of lighting fixtures 1000 in the agricultural environment. FIGS. 20E-1-20E-5 show yet another exemplary implementation of a distributed sensor grid 4000 for numerous plant shelves in an agricultural environment. The X-axis is indexed according to plant shelves with index positions 0 through 15. The Y-axis is indexed according to each lighting fixture 1000 with index positions A through J. An index AA is included corresponding to the edge of the plant shelves. The Z-axis is defined along the vertical height of the environment with index positions L1, L2, and L3. As shown, the X-axis index positions can be defined such that the nodes 4200 cover one or more plant shelves. Nodes 4200 can also be defined to cover regions where no plants are presented, e.g., X-axis indices 7 and 8, which can provide uniform coverage across the environment, e.g., a uniform grid of nodes 4200 can measure air flow, which can be affected by obstacles located between growing areas.

Sensors

One or more sensors 4220 can be deployed at a particular node 4200 to monitor parameters relevant to growth conditions. The sensors 4220 can include, but are not limited to, a visible light sensor, a UV light sensor, an air temperature sensor, a relative humidity sensor, an airflow sensor, a $CO_2$ sensor, an IR temperature sensor, a chemical sensor, a pH sensor, and cameras configured to capture still images or videos of the agricultural environment with various spectral qualities, as described above. In some implementations, multiple sensors 4220 can be packaged into an integrated sensor assembly 3100, as described above to simplify wiring and ease of installation. Each node 4200 in a node array 4100 can also include different combinations of sensors 4220 pertinent to the region of the environment the node 4200 is located in. For example, different types of sensors 4220 may be deployed according to the levels 4300 used in an environment.

The nodes 4200 in the node array 4100 can also be configured to share power and network connections to simplify the integration of multiple sensors 4220 in the distributed sensor grid 4000. As described above, in some implementations a plurality of lighting fixtures 1000 can be used as a connectivity platform for the distributed sensor grid 4000. Sensors 4220 can couple to the PoE ports 1008A-D or the USB ports 1012A and 1012B for power and networking using cables or dongles, exemplary examples of which are shown in FIGS. 18 and 19. In some implementations, multiple sensors 4220 located at various levels 4300 can be connected to a single lighting fixture 1000. For example, a soil sensor can be connected via a long USB extension cable dangled from a USB port 1012B (e.g., an exemplary image is shown in FIG. 33S) and a lighting sensor can be connected directly to a PoE port. By connecting the plurality of lighting fixtures 1000 together, the sensors 4220 can also be connected thus forming a distributed array of sensors.

Control Systems

Distributed sensors in the agricultural environment can also be coupled to one or more control systems such that data acquired by one or more of the distributed sensors may be used to adjust the operating parameters of one or more control systems. The control systems can include, but are not limited to, lighting, heating, air flow, hydronics, and humidity conditioning systems. For many agricultural environments, the control systems may be configured to affect growing conditions from a single or few locations in the environment. For example, HVAC systems affecting air flow may be dispersed intermittently along the wall or ceiling in an environment, thus affecting multiple nodes 4200 when operating parameters are changed. In another example, a lighting fixture 1000 can affect growing conditions at nodes 4200 located directly below and near the lighting fixture 1000. Thus, data acquired by one or more sensors 4220 can be used to adjust the control systems such that growing conditions across multiple nodes 4200 are improved or maintained.

Human Machine Interface

In some implementations, the distributed sensor grid 4000 can be connected to a processor 5000, as shown in FIG. 20A. The processor 5000 can be a computer or a server, which processes and stores various data from the sensors 4220 in the distributed sensor grid 4000. The processor 5000 may also include a HMI 5100, an exemplary implementation of which is shown on a computer in FIG. 21A, that allows users to monitor and control various aspects of the agricultural environment. For example, users may access various data obtained by the sensors 4220, view and display various data, and control one or more control systems, e.g., lighting, heating, air flow, hydronics, and humidity conditioning systems.

Figure 21A:
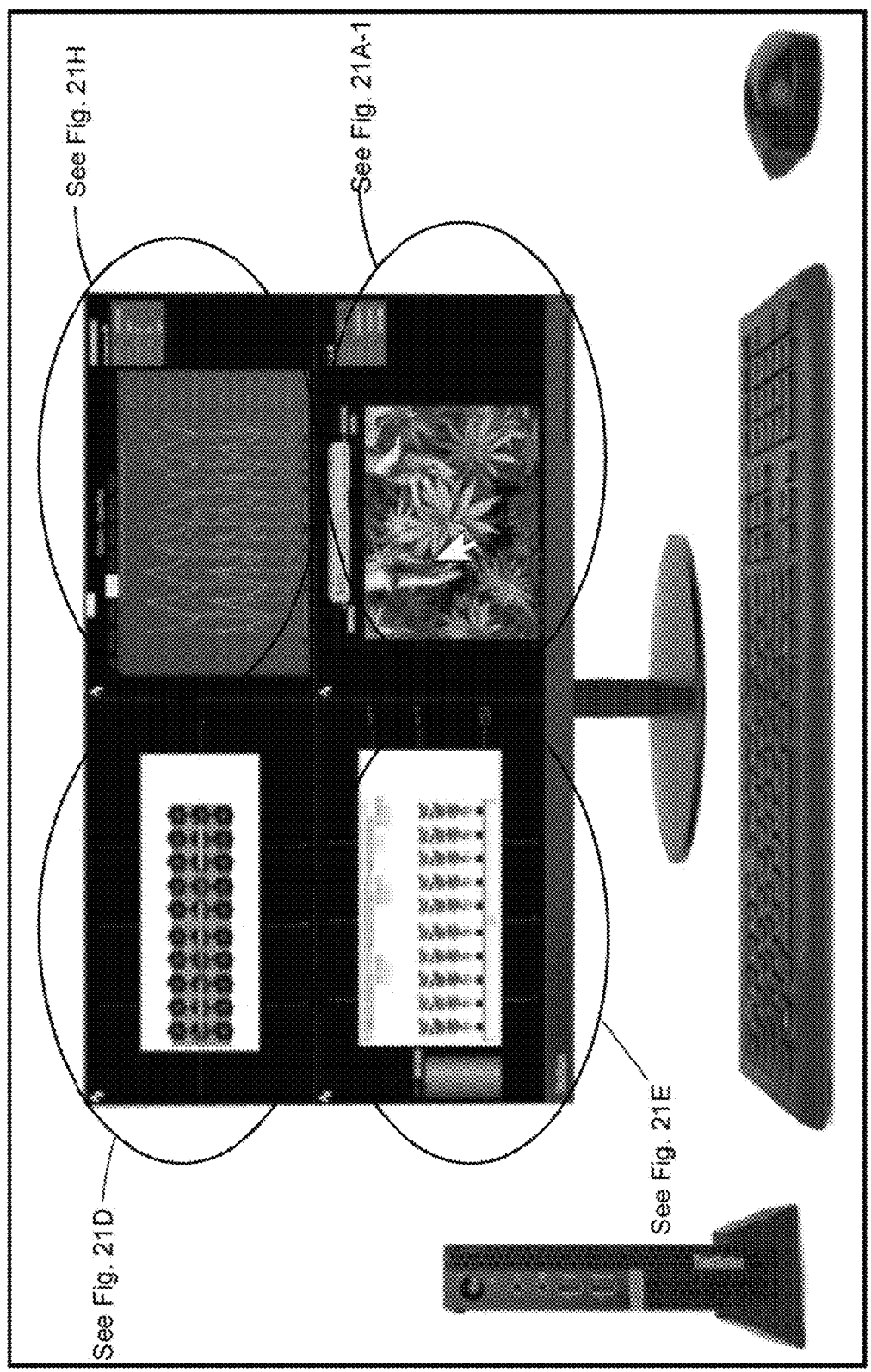
FIG. 21A shows an exemplary human machine interface (HMI) displayed on a monitor of a computer, according to some implementations of the disclosure.
Figures 1, 21A:
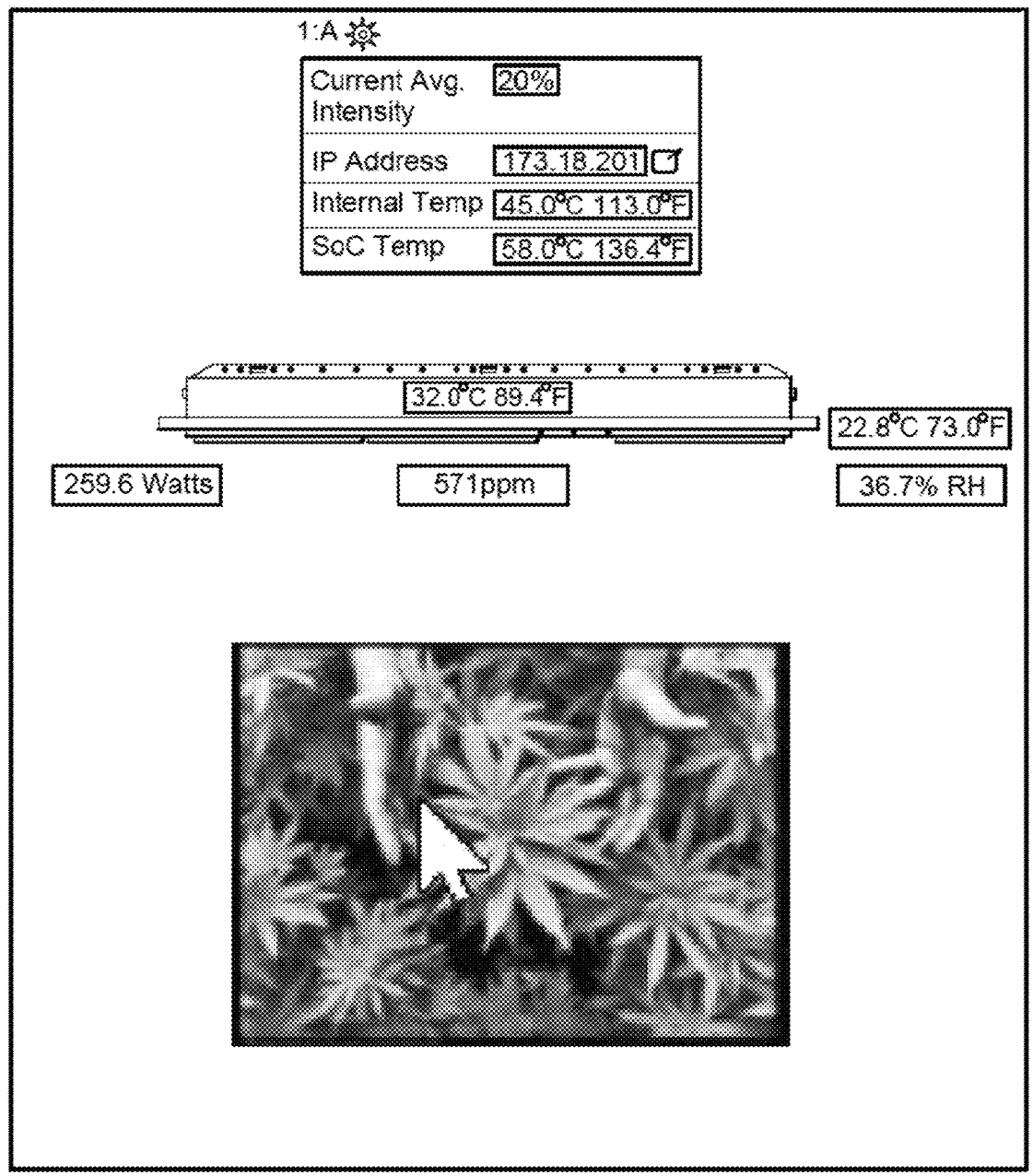
Figure 21C:
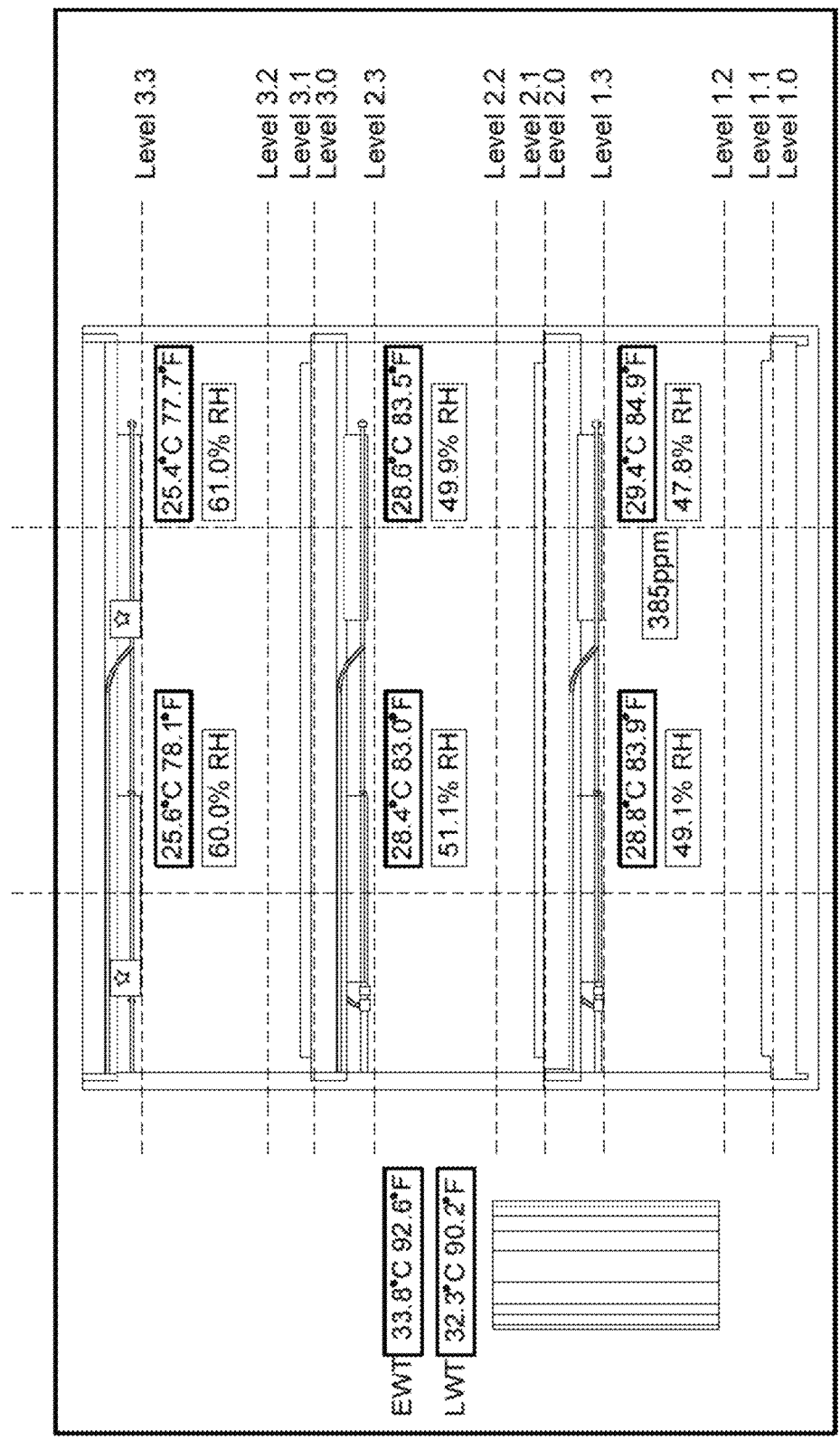
FIG. 21C shows a side view of the plant shelf of FIG. 21B as displayed in the HMI.
Figure 21D:
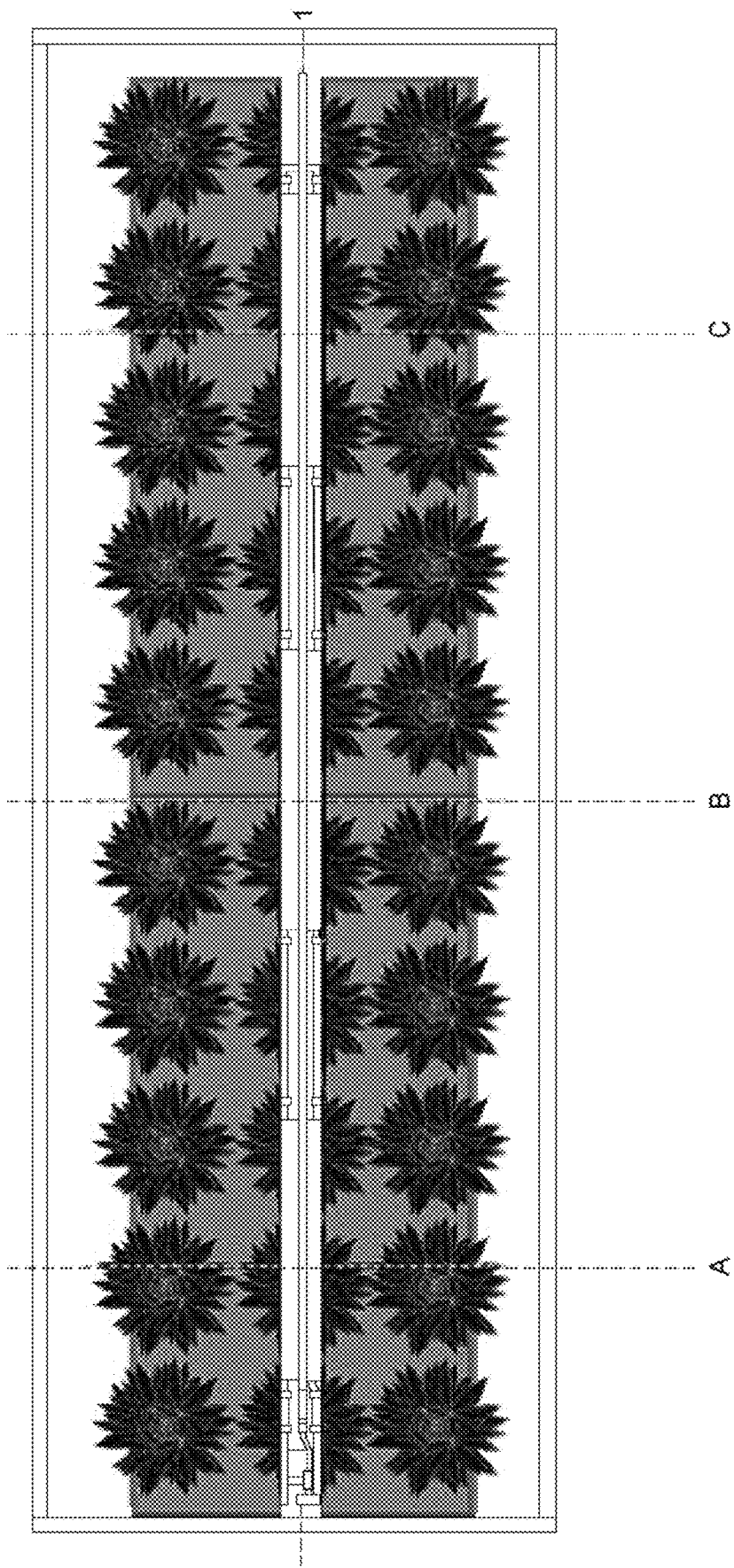
FIG. 21D shows a top view of two exemplary plant shelves as displayed in the HMI of FIG. 21A.
Figure 21E:
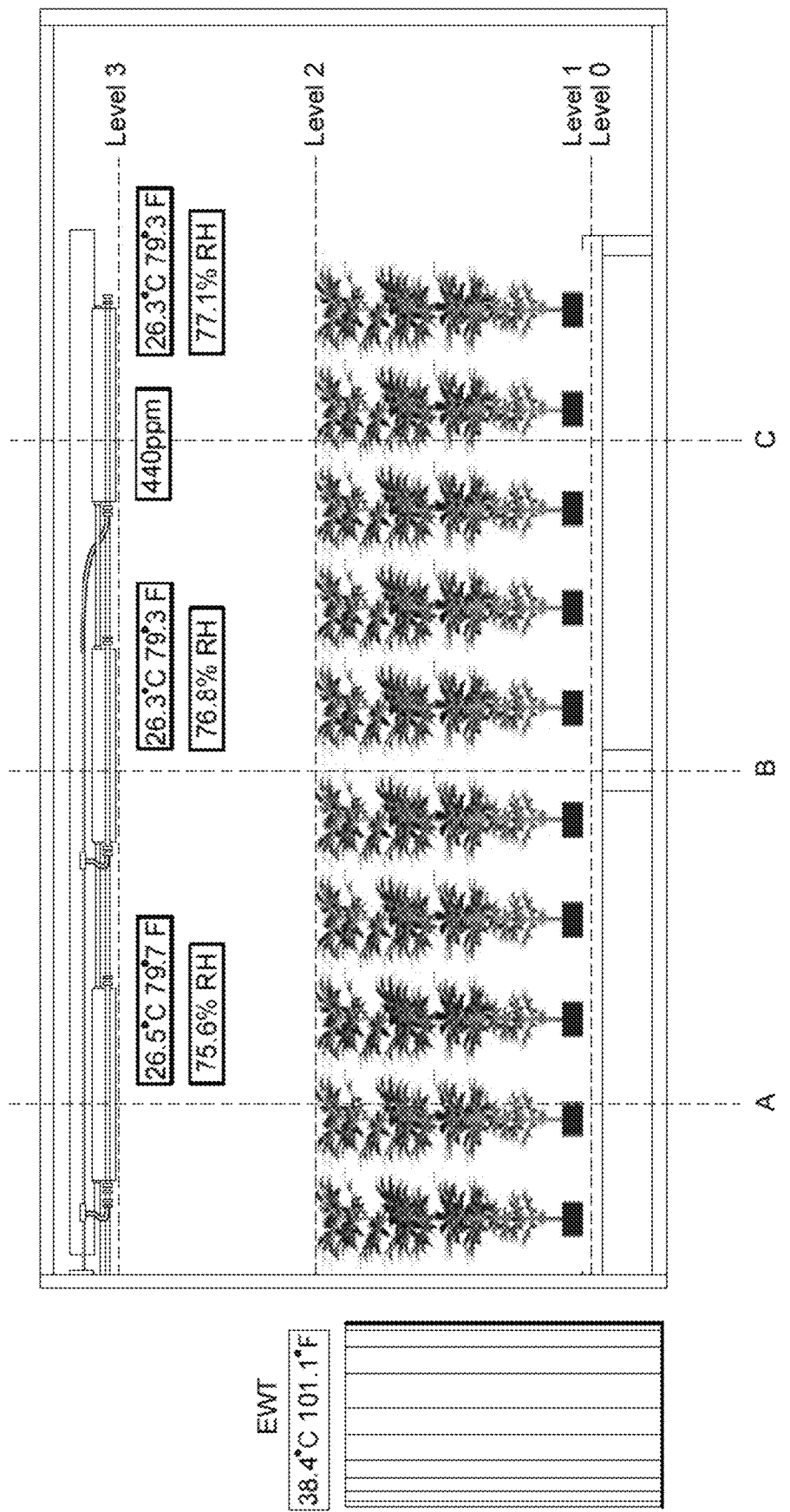
FIG. 21E shows a side view of the plant shelves of FIG. 21D as displayed in the HMI of FIG. 21A.
Figure 21F:
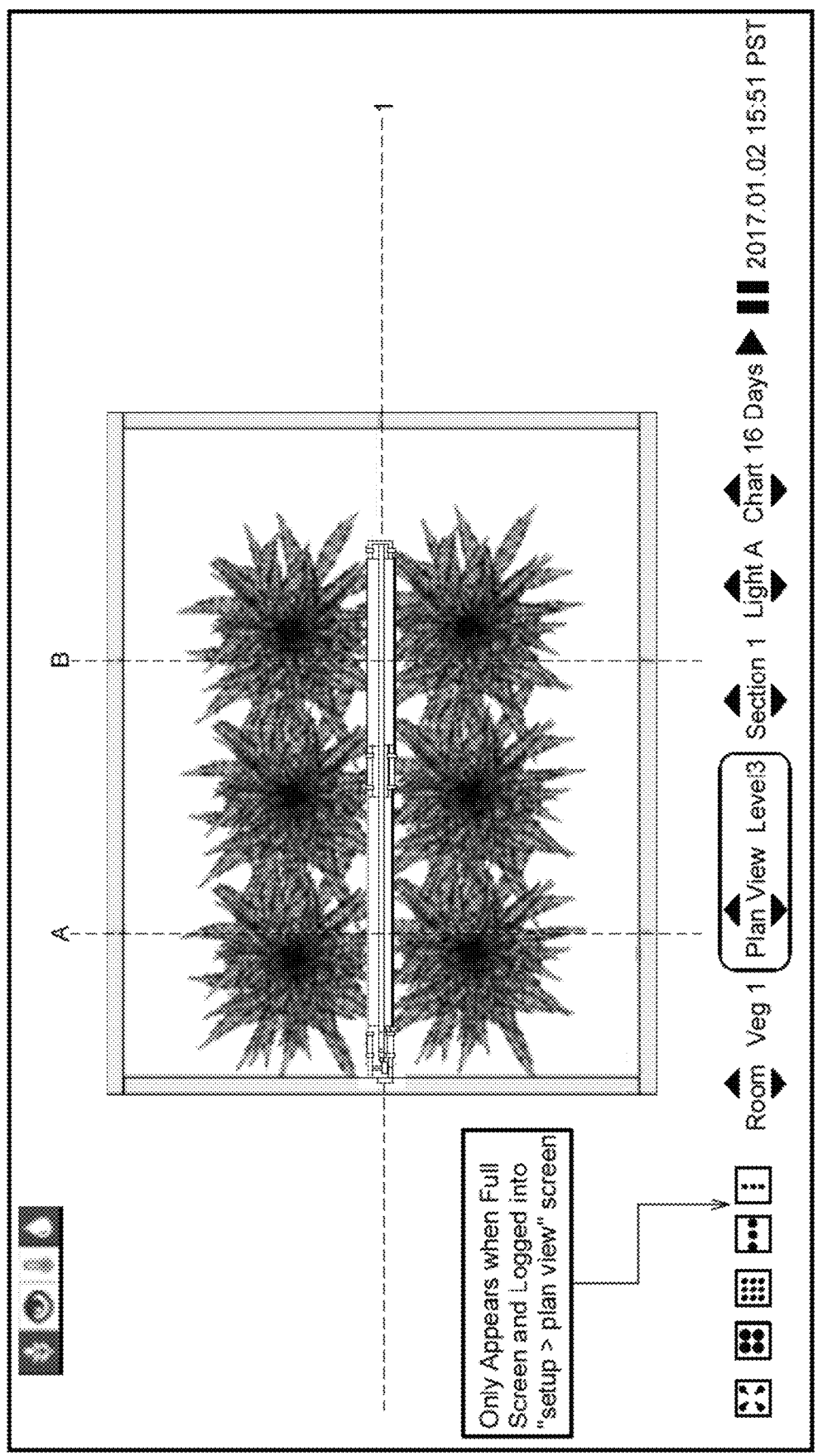
FIG. 21F shows a top view of another exemplary plant shelf as displayed in the HMI of FIG. 21A.
Figure 21G:
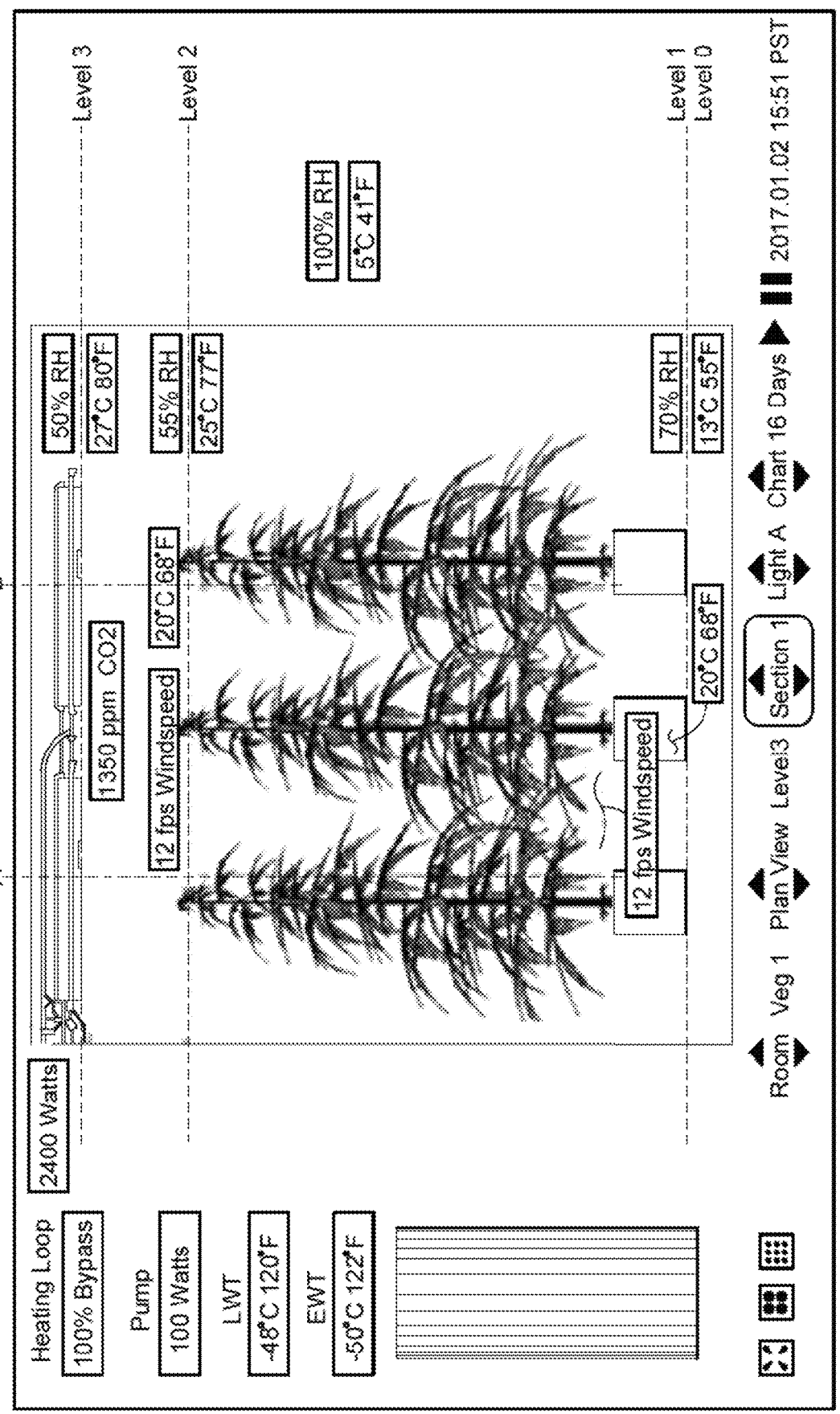
FIG. 21G shows a side view of the plant shelf of FIG. 21F where the nodes are subdivided into levels that correspond to different regions of the agricultural environment.

In some implementations, the HMI 5100 may enable users to select one or more nodes 4200 from an array 4100 in the distributed sensor grid 4000 and display the data collected by these nodes 4200. To facilitate selection of nodes 4200, the HMI 5100 may include a representation of the agricultural environment. For example, FIGS. 21B-21G show various top and side views of different arrangements of plants (e.g., horizontal/vertical farming, one or multiple plant shelves, one or multiple rows of plants per shelf). As shown, the representation of the agricultural environment may be overlaid with data recorded by various sensors disposed in the distributed sensor grid 4000. For instance, FIGS. 21C and 21E show sensory data for each lighting fixture 1000. FIG. 21G shows sensory data at different levels (e.g., the soil level 4310, the plant level 4320, the light canopy level 4330, and the ambient environment level 4340). The data shown may include, but is not limited to, the operating parameters of various control systems (e.g., power draw from lighting fixtures 1000, pump power in a hydronics system) and environmental parameters (e.g., air temperature, leaf temperature, air flow rate, relative humidity, PPFD, pH level). The HMI 5100 may also allow users to select different node arrays 4100 (e.g., separate growing areas or rooms in an environment), views of the environment (e.g., top view, side view, perspective view), and control systems coupled to the sensors 4220 (e.g., various lighting fixtures 1000). Data can also be updated in real-time, selected from list of recorded times, or displayed as an average over a period of time.

Figure 21H:
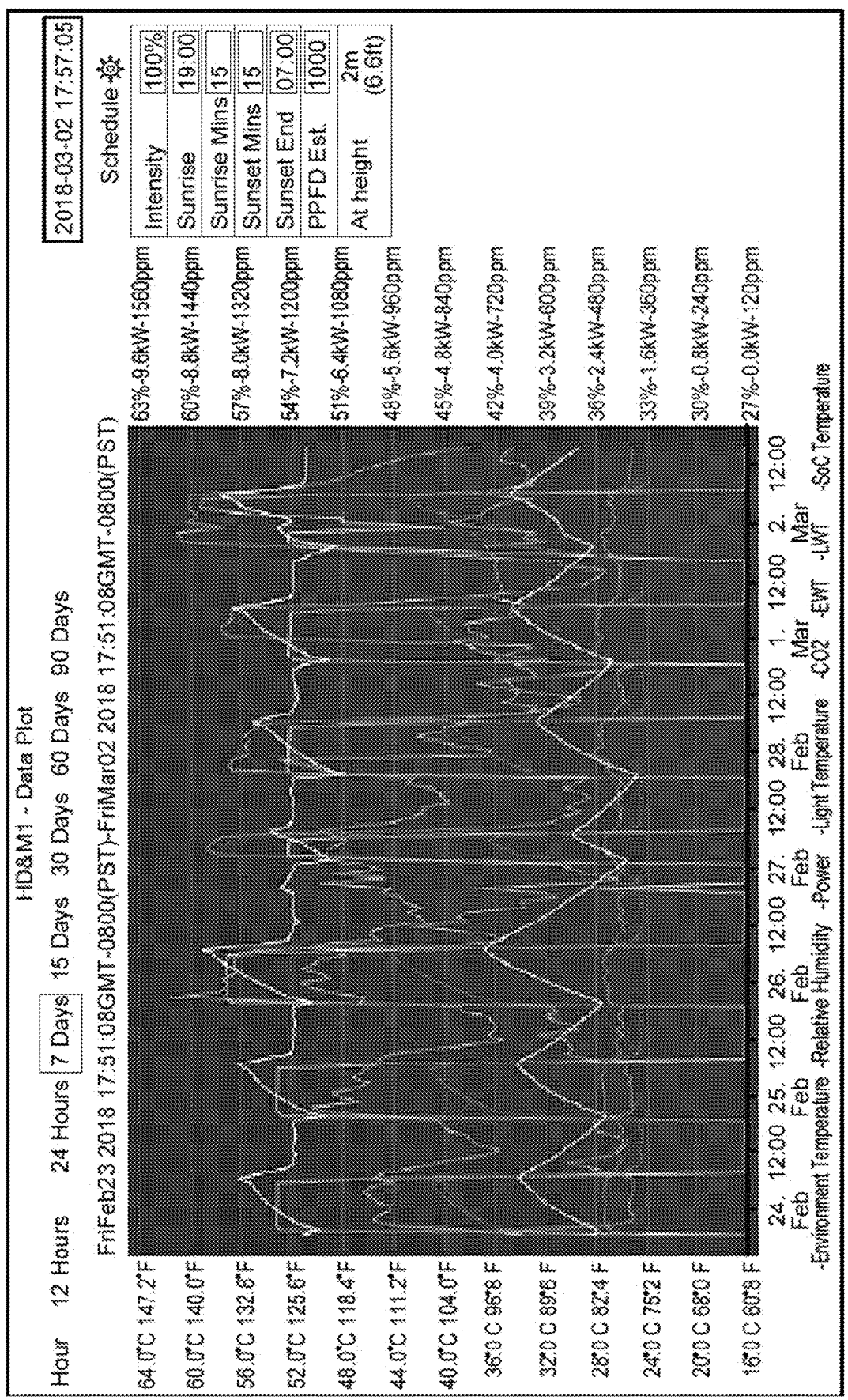
FIG. 21H shows a chart of various sensory data recorded by an integrated sensor assembly as a function of time as displayed in the HMI of FIG. 21A.
Figure 21I:
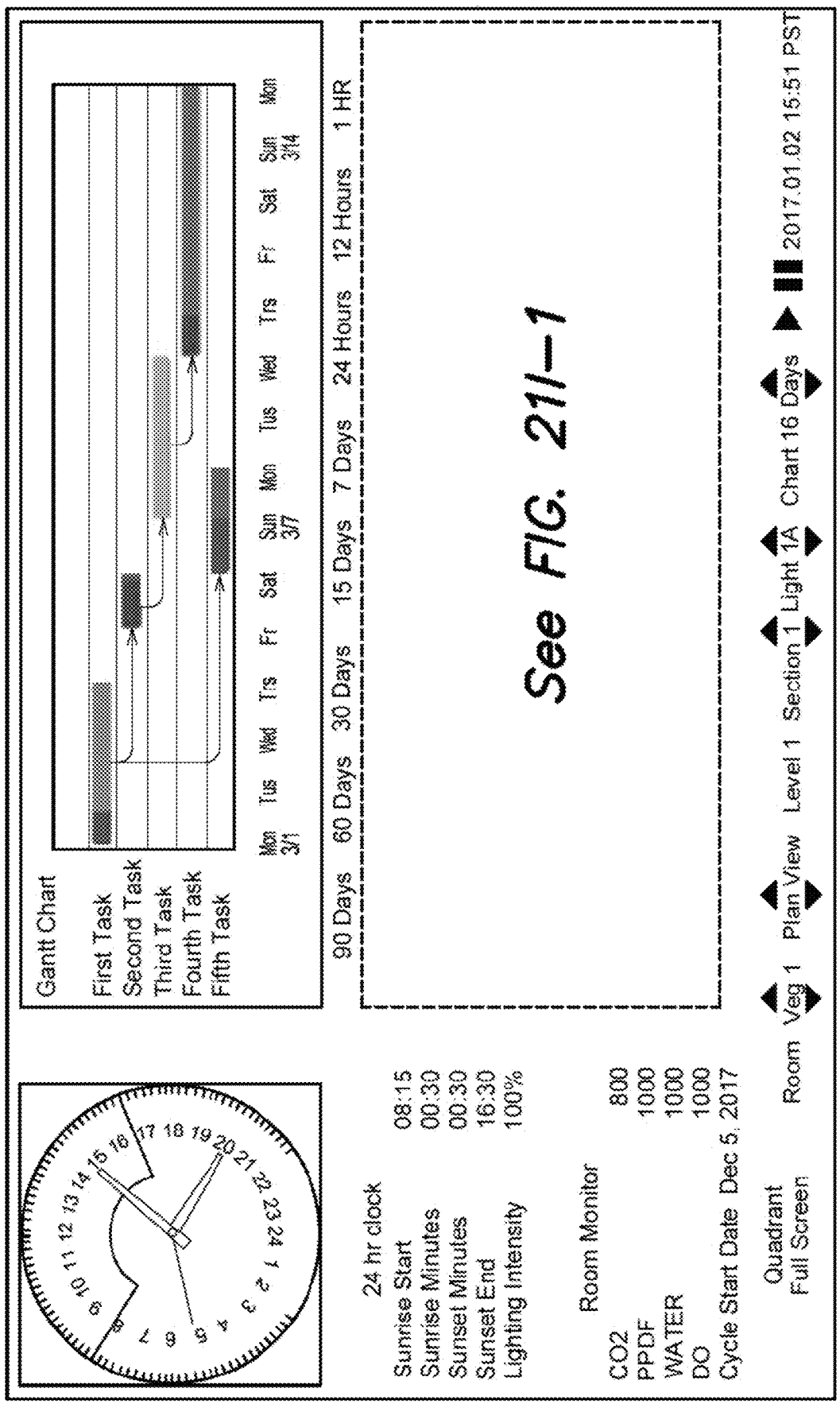
FIG. 21I shows another chart of various sensory data as a function of time and a scheduling chart as displayed in the HMI of FIG. 21A.
Figures 1, 21I:
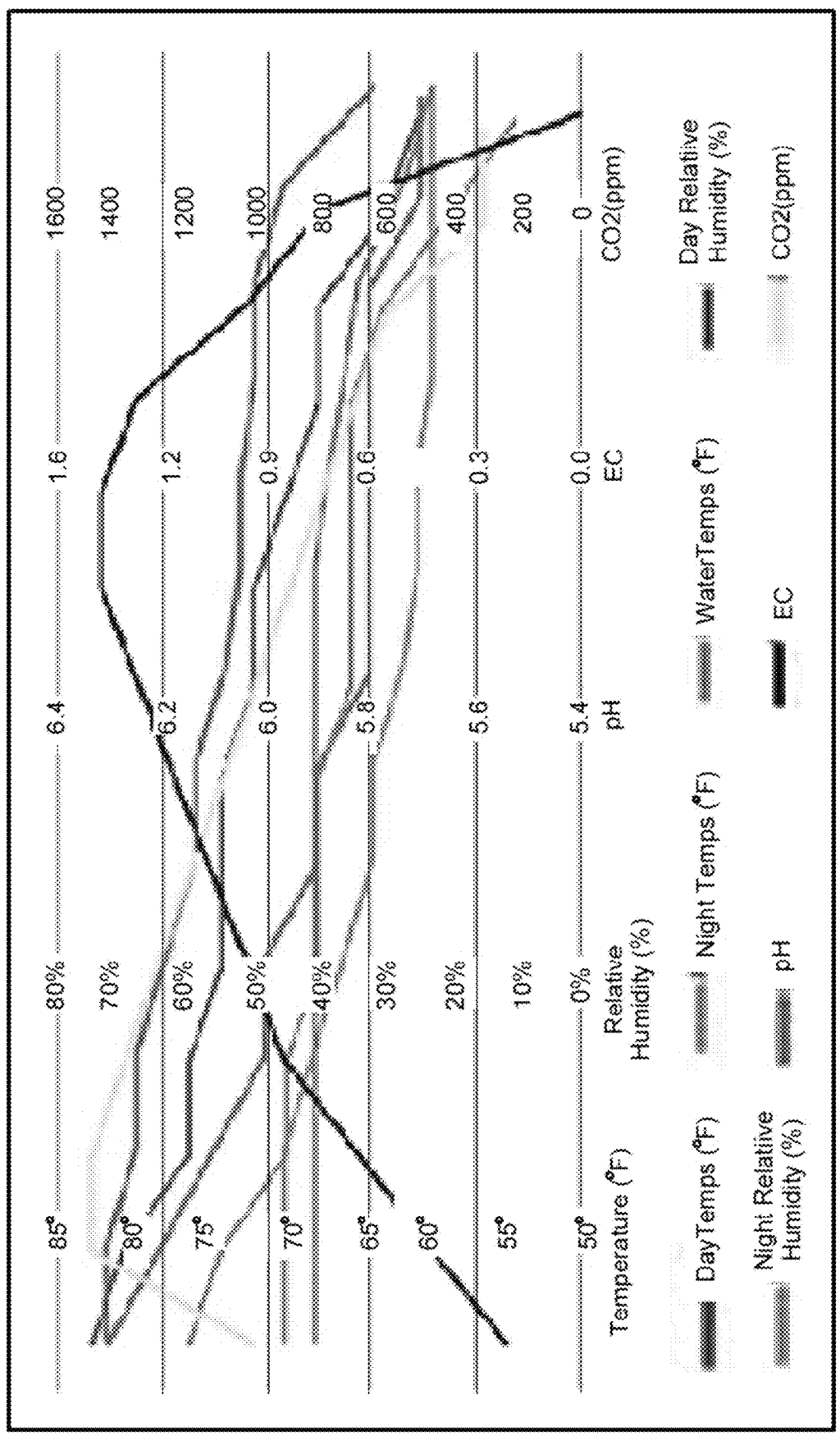
Figure 21J:
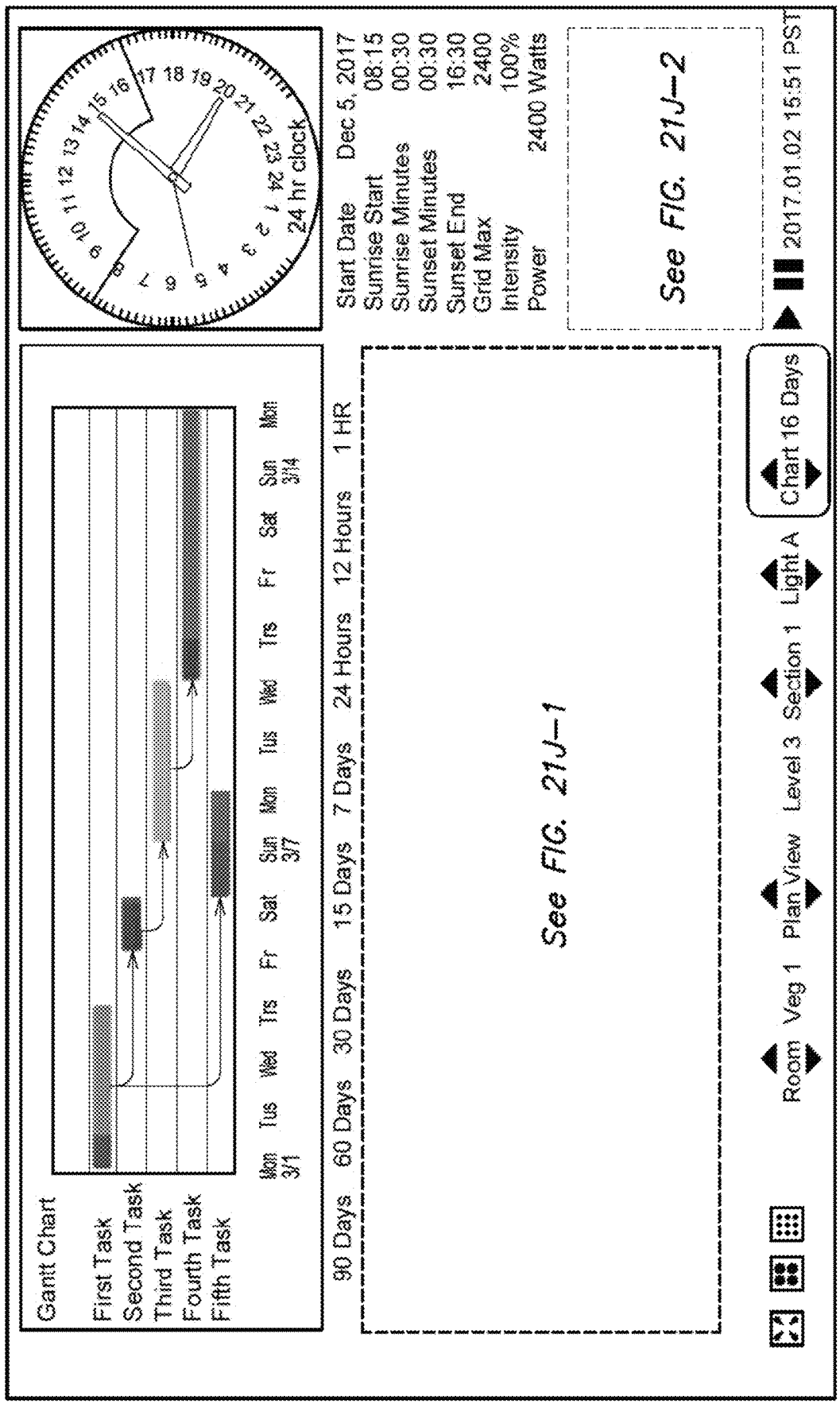
FIG. 21J shows another chart of various sensory data as a function of time, a scheduling chart, and a 3D plot of sensory data as displayed in the HMI of FIG. 21A.
Figures 1, 21J:
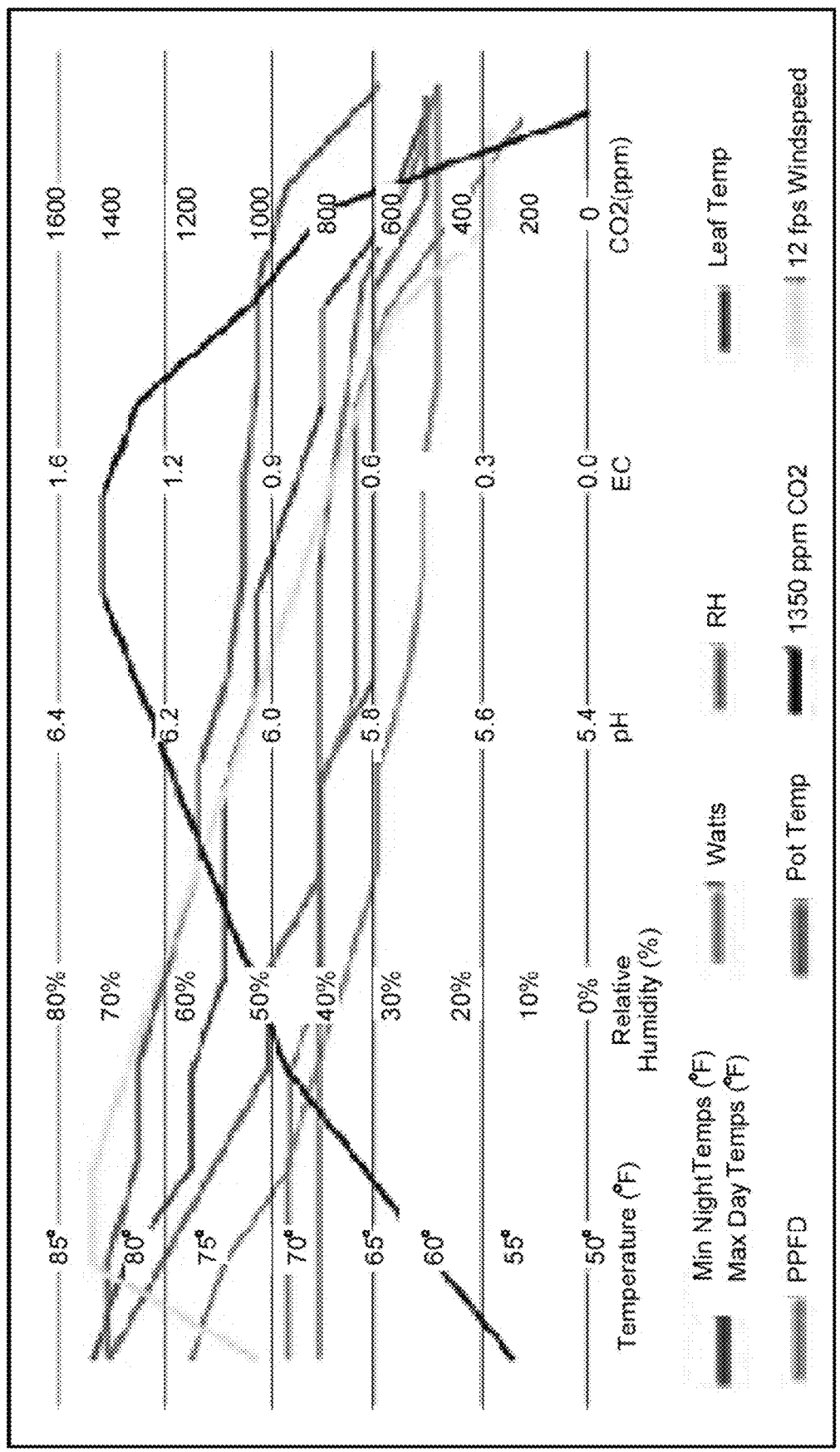
Figures 2, 21J:
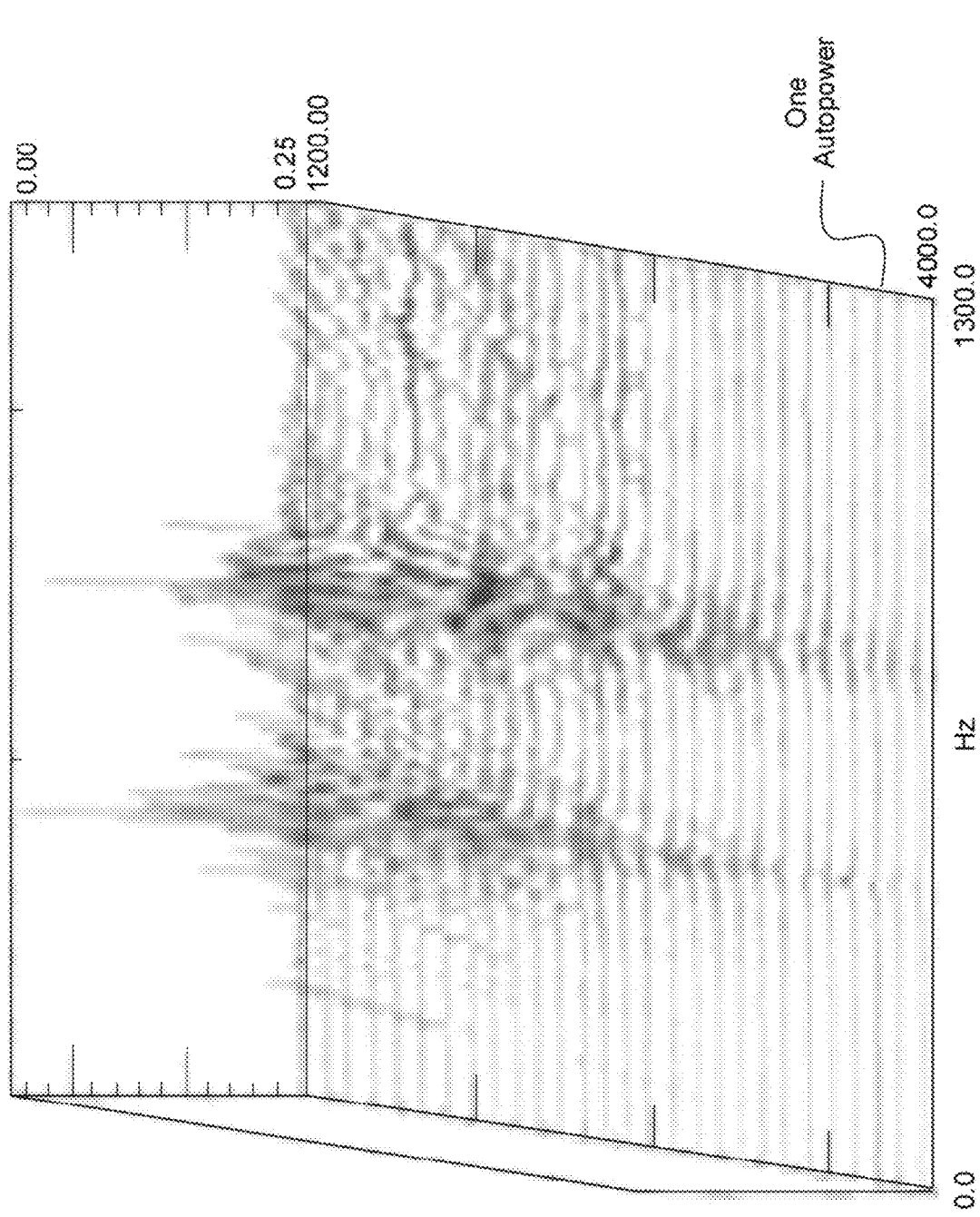

The HMI 5100 may allow users to display historical data as a function of time as shown in FIGS. 21H-J. For instance, FIG. 21H shows the environment temperature, relative humidity, electrical power, temperature of a lighting fixture 1000, carbon dioxide concentration, entering water temperature (EWT), leaving water temperature (LWT), and system on a chip (SoC) temperature over a period of several days. Data can be recorded continuously in real-time or incrementally over set time increments (e.g., every 30 minutes, 60 minutes, and 3 hours). The HMI 5100 may also allow users to control and display a schedule as shown in FIGS. 21I and 21J as a Gantt chart. A schedule can be used to organize tasks to be performed on the environment (e.g., a maintenance schedule for various systems in the environment during a week of operation, periods of the day when hydronics or HVAC systems should turn on). Three-dimensional line plots can also be used to display data as a function of multiple parameters as shown in FIG. 21J-2.

The HMI 5100 may also allow users to adjust control systems (e.g., adjusting the output of a lighting fixture 1000 to simulate a sunrise and sunset). In some implementations, the processor 5000 may automate, at least in part, various controllable conditions based on data from one or more sensors 4420 and user-defined criteria (e.g., set temperature, relative humidity, $CO_2$ concentrations).

Figure 21K:
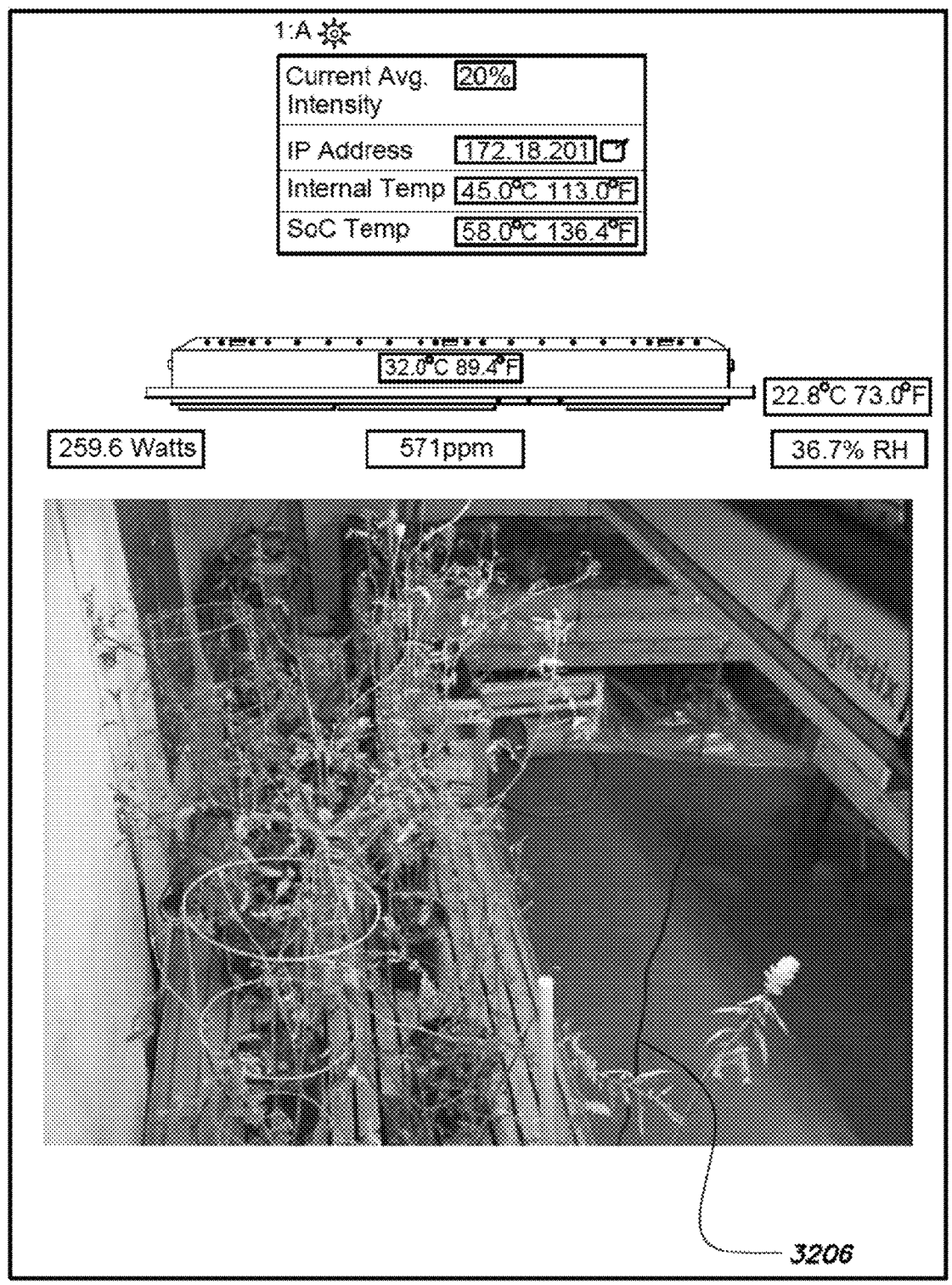
FIG. 21K shows an exemplary image or video frame of the agricultural environment as displayed in the HMI of FIG. 21A.

As described above, one or more cameras may be coupled to the distributed sensor grid 4000 to record still images or video of a portion of the agricultural environment as shown in FIG. 21K to allow users to remotely inspect the environment. In some implementations, the selection of a camera can be based on the proximity and field of view of a camera in relation to the nodes 4200 or a control system, e.g., a lighting fixture 1000, selected by a user. Images or video can be acquired on command by a user or recorded on a preset schedule.

The HMI 5100 can also be configured to display multiple views, data, and images or video of the environment separated in various panels. For example, FIG. 21A shows an exemplary implementation of the HMI 5100 in a quadrant format, which includes different views of a representation of the environment, a time history of various data, and images recorded by a camera are shown (see FIGS. 21A-1, 21D, 21E, 21H).

Figure 22A:
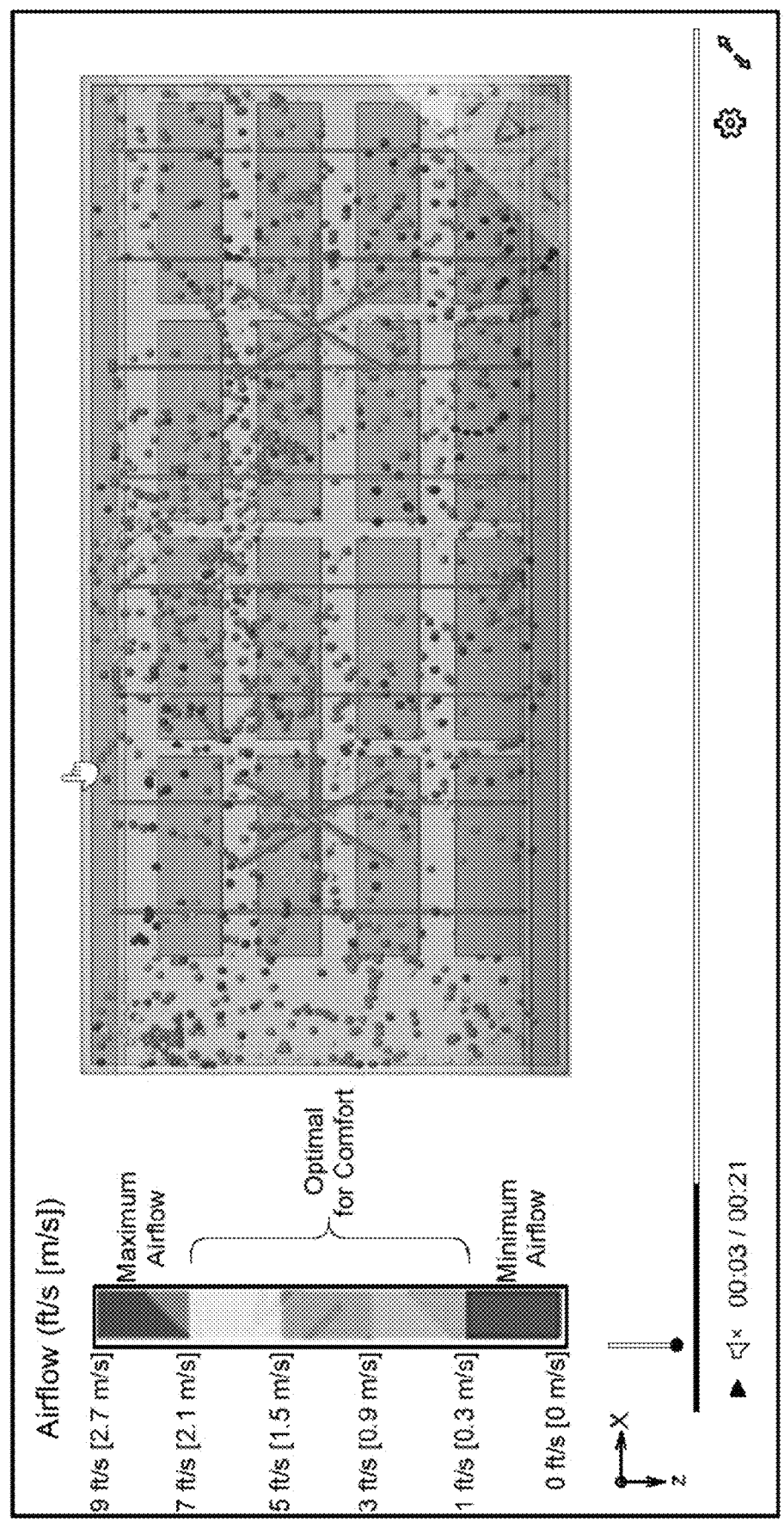
FIG. 22A shows a top view of a simulated air flow distribution in an agricultural environment, according to some implementations of the disclosure.
Figure 22B:
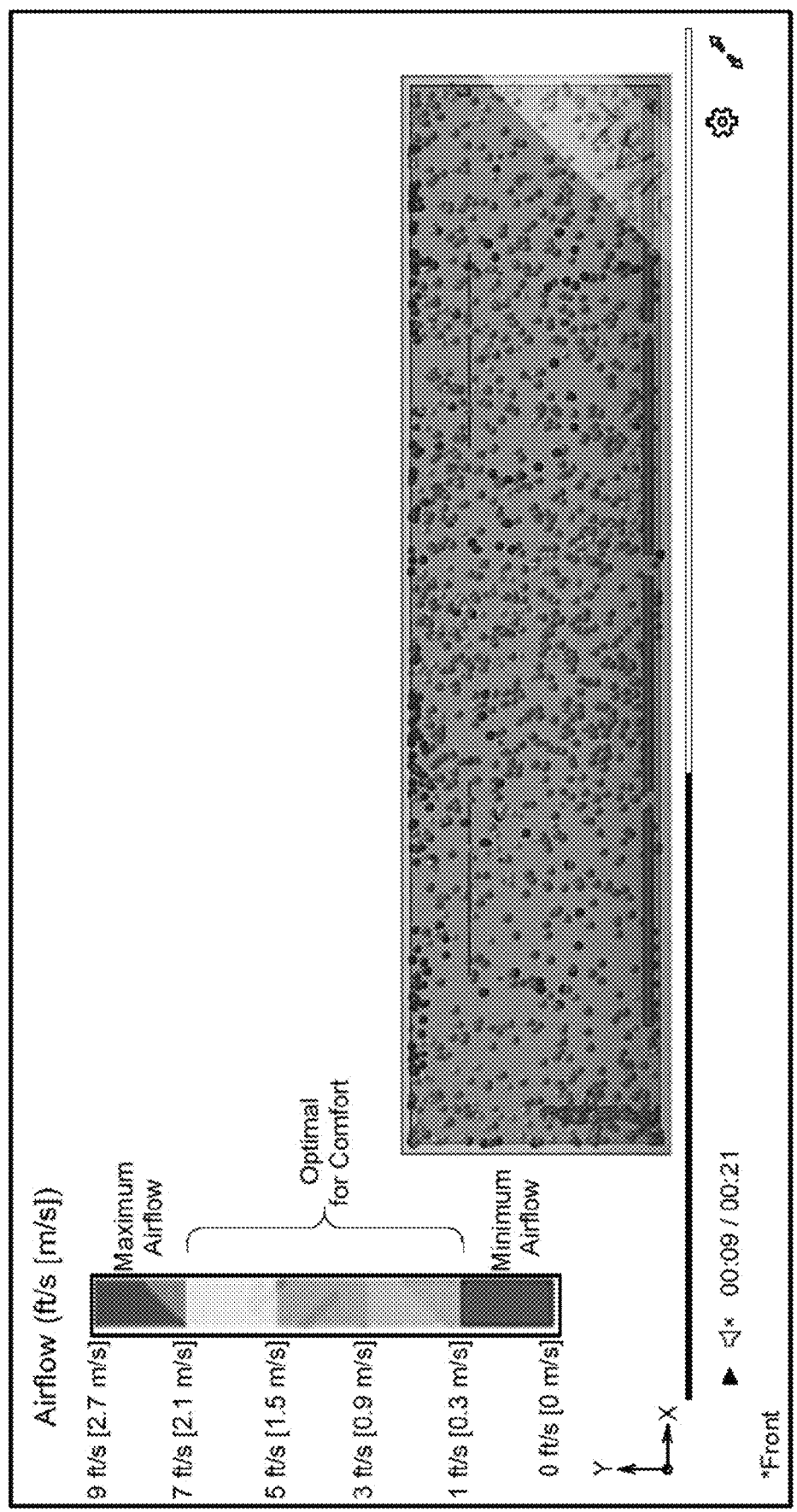
FIG. 22B shows a side view of the air flow distribution of FIG. 22A.
Figure 22C:
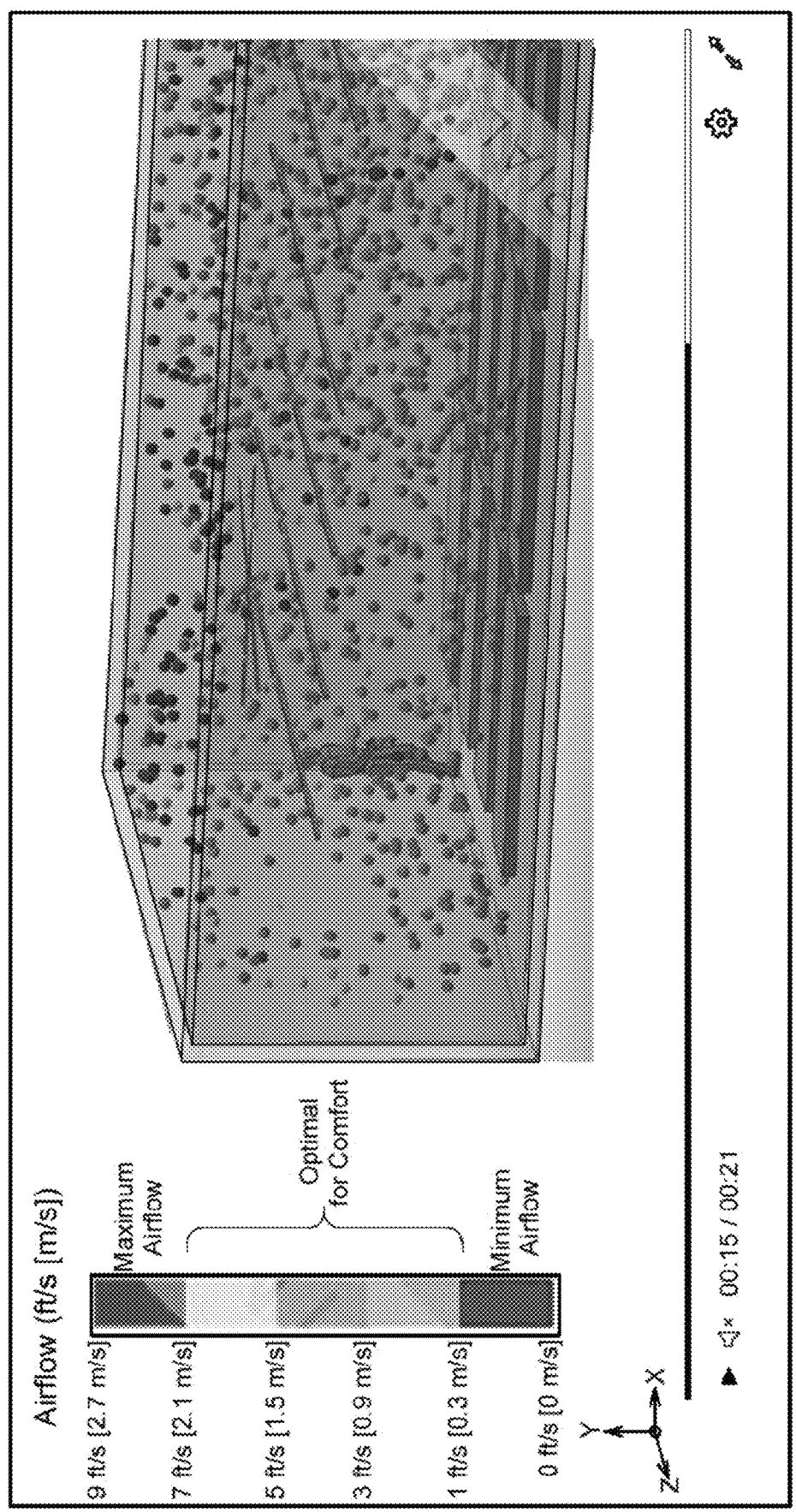
FIG. 22C shows a perspective view of the air flow distribution of FIG. 22A.

In some implementations, the processor 5000 can also perform additional analysis on data collected by the sensors 4420 in the distributed sensor grid 4000. An exemplary illustration of such analysis is shown in FIGS. 22A-C, which shows various views of a three-dimensional air flow distribution in an environment captured at various times.

Root Zone Level Monitoring

Based on the various concepts described above and illustrated in the accompanying drawings, various inventive implementations involving a sensing system configured to monitor a root zone level of a plant system compatible with the distributed sensing techniques will now be described.

With reference again to FIG. 20C, and in particular the soil level 4310 of the node array 4100, in some types of controlled agricultural environments the plants or crops are grown in soil, while in other environments the plants or crops are not grown in soil; instead, the root systems of respective plants may be exposed to a variety of other nutrient sources and/or various techniques to provide nutrients to the root systems. In view of the foregoing, in other implementations of the inventive concepts discussed herein, the soil level discussed above in connection with a node array may be viewed more generally as a "root zone level" (whether the roots be in soil or exposed to one or more other nutrient sources). As noted above, one or more sensors may be situated in the root zone level to measure and monitor various conditions and parameters germane to the health and nutrition of one or more root systems.

In general, the root system of a plant can provide various functions important to the growth and health of the plant. For example, the root system can absorb water and nutrients from the surrounding environment, providing nourishment to the plant. The root system can also store nutrients for future consumption. The degree to which the root system can provide such functions can be affected by the environmental conditions surrounding the root system. For instance, subpar environmental conditions can reduce the uptake of water or nutrients by the plant. By deploying sensors to monitor environmental conditions specific to the root system of the plant, e.g., in the root zone level of a node array, data from the sensors can be used to adjust various control systems in the agricultural environment to improve or maintain the functionality of the root system.

As an alternative to soil (e.g., dirt), "hydroponics" refers to methods of growing plans without soil, and instead using nutrient solutions (e.g., minerals in a water solvent. Plants may be grown with only their roots exposed to the mineral solution, or the roots may be supported by an inert medium (e.g., gravel or perlite). Examples of hydroponics methods that do not use a solid medium include Nutrient Film Techniques (NFT), Deep Water Culture (DWC), wick hydroponics, ebb and flow systems, drip hydroponics, and aeroponic methods (techniques in which plants are grown in an air or mist environment, e.g., fogponics, mistponics, in which a plant's dangling roots and lower stem are spayed with an atomized nutrient-rich solution). A variety of nutrients can be used in hydroponics methods (sometimes also referred to as "fertigation"); examples of such nutrients include, but are not limited to, natural or synthetic fertilizers, byproduct from fish waste, and duck manure.

The environmental conditions that can affect the functionality of the root system can vary depending on the type of the agricultural environment used. For example, in the soil-based environments discussed earlier, the functionality of the root system can depend on various parameters including, but not limited to, (1) the soil temperature, (2) the electrical conductivity of soil, which is an indicator of soil salinity, soil texture, and moisture content (3) the pH value, (4) the water tension, which relates to the force root systems should overcome to extract water from the soil, (5) the air permeability, (6) the soil compaction, which can be an indicator of water and soil quality, and (7) the water content of the soil. For hydroponic environments, the functionality of the root system can depend on various parameters including, but not limited to, (1) solution temperature, (2) the pH value, (3) the electrical conductivity, which is an indicator of solution salinity, and (4) the oxidation-reduction potential, which provides water oxygenation and bio activity.

Various types of sensors can be employed in the root zone level of a node array according to the concepts disclosed herein to monitor the various parameters described above. Examples of sensors that may be employed in the root zone level include, but are not limited to, temperature sensors (e.g., thermocouple, thermistor, resistance temperature detectors), electromagnetic sensors for electrical conductivity, dissolved oxygen sensors, nitrogen sensors, carbon dioxide sensors, optical sensors (e.g., photodetectors configured for visible, near-infrared (NIR), mid-infrared (MIR), and polarized light), mechanical sensors for soil compaction, electrochemical sensors (e.g., pH sensors), airflow sensors for soil air permeability, and water content sensors (e.g., coaxial impedance dielectric reflectometry, frequency domain reflectometry, time domain transmissometry, gypsum blocks, neutron probes).

CONCLUSION

All parameters, dimensions, materials, and configurations described herein are meant to be exemplary and the actual parameters, dimensions, materials, and/or configurations will depend upon the specific application or applications for which the inventive teachings is/are used. It is to be understood that the foregoing embodiments are presented primarily by way of example and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein.

In addition, any combination of two or more such features, systems, articles, materials, kits, and/or methods, if such features, systems, articles, materials, kits, and/or methods are not mutually inconsistent, is included within the inventive scope of the present disclosure. Other substitutions, modifications, changes, and omissions may be made in the design, operating conditions and arrangement of respective elements of the exemplary implementations without departing from the scope of the present disclosure. The use of a numerical range does not preclude equivalents that fall outside the range that fulfill the same function, in the same way, to produce the same result.

The above-described embodiments can be implemented in multiple ways. For example, embodiments may be implemented using hardware, software or a combination thereof. When implemented in software, the software code can be executed on a suitable processor or collection of processors, whether provided in a single computer or distributed among multiple computers.

Further, it should be appreciated that a computer may be embodied in any of a number of forms, such as a rack-mounted computer, a desktop computer, a laptop computer, or a tablet computer. Additionally, a computer may be embedded in a device not generally regarded as a computer but with suitable processing capabilities, including a Personal Digital Assistant (PDA), a smart phone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible format.

Such computers may be interconnected by one or more networks in a suitable form, including a local area network or a wide area network, such as an enterprise network, an intelligent network (IN) or the Internet. Such networks may be based on a suitable technology, may operate according to a suitable protocol, and may include wireless networks, wired networks or fiber optic networks.

The various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine. Some implementations may specifically employ one or more of a particular operating system or platform and a particular programming language and/or scripting tool to facilitate execution.

Also, various inventive concepts may be embodied as one or more methods, of which at least one example has been provided. The acts performed as part of the method may in some instances be ordered in different ways. Accordingly, in some inventive implementations, respective acts of a given method may be performed in an order different than specifically illustrated, which may include performing some acts simultaneously (even if such acts are shown as sequential acts in illustrative embodiments).

All publications, patent applications, patents, and other references mentioned herein are incorporated by reference in their entirety.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of" "only one of" or "exactly one of." "Consisting essentially of" when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:

1. A distributed lighting and sensing system for controlled environment agriculture (CEA) in a growing area space defined by three orthogonal axes including a first axis (x)

along a width of the growing area space, a second axis (y) along a length of the growing area space, and a third axis (z) along a height of the growing area space, the system comprising:
  a lighting system, comprising:
    a first lighting fixture at a first position ($x_1$, $y_1$) in a plane defined by the first axis and the second axis of the growing area space and at a first height ($z_{light}$) along the third axis of the growing area space; and
    a second lighting fixture at a second position ($x_2$, $y_2$) in the plane defined by the first axis and the second axis of the growing area space and at the first height ($z_{light}$) along the third axis of the growing area space,
    wherein the first position ($x_1$, $y_1$) of the first lighting fixture at the first height ($z_{light}$) and the second position ($x_2$, $y_2$) of the second lighting fixture at the first height ($z_{light}$) define a multidimensional grid of nodes in the growing area space at which the lighting system provides at least one of operating power or network communications access to respective nodes of the multidimensional grid of nodes; and
  a sensing system, comprising:
    a first sensor and a second sensor situated at a first node ($x_1$, $y_1$, $z_1$) of the multidimensional grid of nodes, the first sensor and the second sensor coupled to the first lighting fixture to receive the at least one of operating power or network communication access from the first lighting fixture; and
    a third sensor and a fourth sensor situated at a second node ($x_2$, $y_2$, $z_2$) of the multidimensional grid of nodes, the third sensor and the fourth sensor coupled to the second lighting fixture to receive the at least one of operating power or network communication access from the second lighting fixture,
    wherein:
      $z_1$ and $z_2$ are different; and
      at least the first sensor and the third sensor are different.

2. The system of claim 1, wherein $x_1 = x_2$ or $y_1 = y_2$ such that the multidimensional grid of nodes is a two-dimensional array of nodes.

3. The system of claim 1, wherein $x_1$ and $x_2$ are different, and $y_1$ and $y_2$ are different, such that the multidimensional grid of nodes is a three-dimensional array of nodes.

4. The system of claim 1, wherein:
  the growing area space includes multiple vertical levels along the third axis of the growing area space;
  the first node is at one of the multiple vertical levels; and
  the second node is at another of the multiple vertical levels.

5. The system of claim 4, wherein the multiple vertical levels include a root zone level ($z_{root}$), a plant level ($z_{plant}$), a light canopy level ($z_{light}$), and an ambient environment level ($z_{ambient}$).

6. The system of claim 4, wherein the lighting system provides both of the operating power and the network communications access to the first sensor and the second sensor.

7. The system of claim 1, wherein at least the first sensor is a first integrated sensor assembly comprising a plurality of sensors including:
  an air temperature sensor;
  a visible light sensor;
  a near infrared (NIR) sensor;
  a relative humidity sensor;
  a camera;
  a carbon dioxide ($CO_2$) sensor; and/or
  an infrared (IR) sensor.

8. The system of claim 1, wherein the sensing system further comprises:
  a fifth sensor situated at a third node ($x_3$, $y_3$, $z_3$) of the multidimensional grid of nodes, the fifth sensor coupled to one of the first lighting fixture and the second lighting fixture to receive the at least one of the operating power or the network communication access from the one of the first lighting fixture and the second lighting fixture, wherein if $x_3 = x_1$ and $y_3 = y_1$, $z_3$ is different than $z_1$, and if $x_3 = x_2$ and $y_3 = y_2$, $z_3$ is different than $z_2$.

9. A distributed sensing system comprising:
  a first plurality of integrated sensor assemblies distributed along (1) a first horizontal axis and (2) a vertical axis at intervals corresponding to a first set of vertical levels of an agricultural environment,
  wherein:
    the first horizontal axis is substantially orthogonal to the vertical axis;
    a first integrated sensor assembly of the first plurality of integrated sensor assemblies, located at a first level of the first set of vertical levels, comprises at least a first sensor and a second sensor;
    a second integrated sensor assembly of the first plurality of integrated sensor assemblies, located at a second level of the first set of vertical levels, comprises at least a third sensor and a fourth sensor;
    the first level and the second level correspond to different levels of the agricultural environment; and
    at least the first sensor and the third sensor are different.

10. The distributed sensing system of claim 9, wherein the first plurality of integrated sensor assemblies comprises:
  a first subset of integrated sensor assemblies distributed along the first horizontal axis at substantially regular intervals defined by a first pitch and located at the first level of the first set of vertical levels, each integrated sensor assembly of the first subset of integrated sensor assemblies being identical with the first integrated sensor assembly; and
  a second subset of integrated sensor assemblies distributed along the first horizontal axis at substantially regular intervals defined by a second pitch different than the first pitch and located at the second level of the first set of levels, each integrated sensor assembly of the second subset of integrated sensor assemblies being identical with the second integrated sensor assembly.

11. The distributed sensing system of claim 10, wherein:
  the first integrated sensor assembly has a first field of view and the first pitch is chosen such that respective first fields of view of the integrated sensor assemblies of the first subset of integrated sensor assemblies at least partially overlap with one another; and
  the second integrated sensor assembly has a second field of view and the second pitch is chosen such that respective second fields of view of the integrated sensor assemblies of the second subset of integrated sensor assemblies at least partially overlap with one another.

12. The distributed sensing system of claim 9, wherein the first sensor and the second sensor share a first electrical port of the first integrated sensor assembly to receive at least one of operating power or network communications access.

13. The distributed sensing system of claim 12, wherein the third sensor and the fourth sensor share a second electrical port of the second integrated sensor assembly to receive at least one of operating power or network communications access, the second electrical port being different from the first electrical port.

14. The distributed sensing system of claim 9, wherein the first sensor comprises a visible light sensor and the second sensor comprises an infrared (IR) leaf temperature sensor.

15. The distributed sensing system of claim 14, wherein the third sensor comprises a carbon dioxide sensor and the fourth sensor comprises a relative humidity sensor.

16. A distributed sensing system comprising:
a plurality of integrated sensor assemblies distributed at a plurality of nodes along at least one axis in an agricultural environment,
wherein:
the at least one axis is defined with respect to a spatial origin corresponding to at least one of a corner of the agricultural environment, a plant in the agricultural environment, a lighting fixture in the agricultural environment, or a control system in the agricultural environment;
each node of the plurality of nodes is positioned at an indexed location defined by a corresponding distance along the at least one axis with respect to the spatial origin;
each of the integrated sensor assemblies of the plurality of integrated sensor assemblies has at least two sensors;
at least two integrated sensor assemblies of the plurality of the integrated sensor assemblies have at least one different sensor; and
at least one integrated sensor assembly of the plurality of integrated sensor assemblies includes:
a visible light sensor; and
an infrared leaf temperature sensor.

17. The distributed sensing system of claim 16, additionally comprising a processor operatively coupled to the plurality of integrated sensor assemblies,
wherein, upon execution by the processor of processor-executable instructions:
the processor provides a visual representation of the agricultural environment; and
the processor provides sensory data recorded by at least one sensor of at least one integrated sensor assembly of the plurality of integrated sensor assemblies overlaid on the visual representation of the agricultural environment at locations in the visual representation of the agricultural environment corresponding to the indexed locations.

18. The distributed sensing system of claim 17 wherein:
the at least one axis includes a first axis (x) along a width of the agricultural environment, a second axis (y) along a length of the agricultural environment, and a third axis (z) along a height of the agricultural environment, the first, second, and third axes being orthogonal with respect to one another; and
the processor provides multiple views of the visual representation of the agricultural environment, the multiple views comprising:
a side view defined by the third axis (z) and one of the first axis (x) or the second axis (y); and
a top view defined by the first axis (x) and the second axis (y).

19. The distributed sensing system of claim 16, wherein:
the indexed locations of each node in the plurality of nodes are defined by respective distances along three orthogonal axes including a first axis (x) along a width of the agricultural environment, a second axis (y) along a length of the agricultural environment, and third axis (z) along a height of the agricultural environment; and
the plurality of nodes is distributed along (1) at least one of the first axis (x) or the second axis (y) at approximately or substantially regular intervals defined by a pitch and (2) the third axis (z).

20. The distributed sensing system of claim 19, wherein the pitch of the plurality of nodes along the at least one of the first axis (x) or the second axis (y) substantially corresponds to respective positions of a plurality of lighting fixtures disposed in the agricultural environment substantially along the at least one of the first axis (x) or the second axis (y).

21. The distributed sensing system of claim 19, wherein the pitch of the plurality of nodes along the at least one of the first axis (x) or the second axis (y) substantially corresponds to respective positions of a plurality of plant shelves disposed in the agricultural environment substantially along the at least one of the first axis (x) or the second axis (y).

22. The distributed sensing system of claim 19, wherein the plurality of nodes is distributed along the third axis (z) along at a set of vertical levels of the agricultural environment, the set of vertical levels comprising a root zone level, a plant level, a light canopy level, and an ambient environment level.

23. The distributed sensing system of claim 16, wherein:
the plurality of nodes is distributed along at least one axis in the agricultural environment at approximately or substantially regular intervals;
a first integrated sensor assembly of the plurality of integrated sensor assemblies is positioned at a first node of the plurality of nodes;
the first integrated sensor assembly includes a first sensor with a first field of view;
a second integrated sensor assembly of the plurality of integrated sensor assemblies is positioned at a second node of the plurality of nodes, the second node being a nearest adjacent node to the first node along the at least one axis in the agricultural environment;
the second integrated sensor assembly includes a second sensor with a second field of view; and
the first field of view at least partially overlaps with the second field of view.

24. A distributed sensing system for controlled environment agriculture (CEA) in a growing area, the system comprising:
a first plurality of sensors distributed along (1) a first horizontal axis and (2) a vertical axis at intervals corresponding to a first set of vertical levels of an agricultural environment, the first plurality of sensors comprising:
a first subset of sensors distributed along the first horizontal axis at substantially regular intervals defined by a first pitch and located at a first level of the first set of vertical levels; and
a second subset of sensors distributed along the first horizontal axis at substantially regular intervals defined by a second pitch different than the first pitch and located at a second level of the first set of vertical levels,
wherein:
the first horizontal axis is substantially orthogonal to the vertical axis; and
the first level and the second level correspond to different levels of the agricultural environment.

25. The distributed sensing system of claim 24, wherein:
at least some sensors of the first subset of sensors each have a first field of view and the first pitch is chosen such that respective first fields of view of the at least some sensors of the first subset of sensors at least partially overlap with one another; and at least some sensors of the second subset of sensors each have a second field of view different than the first field of view and the second pitch is chosen such that respective second fields of view of the at least some sensors of the second subset of sensors at least partially overlap with one another.

26. The distributed sensing system of claim 24, wherein the first plurality of sensors is further distributed along a second horizontal axis, the second horizontal axis being substantially orthogonal with respect to the first horizontal axis and the vertical axis.

27. The distributed sensing system of claim 24, further comprising:

a first plurality of lighting fixtures disposed within the first level of the growing area and distributed at regular intervals along the first horizontal axis, wherein the first pitch of the first subset of sensors substantially corresponds to the respective positions of the first plurality of lighting fixtures along the first horizontal axis.

28. The distributed sensing system of claim 24, wherein:
the growing area includes a plurality of plants; and
the first plurality of vertical levels comprises a root zone level, a plant level, and a light canopy level.

29. The distributed sensing system of claim 28, wherein:
the first vertical level of the first plurality of vertical levels is the light canopy level and the second vertical level of the first plurality of vertical levels is the plant level;

at least some sensors of the first subset of sensors are one of a visible light sensor or an infrared (IR) leaf temperature sensor; and at least some sensors of the second subset of sensors are one of a carbon dioxide sensor or a relative humidity sensor.

30. The distributed sensing system of claim 24, wherein:
at least some sensors of the first subset of sensors are a visible light sensor; and
the first plurality of sensors further comprises:
a plurality of infrared (IR) leaf temperature sensors located at the first level of the first set of vertical levels and disposed proximate to a corresponding visible light sensor of the at least some sensors of the first subset of sensors.

* * * * *